(12) United States Patent
Kamireddy et al.

(10) Patent No.: US 8,349,870 B2
(45) Date of Patent: Jan. 8, 2013

(54) FUNGICIDAL HETERCYCLIC COMPOUNDS

(75) Inventors: Balreddy Kamireddy, Hockessin, DE (US); Robert James Pasteris, Newark, DE (US); Mary Ann Hanagan, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 50 days.

(21) Appl. No.: 12/863,875

(22) PCT Filed: Jan. 22, 2009

(86) PCT No.: PCT/US2009/031686
§ 371 (c)(1),
(2), (4) Date: Jul. 21, 2010

(87) PCT Pub. No.: WO2009/094445
PCT Pub. Date: Jul. 30, 2009

(65) Prior Publication Data
US 2010/0292275 A1 Nov. 18, 2010

Related U.S. Application Data

(60) Provisional application No. 61/062,395, filed on Jan. 25, 2008.

(51) Int. Cl.
A61K 31/445 (2006.01)
C07D 405/00 (2006.01)

(52) U.S. Cl. ...................................... 514/326; 546/209

(58) Field of Classification Search .................. 514/326; 546/209
See application file for complete search history.

(56) References Cited

U.S. PATENT DOCUMENTS 7,713,998 B2   5/2010   Nakai et al.

FOREIGN PATENT DOCUMENTS

| WO | 2004/056751 A1 | 7/2004 |
|---|---|---|
| WO | 2005/003128 A1 | 1/2005 |
| WO | WO2005/003128 * | 1/2005 |
| WO | 2005/087765 A1 | 9/2005 |
| WO | 2006/051826 A1 | 5/2006 |
| WO | 2007/014290 A2 | 2/2007 |
| WO | 2008/013622 A2 | 1/2008 |
| WO | 2008/013925 A2 | 1/2008 |
| WO | 2008/091580 A2 | 7/2008 |
| WO | 2008/091594 A2 | 7/2008 |
| WO | 2009/055514 A2 | 4/2009 |
| WO | 2009/094407 A2 | 7/2009 |

OTHER PUBLICATIONS

Goldfarb et al. CAS: 151:92845, 2009.*
Griffioen et al. CAS: 147: 277611, 2007.*
Sakano et al. CAS: 96:52331, 1982.*
Lee et al. CAS: 84: 159598, 1976.*
Habashita et al. CAS: 141: 71555, 2004.*
Durant et al. CAS: 127: 90515, 1997.*
Stamford et al. CAS: 135: 61332, 2001.*
Kitajima et al. CAS: 136 :200479, 2002.*
Janssens et al. CAS: 138: 338147, 2003.*
Henriksson et al. CAS: 144:36327, 2005.*

* cited by examiner

Primary Examiner — Rei-tsang Shiao

(57) ABSTRACT

Disclosed are compounds of Formula 1, including all geometric and stereoisomers, N-oxides, and salts thereof,

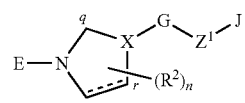

wherein
E, $R^2$, G, $Z^1$, J and n are as defined in the disclosure.
Also disclosed are compositions containing the compounds of Formula 1 and methods for controlling plant disease caused by a fungal pathogen comprising applying an effective amount of a compound or a composition of the invention.

12 Claims, No Drawings

FUNGICIDAL HETERCYCLIC COMPOUNDS

FIELD OF THE INVENTION

This invention relates to certain heterocyclic compounds, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

PCT Patent Publication WO 05/003128 discloses certain thiazolylpiperidines of Formula i

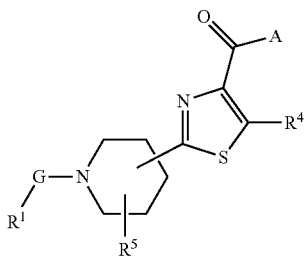

and their use as microsomal triglyceride transfer protein inhibitors.

PCT Patent Publication WO 04/058751 discloses piperidinyl-thiazole carboxamide derivatives for altering vascular tone.

PCT Patent Publication WO 2007/014290 discloses certain carboxamide derivatives of Formula ii

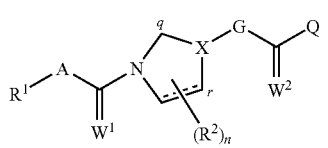

and their use as fungicides.

SUMMARY OF THE INVENTION

This invention is directed to compounds of Formula 1 (including all geometric and stereoisomers), N-oxides, and salts thereof, agricultural compositions containing them and their use as fungicides:

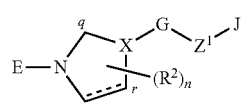

1 wherein
E is a radical selected from the group consisting of

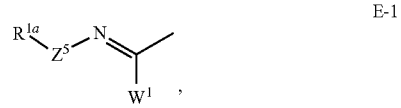

E-1

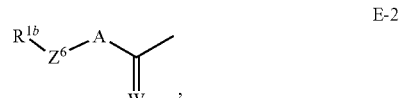

E-2

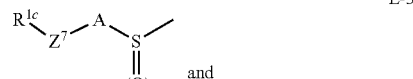

E-3 and

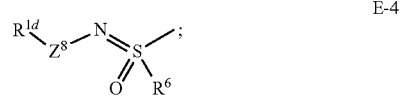

E-4

A is $CHR^{15}$, $NR^{16}$ or $C(=O)$;
G is an optionally substituted 5-membered heterocyclic ring;
J is a 5-, 6- or 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S and up to 4 N, and up to 3 ring members selected from $C(=O)$, $C(=S)$, $S(=O)_s(=NR^{23})_f$ and $SiR^{17}R^{18}$, and optionally substituted with up to 5 substituents independently selected from $R^5$;
$W^1$ is $OR^{30}$, $SR^{31}$, $NR^{32}R^{33}$ or $R^{28}$;
W is O or S;
X is a radical selected from

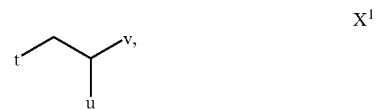

$X^1$

$X^2$

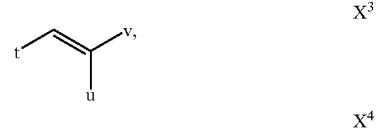

$X^3$

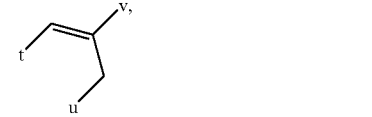

$X^4$

$X^5$

$X^6$

-continued

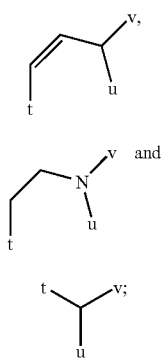

X⁷

X⁸

X⁹ wherein the bond of $X^1$, $X^2$, $X^3$, $X^4$, $X^5$, $X^6$, $X^7$, $X^8$ or $X^9$ which is identified with "t" is connected to the carbon atom identified with "q" of Formula 1, the bond which is identified with "u" is connected to the carbon atom identified with "r" of Formula 1, and the bond which is identified with "v" is connected to G of Formula 1;

$Z^1$ is a direct bond, O, C(=O), S(O)$_m$, CHR$^{20}$ or NR$^{21}$;

$Z^5$, $Z^6$, $Z^7$ and $Z^8$ independently are a direct bond, C(=O) or S(O)$_2$;

$R^{1a}$, $R^{1b}$, $R^{1c}$ and $R^{1d}$ independently are an optionally substituted phenyl, an optionally substituted naphthalenyl or an optionally substituted 5- to 6-membered heteroaromatic ring; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_4$-$C_{10}$ halocycloalkylalkyl, $C_5$-$C_{10}$ alkylcycloalkylalkyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ haloalkylthioalkyl, $C_2$-$C_8$ alkylsulfinylalkyl, $C_2$-$C_8$ alkylsulfonylalkyl, $C_3$-$C_8$ alkoxycarbonylalkyl, $C_3$-$C_8$ haloalkoxycarbonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ haloalkenyloxy, $C_2$-$C_8$ alkynyloxy, $C_3$-$C_8$ haloalkynyloxy, $C_2$-$C_8$ alkoxyalkoxy, $C_2$-$C_8$ alkylcarbonyloxy, $C_1$-$C_8$ alkylcarbonyloxy, $C_2$-$C_8$ haloalkylcarbonyloxy, $C_1$-$C_8$ alkylthio, $C_1$-$C_8$ haloalkylthio, $C_3$-$C_8$ cycloalkylthio, $C_3$-$C_{10}$ trialkylsilyl, $C_1$-$C_8$ alkylamino, $C_2$-$C_8$ dialkylamino, $C_1$-$C_8$ haloalkylamino, $C_2$-$C_8$ halodialkylamino, $C_3$-$C_8$ cycloalkylamino, $C_2$-$C_8$ alkylcarbonylamino, $C_2$-$C_8$ halo alkylcarbonylamino, $C_1$-$C_8$ alkylsulfonylamino, $C_1$-$C_8$ haloalkylsulfonylamino, pyrrolidinyl, piperidinyl or morpholinyl;

each $R^2$ is independently halogen, cyano, hydroxy, $C_1$-$C_4$ alkyl, $C_1$-$C_4$ alkenyl, $C_1$-$C_4$ haloalkyl or $C_1$-$C_4$ alkoxy; or two $R^2$ groups are taken together as $C_1$-$C_4$ alkylene or $C_2$-$C_4$ alkenylene to form a bridged bicyclic or fused bicyclic ring system; or two $R^2$ groups attached to adjacent ring carbon atoms joined by a double bond are taken together as —CH=CH—CH=CH— optionally substituted with up to 3 substituents independently selected from halogen, cyano, hydroxy, amino, nitro, $C_1$-$C_4$ alkyl, $C_1$-$C_4$ haloalkyl, $C_1$-$C_4$ alkoxy and $C_1$-$C_4$ haloalkoxy;

$R^6$ is $C_1$-$C_4$ alkyl, $C_1$-$C_4$ haloalkyl or $C_2$-$C_4$ alkoxyalkyl;

each $R^5$ is independently H, halogen, cyano, hydroxy, amino, nitro, —CHO, —C(=O)OH, —C(=O)NH$_2$, —NR$^{25}$R$^{26}$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_8$ dialkylaminoalkyl, $C_2$-$C_6$ haloalkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_2$-$C_6$ haloalkoxyalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylsulfonylamino, $C_1$-$C_6$ halo alkylsulfonylamino or —Z$^2$Q;

each $Z^2$ is independently a direct bond, —O, —C(=O), —S(O)$_m$, —CHR$^{20}$ or —NR$^{21}$;

each Q is independently phenyl, benzyl, naphthalenyl, a 5- to 6-membered heteroaromatic ring or an 8- to 11-membered heteroaromatic bicyclic ring system, each optionally substituted with up to 2 substituents independently selected from R$^{7a}$ on carbon atom or nitrogen atom ring members, and each optionally substituted with up to 5 substituents independently selected from R$^7$ on carbon atom ring members and R$^{12}$ on nitrogen atom ring members; or a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(=O)$_s$(=NR$^{23}$)$_f$ and SiR$^{17}$R$^{18}$, and each ring or ring system optionally substituted with up to 2 substituents independently selected from R$^{7a}$ on carbon atom or nitrogen atom ring members, and each optionally substituted with up to 5 substituents independently selected from R$^7$ on carbon atom ring members and R$^{12}$ on nitrogen atom ring members;

each $R^{7a}$ is independently —Z$^3$T$^4$, —Z$^3$T$^N$ or —Z$^3$T$^P$;

each $Z^3$ is independently a direct bond, O, NR$^{22}$, C(=O), C(=S), S(O)$_m$, CHR$^{20}$, —CHR$^{20}$—CHR$^{20}$—, —CR$^{24}$=CR$^{27}$—, —OCHR$^{20}$— or —CHR$^{20}$O—;

each $T^4$ is independently phenyl, phenylethynyl or a 5- to 6-membered heteroaromatic ring, each optionally substituted with up to 5 substituents independently selected from R$^{29}$ on carbon atom ring members, and each optionally substituted with up to 2 substituents independently selected from R$^{22}$ on nitrogen atom ring members;

each $T^N$ is independently a 3- to 7-membered nonaromatic ring including ring members selected from the group consisting of $C(R^{29})_2$, O, S, $NR^{22}$, $-C(R^{29})=C(R^{29})-$, $-C(R^{29})=N-$, $-N=N-$, $C(=O)$, $C(=S)$, $-C\equiv C-$, $C(=NR^{23})$, $S(=O)_s(=NR^{23})_f$ and $SiR^{17}R^{18}$;

each $T^p$ is independently an 8- to 10-membered aromatic or a 7- to 11-membered nonaromatic bicyclic ring system, said ring system including ring members selected from the group consisting of $C(R^{29})_2$, O, S, $NR^{22}$, $-C(R^{29})=CC(R^{29})-$, $-C(R^{29})=N-$, $-N=N-$, $C(=O)$, $C(=S)$, $-C\equiv C-$, $C(=NR^{23})$, $S(=O)_s(=NR^{23})_f$ and $SiR^{17}R^{18}$;

each $R^7$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_6$-$C_{14}$ cycloalkylcycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ alkylsulfonyl, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_6$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form an optionally substituted 5- to 7-membered ring containing ring members selected from carbon atoms and optionally up to 3 heteroatoms selected from up to 1 O, up to 1 S and up to 1 N, and up to 3 ring members selected from $C(=O)$, $C(=S)$, $S(=O)_s(=NR^{23})_f$ and $SiR^{17}R^{18}$;

each $R^{12}$ is independently H, $C_1$-$C_3$ alkyl, $C_1$-$C_3$ alkylcarbonyl, $C_1$-$C_3$ alkoxy or $C_1$-$C_3$ alkoxycarbonyl;

$R^{15}$ is H, halogen, cyano, hydroxy, $-CHO$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl;

$R^{16}$ is H, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkylsulfonyl or $C_1$-$C_4$ haloalkylsulfonyl;

each $R^{17}$ and $R^{18}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

each $R^{20}$, $R^{22}$, $R^{24}$ and $R^{27}$ is independently H, $C_1$-$C_4$ alkyl or $C_1$-$C_4$ haloalkyl;

each $R^{21}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each $R^{23}$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_1$-$C_6$ alkoxy, $C_1$-$C_6$ haloalkoxy, $C_1$-$C_6$ alkylamino, $C_2$-$C_8$ dialkylamino, $C_1$-$C_6$ haloalkylamino or phenyl;

each $R^{25}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each $R^{26}$ is independently $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl or $-Z^4Q$;

each $Z^4$ is independently O, $C(=O)$, $S(O)_m$ or $CHR^{20}$;

$R^{28}$ is H, halogen, cyano, $C_1$-$C_4$ alkyl, $C_1$-$C_4$ haloalkyl, $C_2$-$C_4$ alkoxyalkyl, $C_2$-$C_4$ alkylcarbonyl, $C_2$-$C_4$ alkoxycarbonyl, $C_2$-$C_3$ alkylaminocarbonyl or $C_3$-$C_6$ dialkylaminocarbonyl;

each $R^{29}$ is independently H, halogen, cyano, hydroxy, amino, nitro, $-CHO$, $-C(=O)OH$, $-C(=O)NH_2$, $-SO_2NH_2$, $-C(=S)NH_2$, $-C(=O)NHCN$, $-C(=O)NHOH$, $-SH$, $-SO_2NHCN$, $-SO_2NHOH$, $-OCN$, $-SCN$, $-SF_5$, $-NHCHO$, $-NHNH_2$, $-N_3$, $-NHOH$, $-NHCN$, $-NHC(=O)NH_2$, $-N=C=O$, $-N=C=S$, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_4$-$C_{10}$ cycloalkylcarbonyl, $C_4$-$C_{10}$ cycloalkylaminocarbonyl, $C_2$-$C_7$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_4$-$C_{12}$ trialkoxyalkyl, $C_3$-$C_8$ alkoxyalkenyl, $C_3$-$C_8$ alkoxyalkynyl, $C_3$-$C_{10}$ halodialkylaminoalkyl, $C_5$-$C_{12}$ cycloalkyl(alkyl)aminoalkyl, $C_2$-$C_8$ alkyl(thiocarbonyl), $C_3$-$C_{10}$ alkoxyalkylcarbonyl, $C_3$-$C_{10}$ alkoxycarbonylalkyl, $C_2$-$C_8$ haloalkoxycarbonyl, $C_3$-$C_{10}$ alkoxyalkoxycarbonyl, $C_2$-$C_8$ (alkylthio)carbonyl, $C_2$-$C_8$ alkoxy(thiocarbonyl), $C_2$-$C_8$ alkylthio(thiocarbonyl), $C_2$-$C_8$ alkylamino(thiocarbonyl), $C_3$-$C_{10}$ dialkylamino(thiocarbonyl), $C_3$-$C_{10}$ alkoxy(alkyl)aminocarbonyl, $C_2$-$C_8$ alkylsulfonylaminocarbonyl, $C_2$-$C_8$ haloalkylsulfonylaminocarbonyl, $C_2$-$C_8$ alkylamidino, $C_3$-$C_{10}$ dialkylamidino, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ haloalkylcarbonyloxy, $C_4$-$C_{10}$ cycloalkylcarbonyloxy, $C_3$-$C_{10}$ alkylcarbonylalkoxy, $C_3$-$C_8$ cycloalkylthio, $C_3$-$C_8$ cycloalkylsulfonyl, $C_3$-$C_8$ cycloalkenyloxy, $C_3$-$C_8$ halocycloalkenyloxy, $C_2$-$C_8$ haloalkoxyalkoxy, $C_2$-$C_8$ alkoxyhaloalkoxy, $C_2$-$C_8$ haloalkoxyhaloalkoxy, $C_3$-$C_{10}$ alkoxycarbonylalkoxy, $C_2$-$C_8$ alkyl(thiocarbonyl)oxy, $C_2$-$C_8$ alkylcarbonylthio, $C_2$-$C_8$ alkyl(thiocarbonyl)thio, $C_3$-$C_8$ cycloalkylsulfinyl, $C_3$-$C_{10}$ halotrialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, $C_1$-$C_6$ haloalkylamino, $C_2$-$C_8$ halodialkylamino, $C_3$-$C_8$ cycloalkylamino, $C_2$-$C_8$ haloalkylcarbonylamino, $C_1$-$C_6$ haloalkylsulfonylamino, $C_4$-$C_{10}$ cycloalkylalkylamino, $C_4$-$C_{10}$ cycloalkyl(alkyl)amino, $C_3$-$C_{10}$ alkoxycarbonylalkylamino, $C_1$-$C_6$ alkoxyamino, $C_1$-$C_6$ haloalkoxyamino, $C_4$-$C_{12}$ dialkylimido, $C_2$-$C_8$ alkoxycarbonylamino, $C_2$-$C_8$ haloalkoxycarbonylamino, $C_2$-$C_8$ alkylaminocarbonylamino, $C_3$-$C_{10}$ dialkylaminocarbonylamino, $C_3$-$C_{10}$ alkylaminocarbonyl(alkyl)amino, $C_4$-$C_{12}$ dialkylaminocarbonyl(alkyl)amino, $C_2$-$C_8$ alkylamino(thiocarbonyl)amino, $C_3$-$C_{10}$ dialkylamino(thiocarbonyl)amino, $C_3$-$C_{10}$ alkylamino(thiocarbonyl)alkylamino or $C_4$-$C_{12}$ dialkylamino(thiocarbonyl)alkylamino;

each $R^{30}$ and $R^{31}$ is independently $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_4$-$C_8$ halocycloalkylalkyl, $C_5$-$C_8$ alkylcycloalkylalkyl, $C_2$-$C_6$ alkoxyalkyl, $C_4$-$C_8$ cycloalkoxyalkyl, $C_3$-$C_6$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_6$ dialkylaminoalkyl, $C_2$-$C_6$ haloalkylaminoalkyl, $C_4$-$C_8$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ alkylaminocarbonyl, $C_3$-$C_8$ dialkylaminocarbonyl or $C_4$-$C_8$ cycloalkylaminocarbonyl;

$R^{32}$ is H, cyano, hydroxy, amino, $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_4$-$C_8$ cycloalkylalkyl, $C_2$-$C_6$ alkoxyalkyl, $C_1$-$C_6$ alkoxy, $C_1$-$C_6$ haloalkoxy, $C_1$-$C_6$ alkylsulfonyl, $C_1$-$C_6$ haloalkylsulfonyl, $C_2$-$C_6$ alkylcarbonyl, $C_2$-$C_6$ haloalkylcarbonyl, $C_1$-$C_6$ alkylamino, $C_2$-$C_8$ dialkylamino, $C_1$-$C_6$ haloalkylamino or $C_2$-$C_8$ halodialkylamino;

$R^{33}$ is H, $C_1$-$C_6$ alkyl, $C_3$-$C_6$ alkenyl, $C_3$-$C_6$ alkynyl, $C_1$-$C_6$ haloalkyl or $C_3$-$C_6$ cycloalkyl; or $R^{32}$ and $R^{33}$ are taken together as —$(CH_2)_4$—, —$(CH_2)_5$— or —$(CH_2)_2$—O—$(CH_2)_2$—;

d is 1 or 2;

each m is independently 0, 1 or 2;

n is 0, 1 or 2; and s and f are independently 0, 1 or 2 in each instance of $S(=O)_s(=NR^{23})_f$, provided that the sum of s and f is 1 or 2;

provided that:
(i) when $Z^6$ is a direct bond, and A is $CHR^{15}$ or $NR^{16}$, then $R^{1b}$ is other than an optionally substituted phenyl, optionally substituted naphthalenyl or an optionally substituted 5- to 6-membered herteroaromatic ring;
(ii) when A is C(=O), then E is E-2, $Z^6$ is a direct bond and W is O; and
(iii) when E is E-3, $R^{1c}$ is unsubstituted phenyl, X is $X^1$ and the ring containing X is saturated, G is an unsubstituted thiazole ring connected at the 2-position to X and at the 4-position to $Z^1$ in Formula 1, $Z^7$ is a direct bond, A is $CHR^{15}$, $R^{15}$ is H, d is 2 and J is an isoxazole ring connected at the 4-position to $Z^1$ and substituted at the 5-position with methyl and at its 3-position with meta-substituted phenyl, then $Z^1$ is O, C(=O), S(O)$_m$, $CHR^{20}$ or $NR^{21}$.

More particularly, this invention pertains to a compound of Formula 1 (including all geometric and stereoisomers), an N-oxide or a salt thereof.

This invention also relates to a fungicidal composition comprising a fungicidally effective amount of a compound of Formula 1 (or an N-oxide or salt thereof) and at least one additional component selected from the group consisting of surfactants, solid diluents and liquid diluents.

This invention also relates to a fungicidal composition comprising a mixture of a compound of Formula 1 (or an N-oxide or salt thereof) and at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

DETAILS OF THE INVENTION

As used herein, the terms "comprises," "comprising," "includes," "including," "has," "having", "contains" or "containing" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

As referred to herein, the term "broadleaf" used either alone or in words such as "broadleaf crop" means dicot or dicotyledon, a term used to describe a group of angiosperms characterized by embryos having two cotyledons.

As used herein, the term "alkylating agent" refers to a chemical compound in which a carbon-containing radical is bound through a carbon atom to leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified, for example, for $R^{30}$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers. "Alkenylene" denotes a straight-chain or branched alkenediyl containing one olefinic bond. Examples of "alkenylene" include $CH=CH$, $CH_2CH=CH$, $CH=C(CH_3)$ and the different butenylene isomers. "Alkynylene" denotes a straight-chain or branched alkynediyl containing one triple bond. Examples of "alkynylene" include $C\equiv C$, $CH_2C\equiv C$, $C\equiv CCH_2$ and the different butynylene isomers.

"Alkoxy" includes, for example, methoxy, ethoxy, n-propyloxy, isopropyloxy and the different butoxy, pentoxy and hexyloxy isomers. "Alkenyloxy" includes straight-chain or branched alkenyl attached to and linked through an oxygen atom. Examples of "alkenyloxy" include $H_2C=CHCH_2O$, $(CH_3)_2C=CHCH_2O$, $CH_3CH=CHCH_2O$, $CH_3CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$.

"Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes straight-chain or branched alkoxy substitution on a straight-chain or branched alkoxy. Examples of "alkoxyalkoxy" include $CH_3OCH_2O$, $CH_3OCH_2(CH_3)CHCH_2O$ and $(CH_3)_2CHOCH_2CH_2O$. Examples of "alkoxyalkoxyalkyl" include $CH_3OCH_2OCH_2$, $CH_3CH_2—O—(CH_3)CHOCH_2$ and $(CH_3CH_2)_2OCH_2OCH_2$. "Alkoxyalkenyl" denotes alkoxy substitution on straight-chain or branched alkenyl. Examples of "alkoxyalkenyl" include $CH_3OCH=CH$, $CH_3OCH_2CH=CH$, $CH_3CH_2OCH=C(CH_3)$ and $CH_3CH_2OCH=CH_2$. "Alkoxyalkynyl" denotes alkoxy substitution on straight-chain or branched alkenyl. Examples of "alkoxyalkynyl" include $CH_3OC\equiv C$, $CH_3OCH_2C\equiv C$ and $CH_3CH_2OC\equiv CCH_2$.

"Alkylthio" includes straight-chain or branched alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2S(CH_3)_2CHS(O)_2$, and the different butylsulfonyl, pentylsulfonyl and hexylsulfonyl isomers.

"Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylsulfinylalkyl" denotes alkylsulfinyl substitution on alkyl. Examples of "alkylsulfinylalkyl" include $CH_3S(=O)CH_2$, $CH_3S(=O)CH_2CH_2$, $CH_3CH_2S(=O)CH_2$ and $CH_3CH_2S(=O)CH_2CH_2$. "Alkylsulfonylalkyl" denotes alkylsulfonyl substitution on alkyl. Examples of "alkylsulfonylalkyl" include $CH_3S(=O)_2CH_2$, $CH_3S(=O)_2CH_2CH_2$, $CH_3CH_2S(=O)_2CH_2$ and $CH_3CH_2S(=O)_2CH_2CH_2$.

"Cyanoalkyl" denotes an alkyl group substituted with one cyano group. Examples of "cyanoalkyl" include $NCCH_2$, $NCCH_2CH_2$ and $CH_3CH(CN)CH_2$. "Hydroxyalkyl" denotes an alkyl group substituted with one hydroxy group. Examples of "hydroxyalkyl" include $HOCH_2CH_2$, $CH_3CH_2(OH)CH$ and $HOCH_2CH_2CH_2CH_2$.

"Alkylamino" includes an NH radical substituted with straight-chain or branched alkyl. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$. "Alkoxyamino" includes straight-chain or branched alkoxy attached to and linked through an NH radical. Examples of "alkoxyamino" include $CH_3CH(CH_3)ONH$, $CH_3CH_2CHONH$, and $(CH_3)_2CHCH(CH_3)ONH$. "Alkylaminoalkyl" denotes alkylamino substitution on alkyl. Examples of "alkylaminoalkyl" include $CH_3NHCH_2$, $CH_3NHCH_2CH_2$, $CH_3CH_2NHCH_2$, $CH_3CH_2CH_2NHCH_2$ and $CH_3CH_2NHCH_2CH_2$. "Alkylsulfonylamino" denotes an NH radical substituted with alkylsulfonyl. Examples of "alkylsulfonylamino" include $CH_3CH_2S(=O)_2NH$ and $(CH_3)_2CHS(=O)_2NH$. "Alkylaminosulfonyl" includes straight-chain or branched alkylamino attached to and linked through an $S(=O)_2$ radical. Examples of "alkylaminosulfonyl" include $CH_3CH_2NHS(=O)_2$ and $(CH_3)_2CHNHS(=O)_2$.

"Trialkylsilyl" includes 3 branched and/or straight-chain alkyl radicals attached to and linked through a silicon atom, such as trimethylsilyl, triethylsilyl and tert-butyldimethylsilyl.

"Cycloalkyl" includes, for example, cyclopropyl, cyclobutyl, cyclopentyl and cyclohexyl. "Cycloalkenyl" includes groups such as cyclopentenyl and cyclohexenyl as well as groups with more than one double bonds such as 1,3- and 1,4-cyclohexadienyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. "Alkylcycloalkylalkyl" denotes an alkyl group substituted with alkylcycloalkyl. Examples of "alkylcycloalkylalkyl" include 1-, 2-, 3- or 4-methyl or -ethyl cyclohexylmethyl. The term "cycloalkylcycloalkyl" denotes cycloalkyl substitution on another cycloalkyl ring, wherein each cycloalkyl ring independently has from 3 to 7 carbon ring members. Examples of cycloalkylcycloalkyl radicals include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- or trans-cycloalkylcycloalkyl isomers (such as (1R,2S)-1,1'-bicyclopropyl-2-yl and (1R,2R)-1,1'-bicyclopropyl-2-yl).

The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom. Examples of "cycloalkylalkoxy" include cyclopropylmethoxy, cyclopentylethoxy, and other cycloalkyl moieties bonded to straight-chain or branched alkoxy groups. The term "cycloalkoxyalkyl" denotes cycloalkoxy substitution on an alkyl moiety. Examples of "cycloalkoxyalkyl" include cyclopropoxymethyl, cyclopentoxyethyl, and other cycloalkoxy moieties bonded to straight-chain or branched alkyl groups. The term "cycloalkenylalkyl" denotes cycloalkenyl substitution on an alkyl group. Examples of "cycloalkenylalkyl" include 2-cyclohexen-1-ylmethyl, 1-cyclopenten-1 ylmethyl, and other cycloalkenyl moieties bonded to straight-chain or branched alkyl groups.

"Cycloalkylcarbonyl" denotes cycloalkyl bonded to a $C(=O)$ group including, for example, cyclopropylcarbonyl and cyclopentylcarbonyl. "Cycloalkylcarbonyloxy" denotes cycloalkylcarbonyl attached to and linked through an oxygen atom. Examples of "cycloalkylcarbonyloxy" include cyclohexylcarbonyloxy and cyclopentylcarbonyloxy. The term "cycloalkylthio" denotes cycloalkyl attached to and linked through a sulfur atom such as cyclopropylthio and cyclopentylthio; "cycloalkylsulfonyl" includes the corresponding sulfones.

"Cycloalkylamino" denotes cycloalkyl linked through an amine group such as cyclopropylamino, cyclobutylamino, cyclopentylamino and cyclohexylamino. "Cycloalkyl(alkyl)amino" means a cycloalkylamino group where the hydrogen atom is replaced by an alkyl radical. Examples of "cycloalkyl(alkyl)amino" include groups such as cyclopropyl(methyl)amino, cyclobutyl(butyl)amino, cyclopentyl(propyl)amino, cyclohexyl(methyl)amino and the like. The term "cycloalkylaminoalkyl" denotes cycloalkylamino substitution on an alkyl group. Examples of "cycloalkylaminoalkyl" include cyclopropylaminomethyl, cyclopentylaminoethyl, and other cycloalkylamino moieties bonded to straight-chain or branched alkyl groups. "Cycloalkylaminocarbonyl" denotes cycloalkylamino bonded to a $C(=O)$ group, for example, cyclopentylaminocarbonyl and cyclohexylaminocarbonyl.

"Alkylcarbonyl" denotes a straight-chain or branched alkyl group bonded to a $C(=O)$ moiety. Examples of "alkylcarbonyl" include $CH_3C(=O)$, $CH_3CH_2CH_2C(=O)$ and $(CH_3)_2CHC(=O)$. Examples of "alkoxycarbonyl" include $CH_3C(=O)$, $CH_3CH_2C(=O)$, $CH_3CH_2CH_2C(=O)$, $(CH_3)_2CHOC(=O)$ and the different butoxy- or pentoxycarbonyl isomers. "Alkoxyalkylcarbonyl" denotes a straight-chain or branched alkoxyalkyl bonded to a $C(=O)$ moiety. Examples of "alkoxyalkylcarbonyl" include $CH_3OCH_2C(=O)$, $CH_3OCH_2CH_2C(=O)$ and $(CH_3)_2CHOCH_2CH_2C(=O)$. "Alkoxyalkoxycarbonyl" denotes a straight-chain or branched alkoxyalkoxy bonded to a $C(=O)$ moiety. Examples of "alkoxyalkoxycarbonyl" include $CH_3OCH_2C(=O)$ and $(CH_3)_2CHOCH_2CH_2C(=O)$. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $(CH_3)_2CHN(CH_3)C(=O)$ and $CH_3CH_2CH_2(CH_3)NC(=O)$.

The term "alkylcarbonyloxy" denotes straight-chain or branched alkyl bonded to a $C(=O)O$ moiety. Examples of "alkylcarbonyloxy" include $CH_3CH_2C(=O)O$ and $(CH_3)_2CHC(=O)O$. "Alkylcarbonylthio" denotes straight-chain or branched alkylcarbonyl attached to and linked through a sulfur atom. Examples of "alkylcarbonylthio" include $CH_3C(=O)S$, $CH_3CH_2CH_2C(=O)S$ and $(CH_3)_2CHC(=O)S$. The term "alkylcarbonylamino" denotes alkyl bonded to a $C(=O)NH$ moiety. Examples of "alkylcarbonylamino" include $CH_3CH_2C(=O)NH$ and $CH_3CH_2C(=O)NH$.

"Alkoxycarbonylalkyl" denotes alkoxycarbonyl substitution on straight-chain or branched alkyl. Examples of "alkoxycarbonylalkyl" include $CH_3C(=O)CH_2CH(CH_3)$, $CH_3CH_2C(=O)CH_2CH_2$ and $(CH_3)_2CHOC(=O)CH_2$. The term "alkylcarbonylalkoxy" denotes alkylcarbonyl bonded to an alkoxy moiety. Examples of "alkylcarbonylalkoxy" include $CH_3C(=O)CH_2CH_2O$ and $CH_3CH_2C(=O)CH_2O$. Examples of "alkoxycarbonyloxy" include $CH_3CH_2CH_2C(=O)O$ and $(CH_3)_2CHOC(=O)O$. The term "alkoxycarbonylalkoxy" denotes alkoxycarbonyl substitution on straight-chain or branched alkoxy. Examples of "alkoxycarbonylalkoxy" include $CH_3CH_2C(=O)CH_2CH_2O$ and $CH_3CH_2CH(CH_3)OC(=O)CH_2O$.

"Cycloalkylalkoxycarbonyl" denotes a cycloalkylalkyl bonded to a $OC(=O)$ moiety. Examples of "cycloalkylalkoxycarbonyl" include cyclopropyl-$CH_2C(=O)$, cyclopropyl-$CH(CH_3)OC(=O)$ and cyclopentyl-$CH_2C(=O)$.

The term "alkoxycarbonylamino" denotes alkoxy bonded to a $C(=O)NH$ moiety. Examples of "alkoxycarbonylamino" include $CH_3C(=O)NH$ and $CH_3CH_2C(=O)NH$. "Alkoxy(alkyl)aminocarbonyl" denotes a nitrogen atom of aminocarbonyl moiety disubstituted with a straight-chain or branched alkoxy group and a straight-chain or branched alkyl group. Examples of "alkoxy(alkyl)aminocarbonyl" include $CH_3—O(CH_3)NC(=O)$, $CH_3CH_2—O(CH_3)NC(=O)$ and $(CH_3)_2CHO(CH_3)NC(=O)$. "Alkoxycarbonylalkylamino" denotes alkoxycarbonylalkyl bonded to an NH radical. Examples of "alkoxycarbonylalkylamino" include $CH_3C(=O)CH_2NH$ and $CH_3CH_2C(=O)CH_2CH_2NH$.

"Alkyl(thiocarbonyl)" denotes a straight-chain or branched alkyl group bonded to a $C(=S)$ moiety. Examples of "alkyl(thiocarbonyl)" include $CH_3C(=S)$, $CH_3CH_2CH_2C(=S)$ and $(CH_3)_2CHC(=S)$. "Alkyl(thiocarbonyl)thio" denotes a straight-chain or branched alkyl group bonded to a $C(=S)S$ moiety. Examples of "alkyl(thiocarbonyl)thio" include $CH_3C(=S)S$, $CH_3CH_2CH_2C(=S)S$ and $(CH_3)_2CHC(=S)S$. Examples of "alkyl(thiocarbonyl)oxy" include $CH_3C(=S)O$, $CH_3CH_2CH_2C(=S)O$ and $(CH_3)_2CHC(=S)O$. "(Alkylthio)carbonyl" denotes a straight-chain or branched alkylthio group bonded to a $C(=O)$ moiety. Examples of "(alkylthio)carbonyl" include $CH_3SC(=O)$, $CH_3CH_2CH_2SC(=O)$ and $(CH_3)_2CHSC(=O)$. "Alkoxy(thiocarbonyl)" denotes a straight-chain or branched alkoxy group bonded to a $C(=S)$ moiety. Examples of "alkoxy(thiocarbonyl)" include $CH_3C(=S)$, $CH_3CH_2CH_2C(=S)$ and $(CH_3)_2CHOC(=S)$. "Alkylthio(thiocarbonyl)" denotes a straight-chain or branched alkylthio group bonded to a $C(=S)$ moiety. Examples of "alkylthio(thiocarbonyl)" include $CH_3SC(=S)$, $CH_3CH_2CH_2SC(=S)$ and $(CH_3)_2CHSC(=S)$. "Alkylamino(thiocarbonyl)" denotes a straight-chain or branched alkylamino group bonded to a $C(=S)$ moiety. Examples of "alkylamino(thiocarbonyl)" include $CH_3NHC(=S)$, $CH_3CH_2CH_2NHC(=S)$ and $(CH_3)_2CHNHC(=S)$. "Dialkylamino(thiocarbonyl)" denotes a straight-chain or branched dialkylamino group bonded to a $C(=S)$ moiety. Examples of "dialkylamino(thiocarbonyl)" include $(CH_3)_2NC(=S)$, $CH_3CH_2CH_2(CH_3)NC(=S)$ and $(CH_3)_2C(CH_3)NC(=S)$.

The term "alkylaminocarbonylamino" denotes a straight-chain or branched alkylamino group bonded to a $C(=O)NH$ moiety. Examples of "alkylaminocarbonylamino" include $CH_3NHC(=O)NH$ and $CH_3CH_2NHC(=O)NH$. The term "dialkylaminocarbonylamino" denotes a straight-chain or branched dialkylamino group bonded to a $C(=O)NH$ moiety. Examples of "dialkylaminocarbonylamino" include $(CH_3)_2NC(=O)NH$ and $CH_3CH_2(CH_3)NC(=O)NH$. The term "alkylaminocarbonyl(alkyl)amino" means a alkylaminocarbonylamino group where the hydrogen atom on the connecting amino group is replaced by an alkyl radical. Examples of "alkylaminocarbonyl(alkyl)amino" include $CH_3NHC(=O)$ N(CH$_3$) and CH$_3$CH$_2$NHC(=O)N(CH$_3$). The term "dialkylaminocarbonyl(alkyl)amino" means a dialkylaminocarbonylamino group where the hydrogen atom on the connecting amino group is replaced by an alkyl radical. Examples of "dialkylaminocarbonyl(alkyl)amino" include (CH$_3$)$_2$NC(=O)N(CH$_3$) and CH$_3$CH$_2$(CH$_3$)NC(=O)N(CH$_3$). The term "alkylamino(thiocarbonyl)amino" denotes a straight-chain or branched alkylamino group bonded to a C(=S)NH moiety. Examples of "alkylamino(thiocarbonyl)amino" include CH$_3$NHC(=S)NH and CH$_3$CH$_2$NHC(=S)NH.

"Alkylamidino" denotes a straight-chain or branched alkylamino moiety bonded to the carbon atom of the C(=N) moiety, or an unsubstituted amino moiety bonded to the carbon atom of a C(=N) moiety and a straight-chain or branched alkyl moiety bonded to a nitrogen atom of a C(=N) moiety. Examples of "alkylamidino" include CH$_3$NHC(=NH), CH$_3$CH$_2$NHC(=NH) and H$_2$NC(=NCH$_3$). "Dialkylamidino" denotes a straight-chain or branched dialkylamino moiety bonded to the carbon atom of a C(=N) moiety, or a straight-chain or branched alkylamino moiety bonded to the carbon atom of the C(=N) moiety and a straight-chain or branched alkyl moiety bonded to the nitrogen atom of a C(=N) moiety. Examples of "dialkylamidino" include (CH$_3$)$_2$NC(=NH), CH$_3$CH$_2$(CH$_3$)NC(=NH) and CH$_3$NHC(=NCH$_3$). The term "dialkylimido" denotes two straight-chain or branched alkylcarbonyl moieties bonded to the nitrogen atom of an amino moiety. Examples of "dialkylimido" include (CH$_3$C(=O))$_2$N and CH$_3$CH$_2$C(=O)(CH$_3$C(=O))N.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include F$_3$C, ClCH$_2$, CF$_3$CH$_2$ and CF$_3$CCl$_2$. The terms "haloalkenyl", "haloalkynyl" "haloalkoxy", "haloalkylthio", "haloalkylamino", "haloalkylsulfinyl", "haloalkylsulfonyl", "halocycloalkyl", "haloalkoxyalkoxy", "haloalkoxyhaloalkoxy", "haloalkylaminoalkyl", "haloalkylsulfonylaminocarbonyl", "halotrialkylsilyl and the like, are defined analogously to the term "haloalkyl". Examples of "haloalkenyl" include (Cl)$_2$C=CHCH$_2$ and CF$_3$CH$_2$CH=CHCH$_2$. Examples of "haloalkynyl" include HC≡CCHCl, CF$_3$C≡C, CCl$_3$C≡C and FCH$_2$C≡CCH$_2$. Examples of "haloalkoxy" include CF$_3$O, CCl$_3$CH$_2$O, HCF$_2$CH$_2$CH$_2$O and CF$_3$CH$_2$O. Examples of "haloalkylthio" include CCl$_3$S, CF$_3$S, CCl$_3$CH$_2$S and ClCH$_2$CH$_2$CH$_2$S. Examples of "haloalkylamino" include CF$_3$(CH$_3$)CHNH, (CF$_3$)$_2$CHNH and CH$_2$ClCH$_2$NH. Examples of "haloalkylsulfinyl" include CF$_3$S(=O), CCl$_3$S(=O), CF$_3$CH$_2$S(=O) and CF$_3$CF$_2$S(=O). Examples of "haloalkylsulfonyl" include CF$_3$S(=O)$_2$, CCl$_3$S(=O)$_2$, CF$_3$CH$_2$S(=O)$_2$ and CF$_3$CF$_2$S(=O)$_2$. Examples of "halocycloalkyl" include 2-chlorocyclopropyl, 2-fluorocyclobutyl, 3-bromocyclopentyl and 4-chlorocyclohexyl. Examples of "haloalkoxyalkoxy" include CF$_3$OCH$_2$O, ClCH$_2$CH$_2$OCH$_2$CH$_2$O, Cl$_3$CCH$_2$OCH$_2$O as well as branched alkyl derivatives. Examples of "haloalkoxyhaloalkoxy" include CF$_3$OCHClO, ClCH$_2$CH$_2$OCHClCH$_2$O, Cl$_3$CCH$_2$OCHClO as well as branched alkyl derivatives. Examples of "haloalkylaminoalkyl" include CH$_3$NHCHCl, (CH$_3$)$_2$CClNHCH$_2$ and CH$_3$NClCH(CH$_3$). Examples of "haloalkylsulfonylaminocarbonyl" include CF$_3$SO$_2$NH(C=O) and CF$_3$SO$_2$NCl(C=O). Examples of "halotrialkylsilyl" include CF$_3$(CH$_3$)$_2$Si, (CF$_3$)$_3$Si, and CH$_2$Cl(CH$_3$)$_2$Si.

The term "halodialkyl", either alone or in compound words such as "halodialkylamino", means at least one of the two alkyl groups is substituted with at least one halogen atom, and independently each halogenated alkyl group may be partially or fully substituted with halogen atoms which may be the same or different. Examples of "halodialkylamino" include (BrCH$_2$CH$_2$)$_2$N and BrCH$_2$CH$_2$(ClCH$_2$CH$_2$)N.

Unless otherwise indicated, a "ring" or "ring system" as a component of Formula 1 (e.g., substituent J and Q) is carbocyclic or heterocyclic. The term "ring system" denotes two or more connected rings. The term "spirocyclic ring system" denotes a ring system consisting of two rings connected at a single atom (so the rings have a single atom in common). Illustrative of a J moiety that is a spirocyclic ring system is J-29-59 shown in Exhibit A below. The term "bicyclic ring system" denotes a ring system consisting of two rings sharing two or more common atoms. In a "fused bicyclic ring system" the common atoms are adjacent, and therefore the rings share two adjacent atoms and a bond connecting them. In a "bridged bicyclic ring system" the common atoms are not adjacent (i.e. there is no bond between the bridgehead atoms). A "bridged bicyclic ring system" can be formed by bonding a segment of one or more atoms to nonadjacent ring members of a ring.

A ring, a bicyclic ring system or a spirocyclic ring system can be part of an extended ring system containing more than two rings wherein substituents on the ring, bicyclic ring system or spirocyclic ring system are taken together to form the additional rings, which may be in bicyclic and/or spirocyclic relationships with other rings in the extended ring system. For example, the J moiety J-29-26 shown in Exhibit A below consists of a dihydro isoxazoline ring substituted with one $R^5$ substituent which is —$Z^2$Q wherein $Z^2$ is a direct bond and Q is a cyclobutyl ring substituted with two methyl groups (i.e. $R^7$ substituents) and one —CH$_2$— group (i.e. $R^7$ substituent) which is taken together with another —CH$_2$— group (i.e. $R^5$ substituent) on the dihydro isoxazoline ring to form the additional six-membered ring in the ring system.

The term "ring member" refers to an atom (e.g., C, O, N or S) or other moiety (e.g., C(=O), C(=S), SiR$^{17}$R$^{18}$ or S(=O)$_s$ (=NR$^{23}$)$_f$) forming the backbone of a ring or ring system. The term "aromatic" indicates that each of the ring atoms is essentially in the same plane and has a p-orbital perpendicular to the ring plane, and that (4n+2)π electrons, where n is a positive integer, are associated with the ring to comply with Hückel's rule The term "carbocyclic ring" denotes a ring wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring" or "heterocycle" denotes a ring wherein at least one of the atoms forming the ring backbone is other than carbon. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or aromatic heterocyclic ring. "Saturated heterocyclic ring" refers to a heterocyclic ring containing only single bonds between ring members. "Partially saturated heterocyclic ring" refers a heterocyclic ring containing at least one double bond but which is not aromatic.

Unless otherwise indicated, heterocyclic rings and ring systems are attached to the remainder of Formula 1 through any available carbon or nitrogen by replacement of a hydrogen on said carbon or nitrogen.

The dotted line in Formula 1 and in other rings depicted in the present description indicates that the bond can be a single bond or double bond.

As already noted above, J is a 5-, 6- or 7-membered ring, an 8- to 11-membered bicyclic ring system or a 7- to 11-membered spirocyclic ring system, each ring or ring system containing ring members selected from carbon atoms and up to 4 heteroatoms independently selected from up to 2 O, up to 2 S and up to 4 N, and up to 3 ring members selected from C(=O), C(=S), S(=O)$_s$(=NR$^{23}$)$_f$ and SiR$^{17}$R$^{18}$, and optionally substituted with up to 5 substituents independently selected from R$^5$. The definition of J regarding S(=O)$_s$(=NR$^{23}$)$_f$ ring members allows for up to 3 oxidized sulfur moieties (e.g., S(=O) or S(=O)$_2$); this is in addition to the up to 2 S heteroatoms, which in this definition of J are considered to be unoxidized, because the definition of S(=O)$_s$(=NR$^{23}$)$_f$ does not allow for unoxidized sulfur atoms (i.e. s and f cannot simultaneously be zero). In the definition of J, the ring members selected from O, S, S(=O)$_s$(=NR$^{23}$)$_f$, N and SiR$^{17}$R$^{17}$ are optional, and the total number of these ring members may be zero. When none of these ring members are present (i.e. the ring members are all carbon atoms), the ring or ring system is carbocyclic. If at least one of these ring members is present, the ring or ring system is heterocyclic. The nitrogen atom ring members may be oxidized as N-oxides, because compounds relating to Formula 1 also include N-oxide derivatives. The definition allows up to three carbon ring members being in the form of C(=O) and C(=S), subject to limitations due to the presence of S(=O)$_s$(=NR$^{23}$)$_f$ or SiR$^{17}$R$^{18}$, as well as the number of available carbon atoms. The J ring or ring system is optionally substituted on carbon and nitrogen atoms with up to 5 substituents, limited only by the number of available points of attachment, independently selected from R$^5$. The up to 5 R$^5$ substituents are in addition to any C(=O), C(=S), S(=O), S(=NR$^{23}$) and SiR$^{17}$R$^{18}$ moieties. As the R$^5$ substituents are optional, zero substituents may be present. The substituents on silicon atom ring members are separately defined as R$^{17}$ and R$^{18}$.

As already noted above, each Q is, inter alia, independently a 5- to 6-membered heteroaromatic ring or an 8- to 11-membered heteroaromatic bicyclic ring system, each optionally substituted with up to 2 substituents independently selected from R$^{7a}$ on carbon atom or nitrogen atom ring members, and each optionally substituted with up to 5 substituents independently selected from R$^7$ on carbon atom ring members and R$^{12}$ on nitrogen atom ring members. In this definition, each heteroaromatic ring or ring system typically contains no more than 4 heteroatoms independently selected from up to 2 O, up to 2 S and up to 4 N. The nitrogen atom ring members may be oxidized as N-oxides, because compounds relating to Formula 1 also include N-oxide derivatives. As R$^{7a}$, R$^7$ and R$^{12}$ are optional, 0 to 5 substituents may be present, limited only by the number of available points of attachment.

As already noted above, each Q is, inter alia, independently a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(=O)$_s$(=NR$^{23}$)$_f$ and SiR$^{17}$R$^{18}$, and each ring or ring system optionally substituted with up to 2 substituents independently selected from R$^{7a}$ on carbon atom or nitrogen atom ring members, and each optionally substituted with up to 5 substituents independently selected from R$^7$ on carbon atom ring members and R$^{12}$ on nitrogen atom ring members. This definition allows the inclusion as ring members, in addition to carbon atoms, one or more heteroatoms such as, but not limited to, oxygen, nitrogen and sulfur. The number of ring heteroatoms may be zero, and indeed must be by definition in a carbocyclic ring. If at least one ring heteroatom is present, the ring or ring system is heterocyclic. As indicated in the definition, one or more of the ring carbon atoms may be in the form of C(=O) and C(=S), which is in addition to the up to 2 ring substituents selected from R$^{7a}$ and up to 5 substituents selected from R$^7$ and R$^{12}$. Sulfur atom ring members may be unoxidized or oxidized; oxidized sulfur ring atoms are described as S(=O)$_s$(=NR$^{23}$)$_f$, and the S(=O) and S(=NR$^{23}$) moieties are in addition to the up to 2 ring substituents selected from R$^{7a}$ and up to 5 substituents selected from R$^7$ and R$^{12}$. The nitrogen atom ring members may be oxidized as N-oxides, because compounds relating to Formula 1 also include N-oxide derivatives. The substituents on silicon atom ring members are separately defined as R$^{17}$ and R$^{18}$.

Of note is a more particular description of the above noted portion of the definition of Q wherein each Q is, inter alia, 3- to 7-membered nonaromatic carbocyclic ring, a 5-, 6- or 7-membered nonaromatic heterocyclic ring or an 8- to 11-membered heteroaromatic bicyclic ring system, each ring or ring system containing ring members selected from carbon atoms and up to 4 heteroatoms independently selected from up to 2 O, up to 2 S, up to 4 N and up to 2 Si atoms, wherein up to 3 carbon atom ring members are independently selected from C(=O) and C(=S), the sulfur atom ring members are independently selected from S and S(=O)$_s$(=NR$^{23}$)$_f$, and the silicon atom ring members are independently selected from SiR$^{17}$R$^{18}$, each ring or ring system optionally substituted with up to 2 substituents independently selected from R$^{7a}$ on carbon and nitrogen atom ring members, and each ring or ring system optionally substituted with up to 5 substituents independently selected from R$^7$ on carbon atom ring members and R$^{12}$ on nitrogen atom ring members.

As already noted above, R$^5$ and R$^7$, inter alia, are taken together with the atoms linking R$^5$ and R$^7$ to form an optionally substituted 5- to 7-membered ring containing ring members selected from carbon atoms and optionally up to 3 heteroatoms selected from up to 1 O, up to 1 S and up to 1 N, and up to 3 ring members selected from C(=O), C(=S), S(=O)$_s$(=NR$^{23}$)$_f$ and SiR$^{17}$R$^{18}$. This 5- to 7-membered ring includes as ring members the two atoms to which the substituents R$^5$ and R$^7$ are directly attached as well as intervening (i.e. other linking) atoms of J, Z$^2$ and Q, to which R$^5$ and R$^7$ can be regarded as indirectly attached. The other ring members of the ring are provided by the R$^5$ and R$^7$ substituents. This definition regarding S(=O)$_s$(=NR$^{23}$)$_f$ ring members allows for up to 3 oxidized sulfur moieties (e.g., S(=O) or S(=O)$_2$); this is in addition to the up to the 1 S heteroatom, which in this definition is considered to be unoxidized, because the definition of S(=O)$_s$(=NR$^{23}$)$_f$ does not allow for unoxidized sulfur atoms (i.e. s and f cannot simultaneously be zero). In this definition, the ring members selected from O, S, S(=O)$_s$(=NR$^{23}$)$_f$, N and SiR$^{17}$R$^{17}$ are optional, and the total number of these ring members may be zero. When none of these ring members are present (i.e. the ring members are all carbon atoms), the ring is carbocyclic. If at least one of these ring members is present, the ring is heterocyclic. The nitrogen atom ring member may be oxidized as an N-oxide, because compounds relating to Formula 1 also include N-oxide derivatives. The definition allows up to three carbon ring members being in the form of C(=O) and C(=S), subject to limitations due to the presence of $S(=O)_s(=NR^{23})_f$ or $SiR^{17}R^{18}$, as well as the number of available carbon atoms. The optional substituents may be attached to carbon and nitrogen atom ring members having an available point of attachment.

The total number of carbon atoms in a substituent group is indicated by the "$C_i$-$C_j$" prefix where i and j are numbers from 1 to 14. For example, $C_1$-$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "unsubstituted" in connection with a group such as a ring or ring system means the group does not have any substituents other than its one or more attachments to the remainder of Formula 1. The term "optionally substituted" in connection with a group such as a ring or ring system (e.g., 5-membered heterocyclic ring of G, or phenyl, naphthalenyl or 5- or 6-membered heterocyclic ring of $R^{1a}$, $R^{1b}$, $R^{1c}$ and $R^{1d}$) without specifying the number or identity of optional substituents refers to groups that are unsubstituted or have at least one non-hydrogen substituent that does not extinguish fungicidal activity of the unsubstituted analog. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 3.

The number of optional substituents may be restricted by an expressed limitation. For example, the phrase "optionally substituted with up to 2 substituents selected from $R^{7a}$ on carbon or nitrogen ring members means that 0, 1 or 2 substituents can be present (if the number of potential connection points allows). Similarly, the phrase "optionally substituted with up 5 substituents" means that 0, 1, 2, 3, 4 or 5 substituents can be present if the number of available connection points allows. When a range specified for the number of substituents (e.g., x being an integer from 0 to 5 in Exhibit 3) exceeds the number of positions available for substituents on a ring (e.g., 2 positions available for $(R^5)_x$ on J-1 in Exhibit 3), the actual higher end of the range is recognized to be the number of available positions.

When a compound is substituted with a substituent bearing a subscript that indicates the number of said substituents can vary, then when the number of said substituents is greater than 1, said substituents are independently selected from the group of defined substituents. When a group (e.g., J) contains a substituent (e.g., $R^5$) which can be hydrogen, then when this substituent is taken as hydrogen, it is recognized that this is equivalent to said group being unsubstituted. When a position on a group is said to be "not substituted" or "unsubstituted", then hydrogen atoms are attached to take up any free valency.

When $Z^3$ is selected from the radicals —$CR^{24}$=$CR^{27}$—, —$OCHR^{20}$ and —$CHR^{20}O$— the end left of the radicals are connected to the remainder of Q and the right end of the radicals are connected to $T^A$, $T^N$ or $T^P$.

Naming of substituents in the present disclosure uses recognized terminology providing conciseness in precisely conveying to those skilled in the art the chemical structure. For sake of conciseness, locant descriptors may be omitted.

Compounds of Formula 1 can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Compounds of Formula 1 may be present as a mixture of stereoisomers, individual stereoisomers, or as an optically active form. For example, when J is J-29 (see Exhibit 3) bonded at the 3-position to the remainder of Formula 1 and J-29 has one $R^5$ substituent other than H at the 5-position, then Formula 1 possesses a chiral center at the carbon atom to which $R^5$ is bonded. The two enantiomers are depicted as Formula 1' and Formula 1" wherein the chiral center is identified with an asterisk (*).

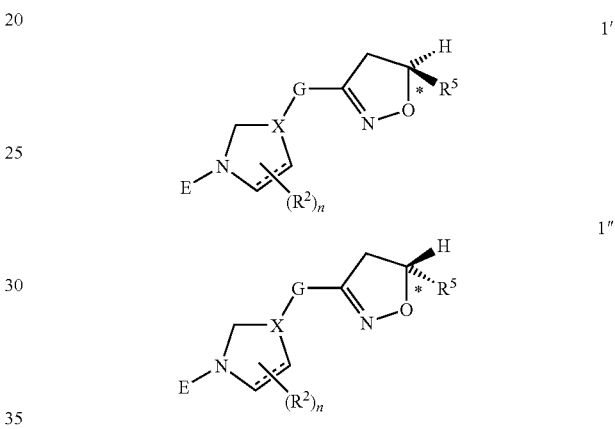

Compounds of Formula 1 comprise racemic mixtures, for example, equal amounts of the enantiomers of Formulae 1' and 1". In addition, compounds of Formula 1 include compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric excess ("ee"), which is defined as $(2x-1) \cdot 100\%$, where x is the mole fraction of the dominant enantiomer in the mixture (e.g., an ee of 20% corresponds to a 60:40 ratio of enantiomers).

Preferably the compositions of this invention of Formula 1 have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as A, $R^{1a}$, $R^{1b}$, $R^{1c}$, $R^{1d}$, G, J, Q, $X^1$ through $X^9$, $Z^1$, $Z^2$ and $Z^3$ may themselves contain chiral centers. Compounds of Formula 1 comprise racemic mixtures as well as enriched and essentially pure stereoconfigurations at these additional chiral centers.

Compounds of Formula 1 can exist as one or more conformational isomers due to restricted rotation about the amide bond (e.g., C(W)—N) in Formula 1. Compounds of Formula 1 comprise mixtures of conformational isomers. In addition, compounds of Formula 1 include compounds that are enriched in one conformer relative to others. One skilled in the art recognizes that compounds of Formula 1 can exist in equilibrium with one or more of its respective tautomeric counterparts. Unless otherwise indicated, reference to a compound by one tautomer description is to be considered to include all tautomers. For example, some of the unsaturated rings and ring systems depicted in Exhibits 1, 2, 3 and 4 can have an arrangement of single and double bonds between ring members different from that depicted. Such differing arrangements of bonds for a particular arrangement of ring atoms correspond to different tautomers. For these unsaturated rings and ring systems, the particular tautomer depicted is to be considered representative of all the tautomers possible for the arrangement of ring atoms shown.

The compounds of the present invention include N-oxide derivatives of Formula 1. One skilled in the art will appreciate that not all nitrogen-containing heterocycles can form N-oxides since the nitrogen requires an available lone pair of electrons for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as tent-butyl hydroperoxide, sodium perborate, and dioxiranes such as dimethyldioxirane. These methods for the preparation of N-oxides have been extensively described and reviewed in the literature, see for example: T. L. Gilchrist in Comprehensive Organic Synthesis, vol. 7, pp 748-750, S. V. Ley, Ed., Pergamon Press; M. Tisler and B. Stanovnik in Comprehensive Heterocyclic Chemistry, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. When the compounds forming the present mixtures and compositions contain acidic or basic moieties, a wide variety of salts can be formed, and these salts are useful in the present mixtures and compositions for controlling plant diseases caused by fungal plant pathogens (i.e. are agriculturally suitable). When a compound contains a basic moiety such as an amine function, salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound contains an acidic moiety such as a carboxylic acid or phenol, salts include those formed with organic or inorganic bases such as pyridine, triethylamine or ammonia, or amides, hydrides, hydroxides or carbonates of sodium, potassium, lithium, calcium, magnesium or barium.

Compounds selected from Formula 1, geometric and stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

Embodiments of the present invention as described in the Summary of the Invention include those described below. In the following Embodiments, Formula 1 includes geometric and stereoisomers, N-oxides, and salts thereof, and reference to "a compound of Formula 1" includes the definitions of substituents specified in the Summary of the Invention unless further defined in the Embodiments.

Embodiment 1

A compound of Formula 1 wherein E is E-1, E-2 or E-3.

Embodiment 2

A compound of Embodiment 1 wherein E is E-1 or E-2.

Embodiment 3

A compound of Embodiment 2 wherein E is E-1.

Embodiment 4

A compound of Embodiment 2 wherein E is E-2.

Embodiment 5

A compound of Formula 1 wherein $R^6$ is $C_1$-$C_2$ alkyl or $C_1$-$C_2$ haloalkyl.

Embodiment 6

A compound of Embodiment 5 wherein $R^6$ is methyl.

Embodiment 7

A compound of Formula 1 wherein A is $CHR^{15}$.

Embodiment 8

A compound of Formula 1 wherein $R^{15}$ is H, halogen, cyano, hydroxy, —CHO, $C_1$-$C_4$ alkyl, $C_1$-$C_4$ haloalkyl, $C_1$-$C_4$ alkoxy or $C_2$-$C_5$ alkoxycarbonyl.

Embodiment 9

A compound of Embodiment 8 wherein $R^{15}$ is H, halogen, cyano, hydroxy, methyl, methoxy or methoxycarbonyl.

Embodiment 10

A compound of Embodiment 9 wherein $R^{15}$ is OH.

Embodiment 11

A compound of Embodiment 9 wherein $R^{15}$ is H.

Embodiment 12

A compound of Formula 1 wherein A is $NR^{16}$.

Embodiment 13

A compound of Formula 1 wherein $R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl.

Embodiment 14

A compound of Embodiment 13 wherein $R^{16}$ is H, methyl, methylcarbonyl or methoxycarbonyl.

Embodiment 15

A compound of Embodiment 14 wherein $R^{16}$ is H.

Embodiment 16

A compound of Formula 1 wherein A is C(=O).

Embodiment 17

A compound of Formula 1 wherein $W^1$ is $OR^{30}$, $SR^{31}$ or $NR^{32}R^{33}$.

Embodiment 18

A compound of Embodiment 17 wherein $W^1$ is $OR^{30}$.

Embodiment 19

A compound of Embodiment 17 wherein $W^1$ is $SR^{31}$.

Embodiment 19a

A compound of Embodiment 17 wherein $W^1$ is $NR^{32}R^{33}$.

Embodiment 20

A compound of Formula 1 wherein $R^{28}$ is H, halogen, cyano or $C_1$-$C_4$ alkyl.

Embodiment 21

A compound of Embodiment 20 wherein $R^{28}$ is H, halogen or cyano.

Embodiment 22

A compound of Embodiment 21 wherein $R^{28}$ is Cl, F or cyano.

Embodiment 23

A compound of Formula 1 or Embodiment 17 wherein each $R^{30}$ and $R^{31}$ is independently selected from $C_1$-$C_6$ alkyl, $C_3$-$C_4$ alkenyl, $C_3$-$C_4$ alkynyl, $C_1$-$C_4$ haloalkyl, $C_3$-$C_6$ haloalkenyl, $C_3$-$C_6$ haloalkynyl, $C_2$-$C_6$ alkoxyalkyl and $C_3$-$C_6$ cycloalkyl.

Embodiment 24

A compound of Embodiment 23 wherein each $R^{30}$ and $R^{31}$ is independently selected from $C_1$-$C_6$ alkyl, $C_3$-$C_4$ alkenyl, $C_3$-$C_4$ alkynyl and $C_1$-$C_4$ haloalkyl.

Embodiment 25

A compound of Embodiment 24 wherein each $R^{30}$ and $R^{31}$ is independently selected from $C_1$-$C_4$ alkyl.

Embodiment 26

A compound of Embodiment 25 wherein each $R^{30}$ and $R^{31}$ is independently ethyl or methyl.

Embodiment 27

A compound of Formula 1 or Embodiment 17 wherein $R^{32}$ when taken alone (i.e. not taken together with $R^{33}$) is H, cyano, hydroxy, amino, $C_1$-$C_6$ alkyl or $C_1$-$C_6$ alkoxy.

Embodiment 28

A compound of Embodiment 27 wherein $R^{32}$ when taken alone is H, cyano, hydroxy, amino, $C_1$-$C_3$ alkyl or $C_1$-$C_3$ alkoxy.

Embodiment 29

A compound of Embodiment 28 wherein $R^{32}$ when taken alone is H, cyano, hydroxy, $C_1$-$C_2$ alkyl or $C_1$-$C_2$ alkoxy.

Embodiment 30

A compound of Formula 1 or Embodiment 17 wherein $R^{33}$ when (i.e. not taken together with $R^{32}$) taken alone is H or $C_1$-$C_6$ alkyl.

Embodiment 31

A compound of Embodiment 30 wherein $R^{33}$ when taken alone is H or methyl.

Embodiment 32

A compound of Embodiment 31 wherein $R^{33}$ when taken alone is H.

Embodiment 32a

A compound of Formula 1 or any one of Embodiments 1 through 32 wherein $R^{32}$ and $R^{33}$ are taken alone.

Embodiment 33

A compound of Formula 1 wherein W is O.

Embodiment 34

A compound of Formula 1 wherein W is S.

Embodiment 35

A compound of Formula 1 wherein X is $X^1$, $X^2$ or $X^3$, $X^4$, $X^5$, $X^6$, $X^7$ or $X^8$.

Embodiment 36

A compound of Embodiment 35 wherein X is $X^1$, $X^2$ or $X^3$.

Embodiment 37

A compound of Embodiment 36 wherein X is $X^1$ or $X^2$.

Embodiment 38

A compound of Embodiment 37 wherein X is $X^1$.

Embodiment 39

A compound of Formula 1 or any one of Embodiments 35 through 38 wherein the ring comprising X is saturated.

Embodiment 40

A compound of Formula 1 wherein $Z^1$ is a direct bond, $CHR^{20}$ or $NR^{21}$.

Embodiment 40a

A compound of Embodiment 40 wherein $Z^1$ is a direct bond or $CHR^{20}$.

Embodiment 41

A compound of Embodiment 40a wherein $Z^1$ is a direct bond.

Embodiment 42

A compound of Formula 1 or Embodiment 40 wherein each $R^{21}$ is independently H, $C_1$-$C_3$ alkyl, $C_1$-$C_3$ alkylcarbonyl or $C_2$-$C_3$ alkoxycarbonyl.

Embodiment 42a

A compound of Embodiment 42 wherein each $R^{21}$ is independently H or methyl.

Embodiment 43

A compound of Formula 1 wherein $Z^5$, $Z^6$, $Z^7$ and $Z^8$ independently each a direct bond.

Embodiment 44

A compound of Formula 1 wherein
each $R^2$ is independently halogen, cyano, hydroxy, $C_1$-$C_4$ alkyl, $C_1$-$C_4$ alkenyl, $C_1$-$C_4$ haloalkyl or $C_1$-$C_4$ alkoxy; or
two $R^2$ groups are taken together as $C_1$-$C_3$ alkylene or $C_2$-$C_3$ alkenylene to form a bridged bicyclic ring system; or
two $R^2$ groups attached to adjacent ring carbon atoms joined by a double bond are taken together as —CH=CH—CH=CH— optionally substituted with up to 2 substituents independently selected from halogen, cyano, hydroxy, amino, nitro, $C_1$-$C_4$ alkyl, $C_1$-$C_4$ haloalkyl, $C_1$-$C_4$ alkoxy and $C_1$-$C_4$ haloalkoxy.

Embodiment 45

A compound of Embodiment 44 wherein each $R^2$ is independently halogen, cyano, hydroxy, $C_1$-$C_2$ alkyl, $C_1$-$C_2$ haloalkyl or $C_1$-$C_2$ alkoxy.

Embodiment 46

A compound of Embodiment 45 wherein each $R^2$ is independently cyano, hydroxy, methyl or methoxy.

Embodiment 47

A compound of Embodiment 46 wherein each $R^2$ is methyl.

Embodiment 48

A compound of Formula 1 wherein n is 0 or 1.

Embodiment 49

A compound of Embodiment 48 wherein n is 0.

Embodiment 50

A compound of Formula 1 wherein $R^{1a}$, $R^{1b}$, $R^{1c}$, $R^{1d}$ independently are optionally substituted phenyl, optionally substituted naphthalenyl or an optionally substituted 5- or 6-membered heteroaromatic ring; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_2$-$C_8$ haloalkylthioalkyl, $C_3$-$C_8$ cycloalkyl, $C_2$-$C_8$ alkoxyalkyl, $C_2$-$C_8$ haloalkoxyalkyl, $C_3$-$C_8$ alkoxycarbonylalkyl, $C_3$-$C_8$ haloalkoxycarbonylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ alkylcarbonyloxy, $C_3$-$C_{10}$ haloalkylcarbonyloxy, $C_3$-$C_{10}$ dialkylaminoalkyl, $C_1$-$C_8$ alkoxy, $C_1$-$C_8$ haloalkoxy, $C_1$-$C_8$ alkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl.

Embodiment 51

A compound of Embodiment 50 wherein independently when $R^{1a}$, $R^{1b}$, $R^{1c}$ and $R^{1d}$ are other than optionally substituted phenyl, optionally substituted naphthalenyl or an optionally substituted 5- or 6-membered heteroaromatic ring then $R^{1a}$, $R^{1b}$, $R^{1c}$ and $R^{1d}$ are independently cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_2$-$C_8$ alkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_1$-$C_8$ alkoxy, $C_1$-$C_8$ haloalkoxy, $C_1$-$C_8$ alkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl.

Embodiment 52

A compound of Embodiment 51 wherein independently when $R^{1a}$, $R^{1b}$, $R^{1c}$ and $R^{1d}$ are other than optionally substituted phenyl, optionally substituted naphthalenyl or an optionally substituted 5- or 6-membered heteroaromatic ring then $R^{1a}$, $R^{1b}$, $R^{1c}$ and $R^{1d}$ are independently $C_1$-$C_8$ alkyl, $C_2$-$C_8$ alkenyl, $C_1$-$C_8$ haloalkyl, $C_2$-$C_8$ alkoxyalkyl, $C_2$-$C_8$ alkylthioalkyl, $C_2$-$C_8$ alkylaminoalkyl, $C_1$-$C_8$ alkoxy, $C_1$-$C_8$ alkylthio, pyrrolidinyl, piperidinyl or morpholinyl.

Embodiment 53

A compound of Embodiment 52 wherein independently when $R^{1a}$, $R^{1b}$, $R^{1c}$ and $R^{1d}$ are other than optionally substituted phenyl, optionally substituted naphthalenyl or an optionally substituted 5- or 6-membered heteroaromatic ring then $R^{1a}$, $R^{1b}$, $R^{1c}$ and $R^{1d}$ are independently $C_1$-$C_6$ alkyl, $C_2$-$C_6$ alkenyl, $C_1$-$C_6$ haloalkyl, $C_1$-$C_6$ alkoxy, pyrrolidinyl, piperidinyl or morpholinyl.

Embodiment 54

A compound of Embodiment 50 wherein independently when $R^{1a}$, $R^{1b}$, $R^{1c}$ and $R^{1d}$ are other than optionally substituted phenyl, optionally substituted naphthalenyl or an optionally substituted 5- or 6-membered heteroaromatic ring then $R^{1a}$, $R^{1b}$, $R^{1c}$ and $R^{1d}$ are independently $C_2$-$C_5$ alkyl, $C_2$-$C_5$ alkenyl, $C_2$-$C_5$ haloalkyl, $C_2$-$C_5$ haloalkenyl, $C_2$-$C_5$ haloalkylthioalkyl, $C_2$-$C_5$ alkoxyalkyl, $C_2$-$C_5$ haloalkoxyalkyl, $C_2$-$C_5$ alkylthioalkyl, $C_2$-$C_5$ alkylaminoalkyl, $C_2$-$C_5$ alkylcarbonyloxy, $C_2$-$C_5$ haloalkylcarbonyloxy, $C_2$-$C_5$ alkoxy, $C_2$-$C_5$ haloalkoxy, $C_2$-$C_5$ alkylthio, $C_2$-$C_5$ alkylamino or $C_2$-$C_5$ alkylcarbonylamino.

Embodiment 55

A compound of Embodiment 54 wherein independently when $R^{1a}$, $R^{1b}$, $R^{1c}$ and $R^{1d}$ are other than optionally substituted phenyl, optionally substituted naphthalenyl or an optionally substituted 5- or 6-membered heteroaromatic ring then $R^{1a}$, $R^{1b}$, $R^{1c}$ and $R^{1d}$ are independently $C_3$-$C_5$ alkyl, $C_3$-$C_5$ alkenyl, $C_3$-$C_5$ haloalkyl, $C_3$-$C_5$ haloalkenyl, $C_2$-$C_4$ haloalkylthioalkyl, $C_2$-$C_4$ alkoxyalkyl, $C_2$-$C_4$ haloalkoxyalkyl, $C_2$-$C_4$ alkylthioalkyl, $C_2$-$C_4$ alkylaminoalkyl, $C_2$-$C_3$ alkylcarbonyloxy, $C_2$-$C_3$ haloalkylcarbonyloxy, $C_2$-$C_4$ alkoxy, $C_2$-$C_4$ haloalkoxy, $C_2$-$C_4$ alkylthio, $C_2$-$C_4$ alkylamino or $C_2$-$C_3$ alkylcarbonylamino.

Embodiment 56

A compound of Embodiment 55 wherein independently when $R^{1a}$, $R^{1b}$, $R^{1c}$ and $R^{1d}$ are other than optionally substituted phenyl, optionally substituted naphthalenyl or an optionally substituted 5- or 6-membered heteroaromatic ring then $R^{1a}$, $R^{1b}$, $R^{1c}$ and $R^{1d}$ are independently $C_3$-$C_5$ haloalkyl, $C_3$-$C_5$ haloalkenyl, $C_3$-$C_5$ haloalkylthioalkyl, $C_3$-$C_5$ haloalkoxyalkyl, $C_2$-$C_3$ haloalkylcarbonyloxy or $C_2$-$C_4$ haloalkoxy.

Embodiment 57

A compound of Embodiment 56 wherein independently when $R^{1a}$, $R^{1b}$, $R^{1c}$ and $R^{1d}$ are other than optionally substituted phenyl, optionally substituted naphthalenyl or optionally substituted 5- or 6-membered heteroaromatic ring then $R^{1a}$, $R^{1b}$, $R^{1c}$ and $R^{1d}$ are independently $C_4$ haloalkyl, $C_4$ haloalkenyl, $C_3$ haloalkoxyalkyl or $C_3$ haloalkoxy.

Embodiment 58

A compound of Formula 1 or Embodiment 50 wherein independently when $R^{1a}$, $R^{1b}$, $R^{1c}$ and $R^{1d}$ are optionally substituted phenyl, optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is optionally substituted with up to 3 independently selected substituents.

Embodiment 59

A compound of Formula 1 or Embodiment 58 wherein independently when $R^{1a}$, $R^{1b}$, $R^{1c}$ and $R^{1d}$ are optionally substituted phenyl, optionally substituted naphthalenyl or an optionally substituted 5- or 6-membered heteroaromatic ring, the optionally substituted phenyl, optionally substituted naphthalenyl or optionally substituted 5- or 6-membered heteroaromatic ring is optionally substituted with up to 2 independently selected substituents.

Embodiment 60

A compound of Formula 1 or Embodiments 58 or 59 wherein independently when $R^{1a}$, $R^{1b}$, $R^{1c}$ and $R^{1d}$ are optionally substituted phenyl, optionally substituted naphthalenyl or an optionally substituted 5- or 6-membered heteroaromatic ring, then the optional substituents on the phenyl, naphthalenyl or 5- or 6-membered heteroaromatic ring are independently selected from $R^{4a}$ on carbon ring members and $R^{4b}$ on nitrogen ring members;
  each $R^{4a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and
  each $R^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl.

Embodiment 61

A compound of Formula 1 or any one of Embodiments 1 through 60 wherein independently $R^{1a}$, $R^{1b}$, $R^{1c}$ and $R^{1d}$ are other than optionally substituted naphthalenyl.

Embodiment 62

A compound of Embodiment 60 wherein each $R^{4a}$ is independently halogen, cyano, nitro, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl.

Embodiment 63

A compound of Embodiment 62 wherein each $R^{4a}$ is independently halogen, cyano, nitro, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, $C_1$-$C_2$ alkoxy or $C_1$-$C_2$ haloalkoxy.

Embodiment 64

A compound of Embodiment 63 wherein each $R^{4a}$ is independently halogen, $C_1$-$C_3$ alkyl, $C_1$-$C_3$ haloalkyl, $C_1$-$C_2$ alkoxy or $C_1$-$C_2$ haloalkoxy.

Embodiment 65

A compound of Embodiment 64 wherein each $R^{4a}$ is independently halogen, $C_1$-$C_2$ alkyl, $C_1$-$C_2$ haloalkyl or $C_1$-$C_2$ alkoxy.

Embodiment 66

A compound of Embodiment 65 wherein each $R^{4a}$ is independently Cl, Br, I, $C_1$-$C_2$ alkyl, trifluoromethyl or methoxy.

Embodiment 67

A compound of Embodiment 66 wherein each $R^{4a}$ is independently Cl, Br, $C_1$-$C_2$ alkyl or trifluoromethyl.

Embodiment 68

A compound of Embodiment 60 wherein each $R^{4b}$ is independently $C_1$-$C_3$ alkyl, $C_3$ alkenyl (e.g., allyl), $C_3$ alkynyl (e.g., propargyl), cyclopropyl, $C_1$-$C_3$ haloalkyl, $C_3$ haloalkenyl, $C_3$ haloalkynyl, halocyclopropyl or $C_2$-$C_3$ alkoxyalkyl.

Embodiment 69

A compound of Embodiment 68 wherein each $R^{4b}$ is independently $C_1$-$C_3$ alkyl, $C_3$ alkenyl, $C_3$ alkynyl, cyclopropyl, $C_1$-$C_3$ haloalkyl, $C_3$ haloalkenyl or halocyclopropyl.

Embodiment 70

A compound of Embodiment 69 wherein each $R^{4b}$ is independently $C_1$-$C_2$ alkyl or $C_1$-$C_2$ haloalkyl.

Embodiment 71

A compound of Embodiment 70 wherein each $R^{4b}$ is independently $C_1$-$C_2$ alkyl or trifluoromethyl.

Embodiment 72

A compound of Embodiment 71 wherein each $R^{4b}$ is independently $C_1$-$C_2$ alkyl.

Embodiment 72a

A compound of Formula 1 or any one of Embodiments 1 through 72 wherein independently $R^{1a}$, $R^{1b}$, $R^{1c}$ and $R^{1d}$ are optionally substituted phenyl, optionally substituted naphthalenyl or an optionally substituted 5- or 6-membered heteroaromatic ring.

Embodiment 73

A compound of any one of Embodiments 60 through 72a wherein independently when $R^{1a}$, $R^{1b}$, $R^{1c}$ and $R^{1d}$ are optionally substituted phenyl, optionally substituted naphthalenyl or an optionally substituted 5- or 6-membered heteroaromatic ring, then $R^{1a}$, $R^{1b}$, $R^{1c}$ and $R^{1d}$ independently are selected from U-1 through U-50 in Exhibit 1.

Exhibit 1

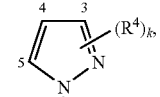
U-1

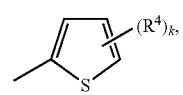
U-2

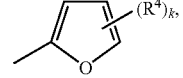
U-3

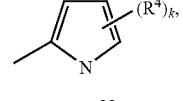
U-4

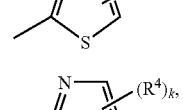
U-5

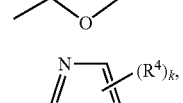
U-6

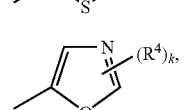
U-7

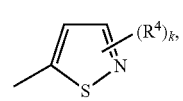
U-8

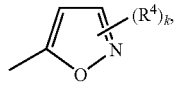
U-9

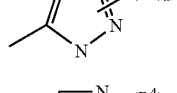
U-10

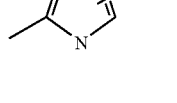
U-11

U-12

| | | | |
|---|---|---|---|
| 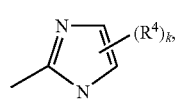 | U-13 | 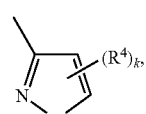 | U-25 |
| 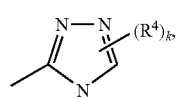 | U-14 | 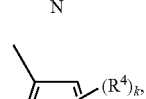 | U-26 |
| 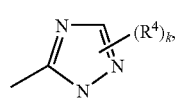 | U-15 | 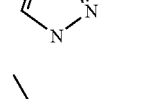 | U-27 |
| 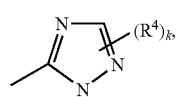 | U-15 | 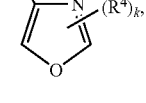 | U-28 |
| 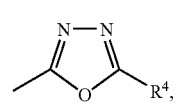 | U-16 | 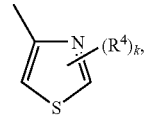 | U-29 |
| 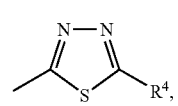 | U-17 | 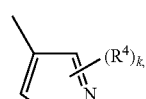 | U-30 |
| 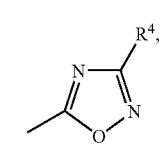 | U-18 | 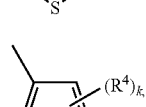 | U-31 |
| 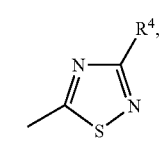 | U-19 | 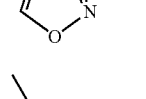 | U-32 |
| 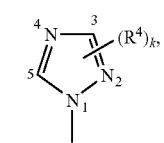 | U-20 | 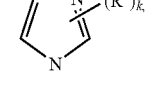 | U-33 |
| 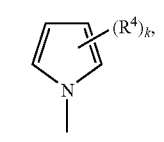 | U-21 | 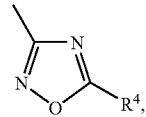 | U-34 |
| 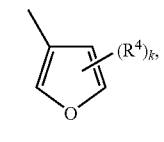 | U-22 | 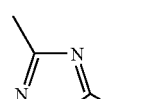 | U-35 |
| 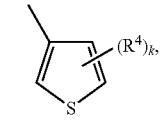 | U-23 | 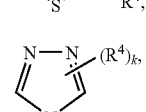 | |
| 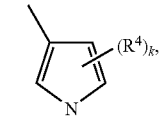 | U-24 |  | U-36 |

-continued

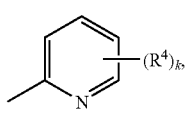 U-37

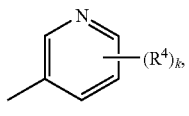 U-38

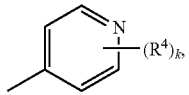 U-39

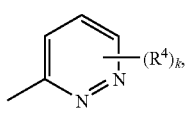 U-40

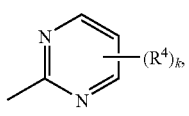 U-41

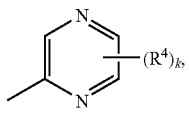 U-42

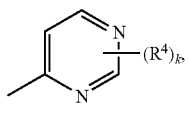 U-43

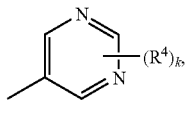 U-44

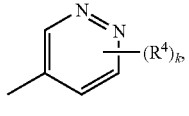 U-45

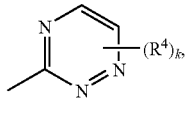 U-46

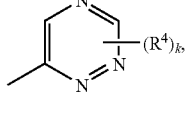 U-47

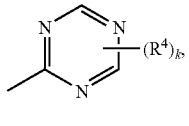 U-48

U-49

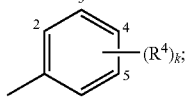 U-50 wherein
when $R^4$ is attached to a carbon ring member, said $R^4$ is selected from $R^{4a}$, and when $R^4$ is attached to a nitrogen ring member (e.g., U-4, U-11, U-12, U-13, U-14, U-15, U-24, U-25, U-26, U-31 or U-35), said $R^4$ is selected from $R^{4b}$; and k is 0, 1 or 2.

Embodiment 74

A compound of Embodiment 73 wherein k is an integer from 1 to 2.

Embodiment 75

A compound of Embodiment 73 wherein $R^{1a}$, $R^{1b}$, $R^{1c}$ and $R^{1d}$ independently are selected from U-1 through U-5, U-8, U-11, U-13, U-15, U-20 through U-28, U-31, U-36 through U-39 and U-50.

Embodiment 76

A compound of Embodiment 75 wherein $R^{1a}$, $R^{1b}$, $R^{1c}$ and $R^{1d}$ independently are selected from U-1 through U-3, U-5, U-8, U-11, U-13, U-20, U-22, U-23, U-25 through U-28, U-36 through U-39 and U-50.

Embodiment 77

A compound of Embodiment 76 wherein $R^{1a}$, $R^{1b}$, $R^{1c}$ and $R^{1d}$ independently are selected from U-1 through U-3, U-11, U-13, U-20, U-22, U-23, U-36 through U-39 and U-50.

Embodiment 78

A compound of Embodiment 77 wherein $R^{1a}$, $R^{1b}$, $R^{1c}$ and $R^{1d}$ independently are selected from U-1, U-20 and U-50.

Embodiment 79

A compound of Embodiment 78 wherein $R^{1a}$, $R^{1b}$, $R^{1c}$ and $R^{1d}$ independently are U-1.

Embodiment 80

A compound of Embodiment 78 wherein $R^{1a}$, $R^{1b}$, $R^{1c}$ and $R^{1d}$ independently are U-20.

Embodiment 81

A compound of Embodiment 78 wherein $R^{1a}$, $R^{1b}$, $R^{1c}$ and $R^{1d}$ independently are U-50.

Embodiment 82

A compound of Embodiment 79 wherein k is 1 and $R^4$ is connected to the 3- or 5-position of U-1.

Embodiment 83

A compound of Embodiment 79 wherein k is 2 and one $R^4$ is connected to the 3-position and the other $R^4$ is connected to the 5-position of U-1.

Embodiment 84

A compound of Embodiment 80 wherein k is 1 and $R^4$ is connected to the 3- or 5-position of U-20.

Embodiment 85

A compound of Embodiment 80 wherein k is 2 and one $R^4$ is connected to the 3-position and the other $R^4$ is connected to the 5-position of U-20.

Embodiment 86

A compound of Embodiment 81 wherein k is 1 and $R^4$ is connected to the 2- or 3-position of U-50.

Embodiment 87

A compound of Embodiment 81 wherein k is 2 and one $R^4$ is connected to the 2-position and the other $R^4$ is connected to the 5-position of U-50.

Embodiment 88

A compound of Formula 1 wherein G is a 5-membered heterocyclic ring optionally substituted with up to 2 substituents selected from $R^3$ on carbon ring members and $R^{11}$ on nitrogen ring members;
each $R^3$ is independently halogen, $C_1$-$C_3$ alkyl or $C_1$-$C_3$ haloalkyl; and
each $R^{11}$ is independently $C_1$-$C_3$ alkyl.

Embodiment 89

A compound of Embodiment 88 wherein G is selected from G-1 through G-59 in Exhibit 2.

Exhibit 2

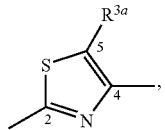
G-1

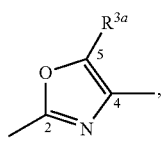
G-2

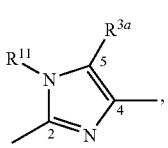
G-3

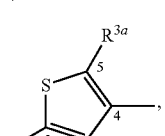
G-4

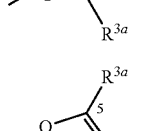
G-5

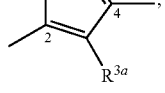

-continued

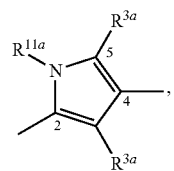
G-6

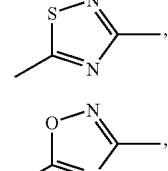
G-7

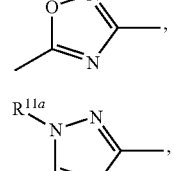
G-8

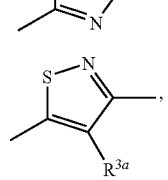
G-9

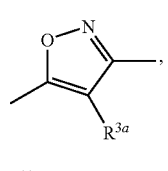
G-10

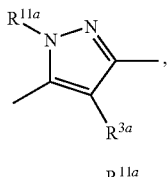
G-11

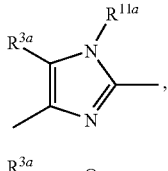
G-12

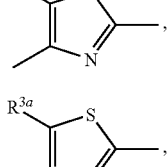
G-13

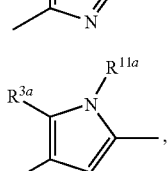
G-14

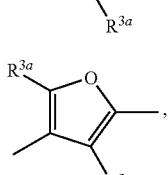
G-15

G-16

G-17

-continued
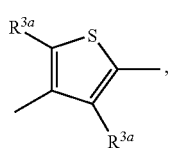 G-18
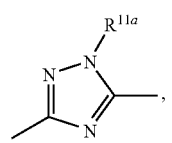 G-19
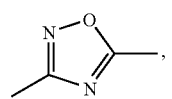 G-20
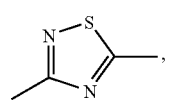 G-21
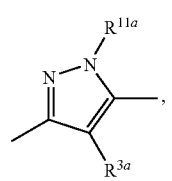 G-22
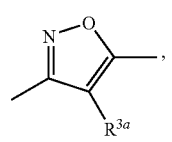 G-23
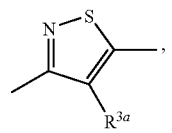 G-24
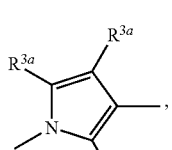 G-25
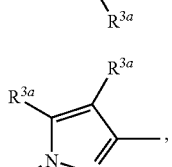 G-26
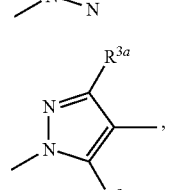 G-27
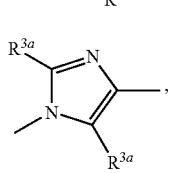 G-28
-continued
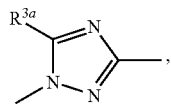 G-29
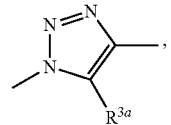 G-30
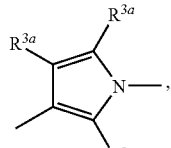 G-31
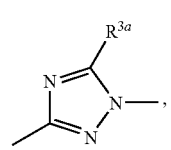 G-32
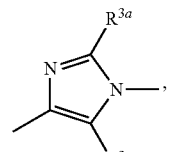 G-33
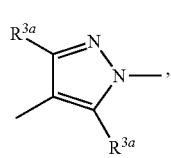 G-34
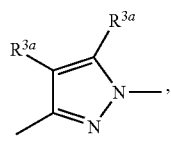 G-35
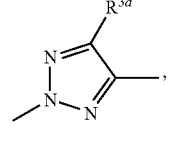 G-36
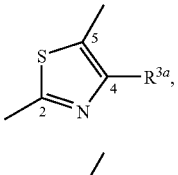 G-37
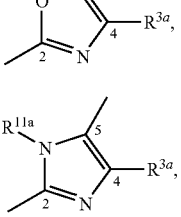 G-38
 G-39

-continued

G-40 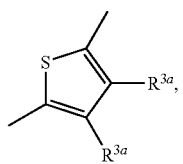

G-41 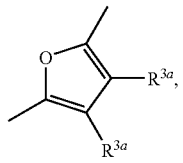

G-42 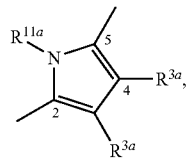

G-43 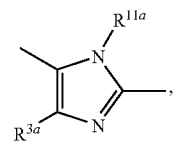

G-44 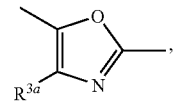

G-45 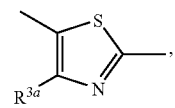

G-46 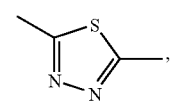

G-47 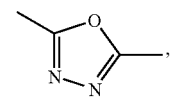

G-48 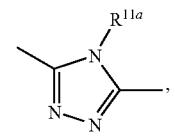

G-49 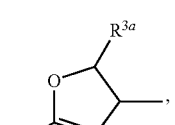

G-50 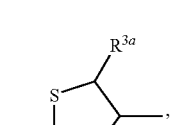

G-51 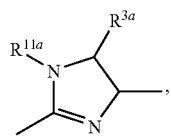

G-52 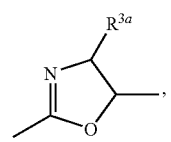

G-53 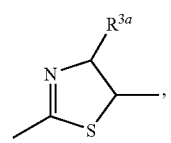

G-54 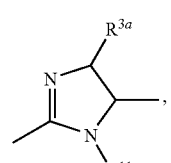

G-55 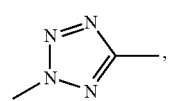

G-56 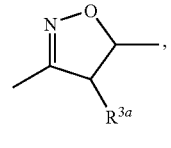

G-57 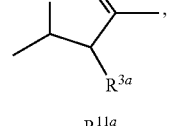

G-58 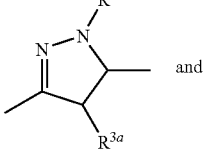

G-59 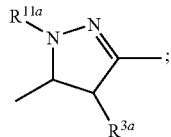

wherein the bond projecting to the left is bonded to X, and the bond projecting to the right is bonded to $Z^1$ in Formula 1; each $R^{1a}$ is independently selected from H and $R^3$; and $R^{11a}$ is selected from H and $R^{11}$;

Embodiment 90

A compound of Embodiment 89 wherein G is selected from G-1 through G-3, G-7, G-8, G-10, G-11, G-14, G-15, G-23, G-24, G-26 through G-28, G-30, G-36 through G-38 and G-49 through G-55.

Embodiment 91

A compound of Embodiment 90 wherein G is selected from G-1, G-2, G-7, G-8, G-14, G-15, G-23, G-24, G-26, G-27, G-36, G-37, G-38, G-49, G-50 and G-55.

Embodiment 92

A compound of Embodiment 91 wherein G is selected from G-1, G-2, G-15, G-26, G-27, G-36, G-37 and G-38.

Embodiment 93

A compound of Embodiment 92 wherein G is selected from G-1, G-2, G-15, G-26 and G-36.

Embodiment 94

A compound of Embodiment 93 wherein G is G-1.

Embodiment 95

A compound of Embodiment 93 wherein G is G-2.

Embodiment 96

A compound of Embodiment 93 wherein G is G-15.

Embodiment 97

A compound of Embodiment 93 wherein G is G-26.

Embodiment 98

A compound of Embodiment 93 wherein G is G-36.

Embodiment 99

A compound of any one of Embodiments 88 through 98 wherein each $R^3$ is independently halogen, $C_1$-$C_3$ alkyl or $C_1$-$C_3$ haloalkyl.

Embodiment 100

A compound of Embodiment 99 wherein each $R^3$ is independently halogen or methyl.

Embodiment 101

A compound of any one of Embodiments 89 through 100 wherein each $R^{1a}$ is H and $R^{11a}$ is H or methyl.

Embodiment 102

A compound of Formula 1 or any one of Embodiments 88 through 98 wherein G is unsubstituted.

Embodiment 103

A compound of Formula 1 wherein J is selected from J-1 through J-82 in Exhibit 3.

Exhibit 3

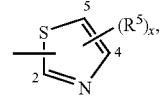
J-1

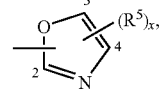
J-2

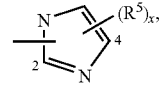
J-3

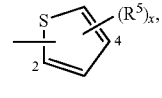
J-4

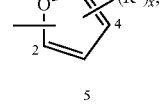
J-5

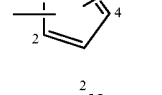
J-6

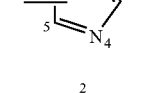
J-7

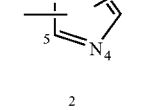
J-8

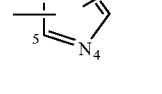
J-9

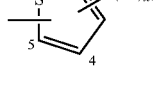
J-10

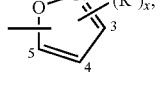
J-11

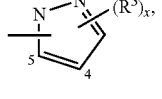
J-12

| | |
|---|---|
| J-13 | 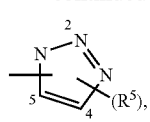 |
| J-14 | 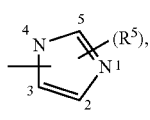 |
| J-15 | 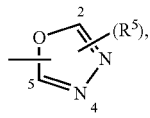 |
| J-16 | 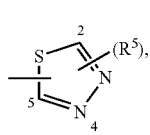 |
| J-17 | 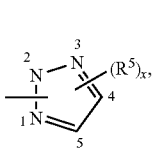 |
| J-18 | 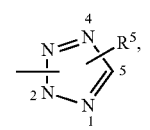 |
| J-19 | 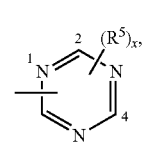 |
| J-20 | 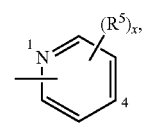 |
| J-21 | 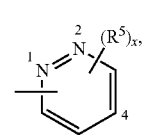 |
| J-22 | 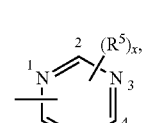 |
| J-23 | 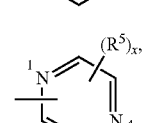 |
| J-24 | 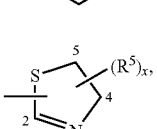 |
| J-25 | 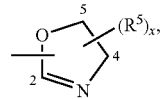 |
| J-26 | 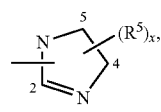 |
| J-27 | 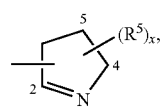 |
| J-28 | 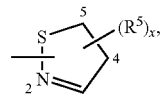 |
| J-29 | 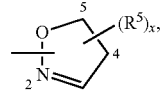 |
| J-30 | 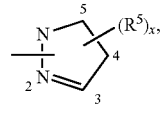 |
| J-31 | 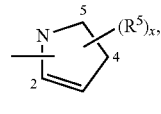 |
| J-32 | 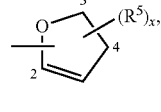 |
| J-33 | 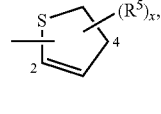 |
| J-34 | 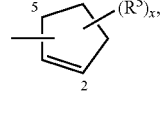 |
| J-35 | 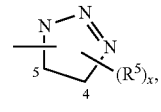 |
| J-36 | 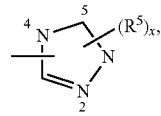 |

J-37 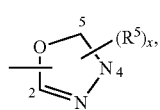
J-38 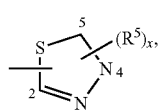
J-39 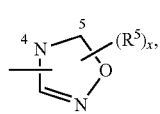
J-40 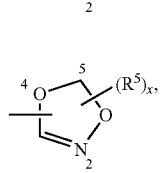
J-41 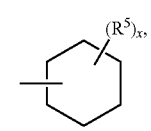
J-42 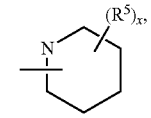
J-43 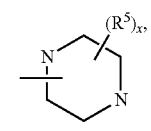
J-44 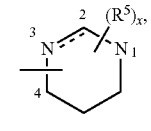
J-45 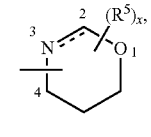
J-46 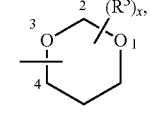
J-47 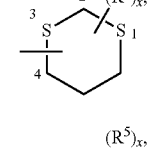
J-48 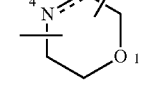
J-49 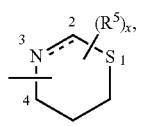
J-50 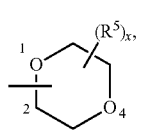
J-51 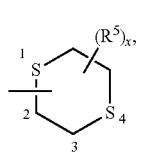
J-52 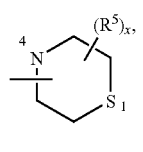
J-53 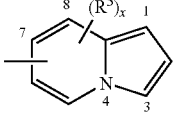
J-54 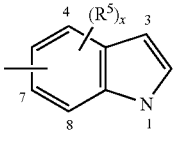
J-55 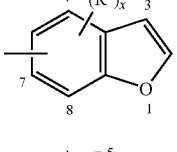
J-56 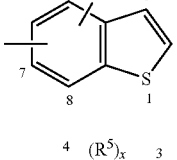
J-57 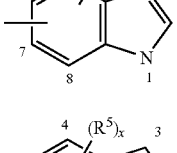
J-58 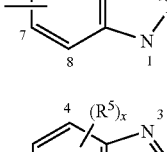
J-59 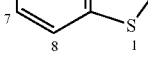

-continued
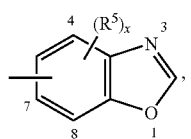 J-60
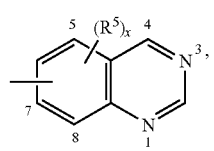 J-61
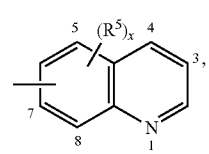 J-62
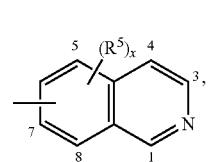 J-63
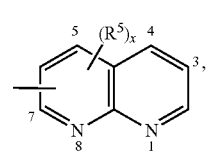 J-64
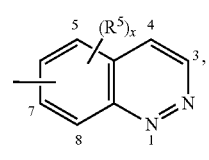 J-65
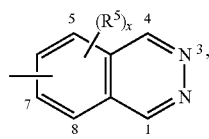 J-66
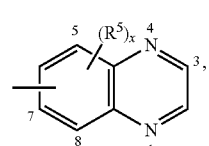 J-67
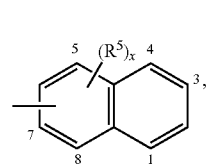 J-68
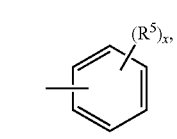 J-69
-continued
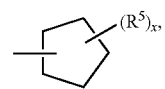 J-70
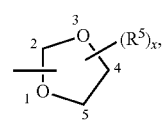 J-71
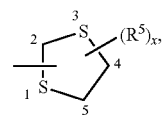 J-72
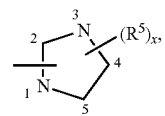 J-73
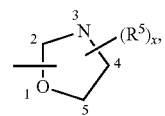 J-74
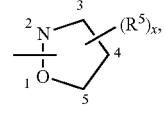 J-75
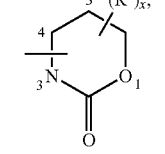 J-76
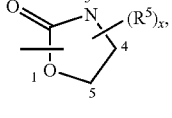 J-77
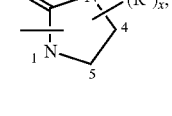 J-78
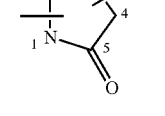 J-79
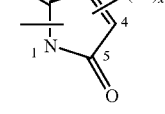 J-80

-continued
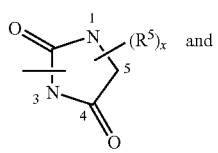
J-81
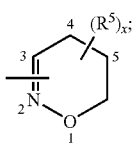
J-82
wherein the bond shown projecting to the left is bonded to Z¹ in Formula 1 and to an available carbon or nitrogen atom ring member in the J ring; and x is an integer from 0 to 5.
Embodiment 104
A compound of Embodiment 103 wherein J is a ring selected from J-29-1 through J-29-60 in Exhibit A.
Exhibit A
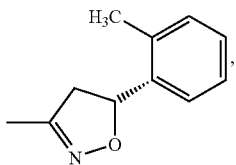
J-29-1
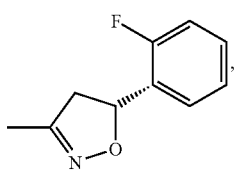
J-29-2
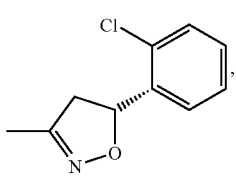
J-29-3
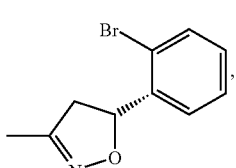
J-29-4
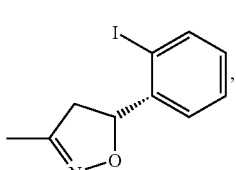
J-29-5
-continued
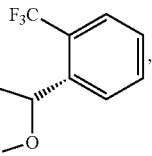
J-29-6
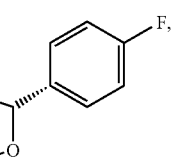
J-29-7
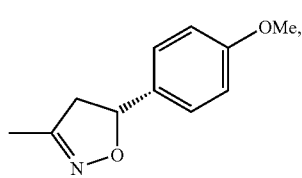
J-29-8
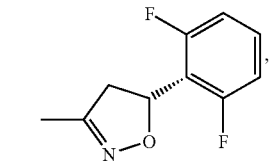
J-29-9
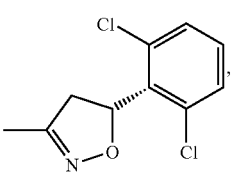
J-29-10
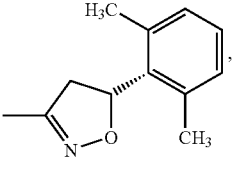
J-29-11
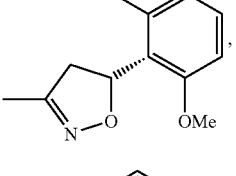
J-29-12
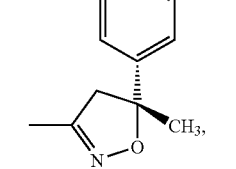
J-29-13
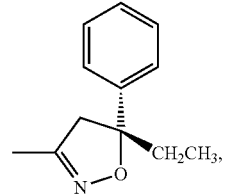
J-29-14

J-29-15
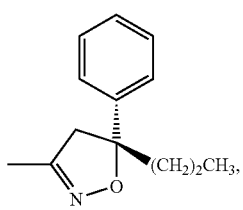
J-29-16
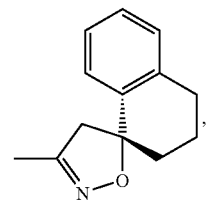
J-29-17
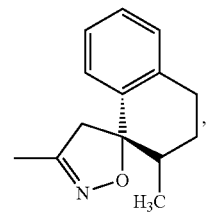
J-29-18
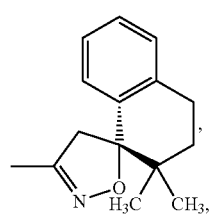
J-29-19
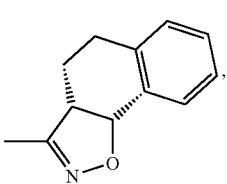
J-29-20
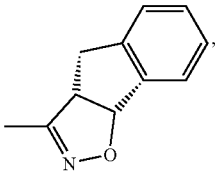
J-29-21
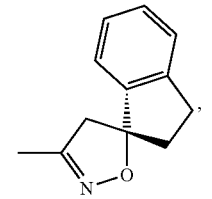
J-29-22
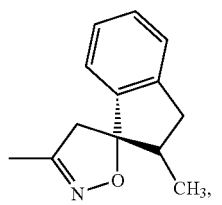
J-29-23
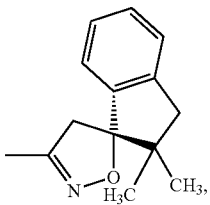
J-29-24
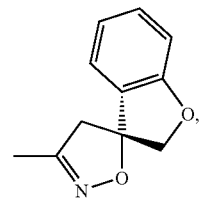
J-29-25
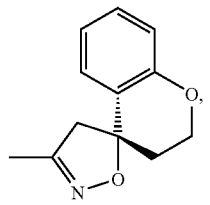
J-29-26
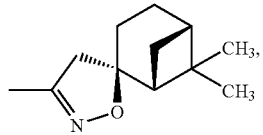
J-29-27
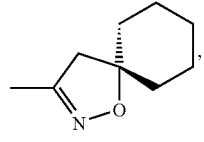
J-29-28
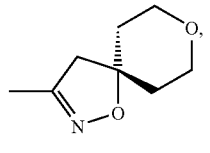
J-29-29
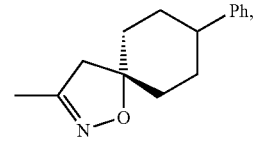
J-29-30
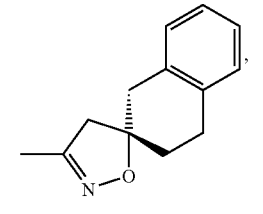
J-29-31
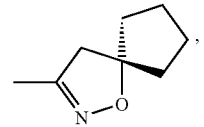

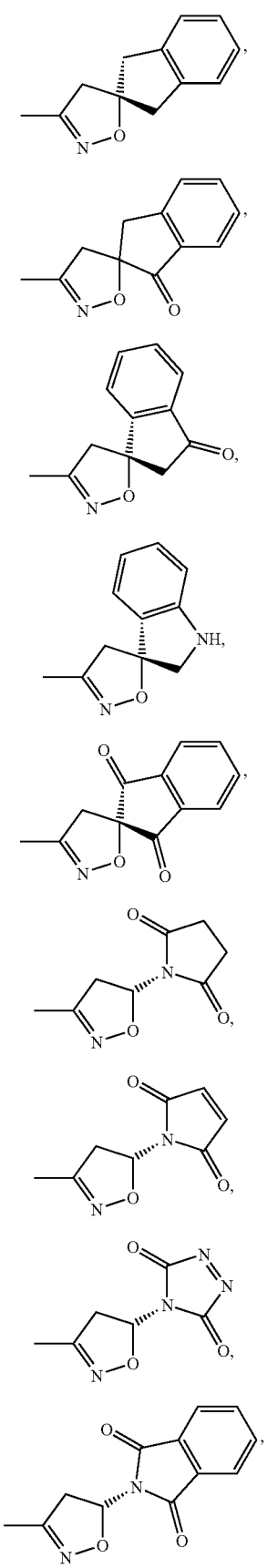
J-29-32
J-29-33
J-29-34
J-29-35
J-29-36
J-29-37
J-29-38
J-29-39
J-29-40
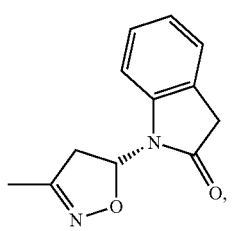
J-29-41
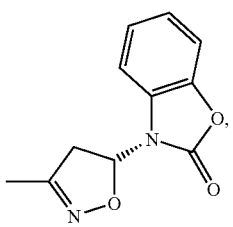
J-29-42
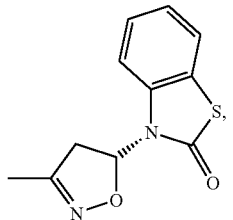
J-29-43
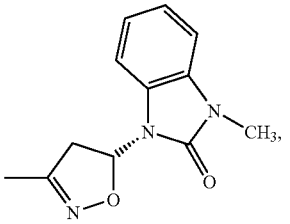
J-29-44
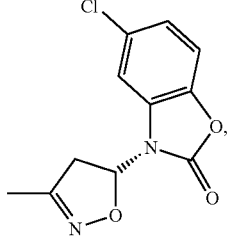
J-29-45
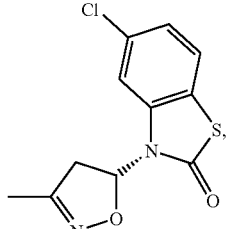
J-29-46
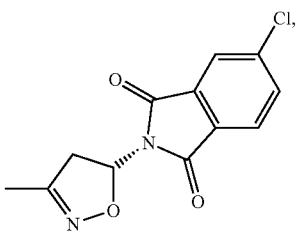
J-29-47

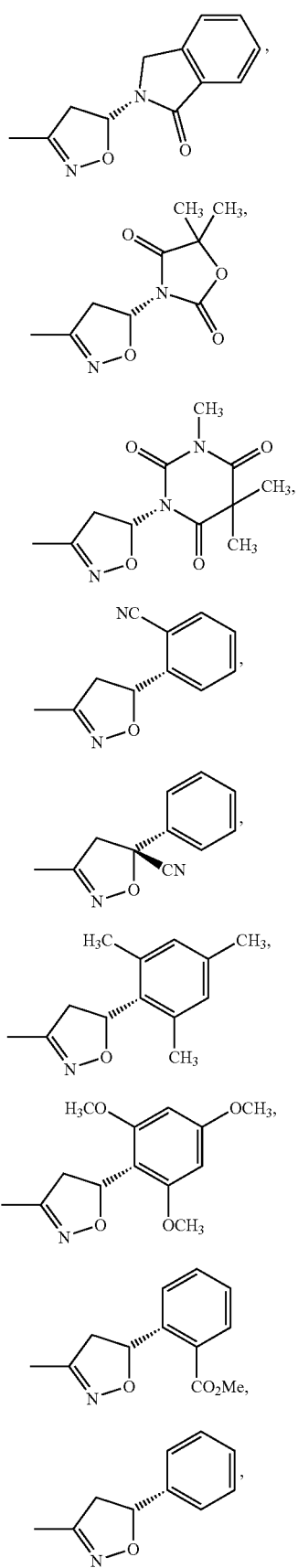

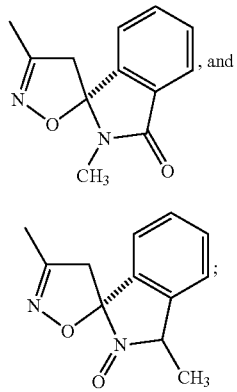

Embodiment 105

A compound of Embodiment 103 wherein J is selected from J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69.

Embodiment 106

A compound of Embodiment 105 wherein J is selected from J-4, J-5, J-8, J-11, J-15, J-16, J-20, J-29, J-30, J-37, J-38 and J-69.

Embodiment 107

A compound of Embodiment 106 wherein J is selected from J-4, J-5, J-11, J-20, J-29, J-37, J-38 and J-69.

Embodiment 108

A compound of Embodiment 107 wherein J is J-11.

Embodiment 109

A compound of Embodiment 107 wherein J is J-29.

Embodiment 110

A compound of Embodiment 107 wherein J is J-69.

Embodiment 111

A compound of any one of Embodiments 103 through 110 wherein x is an integer from 0 to 3.

Embodiment 111a

A compound of any one of Embodiment 111 wherein x is an integer from 0 to 2.

Embodiment 112

A compound of Embodiment 111a wherein x is 1 or 2.

Embodiment 113

A compound of Embodiment 112 wherein x is 1.

Embodiment 114

A compound of Embodiment 108 wherein the 3-position of J-11 is connected to $Z^1$ of Formula 1 and the 5-position of J-11 is substituted with a substituent selected from $R^5$ other than H.

Embodiment 115

A compound of Embodiment 108 wherein the 3-position of J-11 is connected to $Z^1$ of Formula 1 and the 5-position of J-11 is substituted with $-Z^2Q$.

Embodiment 116

A compound of Embodiment 109 wherein the 3-position of J-29 is connected to $Z^1$ of Formula 1 and the 5-position of J-29 is substituted with a substituent selected from $R^5$ other than H.

Embodiment 117

A compound of Embodiment 109 wherein the 3-position of J-29 is connected to $Z^1$ of Formula 1 and the 5-position of J-29 is substituted with $-Z^2Q$.

Embodiment 118

A compound of Formula 1 wherein each $R^5$ when taken alone (i.e. not taken together with $R^7$) is independently H, halogen, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, $-NR^{25}R^{26}$ or $-Z^2Q$.

Embodiment 119

A compound of Embodiment 118 wherein each $R^5$ when taken alone is independently H, halogen, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, $-NR^{25}R^{26}$ or $-Z^2Q$.

Embodiment 120

A compound of Embodiment 119 wherein each $R^5$ when taken alone is independently H, halogen, cyano, $C_1$-$C_6$ alkyl, $C_1$-$C_6$ haloalkyl, $C_1$-$C_6$ alkoxy, $C_1$-$C_6$ haloalkoxy, $-NR^{25}R^{26}$ or $-Z^2Q$.

Embodiment 120a

A compound of Embodiment 120 wherein each $R^5$ when taken alone is independently H, halogen, cyano, $C_1$-$C_6$ alkyl, $C_1$-$C_6$ haloalkyl, $C_1$-$C_6$ alkoxy, $C_1$-$C_6$ haloalkoxy or $-Z^2Q$.

Embodiment 120b

A compound of Embodiment 120a wherein each $R^5$ when taken alone is independently H, cyano, $C_1$-$C_6$ alkyl, $C_1$-$C_6$ alkoxy or $-Z^2Q$.

Embodiment 121

A compound of Embodiment 120b wherein each $R^5$ when taken alone is independently $-Z^2Q$.

Embodiment 121a

A compound of Formula 1 or any one of Embodiments 1 through 121 wherein each $R^5$ is taken alone.

Embodiment 122

A compound of Formula 1 wherein one instance of $R^5$ is $-Z^2Q$ and other instances of $R^5$ are independently selected from H, halogen, cyano, $C_1$-$C_4$ alkyl, $C_1$-$C_4$ haloalkyl and $C_1$-$C_4$ alkylcarbonyl.

Embodiment 123

A compound of Embodiment 122 wherein one instance of $R^5$ is $-Z^2Q$ and other instances of $R^5$ are independently selected from H, cyano and $C_1$-$C_3$ alkyl.

Embodiment 124

A compound of Embodiment 123 wherein the only instance of $R^5$ is $-Z^2Q$.

Embodiment 125

A compound of Formula 1 wherein each $R^{26}$ is independently $C_1$-$C_3$ alkyl or $-Z^4Q$;

Embodiment 126

A compound of Formula 1 or Embodiment 125 wherein each $Z^4$ is independently $C(=O)$ or $S(O)_2$.

Embodiment 127

A compound of Embodiment 126 wherein each $Z^4$ is $C(=O)$.

Embodiment 128

A compound of Formula 1 wherein each $Z^2$ is independently a direct bond, O, $C(=O)$, $S(O)_2$, $CHR^{20}$ or $NR^{21}$.

Embodiment 128a

A compound of Embodiment 128 wherein each $Z^2$ is independently a direct bond or $NR^{21}$.

Embodiment 128b

A compound of Embodiment 128a wherein each $Z^2$ is a direct bond.

Embodiment 129

A compound of Formula 1 wherein each Q is independently phenyl, benzyl, naphthalenyl, a 5- to 6-membered heteroaromatic ring or an 8- to 11-membered heteroaromatic bicyclic ring system, each optionally substituted with up to 1 substituent independently selected from $R^{7a}$ on carbon atom or nitrogen atom ring members, and each optionally substituted with up to 5 substituents independently selected from $R^7$ on carbon atom ring members and $R^{12}$ on nitrogen atom ring members; or a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(=O)$_s$(=NR$^{23}$)$_f$ and SiR$^{17}$R$^{18}$, and each ring or ring system optionally substituted with up to 1 substituent independently selected from $R^{7a}$ on carbon atom or nitrogen atom ring members, and each optionally substituted with up to 5 substituents independently selected from $R^7$ on carbon atom ring members and $R^{12}$ on nitrogen atom ring members.

Embodiment 130

A compound of Embodiment 129 wherein each Q is independently phenyl, benzyl, naphthalenyl, a 5- to 6-membered heteroaromatic ring or an 8- to 11-membered heteroaromatic bicyclic ring system, each optionally substituted with up to 5 substituents independently selected from $R^7$ on carbon atom ring members and $R^{12}$ on nitrogen atom ring members; or a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(=O)$_s$(=NR$^{23}$)$_f$ and SiR$^{17}$R$^{18}$, and each ring or ring system optionally substituted with up to 5 substituents independently selected from $R^7$ on carbon atom ring members and $R^{12}$ on nitrogen atom ring members.

Embodiment 131

A compound of Formula 1 or Embodiments 129 or 130 wherein each Q is independently selected from Q-1 through Q-106 in Exhibit 4.

Exhibit 4

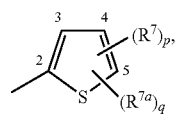
Q-1

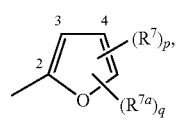
Q-2

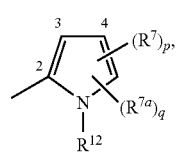
Q-3

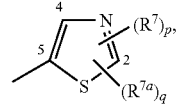
Q-4

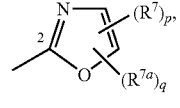
Q-5

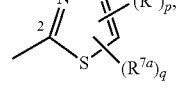
Q-6

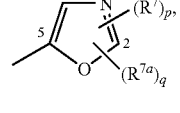
Q-7

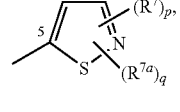
Q-8

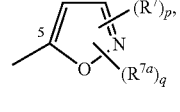
Q-9

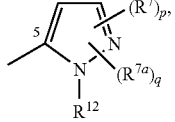
Q-10

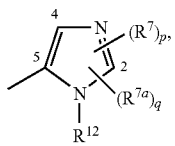
Q-11

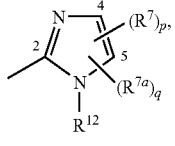
Q-12

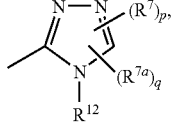
Q-13

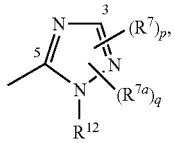
Q-14

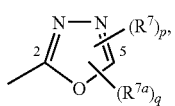
Q-15

US 8,349,870 B2

-continued

Q-16, Q-17, Q-18, Q-19, Q-20, Q-21, Q-22, Q-23, Q-24, Q-25, Q-26, Q-27, Q-28, Q-29, Q-30, Q-31, Q-32, Q-33, Q-34, Q-35, Q-36, Q-37

-continued
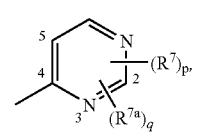 Q-38
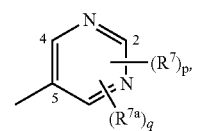 Q-39
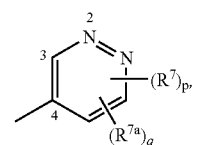 Q-40
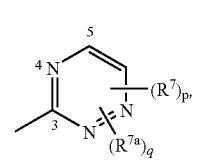 Q-41
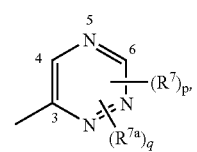 Q-42
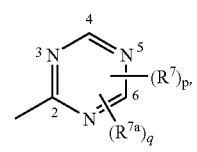 Q-43
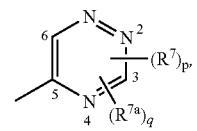 Q-44
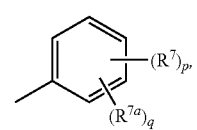 Q-45
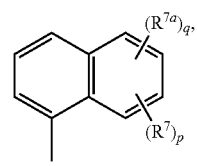 Q-46
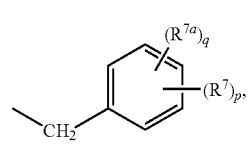 Q-47
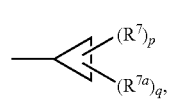 Q-48
-continued
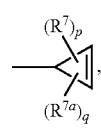 Q-49
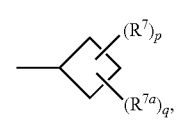 Q-50
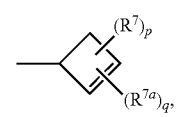 Q-51
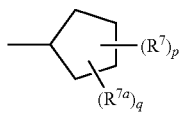 Q-52
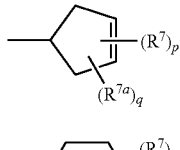 Q-53
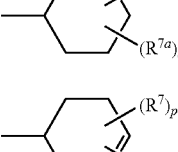 Q-54
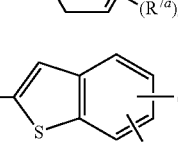 Q-55
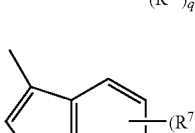 Q-56
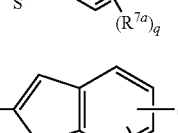 Q-57
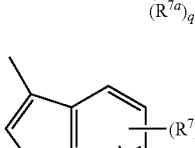 Q-58
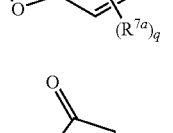 Q-59
Q-60

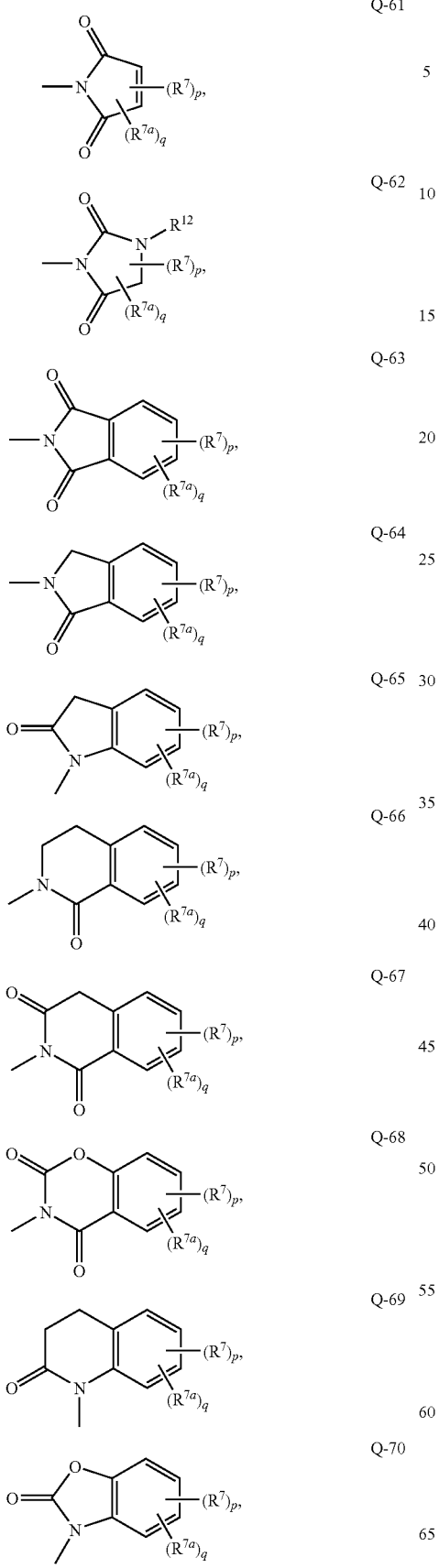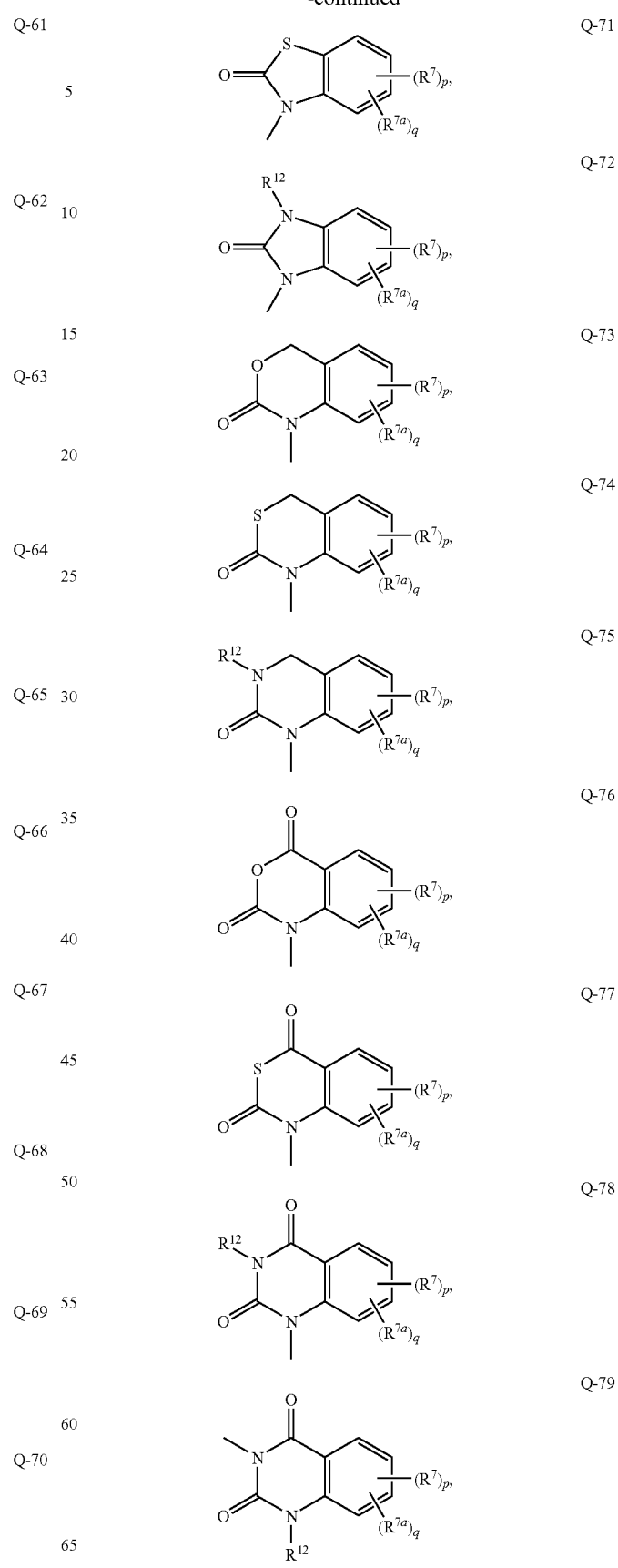

-continued
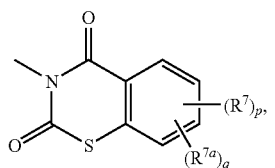 Q-80
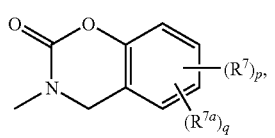 Q-81
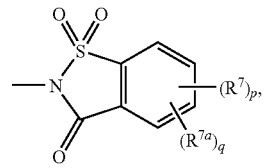 Q-82
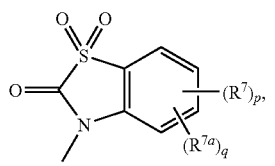 Q-83
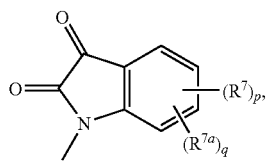 Q-84
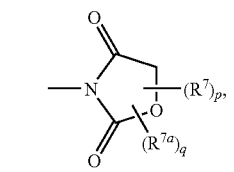 Q-85
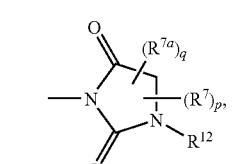 Q-86
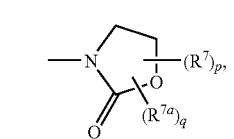 Q-87
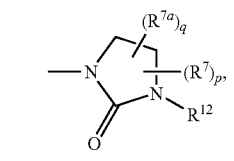 Q-88
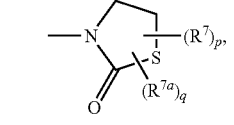 Q-89
-continued
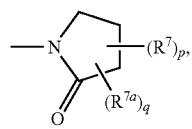 Q-90
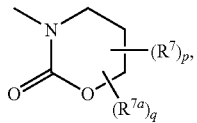 Q-91
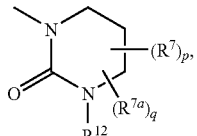 Q-92
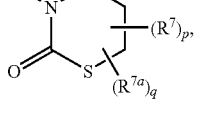 Q-93
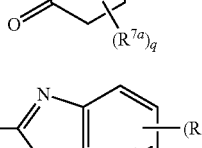 Q-94
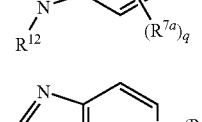 Q-95
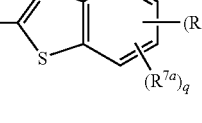 Q-96
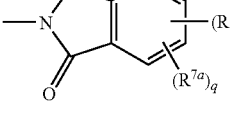 Q-97
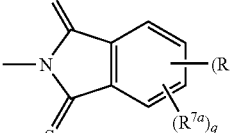 Q-98
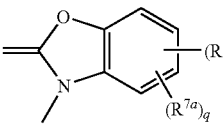 Q-99
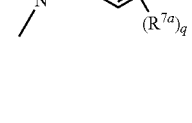 Q-100

-continued

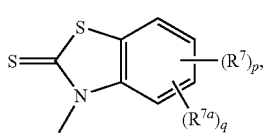 Q-101

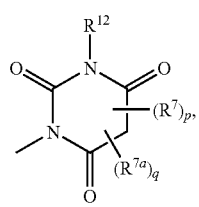 Q-102

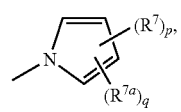 Q-103

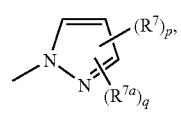 Q-104

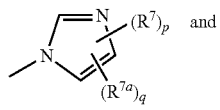 Q-105  and

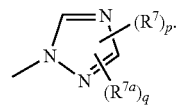 Q-106 wherein p is an integer from 0 to 5 and q is an integer from 0 to 2.

Embodiment 132

A compound of Embodiment 131 wherein p is an integer from 0 to 3.

Embodiment 132a

A compound of Embodiment 131 wherein q is an integer from 0 to 1.

Embodiment 133

A compound of Embodiment 131 wherein each Q is independently selected from Q-1, Q-20, Q-32 through Q-34, Q-45 through Q-47, Q-60 through Q-73, Q-76 through Q-79, Q-84 through Q-94 and Q-98 through Q-106.

Embodiment 134

A compound of Embodiment 133 wherein each Q is independently selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100 and Q-101 through Q-106.

Embodiment 135

A compound of Embodiment 134 wherein each Q is independently selected from Q-45, Q-63, Q-64, Q-65, Q-68, Q-69, Q-70, Q-71, Q-72, Q-84 and Q-85

Embodiment 136

A compound of Embodiment 135 wherein each Q is independently selected from Q-45, Q-63, Q-65, Q-70, Q-71, Q-72, Q-84 and Q-85.

Embodiment 137

A compound of Embodiment 136 wherein each Q is independently selected from Q-45, Q-63, Q-65 or Q-70, Q-71, Q-72 and Q-84.

Embodiment 138

A compound of Formula 1 or any one of Embodiments 129 through 137 wherein each $R^7$ when taken alone (i.e. not taken together with $R^5$) is independently halogen, cyano, hydroxy, amino, nitro, $C_1$-$C_3$ alkyl, $C_1$-$C_3$ haloalkyl, $C_1$-$C_2$ alkoxy or $C_1$-$C_2$ haloalkoxy.

Embodiment 138a

A compound of Embodiment 138 wherein each $R^7$ when taken alone is independently halogen, cyano, hydroxy, $C_1$-$C_3$ alkyl, $C_1$-$C_3$ haloalkyl, $C_1$-$C_2$ $C_1$-$C_2$ alkoxy or $C_1$-$C_2$ haloalkoxy.

Embodiment 138b

A compound of Embodiment 138a wherein each $R^7$ when taken alone is independently F, Cl, Br, cyano, hydroxy, methyl or methoxy.

Embodiment 138c

A compound of Formula 1 or any one of Embodiments 1 through 138b wherein each $R^7$ is taken alone.

Embodiment 139

A compound of Formula 1 wherein when $R^5$ and $R^7$ are taken together with the atoms linking $R^5$ and $R^7$ to form an optionally substituted ring, the ring is a 5- to 7-membered ring, containing ring members selected from carbon atoms and optionally up to 3 heteroatoms selected from up to 1 O, up to 1 S and up to 1 N, and up to 2 ring members selected from $C(=O)$, $C(=S)$, $S(=O)_s(=NR^{23})_f$ and $SiR^{17}R^{18}$.

Embodiment 140

A compound of Embodiment 139 wherein when $R^5$ and $R^7$ are taken together with the atoms linking $R^5$ and $R^7$ to form an optionally substituted 5- to 7-membered ring containing ring members selected from carbon atoms and optionally up to 3 heteroatoms selected from up to 1 O, up to 1 S and up to 1 N, and up to 2 ring members selected from $C(=O)$, $C(=S)$, $S(=O)_s(=NR^{23})_f$ and $SiR^{17}R^{18}$, the ring optionally substituted with substituents selected from $R^8$;

each $R^8$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment 141

A compound of Embodiment 140 wherein the ring is optionally substituted on ring members other than the atoms linking $R^5$ and $R^7$ with up to 4 substituents selected from $R^8$.

Embodiment 142

A compound of Embodiment 141 wherein the ring is optionally substituted on ring members other than the atoms linking $R^5$ and $R^7$ with up to 2 substituents selected from $R^8$.

Embodiment 143

A compound of any one of Embodiments 140 through 142 wherein each $R^8$ is independently $C_1$-$C_3$ alkyl.

Embodiment 144

A compound of Formula 1 wherein each $R^{7a}$ is independently —$Z^3 T^4$.

Embodiment 145

A compound of Formula 1 or Embodiment 144 wherein each $T^4$ is independently phenyl, phenylethynyl or a 5- to 6-membered heteroaromatic ring, each optionally substituted with up to 3 substituents independently selected from $R^{29}$ on carbon atom ring members, and each optionally substituted with up to 1 substituents independently selected from $R^{22}$ on nitrogen atom ring members.

Embodiment 146

A compound of Embodiment 145 wherein each $T^4$ is independently phenyl or a 5- to 6-membered heteroaromatic ring, each optionally substituted with up to 2 substituents independently selected from $R^{29}$ on carbon atom ring members, and each optionally substituted with up to 1 substituents independently selected from $R^{22}$ on nitrogen atom ring members.

Embodiment 147

A compound of Embodiment 146 wherein each $T^4$ is phenyl.

Embodiment 148

A compound of Embodiment 146 wherein each $T^4$ is independently a 5- or 6-membered heteroaromatic ring.

Embodiment 149

A compound of Formula 1 wherein each $R^{7a}$ is independently —$Z^3 T^N$.

Embodiment 150

A compound of Formula 1 wherein $R^{7a}$ is independently —$Z^3 T^P$.

Embodiment 151

A compound of Formula 1 or any one of Embodiments 144 through 150 wherein each $Z^3$ is independently a direct bond, O, C(=O), C(=S), S(O)$_m$, CHR$^{20}$, CHR$^{20}$—CHR$^{20}$, CR$^{24}$=CR$^{27}$ or OCHR$^{20}$.

Embodiment 152

A compound of Embodiment 151 wherein each $Z^3$ is independently a direct bond, O, S(O)$_m$, CHR$^{20}$, CHR$^{20}$—CHR$^{20}$, CR$^{24}$=CR$^{27}$ or OCHR$^{20}$.

Embodiment 153

A compound of Embodiment 152 wherein each $Z^3$ is independently a direct bond, O, S(O)$_m$, CHR$^{20}$, CHR$^{20}$—CHR$^{20}$ or CR$^{24}$=CR$^{27}$.

Embodiment 154

A compound of Embodiment 153 wherein each $Z^3$ is independently a direct bond, O, CHR$^{20}$ or CHR$^{20}$—CHR$^{20}$.

Embodiment 155

A compound of Embodiment 154 wherein each $Z^3$ is independently a direct bond or O.

Embodiment 156

A compound of Embodiment 155 wherein each $Z^3$ is independently a direct bond.

Embodiment 157

A compound of Embodiment 155 wherein each $Z^3$ is independently O.

Embodiment 158

A compound of Formula 1 wherein each $T^4$ is independently selected from $T^4$-1 through $T^4$-49, each $T^N$ is independently selected from $T^N$-1 through $T^N$-32 and each $T^P$ is independently selected from $T^P$-1 through $T^P$-35 in Exhibit 5.

Exhibit 5

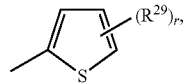 $T^4$-1

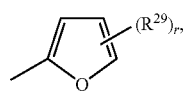 $T^4$-2

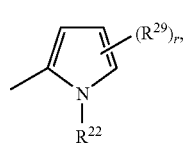 $T^4$-3

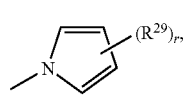 $T^4$-4

-continued
T⁴-5 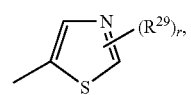
T⁴-6 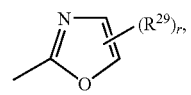
T⁴-7 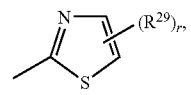
T⁴-8 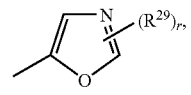
T⁴-9 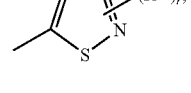
T⁴-10 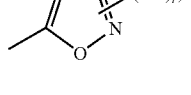
T⁴-11 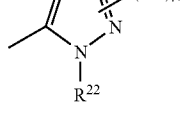
T⁴-12 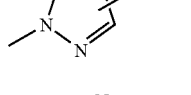
T⁴-13 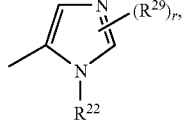
T⁴-14 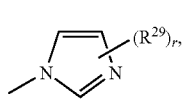
T⁴-15 
T⁴-16 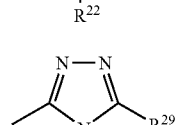
T⁴-17 
-continued
T⁴-18 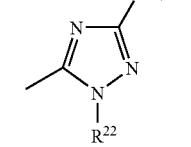
T⁴-19 
T⁴-20 
T⁴-21 
T⁴-22 
T⁴-23 
T⁴-24 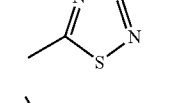
T⁴-25 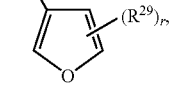
T⁴-26 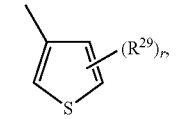
T⁴-27 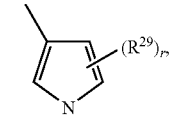
T⁴-28 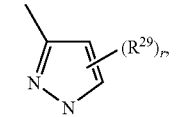
T⁴-29 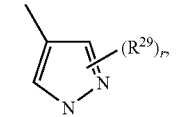

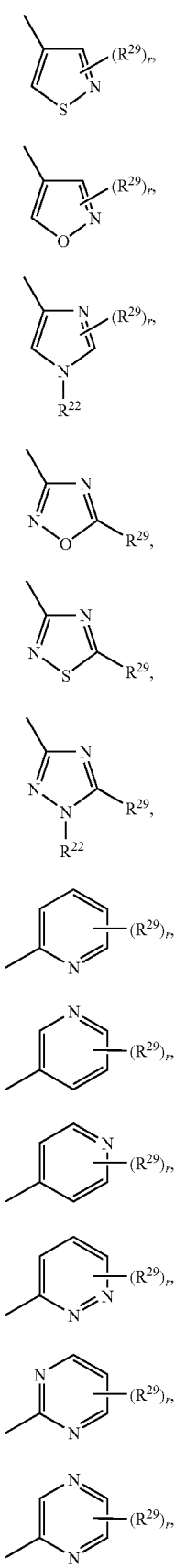
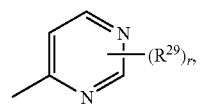
T^A-42
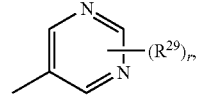
T^A-43
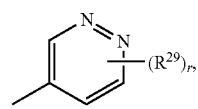
T^A-44
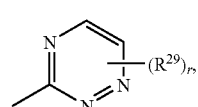
T^A-45
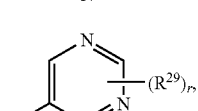
T^A-46
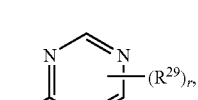
T^A-47
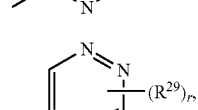
T^A-48
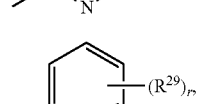
T^A-49
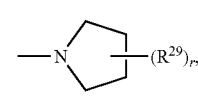
T^N-1
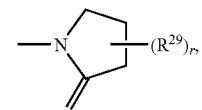
T^N-2
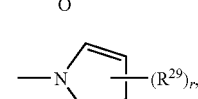
T^N-3
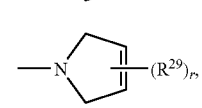
T^N-4
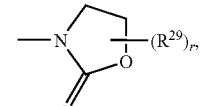
T^N-5
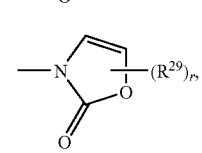
T^N-6

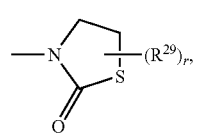 T$^N$-7
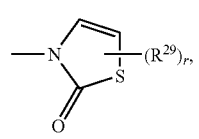 T$^N$-8
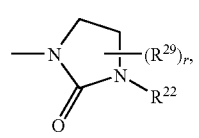 T$^N$-9
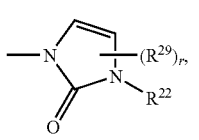 T$^N$-10
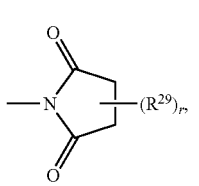 T$^N$-11
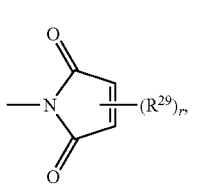 T$^N$-12
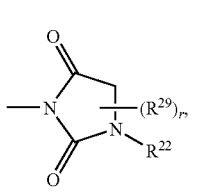 T$^N$-13
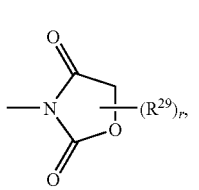 T$^N$-14
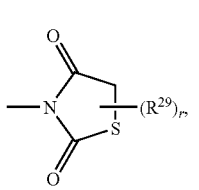 T$^N$-15
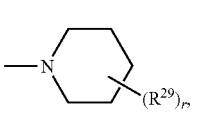 T$^N$-16
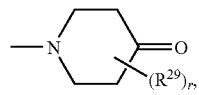 T$^N$-17
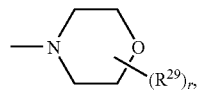 T$^N$-18
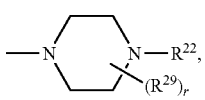 T$^N$-19
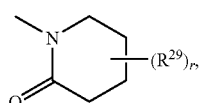 T$^N$-20
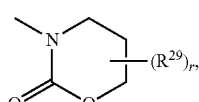 T$^N$-21
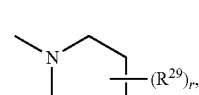 T$^N$-22
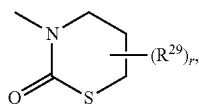 T$^N$-23
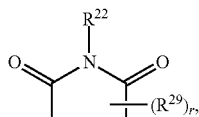 T$^N$-24
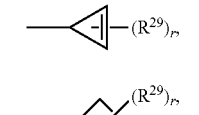 T$^N$-25
T$^N$-26
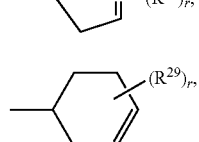 T$^N$-27
T$^N$-28
T$^N$-29
T$^N$-30

| | | | |
|---|---|---|---|
| 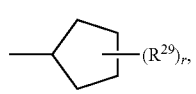 | T$^N$-31 | 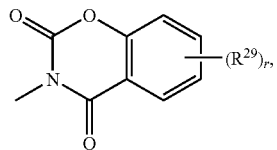 | T$^P$-10 |
|  | T$^N$-32 | 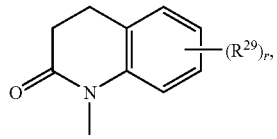 | T$^P$-11 |
| 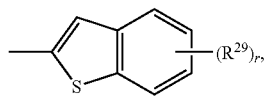 | T$^P$-1 | 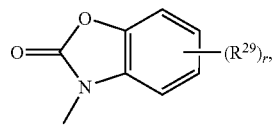 | T$^P$-12 |
| 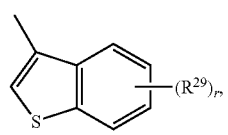 | T$^P$-2 | 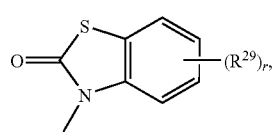 | T$^P$-13 |
| 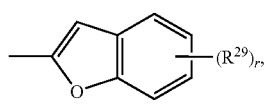 | T$^P$-3 | 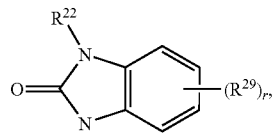 | T$^P$-14 |
| 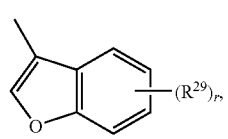 | T$^P$-4 | 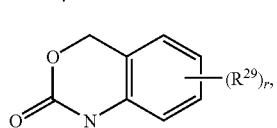 | T$^P$-15 |
| 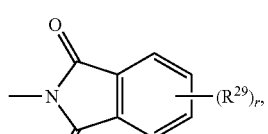 | T$^P$-5 | 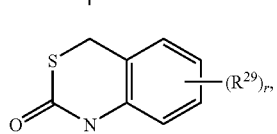 | T$^P$-16 |
| 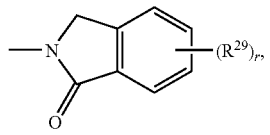 | T$^P$-6 | 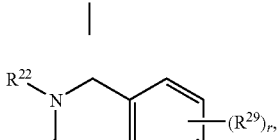 | T$^P$-17 |
| 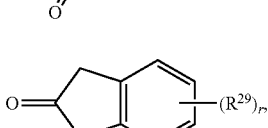 | T$^P$-7 | 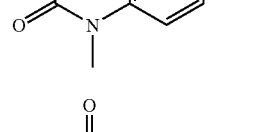 | T$^P$-18 |
|  | T$^P$-8 | 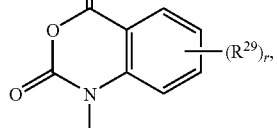 | T$^P$-19 |
| 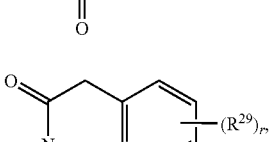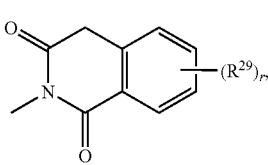 | T$^P$-9 | 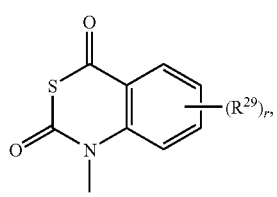 | |

-continued

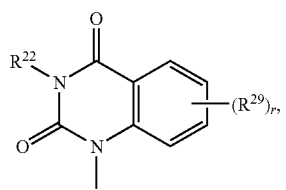 T$^P$-20

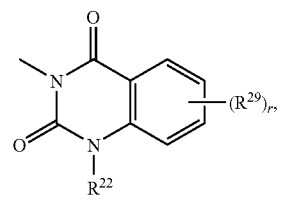 T$^P$-21

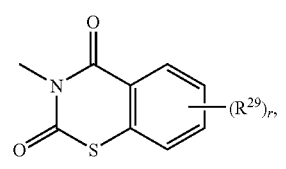 T$^P$-22

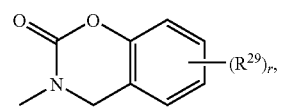 T$^P$-23

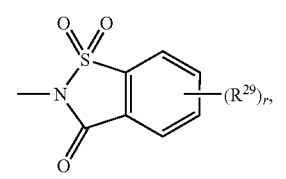 T$^P$-24

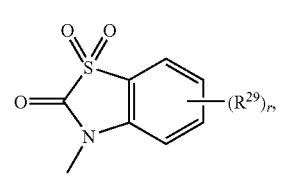 T$^P$-25

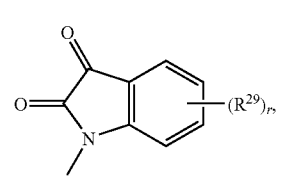 T$^P$-26

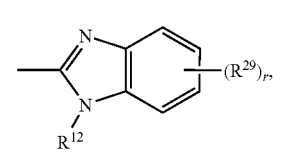 T$^P$-27

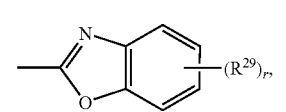 T$^P$-28

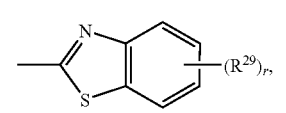 T$^P$-29

-continued

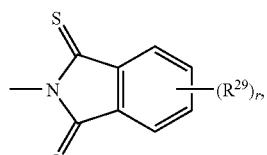 T$^P$-30

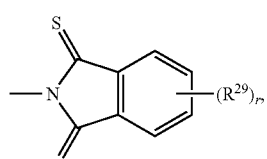 T$^P$-31

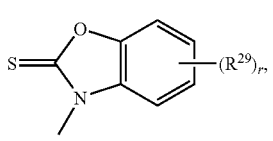 T$^P$-32

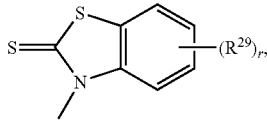 T$^P$-33

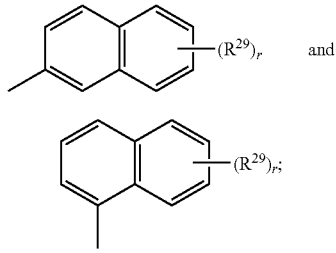 and T$^P$-34

 T$^P$-35 wherein the bond shown projecting to the left is bonded to $Z^3$ in Formula 1; and r is 0, 1, 2, 3, 4 or 5.

Embodiment 159

A compound of Embodiment 158 wherein r is 0, 1, 2 or 3.

Embodiment 160

A compound of Embodiment 158 wherein each $T^A$ is independently selected from $T^A$-1 through $T^A$-18, $T^A$-23 through $T^A$-38 and $T^A$-49, $T^N$ is selected from $T^N$-1, $T^N$-2, $T^N$-5, $T^N$-6, $T^N$-9 through $T^N$-16 and $T^N$-29, or $T^P$ is selected from $T^P$-1 through $T^N$-6, $T^P$-34 and $T^P$-35.

Embodiment 161

A compound of Embodiment 160 wherein each $T^A$ independently is selected from $T^A$-1 through $T^A$-18, $T^A$-23 through $T^A$-38 and $T^A$-49, or $T^N$ is selected from $T^N$-1, $T^N$-2, $T^N$-5, $T^N$-6, $T^N$-9 through $T^N$-16 and $T^N$-29.

Embodiment 162

A compound of Embodiment 161 wherein each $T^A$ is independently selected from $T^A$-18 and $T^A$-49.

Embodiment 163

A compound of Embodiment 162 wherein each $T^4$ is independently $T^4$-18.

Embodiment 164

A compound of Embodiment 162 wherein $T^4$ is $T^4$-49.

Embodiment 165

A compound of Formula 1 wherein each $R^{29}$ is independently H, halogen, cyano, hydroxy, —C(=O)OH, —C(=O)NH$_2$, —SO$_2$NH$_2$, —SH, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_4$-$C_{10}$ cycloalkylcarbonyl, $C_4$-$C_{10}$ cycloalkylaminocarbonyl, $C_2$-$C_7$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_3$-$C_{10}$ alkoxyalkylcarbonyl, $C_3$-$C_{10}$ alkoxycarbonylalkyl, $C_3$-$C_{10}$ alkoxy(alkyl)aminocarbonyl, $C_2$-$C_8$ alkylamidino, $C_3$-$C_{10}$ dialkylamidino, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ alkylaminosulfonyl, $C_2$-$C_8$ dialkylaminosulfonyl, $C_3$-$C_{10}$ trialkylsilyl, $C_2$-$C_8$ alkoxyalkoxy, $C_1$-$C_6$ alkylamino, $C_2$-$C_8$ dialkylamino, $C_2$-$C_8$ alkylcarbonylamino, $C_1$-$C_6$ alkylsulfonylamino or $C_1$-$C_6$ haloalkylamino.

Embodiment 166

A compound of Embodiment 165 wherein each $R^{29}$ is independently H, halogen, cyano, hydroxy, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ alkoxycarbonyl, $C_3$-$C_8$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_2$-$C_8$ alkoxyalkyl, $C_3$-$C_{10}$ dialkylaminoalkyl, $C_2$-$C_7$ cyanoalkyl, $C_1$-$C_6$ hydroxyalkyl, $C_2$-$C_8$ haloalkoxyalkyl, $C_3$-$C_{10}$ alkoxyalkylcarbonyl, $C_3$-$C_{10}$ alkoxycarbonylalkyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ alkylamino or $C_2$-$C_8$ dialkylamino.

Embodiment 167

A compound of Embodiment 166 wherein each $R^{29}$ is independently H, halogen, cyano, hydroxy, $C_1$-$C_2$ alkyl, $C_1$-$C_2$ haloalkyl, $C_1$-$C_2$ alkoxy or $C_1$-$C_2$ haloalkoxy.

Embodiment 167a

A compound of Embodiment 167 wherein each $R^{29}$ is independently halogen, cyano, hydroxy, $C_1$-$C_2$ alkyl, $C_1$-$C_2$ haloalkyl, $C_1$-$C_2$ alkoxy or $C_1$-$C_2$ haloalkoxy.

Embodiment 167b

A compound of Embodiment 167a wherein each $R^{29}$ is independently halogen, $C_1$-$C_2$ alkyl, $C_1$-$C_2$ haloalkyl or $C_1$-$C_2$ alkoxy.

Embodiment 168

A compound of Formula 1 wherein when E is E-2 or E-3, G is an optionally substituted thiazole ring connected at the 2-position to X of Formula 1 and at the 4-position to $Z^1$ of Formula 1, A is CHR$^{15}$, and J is an optionally substituted isoxazole ring connected at the 4-position to $Z^1$ of Formula 1, then $Z^1$ is O, C(=O), S(O)$_m$, CHR$^{20}$ or NR$^{21}$.

Embodiment 169

A compound of Formula 1 wherein when E is E-2 or E-3, G is an optionally substituted thiazole ring connected at the 2-position to X of Formula 1 and at the 4-position to $Z^1$ of Formula 1, and J is an optionally substituted isoxazole ring connected at the 4-position to $Z^1$ of Formula 1, then $Z^1$ is O, C(=O), S(O)$_m$, CHR$^{20}$ or NR$^{21}$.

Embodiment 170

A compound of Formula 1 wherein when E is E-2 or E-3, G is an optionally substituted thiazole ring connected at the 2-position to X of Formula 1 and at the 4-position to $Z^1$ of Formula 1, A is CHR$^{15}$, $Z^1$ is a direct bond, J is an optionally substituted isoxazole ring connected to the remainder of the Formula 1 at the 3- or 5-position of the isoxazole ring.

Embodiment 171

A compound of Formula 1 wherein when E is E-2 or E-3, G is an optionally substituted thiazole ring connected at the 2-position to X of Formula 1 and at the 4-position to $Z^1$ of Formula 1, A is CHR$^{15}$, $Z^1$ is a direct bond, J is an optionally substituted isoxazole ring connected to the remainder of the Formula 1 at the 3-position of the isoxazole ring.

Embodiment 172

A compound of Formula 1 wherein when E is E-2 or E-3, G is an optionally substituted thiazole ring connected at the 2-position to X of Formula 1 and at the 4-position to $Z^1$ of Formula 1, $Z^1$ is a direct bond, and J is an optionally substituted isoxazole ring connected to the remainder of the Formula 1 at the 3-position of the isoxazole ring.

Embodiment 173

A compound of Formula 1 wherein when E is E-2, X is $X^2$ and the ring containing X is saturated, A is CHR$^{15}$, G is an optionally substituted 5-membered heteroaromatic ring, $Z^1$ is a direct bond, J is a phenyl or 5- or 6-membered heteroaromatic ring or a naphthalenyl or 8- to 11-membered heteroaromatic bicyclic ring system, and the J ring or ring system is substituted with at least one $R^5$ that is other than H.

Embodiment 174

A compound of Formula 1 wherein when E is E-2, X is $X^2$ and the ring containing X is saturated, A is CHR$^{15}$, G is an optionally substituted 5-membered heteroaromatic ring, $Z^1$ is a direct bond, J is a phenyl or 5- or 6-membered heteroaromatic ring or a naphthalenyl or 8- to 11-membered heteroaromatic bicyclic ring system, and the J ring or ring system is substituted with at least one $R^5$ that is $Z^2Q$.

Embodiment 175

A compound of Formula 1 wherein when E is E-2 or E-3, X is $X^1$ and the ring containing X is saturated, A is NH, G is an optionally substituted thiazole ring connected at the 2-position to X of Formula 1 and at the 4-position to $Z^1$ of Formula 1, J is an optionally substituted imidazole ring connected at the 2-position to the remainder of Formula 1, and $Z^1$ is O, C(=O), $S(O)_m$, $CHR^{20}$ or $NR^{21}$.

Embodiment 176

A compound of Formula 1 wherein when E is E-2 or E-3, X is $X^1$ and the ring containing X is saturated, A is $NR^{16}$, G is an optionally substituted thiazole ring connected at the 2-position to X of Formula 1 and at the 4-position to $Z^1$ of Formula 1, J is an optionally substituted imidazole ring connected at the 2-position to the remainder of Formula 1, and $Z^1$ is O, C(=O), $S(O)_m$, $CHR^{20}$ or $NR^{21}$.

Embodiment 177

A compound of Formula 1 wherein when E is E-2 or E-3, G is an optionally substituted thiazole ring connected at the 2-position to X of Formula 1 and at the 4-position to $Z^1$ of Formula 1, then J is other than optionally substituted imidazolyl.

Embodiment 178

A compound of Formula 1 or any one of Embodiments 1 through 177 wherein the total molecular weight of the compound is not greater than 850.

Embodiment 179

A compound of Embodiment 17 wherein the total molecular weight of the compound is not greater than 700.

Embodiments of the present invention also include:

Embodiment C1

A compound of Formula 1 wherein E is E-1, E-2 or E-3.

Embodiment C2

A compound of Embodiment C1 wherein E is E-1 or E-2.

Embodiment C3

A compound of Embodiment C2 wherein E is E-1.

Embodiment C4

A compound of Formula 1 wherein E is E-4 and $R^6$ is $C_1$-$C_2$ alkyl or $C_1$-$C_2$ haloalkyl.

Embodiment C4a

A compound of Formula 1 wherein $R^6$ is $C_1$-$C_2$ alkyl or $C_1$-$C_2$ haloalkyl.

Embodiment C5

A compound of Embodiment C4a wherein $R^6$ is methyl.

Embodiment C6

A compound of Formula 1 wherein A is $CHR^{15}$.

Embodiment C7

A compound of Formula 1 wherein $R^{15}$ is H, halogen, cyano, hydroxy, —CHO, $C_1$-$C_4$ alkyl, $C_1$-$C_4$ haloalkyl or $C_2$-$C_5$ alkoxycarbonyl.

Embodiment C8

A compound of Embodiment C7 wherein $R^{15}$ is H, halogen, cyano, hydroxy, methyl or methoxycarbonyl.

Embodiment C9

A compound of Embodiment C8 wherein $R^{15}$ is H.

Embodiment C10

A compound of Formula 1 wherein A is $NR^{16}$.

Embodiment C11

A compound of Formula 1 wherein $R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl.

Embodiment C12

A compound of Embodiment C11 wherein $R^{16}$ is H, methyl, methylcarbonyl or methoxycarbonyl.

Embodiment C13

A compound of Embodiment C12 wherein $R^{16}$ is H.

Embodiment C14

A compound of Formula 1 wherein A is $CH_2$ or NH.

Embodiment C14a

A compound of Formula 1 wherein A is $CH_2$.

Embodiment C15

A compound of Formula 1 wherein $W^1$ is H, CN, halogen, $C_1$-$C_4$ alkyl, $OR^{30}$, $SR^{31}$ or $NR^{32}R^{33}$.

Embodiment C16

A compound of Embodiment C15 wherein $W^1$ is H, CN, halogen, $OR^{30}$, $SR^{31}$ or $NR^{32}R^{33}$ Embodiment C17

A compound of Embodiment C16 wherein $W^1$ is cyano, halogen or $OR^{30}$.

Embodiment C18

A compound of Embodiment C17 wherein $W^1$ is cyano, Cl, F or $OR^{30}$.

Embodiment C19

A compound of Formula 1 wherein each $R^{30}$ and $R^{31}$ independently is selected from $C_1$-$C_6$ alkyl, $C_3$-$C_4$ alkenyl, $C_3$-$C_4$ alkynyl, $C_1$-$C_4$ haloalkyl, $C_3$-$C_6$ haloalkenyl, $C_3$-$C_6$ haloalkynyl, $C_2$-$C_6$ alkoxyalkyl and $C_3$-$C_6$ cycloalkyl.

Embodiment C19a

A compound of Formula 1 wherein $R^{32}$ is selected H, cyano, hydroxy, amino, $C_1$-$C_6$ alkyl.

Embodiment C19b

A compound of Formula 1 wherein $R^{33}$ is selected from H, $C_1$-$C_6$ alkyl.

Embodiment C20

A compound of Embodiment C19 each $R^{30}$ and $R^{31}$ selected from $C_1$-$C_6$ alkyl, $C_3$-$C_4$ alkenyl, $C_3$-$C_4$ alkynyl and $C_1$-$C_4$ haloalkyl.

Embodiment C21

A compound of Embodiment C20 each $R^{30}$ and $R^{31}$ independently is $C_1$-$C_4$ alkyl.

Embodiment C20

A compound of Embodiment C19 each $R^{32}$ and $R^{33}$ selected from $C_1$-$C_6$ alkyl, $C_3$-$C_4$ alkenyl, $C_3$-$C_4$ alkynyl and $C_1$-$C_4$ haloalkyl.

Embodiment C22

A compound of Formula 1 wherein W is O.

Embodiment C23

A compound of Formula 1 wherein W is S.

Embodiment 24

A compound of Formula 1 wherein X is selected from $X^1$, $X^2$, $X^3$, $X^4$, $X^5$, $X^6$, $X^7$ and $X^8$.

Embodiment C25

A compound of Embodiment C24 wherein X is $X^1$, $X^2$ or $X^3$.

Embodiment C26

A compound of Embodiment C25 wherein X is $X^1$ or $X^2$.

Embodiment C27

A compound of Embodiment C26 wherein X is $X^1$.

Embodiment C28

A compound of Formula 1 wherein the ring comprising X is saturated.

Embodiment C29

A compound of Formula 1 wherein $Z^1$ is a direct bond, $CHR^{20}$ or $NR^{21}$.

Embodiment C30

A compound of Embodiment C29 wherein $Z^1$ is a direct bond.

Embodiment C31

A compound of Formula 1 wherein when $R^{21}$ is H, $C_1$-$C_3$ alkyl, $C_1$-$C_3$ alkylcarbonyl or $C_2$-$C_3$ alkoxycarbonyl.

Embodiment C32

A compound of Formula 1 wherein $Z^5$, $Z^6$, $Z^7$ and $Z^8$ are each a direct bond.

Embodiment C33

A compound of Formula 1 wherein
each $R^2$ is independently $C_1$-$C_4$ alkyl, $C_1$-$C_4$ alkenyl, $C_1$-$C_4$ haloalkyl, $C_1$-$C_4$ alkoxy, halogen, cyano or hydroxy; or
two $R^2$ groups are taken together as $C_1$-$C_3$ alkylene or $C_2$-$C_3$ alkenylene to form a bridged bicyclic ring system; or
two $R^2$ groups attached to adjacent ring carbon atoms joined by a double bond are taken together as —CH=CH—CH=CH— optionally substituted with up to 3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro.

Embodiment C34

A compound of Embodiment C33 wherein each $R^2$ is independently $C_1$-$C_4$ alkyl, $C_1$-$C_2$ haloalkyl, $C_1$-$C_2$ alkoxy, halogen, cyano or hydroxy.

Embodiment C35

A compound of Embodiment C34 wherein each $R^2$ is independently methyl, methoxy, cyano or hydroxy.

Embodiment 36

A compound of Embodiment C35 wherein each $R^2$ is independently methyl.

Embodiment C37

A compound of Formula 1 wherein n is 0 or 1.

Embodiment C38

A compound of Embodiment C37 wherein n is 0.

Embodiment C39

A compound of Embodiment C38 wherein n is 1.

Embodiment C40

A compound of Formula 1 wherein $R^{1a}$, $R^{1b}$, $R^{1c}$ and $R^{1d}$ are each cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_2$-$C_8$ alkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_1$-$C_8$ alkoxy, $C_1$-$C_8$ haloalkoxy, $C_1$-$C_8$ alkylthio, $C_3$-$C_{10}$ trialkylsilyl, $C_1$-$C_8$ alkylamino, $C_2$-$C_8$ dialkylamino or $C_2$-$C_8$ alkylcarbonylamino, pyrrolidinyl, piperidinyl or morpholinyl.

Embodiment C41

A compound of Embodiment C40 wherein $R^{1a}$, $R^{1b}$, $R^{1c}$ and $R^{1d}$ are $C_1$-$C_8$ alkyl, $C_2$-$C_8$ alkenyl, $C_1$-$C_8$ haloalkyl, $C_2$-$C_8$ alkoxyalkyl, $C_2$-$C_8$ alkylthioalkyl, $C_2$-$C_8$ alkylaminoalkyl, $C_1$-$C_8$ alkoxy, $C_1$-$C_8$ alkylthio, pyrrolidinyl, piperidinyl or morpholinyl.

Embodiment C42

A compound of Embodiment C41 wherein $R^{1a}$, $R^{1b}$, $R^{1c}$ and $R^{1d}$ are $C_1$-$C_6$ alkyl, $C_2$-$C_6$ alkenyl, $C_1$-$C_6$ haloalkyl, $C_1$-$C_6$ alkoxy, pyrrolidinyl, piperidinyl or morpholinyl.

Embodiment C43

A compound of Formula 1 wherein $R^{1a}$, $R^{1b}$, $R^{1c}$ and $R^{1d}$ are an optionally substituted phenyl, naphthalenyl or 5- or 6-membered heteroaromatic ring.

Embodiment C44

A compound of Embodiment C43 wherein $R^{1a}$, $R^{1b}$, $R^{1c}$ and $R^{1d}$ are an optionally substituted phenyl or 5- or 6-membered heteroaromatic ring.

Embodiment C45

A compound of Embodiment C44 wherein $R^{1a}$, $R^{1b}$, $R^{1c}$ and $R^{1d}$ are a phenyl or 5- or 6-membered heteroaromatic ring optionally substituted with up to 3 substituents independently selected from $R^{4a}$ on carbon ring members and $R^{4b}$ on nitrogen ring members;

each $R^{4a}$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and each $R^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl.

Embodiment C46

A compound of Embodiment C45 wherein $R^{1a}$, $R^{1b}$, $R^{1c}$ and $R^{1d}$ are a phenyl or 5- or 6-membered heteroaromatic ring optionally substituted with up to 2 substituents independently selected from $R^{4a}$ on carbon ring members and $R^{4b}$ on nitrogen ring members.

Embodiment C47

A compound Embodiment C45 wherein $R^{1a}$, $R^{1b}$, $R^{1c}$ and $R^{1d}$ are selected from U-1 through U-50 in Exhibit 1.

Exhibit 1

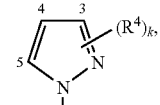 U-1

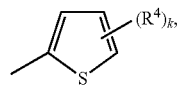 U-2

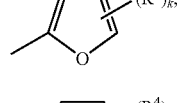 U-3

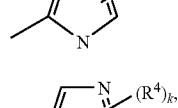 U-4

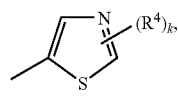 U-5

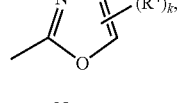 U-6

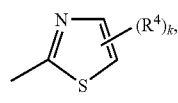 U-7

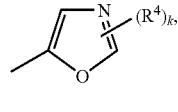 U-8

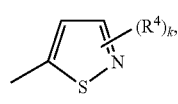 U-9

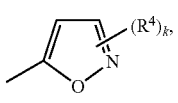 U-10

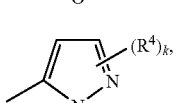 U-11

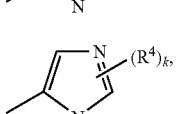 U-12

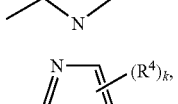 U-13

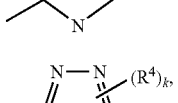 U-14

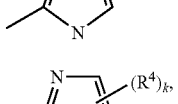 U-15

U-16 through U-40: heterocyclic substituent structures, each bearing a methyl group and an $(R^4)_k$ substituent.

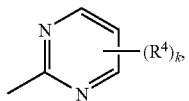 U-41

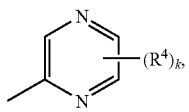 U-42

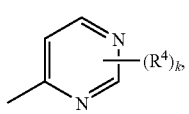 U-43

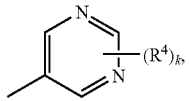 U-44

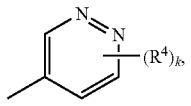 U-45

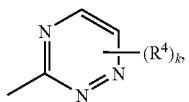 U-46

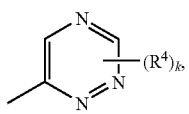 U-47

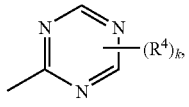 U-48

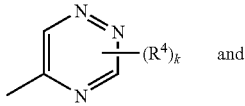 U-49 and

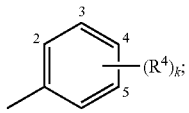 U-50;

wherein when $R^4$ is attached to a carbon ring member, said $R^4$ is selected from $R^{4a}$, and when $R^4$ is attached to a nitrogen ring member (e.g., U-4, U-14, U-15, U-24, U-25, U-26, U-31 or U-35 through U-15, U-24 through U-26, U-31 or U-35), said $R^4$ is selected from $R^{4b}$; and k is 0, 1 or 2.

Embodiment C48

A compound of Embodiment C47 wherein $R^{1a}$, $R^{1b}$, $R^{1c}$ and $R^{1d}$ are selected from U-1 through U-5, U-8, U-11, U-13, U-15, U-20 through U-28, U-31, U-36 through U-39 and U-50.

Embodiment C49

A compound of Embodiment C48 wherein $R^{1a}$, $R^{1b}$, $R^{1c}$ and $R^{1d}$ are selected from U-1 through U-3, U-5, U-8, U-11, U-13, U-20, U-22, U-23, U-25 through U-28, U-36 through U-39 and U-50.

Embodiment C50

A compound of Embodiment C49 wherein $R^{1a}$, $R^{1b}$, $R^{1c}$ and $R^{1d}$ are selected from U-1 through U-3, U-11, U-13, U-20, U-22, U-23, U-36 through U-39 and U-50.

Embodiment C51

A compound of Embodiment C50 wherein $R^{1a}$, $R^{1b}$, $R^{1c}$ and $R^{1d}$ are selected from U-1, U-20 and U-50.

Embodiment 52

A compound of Embodiment C51 wherein $R^{1a}$, $R^{1b}$, $R^{1c}$ and $R^{1d}$ are U-1.

Embodiment C53

A compound of Embodiment C52 wherein $R^{1a}$, $R^{1b}$, $R^{1c}$ and $R^{1d}$ are U-20.

Embodiment C54

A compound of Embodiment 53 wherein $R^{1a}$, $R^{1b}$, $R^{1c}$ and $R^{1d}$ are U-50.

Embodiment C55

A compound of Embodiment C47 wherein each $R^{4a}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl.

Embodiment C56

A compound of Embodiment C55 wherein each $R^{4a}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy.

Embodiment C57

A compound of Embodiment C56 wherein each $R^{4a}$ is independently $C_1$-$C_3$ alkyl, $C_1$-$C_3$ haloalkyl, halogen, $C_1$-$C_2$ alkoxy or $C_1$-$C_2$ haloalkoxy.

Embodiment C58

A compound of Embodiment C57 wherein each $R^{4a}$ is independently $C_1$-$C_2$ alkyl, $C_1$-$C_2$ haloalkyl, halogen or $C_1$-$C_2$ alkoxy.

Embodiment C59

A compound of Embodiment C58 wherein each $R^{4a}$ is independently $C_1$-$C_2$ alkyl, trifluoromethyl, Cl, Br, I or methoxy.

Embodiment C60

A compound of Embodiment C59 wherein each $R^{4a}$ is independently $C_1$-$C_2$ alkyl, trifluoromethyl, Cl or Br.

Embodiment C61

A compound of Embodiment C47 wherein each $R^{4b}$ is independently $C_1$-$C_3$ alkyl, $C_3$ alkenyl (e.g., allyl), $C_3$ alkynyl (e.g., propargyl), cyclopropyl, $C_1$-$C_3$ haloalkyl, $C_3$ haloalkenyl, $C_3$ haloalkynyl, halocyclopropyl or $C_2$-$C_3$ alkoxyalkyl.

Embodiment C62

A compound of Embodiment C61 wherein each $R^{4b}$ is independently $C_1$-$C_3$ alkyl, $C_3$ alkenyl, $C_3$ alkynyl, cyclopropyl, $C_1$-$C_3$ haloalkyl, $C_3$ haloalkenyl or halocyclopropyl.

Embodiment C63

A compound of Embodiment C62 wherein each $R^{4b}$ is independently $C_1$-$C_2$ alkyl or $C_1$-$C_2$ haloalkyl.

Embodiment C64

A compound of Embodiment C63 wherein each $R^{4b}$ is independently $C_1$-$C_2$ alkyl or trifluoromethyl.

Embodiment C65

A compound of Embodiment C64 wherein each $R^{4b}$ is independently $C_1$-$C_2$ alkyl.

Embodiment C66

A compound of Embodiment C47 wherein k is 1 or 2.

Embodiment C66a

A compound of Embodiment C66 wherein at least one $R^4$ is Cl.

Embodiment C67

A compound of Embodiment C66 wherein least one $R^4$ is Br.

Embodiment C68

A compound of Embodiment C66 wherein at least one $R^4$ is methyl.

Embodiment C69

A compound of Embodiment 66 wherein k is 1 or 2 and at least one $R^4$ is ethyl.

Embodiment C70

A compound of Embodiment C66 wherein at least one $R^4$ is trifluoromethyl.

Embodiment C71

A compound of Embodiment C66 wherein at least one $R^4$ is methoxy.

Embodiment C72

A compound of Embodiment 52 wherein k is 1 and $R^4$ is connected to the 3- or 5-position of U-1.

Embodiment C73

A compound of Embodiment C52 wherein k is 2 and one $R^4$ is connected to the 3-position and the other $R^4$ is connected to the 5-position of U-1.

Embodiment C74

A compound of Embodiment C53 wherein k is 1 and $R^4$ is connected to the 3- or 5-position of U-20.

Embodiment C75

A compound of Embodiment C53 wherein k is 2 and one $R^4$ is connected to the 3-position and the other $R^4$ is connected to the 5-position of U-20.

Embodiment C76

A compound of Embodiment C54 wherein k is 1 and $R^4$ is connected to the 2- or 3-position of U-50.

Embodiment C77

A compound of Embodiment C54 wherein k is 2 and one $R^4$ is connected to the 2-position and the other $R^4$ is connected to the 5-position of U-50.

Embodiment C78

A compound of Formula 1 wherein G is a 5-membered heterocyclic ring optionally substituted with up to 2 substituents selected from $R^3$ on carbon ring members and selected from $R^{11}$ on nitrogen ring members;
each $R^3$ is independently $C_1$-$C_3$ alkyl, $C_1$-$C_3$ haloalkyl or halogen; and
each $R^{11}$ is independently $C_1$-$C_3$ alkyl.

Embodiment C79

A compound of Embodiment C78 wherein G is selected from G-1 through G-59 in Exhibit 2.

Exhibit 2

G-1

-continued
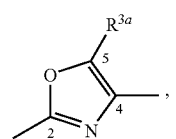 G-2
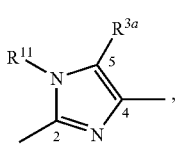 G-3
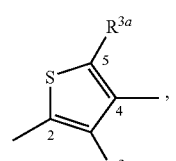 G-4
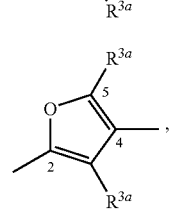 G-5
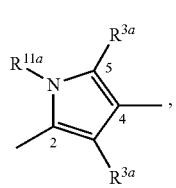 G-6
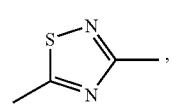 G-7
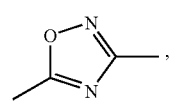 G-8
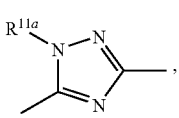 G-9
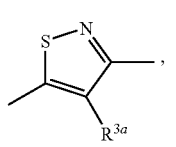 G-10
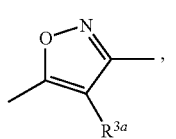 G-11
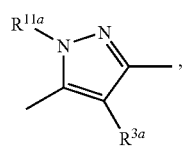 G-12
-continued
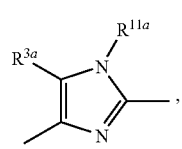 G-13
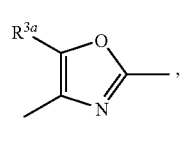 G-14
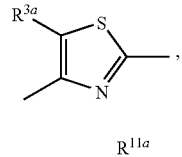 G-15
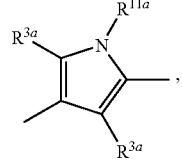 G-16
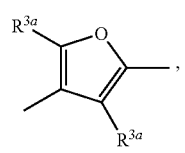 G-17
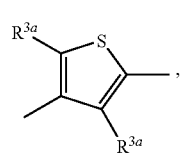 G-18
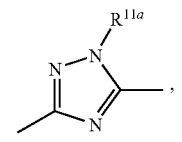 G-19
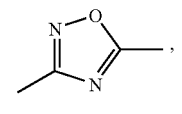 G-20
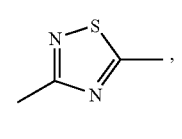 G-21
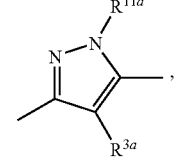 G-22
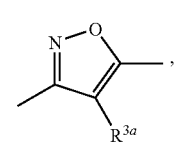 G-23

-continued
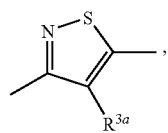 G-24
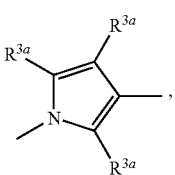 G-25
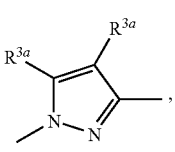 G-26
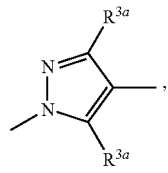 G-27
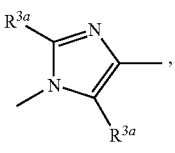 G-28
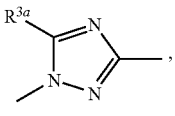 G-29
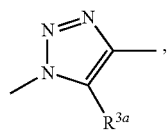 G-30
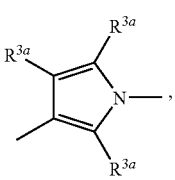 G-31
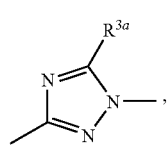 G-32
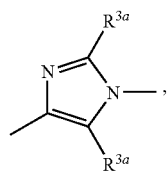 G-33
-continued
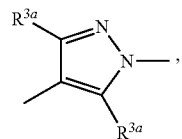 G-34
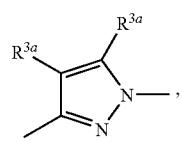 G-35
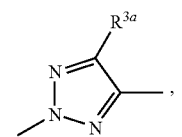 G-36
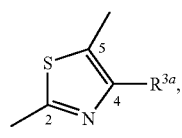 G-37
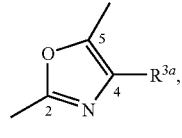 G-38
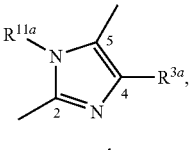 G-39
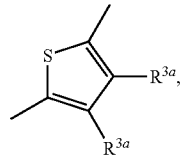 G-40
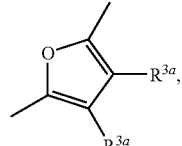 G-41
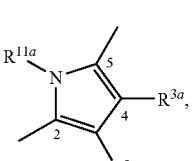 G-42
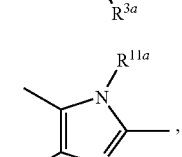 G-43
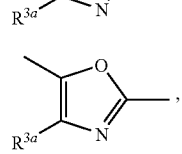 G-44

-continued

| | | |
|---|---|---|
| 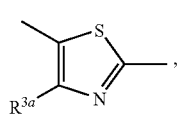 | G-45 | 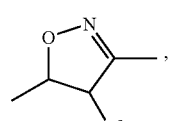 G-57 |
| 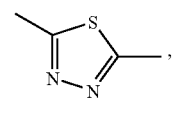 | G-46 | |
| 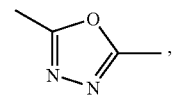 | G-47 | 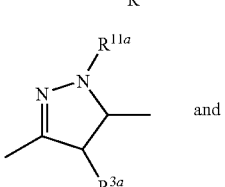 G-58 and |
| 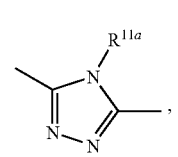 | G-48 | 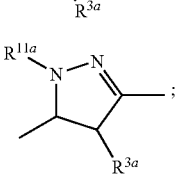 G-59 ; |
| 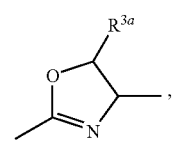 | G-49 | |
| 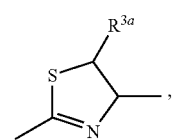 | G-50 | |
| 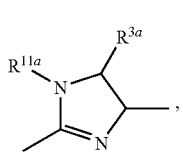 | G-51 | |
| 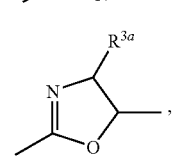 | G-52 | |
| 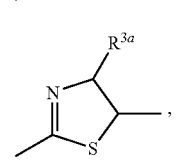 | G-53 | |
| 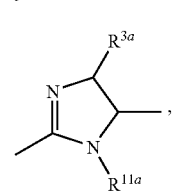 | G-54 | |
| 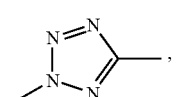 | G-55 | |
| 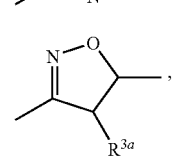 | G-56 | | wherein the bond projecting to the left is bonded to X, and the bond projecting to the right is bonded to $Z^1$; each $R^{1a}$ is independently selected from H or $R^3$; and $R^{11a}$ is selected from H and $R^{11}$;

Embodiment C80

A compound of Embodiment C79 wherein G is selected from G-1 through G-3, G-7, G-8, G-10, G-11, G-14, G-15, G-23, G-24, G-26 through G-28, G-30, G-36 through G-38 and G-49 through G-55.

Embodiment C81

A compound of Embodiment C80 wherein G is selected from G-1, G-2, G-7, G-8, G-14, G-15, G-23, G-24, G-26, G-27, G-36, G-37, G-38, G-49, G-50 and G-55.

Embodiment C82

A compound of Embodiment C81 wherein G is selected from G-1, G-2, G-15, G-26, G-27, G-36, G-37 and G-38.

Embodiment 83

A compound of Embodiment C82 wherein G is selected from G-1, G-2, G-15, G-26 and G-36.

Embodiment C84

A compound of Embodiment C83 wherein G is G-1.

Embodiment 85

A compound of Embodiment C83 wherein G is G-2.

Embodiment C86

A compound of Embodiment C83 wherein G is G-15.

Embodiment C87

A compound of Embodiment C83 wherein G is G-26.

Embodiment C88

A compound of Embodiment C83 wherein G is G-36.

Embodiment 89

A compound of any one of Embodiments C79 through C88 wherein $R^{1a}$ is H, $C_1$-$C_3$ alkyl or halogen.

Embodiment C90

A compound of Embodiment C89 wherein $R^{1a}$ is H, methyl or halogen.

Embodiment C91

A compound of any one of Embodiments C79 through C88 wherein $R^{3a}$ is H and $R^{11a}$ is H or methyl.

Embodiment C92

A compound of Formula 1 or any one of Embodiments C79 through C88 wherein G is unsubstituted.

Embodiment C93

A compound of Formula 1 wherein J is a 5- or 6-membered ring, an 8- to 11-membered bicyclic ring system or a 7- to 11-membered spirocyclic ring system, each ring or ring system containing ring members selected from carbon, up to 3 heteroatoms selected from up to 1 O, up to 1 S and up to 3 N, and up to 3 ring members selected from C(=O), C(=S), S(O) and S(O)$_2$, each ring or ring system optionally substituted with up to 5 substituents independently selected from $R^5$.

Embodiment C94

A compound of Formula 1 wherein J is a phenyl or 5- or 6-membered heteroaromatic ring, or a naphthalenyl or 8- to 11-membered heteroaromatic bicyclic ring system, each ring or ring system optionally substituted with up to 5 substituents independently selected from $R^5$; or J is a 5-, 6- or 7-membered nonaromatic ring, an 8- to 11-membered nonaromatic bicyclic or a 7- to 11-membered spirocyclic ring system, each ring or ring system containing ring members selected from carbon, and up to 3 ring members selected C(=O), C(=S), S(O), S(O)$_2$ and SiR$^{17}$R$^{18}$, and optionally substituted with up to 5 substituents independently selected from $R^5$.

Embodiment C95

A compound of Formula 1 wherein J is selected from J-1 through J-82 in Exhibit 3.

Exhibit 3

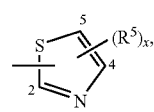
J-1

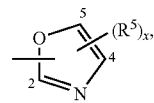
J-2

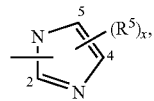
J-3

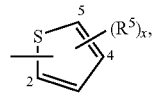
J-4

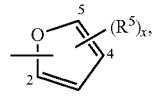
J-5

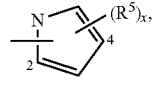
J-6

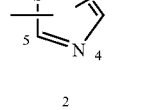
J-7

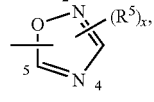
J-8

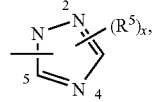
J-9

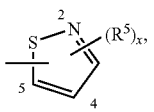
J-10

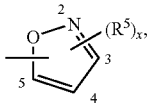
J-11

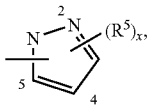
J-12

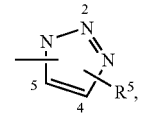
J-13

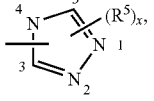
J-14

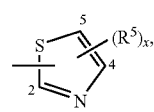
J-15

| | | |
|---|---|---|
| 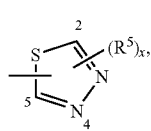 | J-16 | 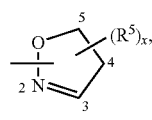 J-29 |
| 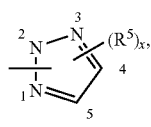 | J-17 | 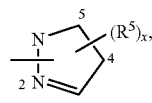 J-30 |
| 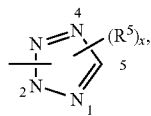 | J-18 | 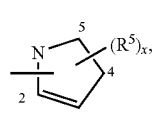 J-31 |
| 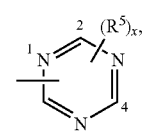 | J-19 | 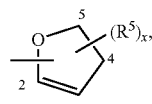 J-32 |
| 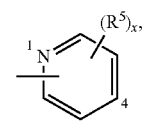 | J-20 | 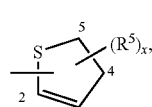 J-33 |
| 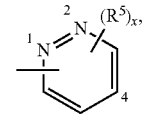 | J-21 | 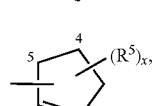 J-34 |
| 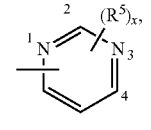 | J-22 | 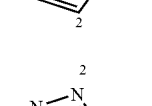 J-35 |
| 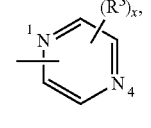 | J-23 | 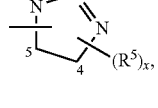 J-36 |
| 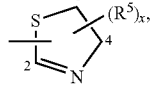 | J-24 | 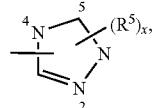 J-37 |
| 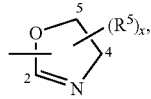 | J-25 | 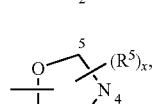 J-38 |
| 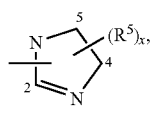 | J-26 | 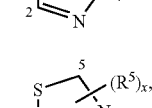 J-39 |
| 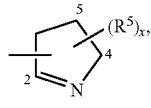 | J-27 | 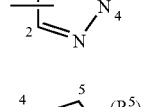 J-40 |
| 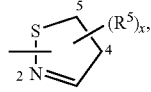 | J-28 | 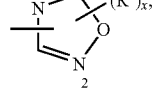 J-41 |
| | | 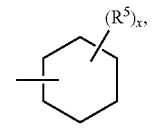 |

| | | |
|---|---|---|
| J-42 | 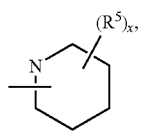 | |
| J-43 | 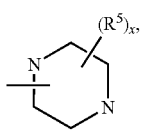 | |
| J-44 | 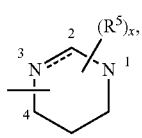 | |
| J-45 | 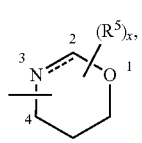 | |
| J-46 | 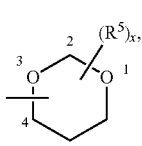 | |
| J-47 | 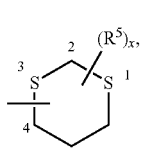 | |
| J-48 | 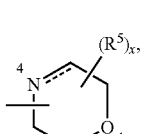 | |
| J-49 | 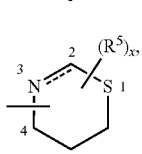 | |
| J-50 | 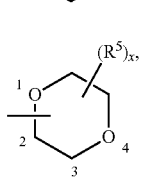 | |
| J-51 | 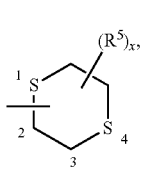 | |
| J-52 | 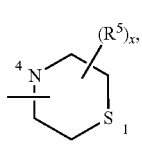 | |
| | | |
|---|---|---|
| J-53 | 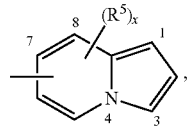 | |
| J-54 | 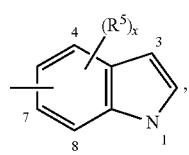 | |
| J-55 | 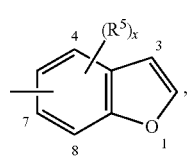 | |
| J-56 | 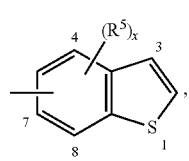 | |
| J-57 | 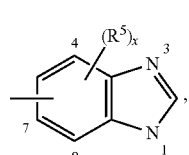 | |
| J-58 | 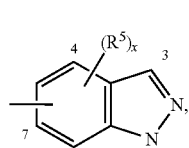 | |
| J-59 | 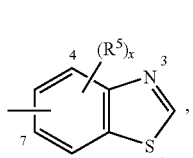 | |
| J-60 | 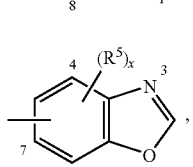 | |
| J-61 | 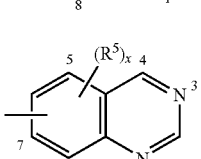 | |
| J-62 | 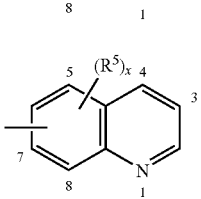 | |

-continued
J-63 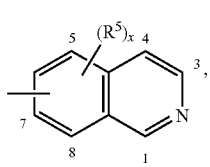
J-64 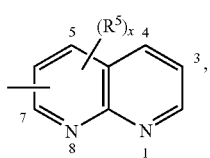
J-65 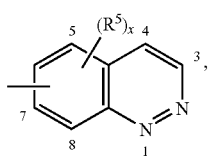
J-66 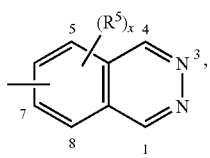
J-67 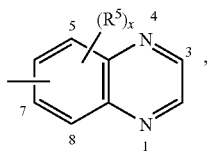
J-68 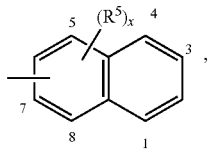
J-69 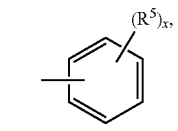
J-70 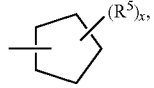
J-71 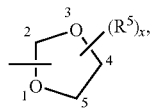
J-72 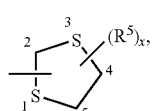
J-73 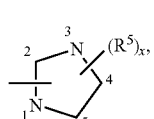
-continued
J-74 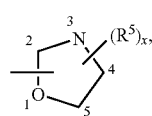
J-75 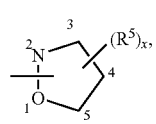
J-76 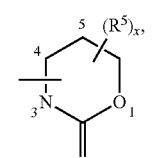
J-77 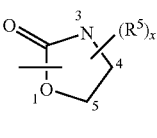
J-78 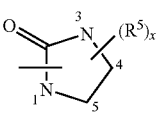
J-79 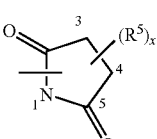
J-80 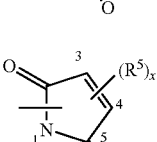
J-81 and 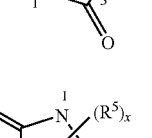
J-82 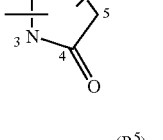
wherein the bond shown projecting to the left is bonded to $Z^1$; and x is an integer from 0 to 3.
Embodiment C96
A compound of Embodiment C95 wherein J is a ring selected from J-29-1 through J-29-60, shown below in Exhibit A.

Exhibit A
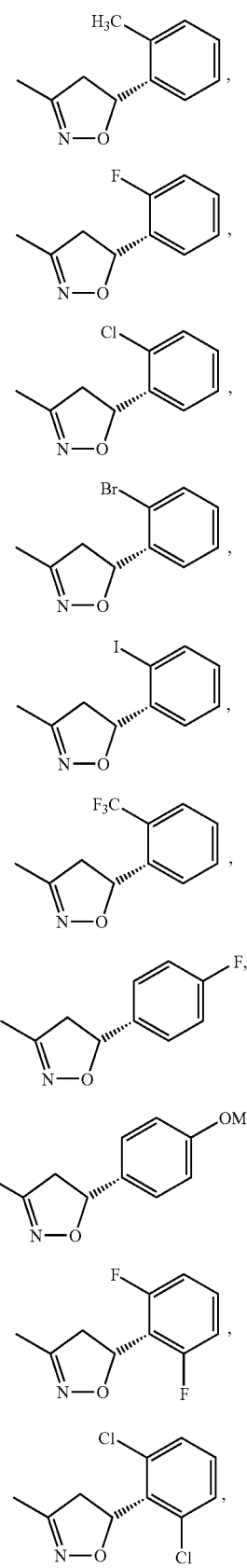
J-29-1
J-29-2
J-29-3
J-29-4
J-29-5
J-29-6
J-29-7
J-29-8
J-29-9
J-29-10
-continued
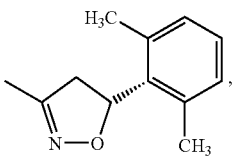 J-29-11
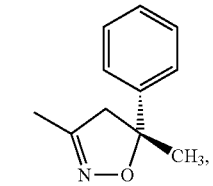 J-29-12
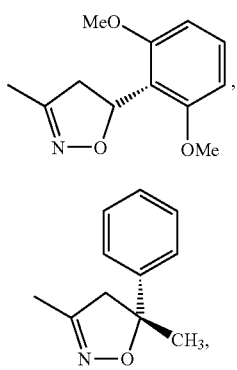 J-29-13
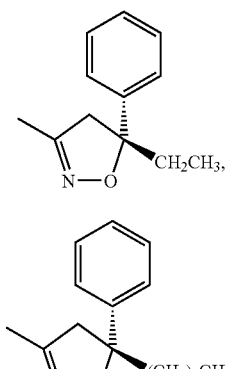 J-29-14
J-29-15
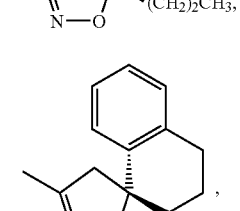 J-29-16
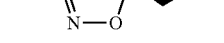
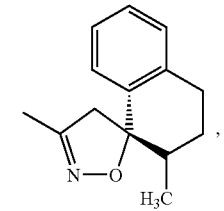 J-29-17
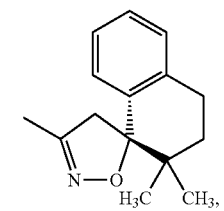 J-29-18

J-29-19
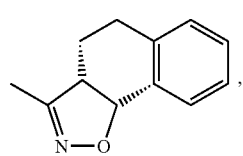
J-29-20
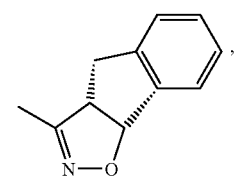
J-29-21
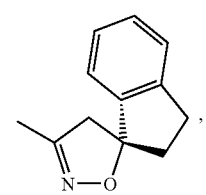
J-29-22
J-29-23
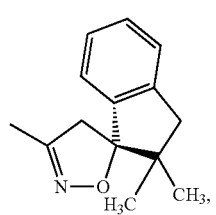
J-29-24
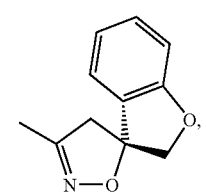
J-29-25
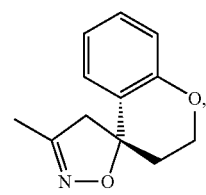
J-29-26
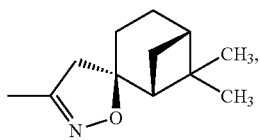
J-29-27
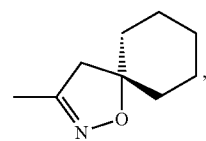
J-29-28
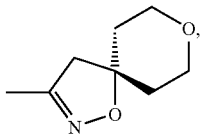
J-29-29
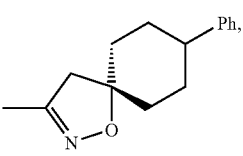
J-29-30
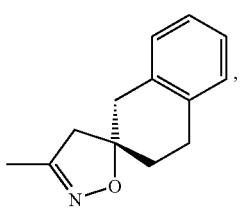
J-29-31
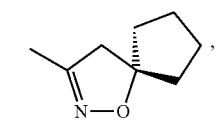
J-29-32
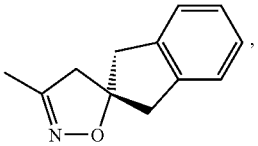
J-29-33
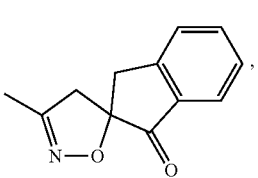
J-29-34
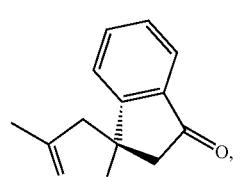
J-29-35
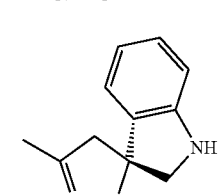
J-29-36
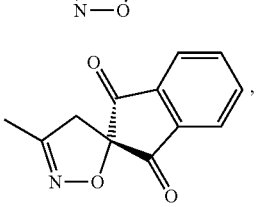

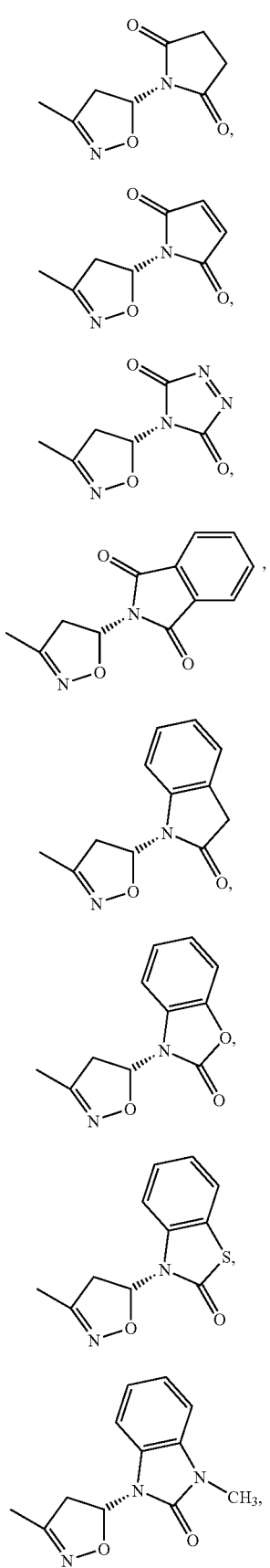
J-29-37
J-29-38
J-29-39
J-29-40
J-29-41
J-29-42
J-29-43
J-29-44
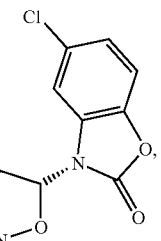
J-29-45
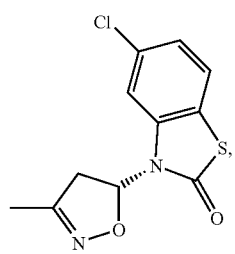
J-29-46
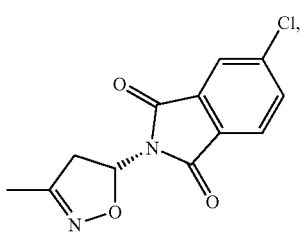
J-29-47
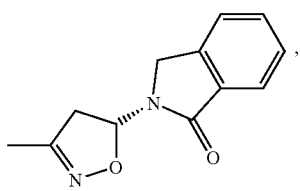
J-29-48
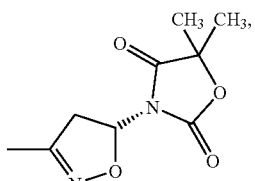
J-29-49
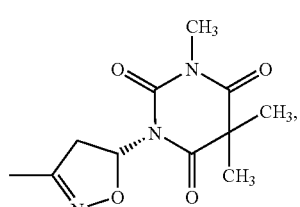
J-29-50
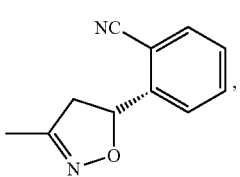
J-29-51

115
-continued

J-29-52 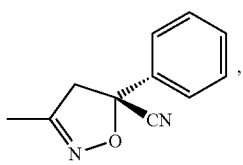

J-29-53 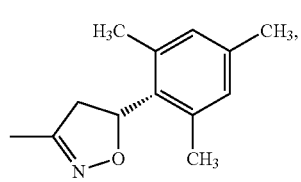

J-29-54 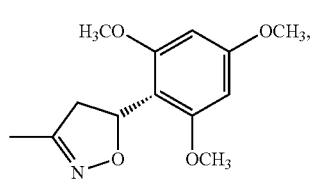

J-29-55 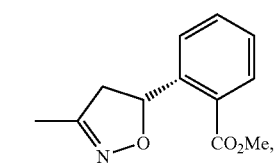

J-29-56 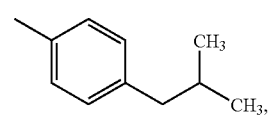

J-29-57 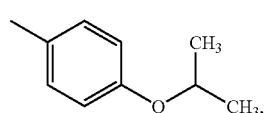

J-29-58 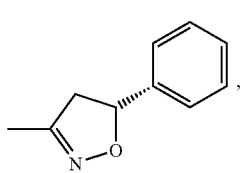

J-29-59 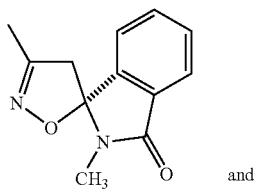
and
J-29-60 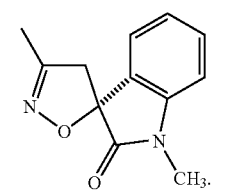

116

Embodiment C97

A compound of Embodiment C95 wherein J is selected from J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69.

Embodiment C98

A compound of Embodiment C97 wherein J is selected from J-4, J-5, J-8, J-11, J-15, J-16, J-20, J-29, J-30, J-37, J-38 and J-69.

Embodiment C99

A compound of Embodiment C98 wherein J is selected from J-4, J-5, J-11, J-20, J-29, J-37, J-38 and J-69.

Embodiment C100

A compound of Embodiment C99 wherein J is J-11.

Embodiment C101

A compound of Embodiment C99 wherein J is J-29.

Embodiment C102

A compound of Embodiment C99 wherein J is J-69.

Embodiment 103

A compound of Embodiment C96 wherein J is selected from any one of J-29-1 through J-29-60, as depicted in Table A.

Embodiment C104

A compound of Embodiment C95 wherein x is 0, 1 or 2.

Embodiment C104a

A compound of Embodiment C95 wherein x is 1 or 2.

Embodiment C105

A compound of Embodiment C104 wherein x is 0.

Embodiment C106

A compound of Embodiment C95 wherein $R^5$ is $Z^2Q$.

Embodiment C107

A compound of Embodiment C100 wherein the 3-position of J-11 is connected to $Z^1$ of Formula 1 and the 5-position of J-11 is substituted with a substituent selected from $R^5$ other than H.

Embodiment C108

A compound of Embodiment C100 wherein the 3-position of J-11 is connected to $Z^1$ of Formula 1 and the 5-position of J-11 is substituted with $Z^2Q$.

Embodiment C109

A compound of Embodiment C101 wherein the 3-position of J-29 is connected to $Z^1$ of Formula 1 and the 5-position of J-29 is substituted with a substituent selected from $R^5$ other than H.

Embodiment C110

A compound of Embodiment C101 wherein the 3-position of J-29 is connected to $Z^1$ of Formula 1 and the 5-position of J-29 is substituted with $Z^2Q$.

Embodiment C111

A compound of Formula 1 or Embodiment C95 wherein each $R^5$ is independently H, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —NR$^{25}$R$^{26}$ or $Z^2Q$.

Embodiment 112

A compound of Embodiment C111 wherein each $R^5$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —NR$^{25}$R$^{26}$ or $Z^2Q$.

Embodiment C113

A compound of Embodiment C112 wherein each $R^5$ is independently H, cyano, $C_1$-$C_6$ alkyl, $C_1$-$C_6$ haloalkyl, $C_1$-$C_6$ alkoxy, $C_1$-$C_6$ haloalkoxy, —NR$^{25}$R$^{26}$ or $Z^2Q$.

Embodiment C114

A compound of Formula 1 or Embodiment 95 wherein one instance of $R^5$ is $Z^2Q$ and other instances of $R^5$ are independently selected from H, cyano, $C_1$-$C_4$ alkyl, $C_1$-$C_4$ haloalkyl, $C_1$-$C_4$ alkylcarbonyl and halogen.

Embodiment C115

A compound of Embodiment C114 wherein one instance of $R^5$ is $Z^2Q$ and other instances of $R^5$ are independently selected from H, cyano and $C_1$-$C_3$ alkyl.

Embodiment C115a

A compound of Embodiment C114 wherein the only instance of $R^5$ is $Z^2Q$,

Embodiment C116

A compound of Formula 1 wherein when each $R^5$ is —NR$^{26}$R$^{25}$, then each R$^{26}$ is independently $C_1$-$C_3$ alkyl or —$Z^4Q$;

Embodiment C117

A compound of Formula 1 or Embodiment C116 wherein each $Z^4$ is independently C(=O) or S(O)$_2$.

Embodiment C118

A compound of Embodiment C117 wherein each $Z^4$ is C(=O).

Embodiment C119

A compound of Formula 1 wherein each $Z^2$ is independently a direct bond, O, C(=O), S(O)$_2$ or CHR$^{20}$.

Embodiment C120

A compound of Embodiment C119 wherein $Z^2$ is direct bond.

Embodiment C121

A compound of Formula 1 wherein each Q is independently a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(O), S(O)$_2$ and SiR$^{17}$R$^{18}$, and optionally substituted with up to 5 substituents independently selected from R$^7$ on carbon atom ring members and R$^{12}$ on nitrogen atom ring members.

Embodiment C122

A compound of Formula 1 wherein each Q is independently an 8- to 11-membered heteroaromatic bicyclic ring system substituted with one R$^7$.

Embodiment C123

A compound of Formula 1 wherein each Q is independently an optionally substituted phenyl, benzyl, naphthalenyl or 5- or 6-membered heteroaromatic ring, each optionally substituted with up to 3 substituents selected from R$^7$ on carbon ring members and R$^{12}$ on nitrogen ring members.

Embodiment C124

A compound of Embodiment C123 wherein each Q is independently phenyl substituted with one R$^7$.

Embodiment C125

A compound of Embodiment C124 wherein each Q is independently benzyl substituted with one R$^7$.

Embodiment C126

A compound of Formula 1 wherein each Q is independently selected from Q-1 through Q-106, in Exhibit 4.

Exhibit 4
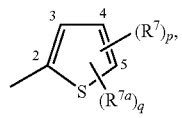 Q-1
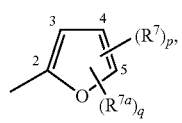 Q-2
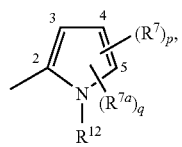 Q-3
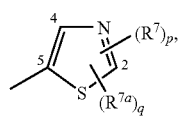 Q-4
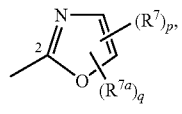 Q-5
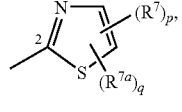 Q-6
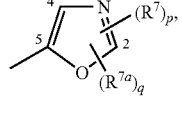 Q-7
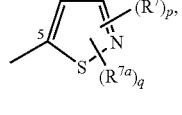 Q-8
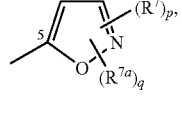 Q-9
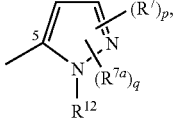 Q-10
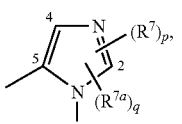 Q-11
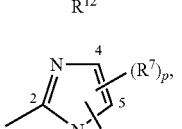 Q-12
-continued
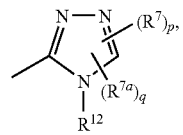 Q-13
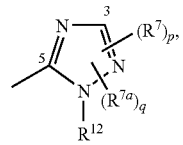 Q-14
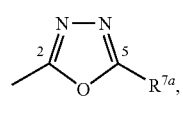 Q-15
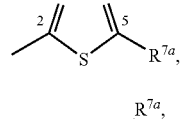 Q-16
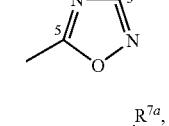 Q-17
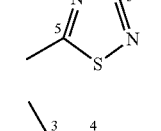 Q-18
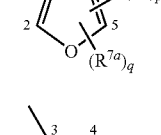 Q-19
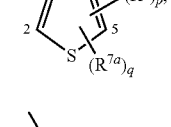 Q-20
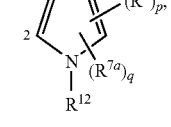 Q-21
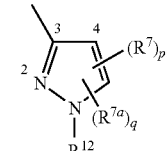 Q-22
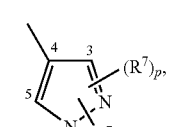 Q-23

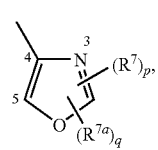 Q-24
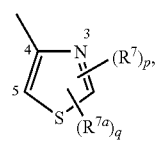 Q-25
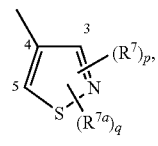 Q-26
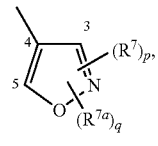 Q-27
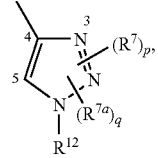 Q-28
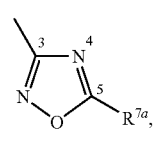 Q-29
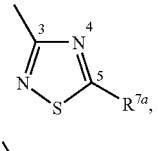 Q-30
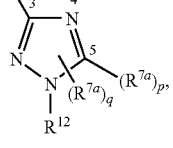 Q-31
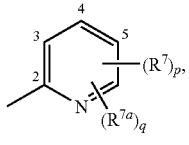 Q-32
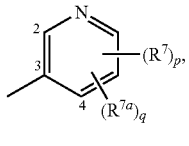 Q-33
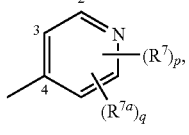 Q-34
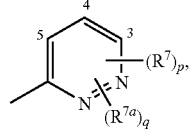 Q-35
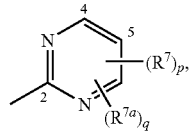 Q-36
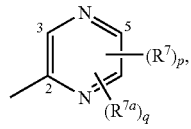 Q-37
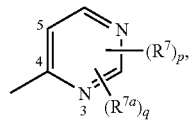 Q-38
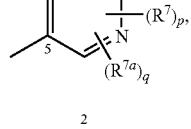 Q-39
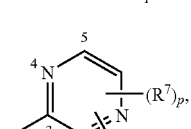 Q-40
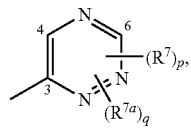 Q-41
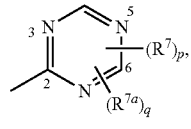 Q-42
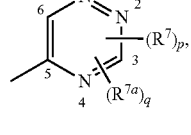 Q-43
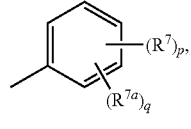 Q-44
Q-45

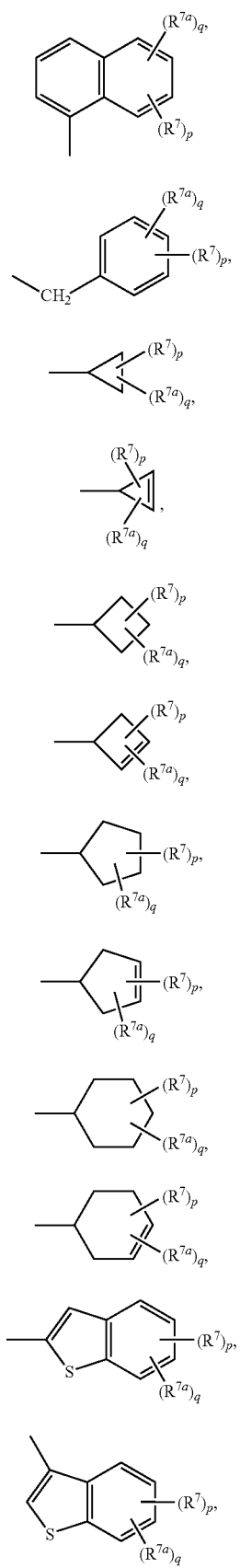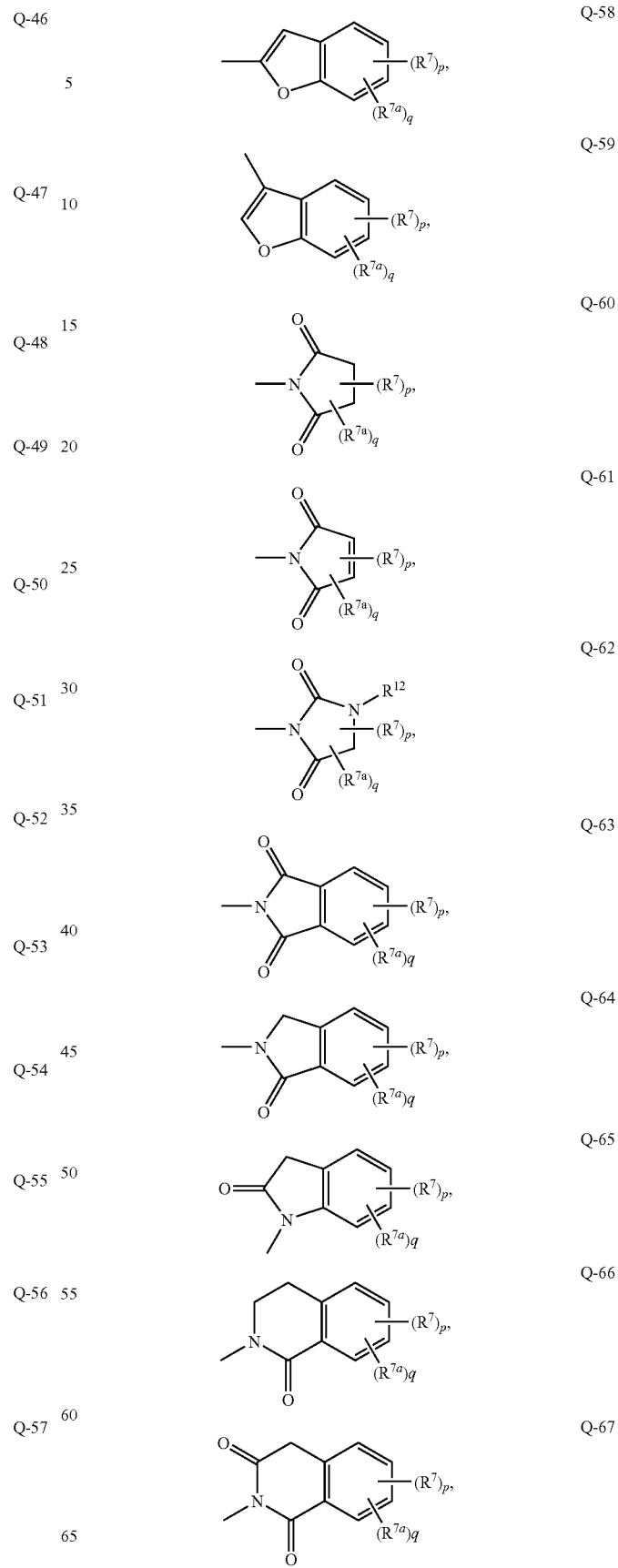

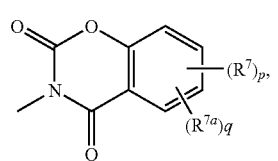 Q-68
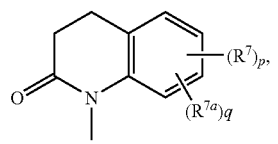 Q-69
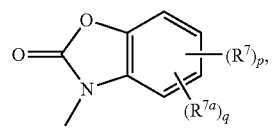 Q-70
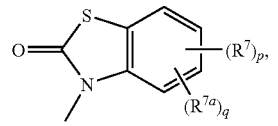 Q-71
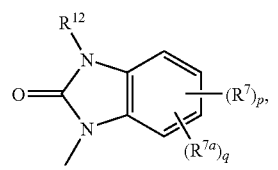 Q-72
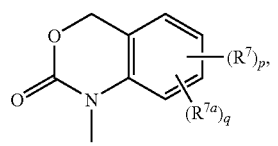 Q-73
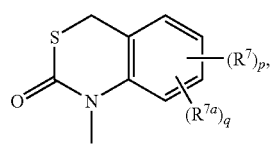 Q-74
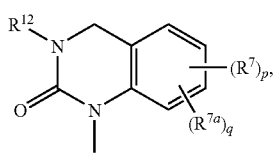 Q-75
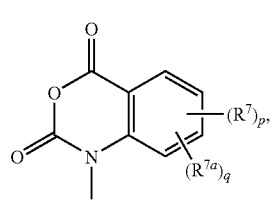 Q-76
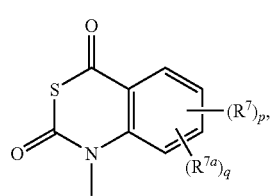 Q-77
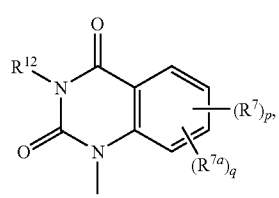 Q-78
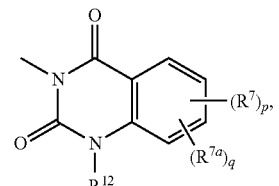 Q-79
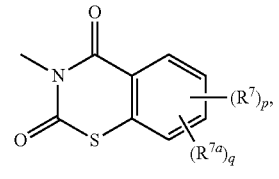 Q-80
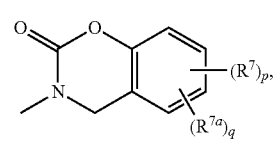 Q-81
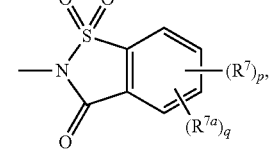 Q-82
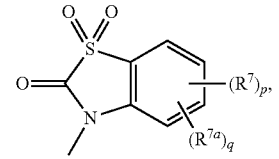 Q-83
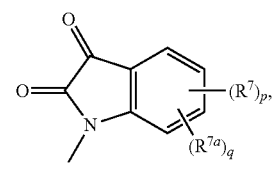 Q-84
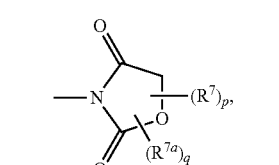 Q-85
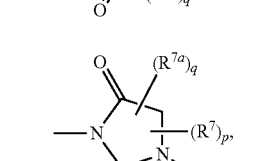 Q-86

Q-87 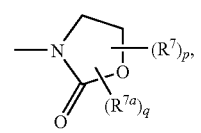
Q-88 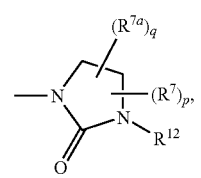
Q-89 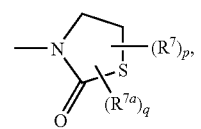
Q-90 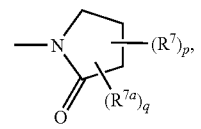
Q-91 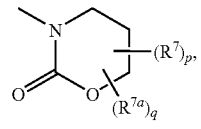
Q-92 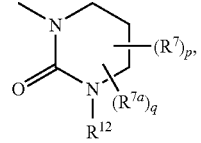
Q-93 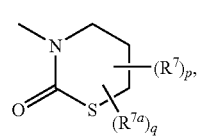
Q-94 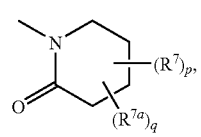
Q-95 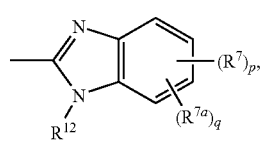
Q-96 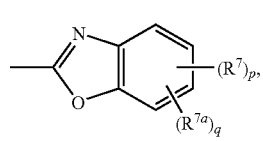
Q-97 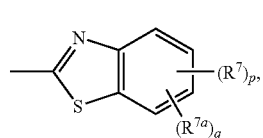
Q-98 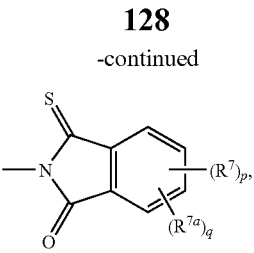
Q-99 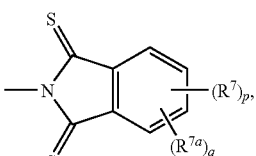
Q-100 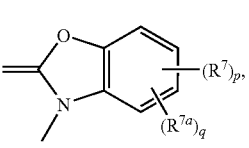
Q-101 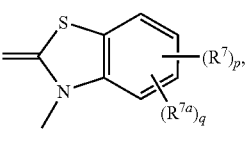
Q-102 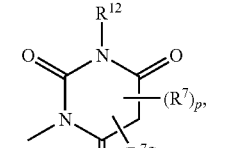
Q-103 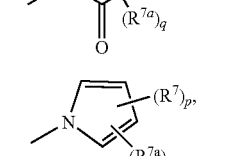
Q-104 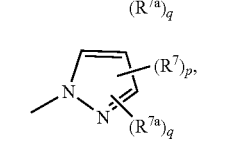
Q-105 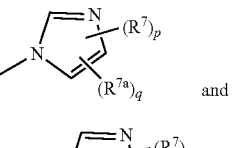 and
Q-106 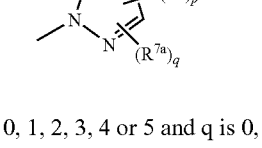
wherein p is 0, 1, 2, 3, 4 or 5 and q is 0, 1 or 2.
Embodiment C127
A compound of Embodiment C126 wherein p is 0, 1, 2 or 3.
Embodiment C128
A compound of Embodiment C126 wherein each Q is independently selected from Q-1, Q-20, Q-32 through Q-34, Q-45 through Q-47, Q-60 through Q-73, Q-76 through Q-79, Q-84 through Q-94 and Q-98 through Q-106.

Embodiment C129

A compound of Embodiment C128 wherein each Q is independently selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100 and Q-101 through Q-106.

Embodiment C130

A compound of Embodiment C129 wherein each Q is independently selected from Q-45, Q-63, Q-64, Q-65, Q-68, Q-69, Q-70, Q-71, Q-72, Q-84 and Q-85.

Embodiment C131

A compound of Embodiment C130 wherein each Q is independently selected from Q-45, Q-63, Q-65, Q-70, Q-71, Q-72, Q-84 and Q-85.

Embodiment C132

A compound of Embodiment C131 wherein each Q is independently selected from Q-45, Q-63, Q-65 or Q-70, Q-71, Q-72 and Q-84.

Embodiment C133

A compound of Formula 1 or Embodiment C126 wherein each $R^7$ is independently $C_1$-$C_3$ alkyl, $C_1$-$C_3$ haloalkyl, halogen, hydroxy, amino, cyano, nitro, $C_1$-$C_2$ alkoxy or $C_1$-$C_2$ haloalkoxy.

Embodiment C134

A compound of Embodiment C133 wherein each $R^7$ is independently $C_1$-$C_3$ alkyl, $C_1$-$C_3$ haloalkyl, $C_1$-$C_2$ haloalkoxy, halogen, hydroxy, cyano or $C_1$-$C_2$ alkoxy.

Embodiment C135

A compound of Embodiment C134 wherein each $R^7$ is independently methyl, F, Cl, Br, hydroxy, cyano or methoxy.

Embodiment C136

A compound of Formula 1 wherein when $R^5$ and $R^7$ are taken together with the atoms linking $R^5$ and $R^7$ to form an optionally substituted 5- to 7-membered ring, the ring members are selected from carbon and optionally up to 3 heteroatoms selected from up to 1 O, up to 1 S and up to 1 N and optionally include 1 to 3 ring members selected from the group consisting of C(=O), C(=S), 17$R^{18}$. S(O), S(O)$_2$ and SiR

Embodiment C137

A compound of Embodiment C136 wherein when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing ring members selected from carbon and optionally 1 to 3 heteroatoms selected from up to 1 O, up to 1 S and up to 1 N, and optionally including up to 3 ring members selected from the group consisting of C(=O), C(=S), S(O), S(O)$_2$ and SiR$^{17}$R$^{18}$, the ring optionally substituted on ring members other than the atoms linking $R^5$ and $R^7$ with substituents selected from $R^8$; and each $R^8$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment C138

A compound of Embodiment C137 wherein the ring is optionally substituted on ring members other than the atoms linking $R^5$ and $R^7$ with up to 4 substituents selected from $R^8$.

Embodiment C139

A compound of Embodiment C138 wherein the ring is optionally substituted on ring members other than the atoms linking $R^5$ and $R^7$ with up to 2 substituents selected from $R^8$.

Embodiment C140

A compound of any one of Embodiments C137, C138 and C39 wherein each $R^8$ is independently $C_1$-$C_3$ alkyl.

Embodiment C141

A compound of Formula 1 or Embodiment C26 wherein $R^{7a}$ is —$Z^3T^4$.

Embodiment C142

A compound of Embodiment C141 wherein each $Z^3$ is independently a direct bond, O, NR$^{22}$, C(=O), C(=S), S(O)$_m$, CHR$^{20}$, CHR$^{20}$—CHR$^{20}$, CR$^{24}$=CR$^{27}$, or OCHR$^{20}$.

Embodiment C143

A compound of Embodiment C142 wherein each $Z^3$ is independently a direct bond, O, NR$^{22}$, S(O)$_m$, CHR$^{20}$, CHR$^{20}$—CHR$^{20}$, CR$^{24}$=CR$^{27}$, or OCHR$^{20}$.

Embodiment C14

A compound of Embodiment C143 wherein each $Z^3$ is independently a direct bond, O, NR$^{22}$, S(O)$_m$, CHR$^{20}$, CHR$^{20}$—CHR$^{20}$ or CR$^{24}$=CR$^{27}$.

Embodiment C145

A compound of Embodiment C144 wherein each $Z^3$ is independently a direct bond, O, NR$^{22}$, CHR$^{20}$ or CHR$^{20}$—CHR$^{20}$.

Embodiment C146

A compound of Embodiment 145 wherein each $Z^3$ is independently a direct bond, O or NR$^{22}$.

Embodiment C147

A compound of Embodiment 146 wherein each $Z^3$ is independently a direct bond.

Embodiment C148

A compound of Embodiment C147 wherein each $Z^3$ is independently a O.

Embodiment C149

A compound of Embodiment C141 wherein $T^4$ is phenyl.

Embodiment C150

A compound of Embodiment C149 wherein $T^4$ is a 5- or 6-membered heteroaromatic ring.

Embodiment C151

A compound of Formula 1 or Embodiment C126 wherein $R^{7a}$ is —$Z^3T^A$.

Embodiment C152

A compound of Formula 1 or Embodiment C126 wherein $R^{7a}$ is —$Z^3T^N$.

Embodiment C153

A compound of Formula 1 or Embodiment C126 wherein $R^{7a}$ is —$Z^3T^P$.

Embodiment C154

A compound of Formula 1 wherein each $T^A$ is independently selected from $T^A$-1 through $T^A$-49, each $T^N$ is independently selected from $T^N$-1 through $T^N$-32 and each $T^P$ is independently selected from $T^P$-1 through $T^P$-35 in Exhibit 5.

Exhibit 5

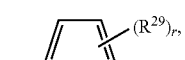  $T^A$-1

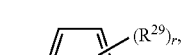  $T^A$-2

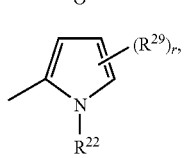  $T^A$-3

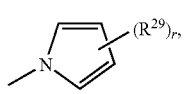  $T^A$-4

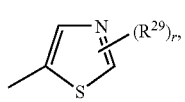  $T^A$-5

-continued

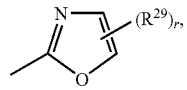  $T^A$-6

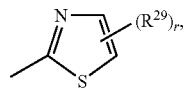  $T^A$-7

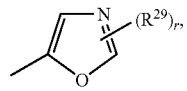  $T^A$-8

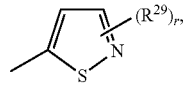  $T^A$-9

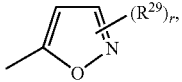  $T^A$-10

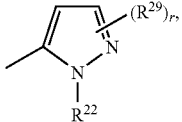  $T^A$-11

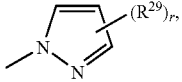  $T^A$-12

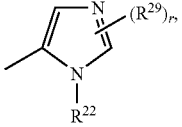  $T^A$-13

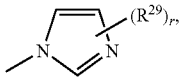  $T^A$-14

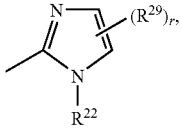  $T^A$-15

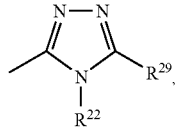  $T^A$-16

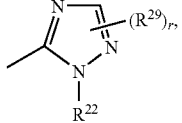  $T^A$-17

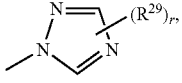  $T^A$-18

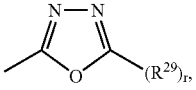  $T^A$-19

-continued
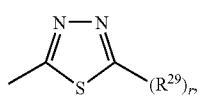 T^A-20
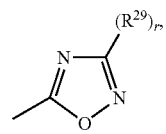 T^A-21
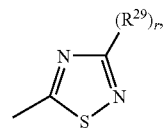 T^A-22
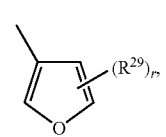 T^A-23
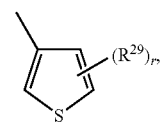 T^A-24
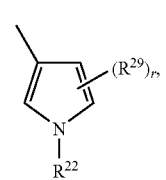 T^A-25
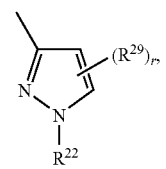 T^A-26
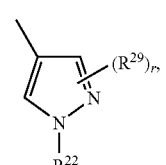 T^A-27
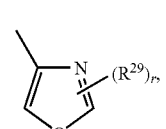 T^A-28
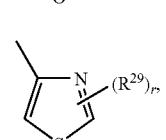 T^A-29
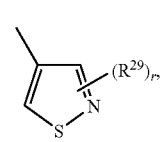 T^A-30
-continued
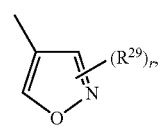 T^A-31
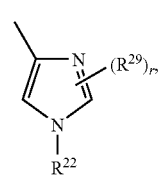 T^A-32
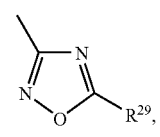 T^A-33
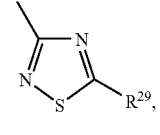 T^A-34
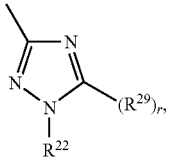 T^A-35
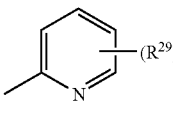 T^A-36
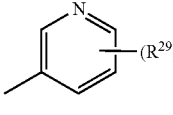 T^A-37
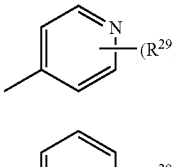 T^A-38
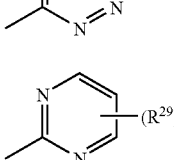 T^A-39
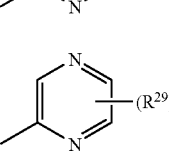 T^A-40
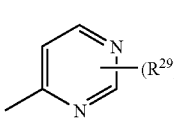 T^A-41
T^A-42

| | |
|---|---|
| 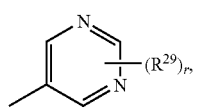 T<sup>A</sup>-43 | 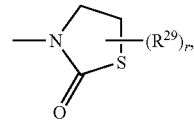 T<sup>N</sup>-7 |
| 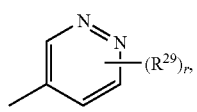 T<sup>A</sup>-44 | 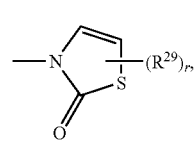 T<sup>N</sup>-8 |
| 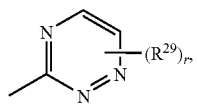 T<sup>A</sup>-45 | 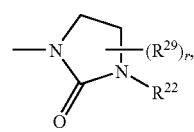 T<sup>N</sup>-9 |
| 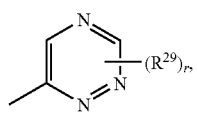 T<sup>A</sup>-46 | 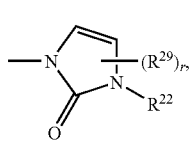 T<sup>N</sup>-10 |
| 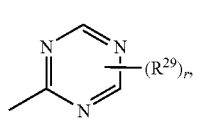 T<sup>A</sup>-47 | 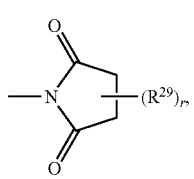 T<sup>N</sup>-11 |
| 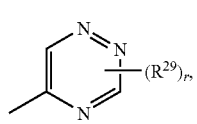 T<sup>A</sup>-48 | 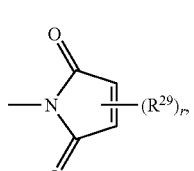 T<sup>N</sup>-12 |
| 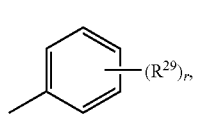 T<sup>A</sup>-49 | 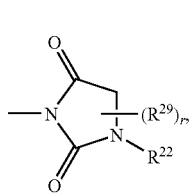 T<sup>N</sup>-13 |
| 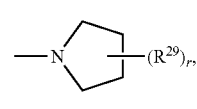 T<sup>N</sup>-1 | 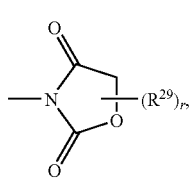 T<sup>N</sup>-14 |
| 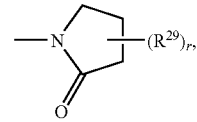 T<sup>N</sup>-2 | 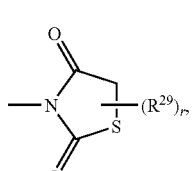 T<sup>N</sup>-15 |
| 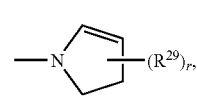 T<sup>N</sup>-3 | |
| 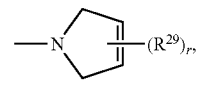 T<sup>N</sup>-4 | |
| 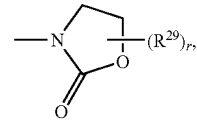 T<sup>N</sup>-5 | |
| 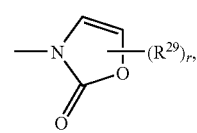 T<sup>N</sup>-6 | T<sup>N</sup>-16 |

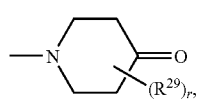 T$^N$-17
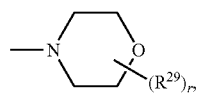 T$^N$-18
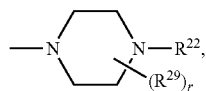 T$^N$-19
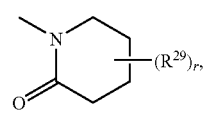 T$^N$-20
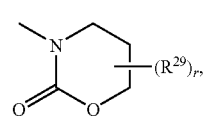 T$^N$-21
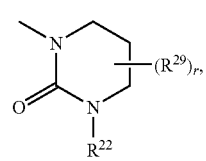 T$^N$-22
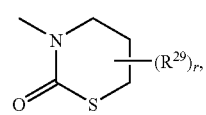 T$^N$-23
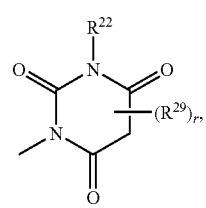 T$^N$-24
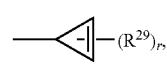 T$^N$-25
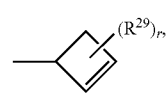 T$^N$-26
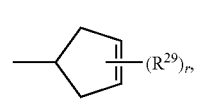 T$^N$-27
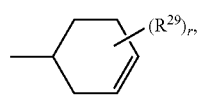 T$^N$-28
 T$^N$-29
 T$^N$-30
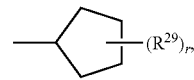 T$^N$-31
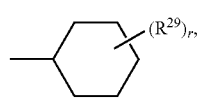 T$^N$-32
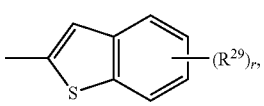 T$^P$-1
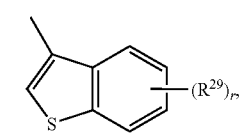 T$^P$-2
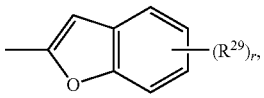 T$^P$-3
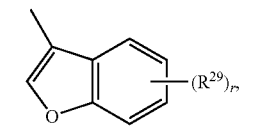 T$^P$-4
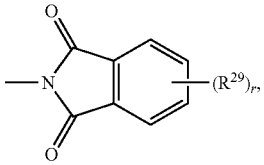 T$^P$-5
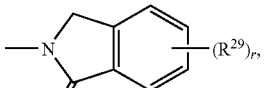 T$^P$-6
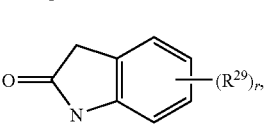 T$^P$-7
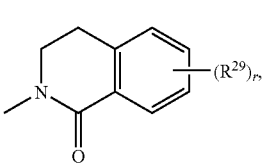 T$^P$-8
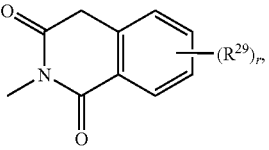 T$^P$-9

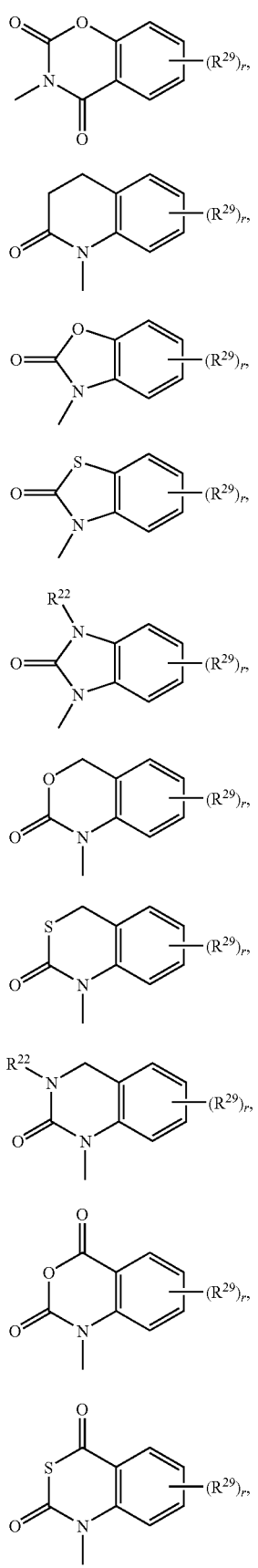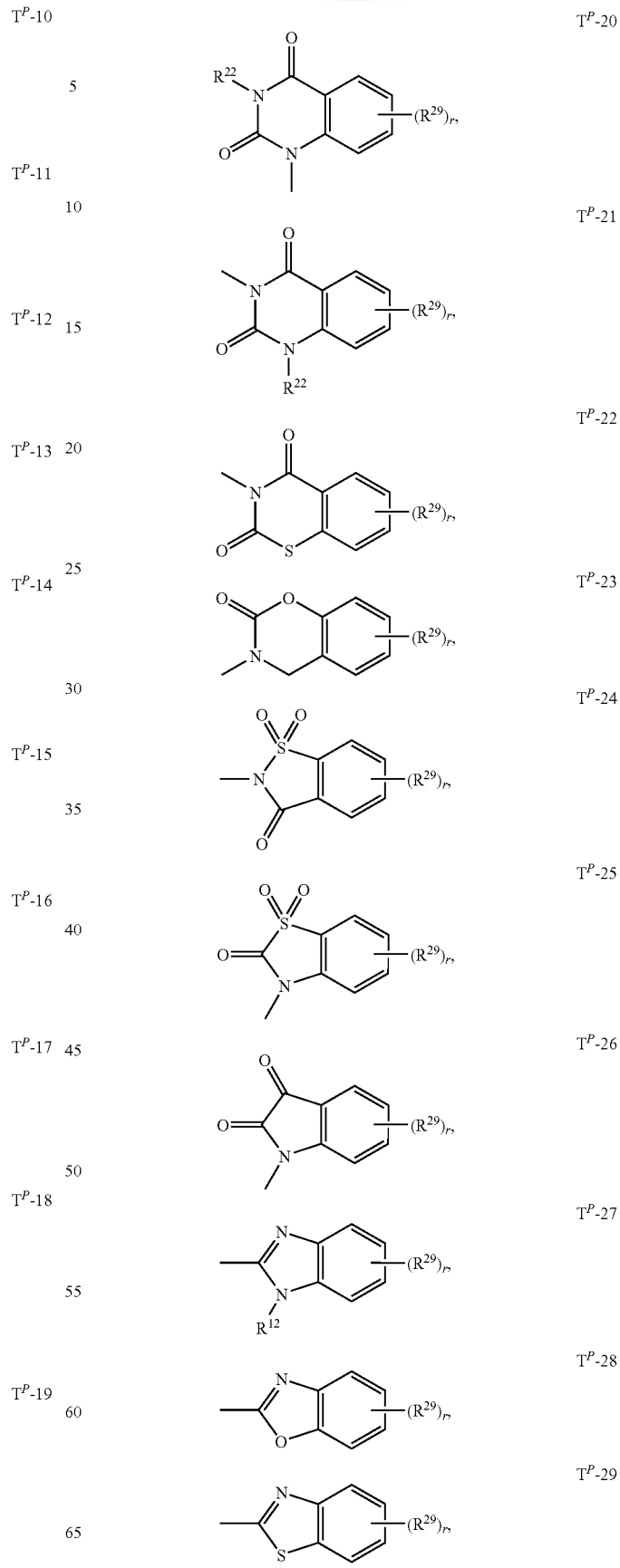

-continued

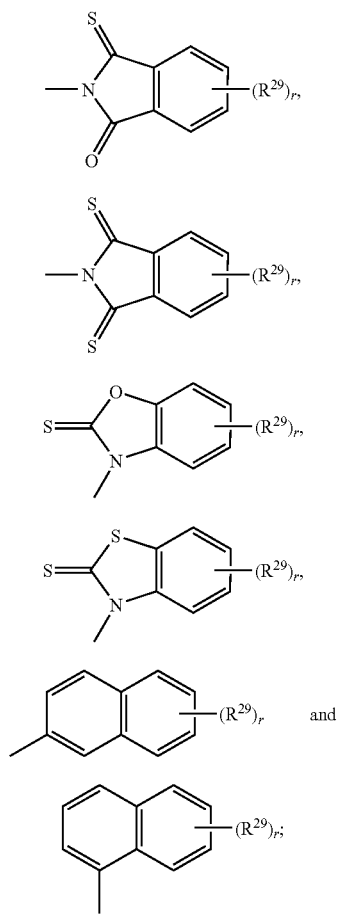

wherein the bond shown projecting to the left is bonded to $Z^3$; and r is 0, 1, 2, 3, 4 or 5.

Embodiment C155

A compound of Embodiment C154 wherein r is 0, 1, 2 or 3.

Embodiment C156

A compound of Embodiment C154 wherein $T^A$ is selected from $T^A$-1 through $T^A$-18, $T^A$-23 through $T^A$-38 and $T^A$-49, $T^N$ is selected from $T^N$-1, $T^N$-2, $T^N$-5, $T^N$-6, $T^N$-9 through $T^N$-16 and $T^N$-29, or $T^P$ is selected from $T^P$-1 through $T^N$-6, $T^P$-34 and $T^P$-38.

Embodiment C157

A compound of Embodiment C156 wherein $T^A$ is selected from $T^A$-1 through $T^A$-18, $T^A$-23 through $T^A$-38 and $T^A$-49, or $T^N$ is selected from $T^N$-1, $T^N$-2, $T^N$-5, $T^N$-6, $T^N$-9 through $T^N$-16 and $T^N$-29.

Embodiment C158

A compound of Embodiment C157 wherein $T^A$ is selected from $T^A$-18 and $T^A$-49.

Embodiment C159

A compound of Embodiment C158 wherein $T^A$ is $T^A$-18.

Embodiment C160

A compound of Embodiment C158 wherein $T^A$ is $T^A$-49.

Embodiment C161

A compound of Formula 1 wherein each $R^{29}$ is independently H, halogen, cyano, hydroxy, —C(=O)OH, —C(=O)NH$_2$, —SO$_2$NH$_2$, —SH, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_4$-$C_{10}$ cycloalkylcarbonyl, $C_4$-$C_{10}$ cycloalkylaminocarbonyl, $C_2$-$C_7$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_3$-$C_{10}$ alkoxyalkylcarbonyl, $C_3$-$C_{10}$ alkoxycarbonylalkyl, $C_3$-$C_{10}$ alkoxy(alkyl)aminocarbonyl, $C_2$-$C_8$ alkylamidino, $C_3$-$C_{10}$ dialkylamidino, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ alkylaminosulfonyl, $C_2$-$C_8$ dialkylaminosulfonyl, $C_3$-$C_{10}$ trialkylsilyl, $C_2$-$C_8$ alkoxyalkoxy, $C_1$-$C_6$ alkylamino, $C_2$-$C_8$ dialkylamino, $C_2$-$C_8$ alkylcarbonylamino, $C_1$-$C_6$ alkylsulfonylamino or $C_1$-$C_6$ haloalkylamino.

Embodiment C162

A compound of Embodiment C161 wherein each $R^{29}$ is independently H, halogen, cyano, hydroxy, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ alkoxycarbonyl, $C_3$-$C_8$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_2$-$C_8$ alkoxyalkyl, $C_3$-$C_{10}$ dialkylaminoalkyl, $C_2$-$C_7$ cyanoalkyl, $C_1$-$C_6$ hydroxyalkyl, $C_2$-$C_8$ haloalkoxyalkyl, $C_3$-$C_{10}$ alkoxyalkylcarbonyl, $C_3$-$C_{10}$ alkoxycarbonylalkyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ alkylsulfonyl, $C_1$-$C_6$ alkylamino or $C_2$-$C_8$ dialkylamino.

Embodiment C163

A compound of Embodiment C162 wherein each $R^{29}$ is independently H, halogen, cyano, hydroxy, $C_1$-$C_2$ alkyl, $C_1$-$C_2$ haloalkyl, $C_1$-$C_2$ alkoxy or $C_1$-$C_2$ haloalkoxy.

Embodiment C164

A compound of Formula 1 wherein when G is an optionally substituted thiazole ring connected at the 2-position to X of Formula 1 and at the 4-position to $Z^1$ of Formula 1, A is CHR$^{15}$, and J is an optionally substituted isoxazole ring connected at the 4-position to $Z^1$ of Formula 1, then $Z^1$ is O, C(=O), S(O)$_m$, CHR$^{20}$ or NR$^{21}$.

Embodiment C165

A compound of Formula 1 wherein when G is an optionally substituted thiazole ring connected at the 2-position to X of Formula 1 and at the 4-position to $Z^1$ of Formula 1, and J is an optionally substituted isoxazole ring connected at the 4-position to $Z^1$ of Formula 1, then $Z^1$ is O, C(=O), S(O)$_m$, CHR$^{20}$ or NR$^{21}$.

Embodiment C166

A compound of Formula 1 wherein when G is an optionally substituted thiazole ring connected at the 2-position to X of Formula 1 and at the 4-position to $Z^1$ of Formula 1, A is CHR$^{15}$, $Z^1$ is a direct bond, J is an optionally substituted isoxazole ring connected to the remainder of the Formula 1 at the 3- or 5-position of the isoxazole ring.

Embodiment 167

A compound of Formula 1 wherein when G is an optionally substituted thiazole ring connected at the 2-position to X of Formula 1 and at the 4-position to $Z^1$ of Formula 1, A is CHR$^{15}$, $Z^1$ is a direct bond, J is an optionally substituted isoxazole ring connected to the remainder of the Formula 1 at the 3-position of the isoxazole ring.

Embodiment 168

A compound of Formula 1 wherein when G is an optionally substituted thiazole ring connected at the 2-position to X of Formula 1 and at the 4-position to $Z^1$ of Formula 1, $Z^1$ is a direct bond, and J is an optionally substituted isoxazole ring connected to the remainder of the Formula 1 at the 3-position of the isoxazole ring.

Embodiment C169

A compound of Formula 1 wherein when X is $X^2$ and the ring containing X is saturated, A is CHR$^{15}$, G is an optionally substituted 5-membered heteroaromatic ring, $Z^1$ is a direct bond, J is a phenyl or 5- or 6-membered heteroaromatic ring or a naphthalenyl or 8- to 11-membered heteroaromatic bicyclic ring system, and the J ring or ring system is substituted with at least one $R^5$ that is other than H.

Embodiment C170

A compound of Formula 1 wherein when X is $X^2$ and the ring containing X is saturated, A is CHR$^{15}$, G is an optionally substituted 5-membered heteroaromatic ring, $Z^1$ is a direct bond, J is a phenyl or 5- or 6-membered heteroaromatic ring or a naphthalenyl or 8- to 11-membered heteroaromatic bicyclic ring system, and the J ring or ring system is substituted with at least one $R^5$ that is $Z^2Q$.

Embodiment C171

A compound of Formula 1 wherein when X is $X^1$ and the ring containing X is saturated, A is NH, G is an optionally substituted thiazole ring connected at the 2-position to X of Formula 1 and at the 4-position to $Z^1$ of Formula 1, J is an optionally substituted imidazole ring connected at the 2-position to the remainder of Formula 1, and $Z^1$ is O, C(=O), S(O)$_m$, CHR$^{20}$ or NR$^{21}$.

Embodiment C172

A compound of Formula 1 wherein when X is $X^1$ and the ring containing X is saturated, A is NR$^{16}$, G is an optionally substituted thiazole ring connected at the 2-position to X of Formula 1 and at the 4-position to $Z^1$ of Formula 1, J is an optionally substituted imidazole ring connected at the 2-position to the remainder of Formula 1, and $Z^1$ is O, C(=O), S(O)$_m$, CHR$^{20}$ or NR$^{21}$.

Embodiment C173

A compound of Formula 1 wherein when G is an optionally substituted thiazole ring connected at the 2-position to X of Formula 1 and at the 4-position to $Z^1$ of Formula 1, then J is other than optionally substituted imidazolyl.

Embodiments of this invention, including Embodiments 1-179 above as well as any other embodiments described herein, can be combined in any manner, and the descriptions of variables in the embodiments pertain not only to the compositions comprising the compounds of Formula 1 but also to the compounds of Formula 1, the starting compounds and intermediate compounds useful for preparing the compounds of Formula 1 unless further defined in the Embodiments. In addition, embodiments of this invention, including Embodiments 1-179 above as well as any other embodiments described herein, and any combination thereof, pertain to the compounds, compositions and methods of the present invention. Combinations of Embodiments 1-179 are illustrated by:

Embodiment A1

A compound of Formula 1 wherein
E is E-1 or E-2;
G is a 5-membered heterocyclic ring optionally substituted with up to 2 substituents selected from $R^3$ on carbon ring members and selected from $R^{11}$ on nitrogen ring members;
each $R^3$ is independently halogen, $C_1$-$C_3$ alkyl or $C_1$-$C_3$ haloalkyl;
each $R^{11}$ is independently $C_1$-$C_3$ alkyl;
J is one of J-1 through J-82 shown in Exhibit 3 wherein the bond shown projecting to the left is bonded to $Z^1$ in Formula 1 and to an available carbon or nitrogen atom ring member in the J ring; and x is an integer from 0 to 5;
X is $X^1$, $X^2$, $X^3$, $X^4$, $X^5$, $X^6$, $X^7$ or $X^8$;
$Z^1$ is a direct bond, CHR$^{20}$ or NR$^{21}$;
each $R^{21}$ is independently H, $C_1$-$C_3$ alkyl, $C_1$-$C_3$ alkylcarbonyl or $C_2$-$C_3$ alkoxycarbonyl;
$R^{1a}$, $R^{1b}$ and $R^{1c}$ independently are optionally substituted phenyl, optionally substituted naphthalenyl or an optionally substituted 5- or 6-membered heteroaromatic ring; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_2$-$C_8$ haloalkylthioalkyl, $C_3$-$C_8$ cycloalkyl, $C_2$-$C_8$ alkoxyalkyl, $C_2$-$C_8$ haloalkoxyalkyl, $C_3$-$C_8$ alkoxycarbonylalkyl, $C_3$-$C_8$ haloalkoxycarbonylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ alkylcarbonyloxy, $C_2$-$C_8$ haloalkylcarbonyloxy, $C_3$-$C_{10}$ dialkylaminoalkyl, $C_1$-$C_8$ alkoxy, $C_1$-$C_8$ haloalkoxy, $C_1$-$C_8$ alkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl;

each $R^2$ is independently halogen, cyano, hydroxy, $C_1$-$C_2$ alkyl, $C_1$-$C_2$ haloalkyl or $C_1$-$C_2$ alkoxy;

$R^5$ is independently H, halogen, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —$NR^{25}R^{26}$ or —$Z^2Q$;

each $R^{26}$ is independently $C_1$-$C_3$ alkyl or —$Z^4Q$;

each $Z^4$ is independently $C(=O)$ or $S(=O)_2$;

each $Z^2$ is independently a O, $C(=O)$, $S(O)_2$, $CHR^{20}$ or $NR^{21}$;

each Q is independently phenyl, benzyl, naphthalenyl, a 5- to 6-membered heteroaromatic ring or an 8- to 11-membered heteroaromatic bicyclic ring system, each optionally substituted with up to 1 substituent independently selected from $R^{7a}$ on carbon atom or nitrogen atom ring members, and each optionally substituted with up to 5 substituents independently selected from $R^7$ on carbon atom ring members and $R^{12}$ on nitrogen atom ring members; or a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of $C(=O)$, $C(=S)$, $S(=O)_s$ $(=NR^{23})_f$ and $SiR^{17}R^{18}$, and each ring or ring system optionally substituted with up to 1 substituent independently selected from $R^{7a}$ on carbon atom or nitrogen atom ring members, and each optionally substituted with up to 5 substituents independently selected from $R^7$ on carbon atom ring members and $R^{12}$ on nitrogen atom ring members;

each $R^7$ is independently halogen, cyano, hydroxy, amino, nitro, $C_1$-$C_3$ alkyl, $C_1$-$C_3$ haloalkyl, $C_1$-$C_2$ alkoxy or $C_1$-$C_2$ haloalkoxy; or $R^5$ and $R^7$ are taken together with the atoms linking R5 and R7 to form an optionally substituted 5- to 7-membered ring containing ring members selected from carbon atoms and optionally up to 3 heteroatoms selected from up to 1 O, up to 1 S and up to 1 N, and up to 2 ring members selected from $C(=O)$, $C(=S)$, $S(=O)_s$ $(=NR^{23})_f$ and $SiR^{17}R^{18}$, the ring optionally substituted with substituents selected from $R^8$;

each $R^8$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsily8;

each $R^{7a}$ is independently —$Z^3T^4$;

each $R^{29}$ is independently H, halogen, cyano, hydroxy, $C_1$-$C_2$ alkyl, $C_1$-$C_2$ haloalkyl, $C_1$-$C_2$ alkoxy or $C_1$-$C_2$ haloalkoxy;

each $T^4$ is independently selected from $T^A$-18 and $T^A$-49 shown in Exhibit 5 wherein the bond shown projecting to the left is bonded to $Z^3$ in Formula 1 and; r is 0, 1, 2, 3, 4 or 5;

$R^{15}$ is H, halogen, cyano, hydroxy, —CHO, $C_1$-$C_4$ alkyl, $C_1$-$C_4$ haloalkyl, $C_1$-$C_4$ alkoxy or $C_2$-$C_5$ alkoxycarbonyl; and $R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl.

Embodiment A2

A compound of Embodiment A1 wherein

G is one of G-1 through G-59 shown in Exhibit 2 wherein the bond projecting to the left is bonded to X, and the bond projecting to the right is bonded to $Z^1$ in Formula 1;

each $R^{1a}$ is independently selected from H and $R^3$;

$R^{11a}$ is selected from H and $R^{11}$;

J is selected from J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69;

x is and integer from 0 to 3;

X is $X^1$, $X^2$ or $X^3$;

$Z^1$ is a direct bond or $CHR^{20}$;

each $R^{21}$ is independently H or methyl;

$Z^5$ and $Z^6$ independently are each a direct bond;

$R^{1a}$ and $R^{1b}$ independently are phenyl, naphthalenyl or a 5- or 6-membered heteroaromatic ring, each optionally substituted with up to 3 substituents selected from $R^{4a}$ on carbon ring members and $R^{4b}$ on nitrogen ring members; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_2$-$C_8$ haloalkylthioalkyl, $C_3$-$C_8$ cycloalkyl, $C_2$-$C_8$ alkoxyalkyl, $C_2$-$C_8$ haloalkoxyalkyl, $C_3$-$C_8$ alkoxycarbonylalkyl, $C_3$-$C_8$ haloalkoxycarbonylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ alkylcarbonyloxy, $C_2$-$C_8$ haloalkylcarbonyloxy, $C_3$-$C_{10}$ dialkylaminoalkyl, $C_1$-$C_8$ alkoxy, $C_1$-$C_8$ haloalkoxy, $C_1$-$C_8$ alkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl;

each $R^{4a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

each $R^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl;

each $R^2$ is independently cyano, hydroxy, methyl or methoxy;

each $R^5$ is independently H, halogen, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —$NR^{25}R^{26}$ or —$Z^2Q$;

each $Z^2$ is independently a direct bond or $NR^{21}$;

Q is one of Q-1 through Q-106 shown in Exhibit 4 wherein p is an integer from 0 to 5 and q is an integer from 0 to 2;

each $R^7$ is independently halogen, cyano, hydroxy, $C_1$-$C_3$ alkyl, $C_1$-$C_3$ haloalkyl, $C_1$-$C_2$ alkoxy or $C_1$-$C_2$ haloalkoxy;

each $R^{29}$ is independently H, halogen, $C_1$-$C_2$ alkyl, $C_1$-$C_2$ haloalkyl or $C_1$-$C_2$ alkoxy;

$R^{15}$ is H, halogen, cyano, hydroxy, methyl, methoxy or methoxycarbonyl;

$R^{16}$ is H, methyl, methylcarbonyl or methoxycarbonyl;

$R^{28}$ is H, halogen, cyano or $C_1$-$C_4$ alkyl;

each $R^{30}$ and $R^{31}$ is independently selected from $C_1$-$C_6$ alkyl, $C_3$-$C_4$ alkenyl, $C_3$-$C_4$ alkynyl, $C_1$-$C_4$ haloalkyl, $C_3$-$C_6$ haloalkenyl, $C_3$-$C_6$ haloalkynyl, $C_2$-$C_6$ alkoxyalkyl and $C_3$-$C_6$ cycloalkyl;

$R^{32}$ is H, cyano, hydroxy, amino, $C_1$-$C_6$ alkyl or $C_1$-$C_6$ alkoxy; and $R^{33}$ is H or $C_1$-$C_6$ alkyl.

Embodiment A3

A compound of Embodiment A2 wherein

G is selected from G-1, G-2, G-7, G-8, G-14, G-15, G-23, G-24, G-26, G-27, G-36, G-37, G-38, G-49, G-50 and G-55;

G is unsubstituted;

J is selected from J-4, J-5, J-8, J-11, J-15, J-16, J-20, J-29, J-30, J-37, J-38 and J-69;

x is an integer from 0 to 2;

W is O;

X is $X^1$ or $X^2$;

$Z^1$ is a direct bond;

$R^{1a}$ and $R^{1b}$ independently are selected from U-1 through U-50 shown in Exhibit 1 wherein when $R^4$ is attached to a carbon ring member, said $R^4$ is selected from $R^{4a}$, and when $R^4$ is attached to a nitrogen ring member, said $R^4$ is selected from $R^{4b}$, and k is 0, 1 or 2; or $C_2$-$C_5$ alkyl, $C_2$-$C_5$ alkenyl, $C_2$-$C_5$ haloalkyl, $C_2$-$C_5$ haloalkenyl, $C_2$-$C_5$ haloalkylthioalkyl, $C_2$-$C_5$ alkoxyalkyl, $C_2$-$C_5$ haloalkoxyalkyl, $C_2$-$C_5$ alkylthioalkyl, $C_2$-$C_5$ alkylaminoalkyl, $C_2$-$C_5$ alkylcarbonyloxy, $C_2$-$C_5$ haloalkylcarbonyloxy, $C_2$-$C_5$ alkoxy, $C_2$-$C_5$ haloalkoxy, $C_2$-$C_5$ alkylthio, $C_2$-$C_5$ alkylamino or $C_2$-$C_5$ alkylcarbonylamino;

each $R^5$ is independently H, halogen, cyano, $C_1$-$C_6$ alkyl, $C_1$-$C_6$ haloalkyl, $C_1$-$C_6$ alkoxy, $C_1$-$C_6$ haloalkoxy, —$NR^{25}R^{26}$ or —$Z^2Q$;

each $Z^2$ is a direct bond;

each Q is independently Q-1, Q-20, Q-32 through Q-34, Q-45 through Q-47, Q-60 through Q-73, Q-76 through Q-79, Q-84 through Q-94 and Q-98 through Q-106;

p is an integer from 0 to 3;

q is an integer from 0 to 1;

each $R^7$ is independently F, Cl, cyano, hydroxy, methyl or methoxy;

$R^{28}$ is H, halogen or cyano;

each $R^{30}$ and $R^{31}$ is independently selected from $C_1$-$C_6$ alkyl, $C_3$-$C_4$ alkenyl, $C_3$-$C_4$ alkynyl and $C_1$-$C_4$ haloalkyl;

$R^{32}$ is selected H, cyano, hydroxy, amino, $C_1$-$C_3$ alkyl or $C_1$-$C_3$ alkoxy;

$R^{33}$ is selected from H or methyl; and n is 0.

Embodiment A4

A compound of Embodiment A3 wherein

G is selected from G-1, G-2, G-15, G-26, G-27, G-36, G-37 and G-38;

J is J-29;

X is $X^1$ or $X^2$; and the ring comprising X is saturated;

$R^{1a}$ and $R^{1b}$ independently are selected from U-1 through U-3, U-11, U-13, U-20, U-22, U-23, U-36 through U-39 and U-50 in Exhibit 1 wherein when $R^4$ is attached to a carbon ring member, said $R^4$ is selected from $R^{4a}$, and when $R^4$ is attached to a nitrogen ring member, said $R^4$ is selected from $R^{4b}$, and k is 0, 1 or 2; or $C_3$-$C_5$ alkyl, $C_3$-$C_5$ alkenyl, $C_3$-$C_5$ haloalkyl, $C_3$-$C_5$ haloalkenyl, $C_2$-$C_4$ haloalkylthioalkyl, $C_2$-$C_4$ alkoxyalkyl, $C_2$-$C_4$ haloalkoxyalkyl, $C_2$-$C_4$ alkylthioalkyl, $C_2$-$C_4$ alkylaminoalkyl, $C_2$-$C_3$ alkylcarbonyloxy, $C_2$-$C_3$ haloalkylcarbonyloxy, $C_2$-$C_4$ alkoxy, $C_2$-$C_4$ haloalkoxy, $C_2$-$C_4$ alkylthio, $C_2$-$C_4$ alkylamino or $C_2$-$C_3$ alkylcarbonylamino;

each $R^5$ is independently H, halogen, cyano, $C_1$-$C_6$ alkyl, $C_1$-$C_6$ haloalkyl, $C_1$-$C_6$ alkoxy, $C_1$-$C_6$ haloalkoxy or —$Z^2Q$;

Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100 and Q-101 through Q-106;

$R^{28}$ is Cl, F or cyano;

each $R^{30}$ and $R^{31}$ is independently selected from $C_1$-$C_4$ alkyl;

$R^{32}$ is H, cyano, hydroxy, $C_1$-$C_2$ alkyl or $C_1$-$C_2$ alkoxy; and $R^{33}$ is H.

Embodiment A5

A compound of Embodiment A4 wherein

G is selected from G-1, G-2, G-15, G-26 and G-36;

J is any one of J-29-1 to J-29-60 as shown in Exhibit A;

X is $X^1$;

$R^{1a}$ and $R^{1b}$ are each selected from U-1, U-20 and U-50 in Exhibit 1 wherein when $R^4$ is selected from $R^{4a}$, and k is 0, 1 or 2; or $C_3$-$C_5$ haloalkyl, $C_3$-$C_5$ haloalkenyl, $C_3$-$C_5$ haloalkylthioalkyl, $C_3$-$C_5$ haloalkoxyalkyl, $C_2$-$C_3$ haloalkylcarbonyloxy or $C_2$-$C_4$ haloalkoxy;

each $R^5$ is independently cyano, $C_1$-$C_6$ alkyl, $C_1$-$C_6$ alkoxy or —$Z^2Q$;

Q is selected from Q-45, Q-63, Q-64, Q-65, Q-68, Q-69, Q-70, Q-71, Q-72, Q-84 and Q-85; and each $R^{30}$ and $R^{31}$ is independently ethyl or methyl.

Specific embodiments include compounds of Formula 1 selected from the group consisting of:

methyl 4-[4-(2,3-dihydrospiro[1H-indene-1,5'(4'H)-isoxazol]-3'-yl)-2-thiazolyl]-N-(2,5-dimethylphenyl)-1-piperidinecarboximidate, methyl 4-[4-[5-(2,6-difluorophenyl)-4,5-dihydro-3-isoxazolyl]-2-thiazolyl]-N-(2,5-dimethylphenyl)-1-piperidinecarboximidate, methyl 4-[4-[4,5-dihydro-5-(2-oxo-3(2H)-benzoxazolyl)-3-isoxazolyl]-2-thiazolyl]-N-(2,5-dimethylphenyl)-1-piperidinecarboximidate, methyl N-(2,5-dimethylphenyl)-4-[4-[5-(2,6-dimethyylphenyl)-4,5-dihydro-3-isoxazolyl]-2-thiazolyl]-1-piperidinecarboximidate, methyl 4-[4-(3',4'-dihydrospiro[isoxazole-5(4H), 1'(2'H)-naphthalen]-3-yl)-2-thiazolyl]-N-(2,5-dimethylphenyl)-1-piperidinecarboximidate, methyl N-(2,5-dimethylphenyl)-4-[4-[5-(2-fluorophenyl)-4,5-dihydro-3-isoxazolyl]-2-thiazolyl]-1-piperidinecarboximidate, methyl 4-[4-(5-cyano-4,5-dihydro-5-phenyl-3-isoxazolyl)-2-thiazolyl]-N-(2,5-dimethylphenyl)-1-piperidinecarboximidate, methyl 4-[4-[5-(2-cyanophenyl)-4,5-dihydro-3-isoxazolyl]-2-thiazolyl]-N-(2,5-dimethylphenyl)-1-piperidinecarboximidate, and 4-[4-(4,5-dihydro-5-phenyl-3-isoxazolyl)-2-thiazolyl]-N-(2,5-dimethylphenyl)-1-piperidinecarboximidamide.

Combinations of Embodiments 1-179 further are illustrated by:

Embodiment B1

A compound of Formula 1 wherein

E is E-1, E-2 or E-3;

$R^{1a}$, $R^{1b}$, $R^{1c}$ and $R^{1d}$ are a phenyl or 5- or 6-membered heteroaromatic ring optionally substituted with up to 3 substituents independently selected from $R^{4a}$ on carbon ring members and $R^{4b}$ on nitrogen ring members; or $C_1$-$C_8$ alkyl, $C_2$-$C_8$ alkenyl, $C_1$-$C_8$ haloalkyl, $C_2$-$C_8$ alkoxyalkyl, $C_2$-$C_8$ alkylthioalkyl, $C_2$-$C_8$ alkylaminoalkyl, $C_1$-$C_8$ alkoxy, $C_1$-$C_8$ alkylthio, pyrrolidinyl, piperidinyl or morpholinyl;

G is a 5-membered heterocyclic ring optionally substituted with up to 2 substituents selected from $R^3$ on carbon ring members and selected from $R^{11}$ on nitrogen ring members;

J is one of J-1 through J-82 (as depicted in Exhibit 3) wherein the bond shown projecting to the left is bonded to $Z^1$;

each $R^2$ is independently $C_1$-$C_2$ alkyl, $C_1$-$C_2$ haloalkyl, $C_1$-$C_2$ alkoxy, halogen, cyano or hydroxy;

each $R^3$ is independently $C_1$-$C_3$ alkyl, $C_1$-$C_3$ haloalkyl or halogen;

each $R^{4a}$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

each $R^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl;

each $R^{11}$ is independently $C_1$-$C_3$ alkyl;

$R^{15}$ is H, halogen, cyano, hydroxy, —CHO, $C_1$-$C_4$ alkyl, $C_1$-$C_4$ haloalkyl or $C_2$-$C_5$ alkoxycarbonyl;

$R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl; and x is 0, 1, 2, 3, 4 or 5.

Embodiment B2

A compound of Embodiment B1 wherein

E is E-1 or E-2;

$W^1$ is H, cyano, halogen, $OR^{30}$, $SR^{31}$ or $NR^{32}R^{33}$;

$Z^5$ and $Z^6$ are each a direct bond;

G is one of G-1 through G-59 (as depicted in Exhibit 2) wherein the bond projecting to the left is bonded to X, and the bond projecting to the right is bonded to $Z^1$; each $R^{3a}$ is independently selected from H and $R^3$; and $R^{11a}$ is selected from H and $R^{11}$;

J is selected from J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69;

Q is Q-1 through Q-106 (as depicted in Exhibit 4);

$R^{1a}$ and $R^{1b}$ are selected from of U-1 through U-50 (as depicted in Exhibit 1);

each $R^2$ is independently methyl, methoxy, cyano or hydroxy;

each $R^5$ is independently H, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —$NR^{25}R^{26}$ or $Z^2Q$;

$R^{15}$ is H, cyano, halogen, hydroxy, methyl or methoxycarbonyl;

$R^{16}$ is H, methyl, methylcarbonyl or methoxycarbonyl;

each $R^{30}$ and $R^{31}$ independently is selected from $C_1$-$C_6$ alkyl, $C_3$-$C_4$ alkenyl, $C_3$-$C_4$ alkynyl, $C_1$-$C_4$ haloalkyl, $C_3$-$C_6$ haloalkenyl, $C_3$-$C_6$ haloalkynyl, $C_2$-$C_6$ alkoxyalkyl and $C_3$-$C_6$ cycloalkyl;

$R^{32}$ is selected H, cyano, hydroxy, amino, $C_1$-$C_6$ alkyl;

$R^{33}$ is selected from H, $C_1$-$C_6$ alkyl;

each $Z^4$ is C(=O);

k is 0, 1 or 2;

p is 0, 1, 2 or 3; and q is 0, 1 or 2;

Embodiment B3

A compound of Embodiment B2 wherein

G is selected from G-1, G-2, G-7, G-8, G-14, G-15, G-23, G-24, G-26, G-27, G-36, G-37, G-38, G-49, G-50 and G-55;

J is selected from J-4, J-5, J-8, J-11, J-15, J-16, J-20, J-29, J-30, J-37, J-38 and J-69;

each Q is independently Q-1, Q-20, Q-32 through Q-34, Q-45 through Q-47, Q-60 through Q-73, Q-76 through Q-79, Q-84 through Q-94 and Q-98 through Q-106;

A is CH$_2$ or NH;
W$^1$ is cyano, Cl, F, Br or OR$^{30}$;
W is O;
X is X$^1$, X$^2$ or X$^3$;
each R$^5$ is independently H, cyano, C$_1$-C$_6$ alkyl, C$_1$-C$_6$ haloalkyl, C$_3$-C$_8$ cycloalkyl, C$_3$-C$_8$ halocycloalkyl, C$_2$-C$_6$ alkoxyalkyl, C$_1$-C$_6$ alkoxy, C$_1$-C$_6$ haloalkoxy, C$_3$-C$_8$ cycloalkoxy, C$_2$-C$_6$ alkenyloxy, C$_2$-C$_6$ haloalkenyloxy, C$_2$-C$_6$ alkynyloxy, C$_2$-C$_6$ alkoxyalkoxy, C$_2$-C$_6$ alkylcarbonyloxy, C$_2$-C$_6$ haloalkylcarbonyloxy, C$_1$-C$_6$ alkylthio, C$_1$-C$_6$ haloalkylthio, C$_3$-C$_{10}$ trialkylsilyl, —NR$^{25}$R$^{26}$ or Z$^2$Q;
Z$^1$ is a direct bond;
Z$^2$ is a direct bond or NR$^{21}$;
R$^{1a}$ and R$^{1b}$ are selected from U-1 through U-3, U-11, U-13, U-20, U-22, U-23, U-36 through U-39 and U-50;
each R$^3$ is independently methyl or halogen;
each R$^{4a}$ is independently C$_1$-C$_2$ alkyl, C$_1$-C$_2$ haloalkyl, halogen, C$_1$-C$_2$ alkoxy or C$_1$-C$_2$ haloalkoxy;
each R$^{4b}$ is independently C$_1$-C$_2$ alkyl or C$_1$-C$_2$ haloalkyl;
each R$^7$ is independently halogen, cyano, C$_1$-C$_3$ alkyl, C$_1$-C$_3$ haloalkyl, hydroxy, C$_1$-C$_2$ alkoxy or C$_1$-C$_2$ haloalkoxy;
R$^{30}$ and R$^{31}$ selected from C$_1$-C$_6$ alkyl, C$_3$-C$_4$ alkenyl, C$_3$-C$_4$ alkynyl and C$_1$-C$_4$ haloalkyl;
k is 1 or 2;
n is 0; and
x is 1 or 2.

Embodiment B4

A compound of Embodiment B3 wherein
G is selected from G-1, G-2, G-15, G-26, G-27, G-36, G-37 and G-38; and G is unsubstituted;
J is J-29;
Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100 and Q-101 through Q-106.
X is X$^1$ or X$^2$; and the ring comprising X is saturated;
R$^{1a}$ and R$^{1b}$ are selected from U-1, U-20 or U-50;
each R$^{4a}$ is independently C$_1$-C$_2$ alkyl, trifluoromethyl, Cl, Br, I or methoxy;
each R$^{4b}$ is independently C$_1$-C$_2$ alkyl or trifluoromethyl; and
each R$^5$ is independently H, cyano, C$_1$-C$_6$ alkyl, C$_1$-C$_6$ haloalkyl, C$_1$-C$_6$ alkoxy, C$_1$-C$_6$ haloalkoxy, —NR$^{25}$R$^{26}$ or Z$^2$Q.

Embodiment B5

A compound of Embodiment B4 wherein
E is E-1;
G is selected from G-1, G-2, G-15, G-26 and G-36;
J is any one of J-29-1 to J-29-60 (depicted in Exhibit A);
Q is selected from Q-45, Q-63, Q-64, Q-65, Q-68, Q-69, Q-70, Q-71, Q-72, Q-84 and Q-85; and
X is X$^1$.

Of particular note are compounds of Formula 1 including geometric and stereoisomers, N-oxides, and salts thereof (including but not limited to Embodiments 1-179, C1-C173, A1-A5, and B1-5 above) wherein A is CHR$^{15}$ or NR$^{16}$.

Of note are compounds of Formula 1 including geometric and stereoisomers, N-oxides, and salts thereof (including but not limited to Embodiments 1-179, C1-C173, A1-A5, and B1-5 above) wherein R$^{1a}$, R$^{1b}$, R$^{1c}$ and R$^{1d}$ are an optionally substituted phenyl, optionally substituted naphthalenyl or an optionally substituted 5- to 6-membered heteroaromatic ring;

or cyano, C$_1$-C$_8$ alkyl, C$_2$-C$_8$ alkenyl, C$_2$-C$_8$ alkynyl, C$_1$-C$_8$ haloalkyl, C$_2$-C$_8$ haloalkenyl, C$_2$-C$_8$ haloalkynyl, C$_3$-C$_8$ cycloalkyl, C$_3$-C$_8$ halocycloalkyl, C$_4$-C$_{10}$ alkylcycloalkyl, C$_4$-C$_{10}$ cycloalkylalkyl, C$_4$-C$_{10}$ halocycloalkylalkyl, C$_5$-C$_{10}$ alkylcycloalkylalkyl, C$_2$-C$_8$ alkoxyalkyl, C$_4$-C$_{10}$ cycloalkoxyalkyl, C$_3$-C$_{10}$ alkoxyalkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylaminoalkyl, C$_3$-C$_{10}$ dialkylaminoalkyl, C$_2$-C$_8$ haloalkylaminoalkyl, C$_4$-C$_{10}$ cycloalkylaminoalkyl, C$_1$-C$_8$ alkoxy, C$_1$-C$_8$ haloalkoxy, C$_3$-C$_8$ cycloalkoxy, C$_1$-C$_8$ halocycloalkoxy, C$_4$-C$_{10}$ cycloalkylalkoxy, C$_2$-C$_8$ alkenyloxy, C$_2$-C$_8$ haloalkenyloxy, C$_2$-C$_8$ alkynyloxy, C$_3$-C$_8$ haloalkynyloxy, C$_2$-C$_8$ alkoxyalkoxy, C$_1$-C$_8$ alkylthio, C$_1$-C$_8$ haloalkylthio, C$_3$-C$_8$ cycloalkylthio, C$_3$-C$_{10}$ trialkylsilyl, C$_1$-C$_8$ alkylamino, C$_2$-C$_8$ dialkylamino, C$_1$-C$_8$ haloalkylamino, C$_2$-C$_8$ halodialkylamino, C$_3$-C$_8$ cycloalkylamino, C$_2$-C$_8$ alkylcarbonylamino, C$_2$-C$_8$ halo alkylcarbonylamino, C$_1$-C$_8$ alkylsulfonylamino, C$_1$-C$_8$ halo alkylsulfonylamino, pyrrolidinyl, piperidinyl or morpholinyl.

Of further note are compounds of Formula 1 including geometric and stereoisomers, N-oxides, and salts thereof (including but not limited to Embodiments 1-179, C1-C173, A1-A5, and B1-5 above) wherein each T$^4$ is independently phenyl, phenylethynyl or a 5- to 6-membered heteroaromatic ring, each optionally substituted with up to 5 substituents independently selected from R$^{29}$.

Also of note are compounds of Formula 1 including geometric and stereoisomers, N-oxides, and salts thereof (including but not limited to Embodiments 1-179, C1-C173, A1-A5, and B1-5 above) wherein R$^{32}$ is H, cyano, hydroxy, amino, C$_1$-C$_6$ alkyl, C$_3$-C$_6$ alkenyl, C$_3$-C$_6$ alkynyl, C$_1$-C$_6$ haloalkyl, C$_3$-C$_6$ haloalkenyl, C$_3$-C$_6$ haloalkynyl, C$_3$-C$_6$ cycloalkyl, C$_4$-C$_8$ cycloalkylalkyl, C$_2$-C$_6$ alkoxyalkyl, C$_1$-C$_6$ alkoxy, C$_1$-C$_6$ haloalkoxy, C$_1$-C$_6$ alkylsulfonyl, C$_1$-C$_6$ haloalkylsulfonyl, C$_1$-C$_6$ alkylamino, C$_2$-C$_8$ dialkylamino, C$_1$-C$_6$ haloalkylamino or C$_2$-C$_8$ halodialkylamino.

Also of note are compounds of Formula 1 including geometric and stereoisomers, N-oxides, and salts thereof (including but not limited to Embodiments 1-179, C1-C173, A1-A5, and B1-5 above) wherein R$^{29}$ is other then H.

Of further note are compounds of Formula 1 including geometric and stereoisomers, N-oxides, and salts thereof (including but not limited to Embodiments 1-179, C1-C173, A1-A5, and B1-5 above) wherein each Z$^3$ is a direct bond, O, C(=O), C(=S), S(O)$_m$, CHR$^{20}$, —CR$^{24}$=CR$^{27}$—, —OCHR$^{20}$— or —CHR$^{20}$O—.

Also noteworthy are compounds of Formula 1 including but not limited to Embodiments 1-179, C1-C173, A1-A5, and B1-5 above.

This invention provides a fungicidal composition comprising a compound of Formula 1 (including all geometric and stereoisomers, N-oxides, and salts thereof), and at least one other fungicide. Of note as embodiments of such compositions are compositions comprising a compound corresponding to any of the compound embodiments described above.

This invention provides a fungicidal composition comprising a fungicidally effective amount of a compound of Formula 1 (including all geometric and stereoisomers, N-oxides, and salts thereof), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all geometric and stereoisomers, N-oxides, and salts thereof). Of note as embodiment of such methods are methods comprising applying a fungicidally effective amount of a compound corresponding to any of the compound embodiments describe above. Of particular notes are embodiment where the compounds are applied as compositions of this invention.

One or more of the following methods and variations as described in Schemes 1-36 can be used to prepare the compounds of Formula 1. The definitions of A, E, G, J, $T^4$, Q, W, $W^1$, X, $Z^1$, $Z^2$, $Z^3$, $Z^5$, $Z^6$, $Z^7$, $Z^8$, $R^{1a}$, $R^{1b}$, $R^{1c}$, $R^{1d}$, $R^2$, $R^5$, $R^{15}$, $R^{16}$, $R^{31}$, $R^{32}$, d and n in the compounds of Formulae 1-57 below are as defined above in the Summary of the Invention unless otherwise noted. Formulae 1a-1u are subsets of the compounds of Formula 1, and all substituents for Formulae 1a-1u are as defined above for Formula 1.

As shown in Scheme 1 certain compounds of Formulae 1a-1d (Formula 1 wherein E is E-1 and $W^1$ is $OR^{30}$, $SR^{31}$, $NR^{32}R^{33}$ or CN) can be prepared by reacting an imidoyl chloride of Formula 2 with a compound of Formula 3 in the presence of an acid scavenger. Suitable acid scavengers include, but are not limited to, amine bases such as triethylamine, N,N-diisopropylethylamine and pyridine, hydroxides such as sodium and potassium hydroxide, and carbonates such as sodium carbonate and potassium carbonate. Alternatively, the compounds of Formulae 2 and 3 can be contacted in the absence of an acid scavenger to provide compounds Formulae 1a-1c as the corresponding HCl salts, which are also compounds of the present invention. If desired, the HCl salts can be free-based by standard methods to give compounds of Formulae 1a-d. Regardless of whether the reaction is conducted with or without an acid scavenger, it is typically conducted in a suitable organic solvent at a temperature between about −20 and 100° C. A variety of solvents can be used to form the suitable solvent for this method, for example nitriles, such as acetonitrile, ethers such as tetrahydrofuran, and halogenated hydrocarbons such as dichloromethane, and amides such as N,N-dimethylformamide, and mixtures thereof. Compounds of Formulae 1a-1d can be generally classified as isoureas, isothioureas, guanidines and cyanoamidines, respectively. For leading references on these classes of compounds see J. Lon Mathias, *Organic Preparations and Procedures International* 1980, 12(5), 309-326; *Comprehensive Organic Chemistry*, vol. 2, I. O, Sutherland, Ed., Pergamon Press, Oxford; *Rodd's Chemistry of Carbon Compounds*, vol. 1C, Elsevier, N.Y.; A. R. Katritzky et al., *J. Organic Chem.* 2004, 69, 309-313. One skilled in the art will recognize that certain compounds of Formulae 1a, 1c, and 1d can be prepared from the corresponding compound of Formula 1b by treatment with an appropriate compound of Formula 3. For example, the preparation of thiuronium salts and their conversion to guanidines is described in the literature, see C. R. Rasmussen et al., *Synthesis* 1988, 6, 460-466. Also, the method is demonstrated in Example 3 and Step C of Example 9. Imidoyl chlorides of Formula 2 can be prepared as described below (see paragraph below Scheme 7). Many compounds of Formula 3 are commercially available and can be prepared by methods well documented in the chemistry art.

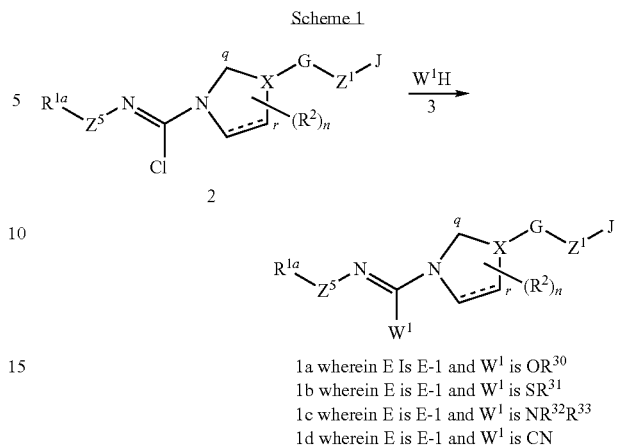

1a wherein E Is E-1 and $W^1$ is $OR^{30}$
1b wherein E is E-1 and $W^1$ is $SR^{31}$
1c wherein E is E-1 and $W^1$ is $NR^{32}R^{33}$
1d wherein E is E-1 and $W^1$ is CN In an alternate procedure, as shown in Scheme 2, certain compounds of Formulae 1a-1c and Formula 1e (Formula 1 wherein E is E-1 and $W^1$ is $R^{28}$) can be prepared by reacting an amine of Formula 4 with an imidoyl chloride of Formula 5 using conditions analogous to those described in Scheme 1. Many imidoyl chlorides of Formula 5 can be prepared by methods disclosed in the art, for example, see R. Bonnett in The Chemistry of the Carbon-Nitrogen Double Bond, S. Patei, Ed., Interscience Publishers, and references cited therein. Some imidoyl chlorides of Formula 5 are commercially available (e.g., Formula 5 wherein $R^{1a}$ is phenyl, substituted phenyl or lower alkyl, $Z^5$ is a direct bond and W is OMe, SMe, or $N(Me)_2$ can be commercial obtained) and can be prepared by methods documented in the chemistry art. A method for preparing compounds of Formula 4 is described below in Scheme 20.

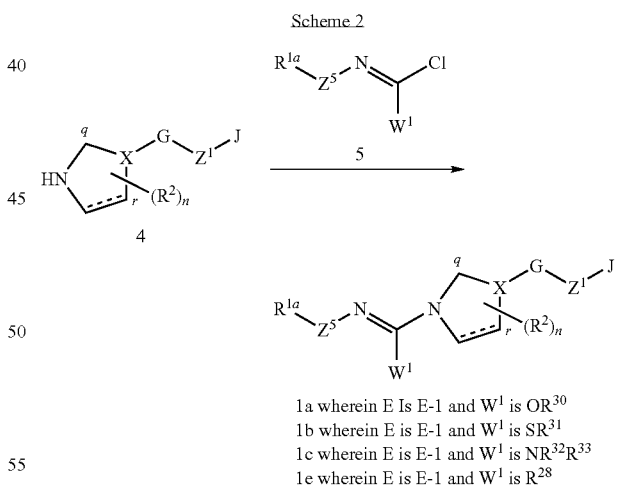

1a wherein E Is E-1 and $W^1$ is $OR^{30}$
1b wherein E is E-1 and $W^1$ is $SR^{31}$
1c wherein E is E-1 and $W^1$ is $NR^{32}R^{33}$
1e wherein E is E-1 and $W^1$ is $R^{28}$ Schemes 1 and 2 are representative of just two methods of preparing compounds of Formula 1b. In another method, as shown in Scheme 3, compounds of Formula 1b can be prepared by reacting a thiourea of Formula 1f (Formula 1 wherein E is E-2, A is NH and W is S) with an alkylating or acylating agent of a Formula 6 wherein $Y^1$ is a nucleophic reaction leaving group such as halide (e.g., Cl, Br, I) or sulfonate (e.g., mesylate, triflate, p-toluenesulfonate), and the like. The method is conducted in the presence of an acid scavenger and a suitable organic solvent at a temperature between about 0 and 100° C. Suitable solvents include, for example, dichloromethane, tetrahydrofuran, acetonitrile, N,N-dimethylformamide, and mixtures thereof. Suitable acid scavengers comprise, for example, amine bases such as triethylamine, N,N-diisopropylethylamine and pyridine, hydroxides such as sodium and potassium hydroxide and carbonates such as sodium carbonate and potassium carbonate. Alternatively, compounds of Formulae 1f and 6 can be contacted in the absence of an acid scavenger to provide the corresponding isothiuronium salts of Formula 1b, which are also compounds of the present invention. In a subsequent reaction the salt can be free-based using standard methods described in the art to provide compounds of Formula 1b. For an example illustrating the preparation of thiuronium salts and their conversion guanidines see C. R. Rasmussen et al., *Synthesis* 1988, 6, 460-466. Also, Step D of Example 1 illustrates the method of Scheme 3.

Many compounds of Formula 6 are known and can be prepared by general methods disclosed in the art. For the preparation of Compounds of Formula 1f see Scheme 6.

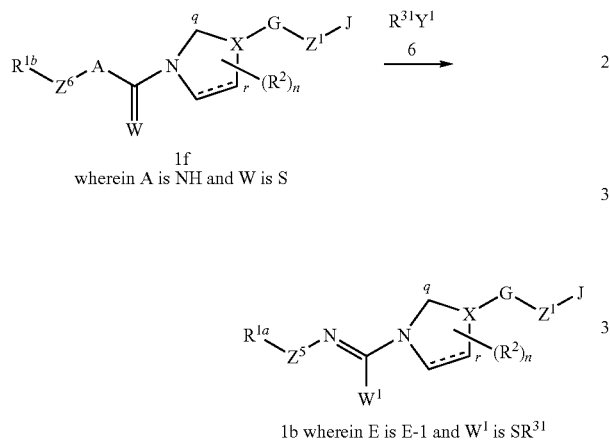

Compounds of Formula 1b can also be prepare by reacting an amine of Formula 4 with a dithiocarbamic acid of Formula 7 as illustrated in Scheme 4. The reaction of Scheme 4 is typically conducted in a suitable solvent at a temperature between about 0 to 100° C. Examples of suitable solvents include acetonitrile, tetrahydrofuran, dichloromethane, N,N-dimethylformamide, and mixtures thereof.

Dithiocarbamic acids of Formula 7 can be prepared from the corresponding amines, carbon disulfide and two equivalents of a base, followed by treatment with an alkylating agent according to the general method of Alvarez-Ibarra et al., *Organic Preparations and Procedures* 1991, 23(5), 611-616.

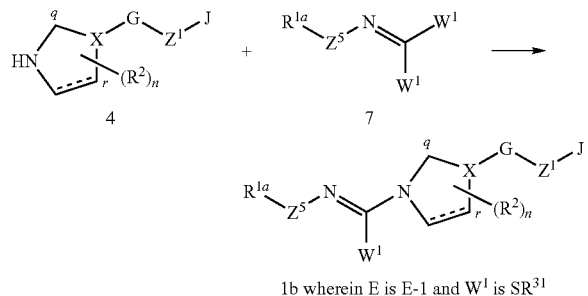

Certain compounds of Formula 1e wherein $R^{28}$ is H can be prepared by treating an amine of Formula 4 with a methoxy or ethoxy imine of Formula 8 as shown in Scheme 5. Imines of Formula 8 can be obtained from the corresponding amines. The procedure involves heating the amines with trimethylorthoformate or triethylorthoformate in toluene or xylenes in the presence of a catalytic amount of p-toluenesulfonate. The method of Scheme 5 is illustrated in Example 2.

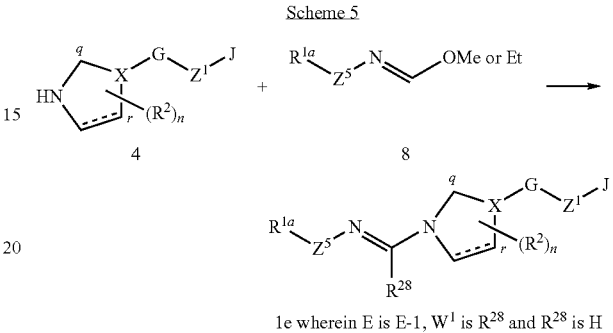

Compounds of Formula 1f (Formula 1 wherein E is E-2 and A is NH) can be prepared by reacting an amine of Formula 4 with an isocyanate or isothiocyanate of Formula 9 as depicted in Scheme 6. This reaction is typically carried out at an ambient temperature in an aprotic solvent such as dichloromethane or acetonitrile. The method of Scheme 6 is illustrated in Step C of Example 1, Example 4, Example 5 and Step A of Example 9.

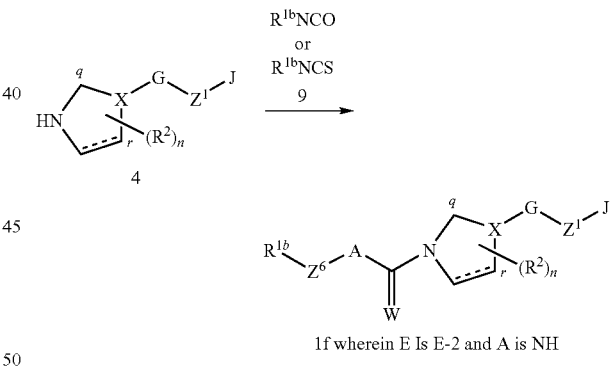

Compounds of Formula 1f can also be prepared by the reaction of an amine of Formula 10 with a carbamoyl or thiocarbamoyl chloride or imidazole of Formula 11 ($Y^2$ is Cl or imidazol-1-yl) as shown in Scheme 7. When $Y^2$ is chlorine, the reaction is typically carried out in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. The carbamoyl or thiocarbamoyl chlorides of Formula 11 (wherein $Y^2$ is Cl) can be prepared from amines of Formula 4 by treatment with phosgene or thiophosgene, respectively, or their equivalents; while carbamoyl or thiocarbamoyl imidazoles of Formula 11 (when $Y^2$ is imidazol-1-yl) can be prepared from amines of Formula 3 by treatment with 1,1'-carbonyldiimidazole or 1,1'-thiocarbonyldiimidazole, respectively, according to general methods known to one skilled in the art.

Scheme 7

R$^{1b}$Z$^6$NH$_2$ +
10

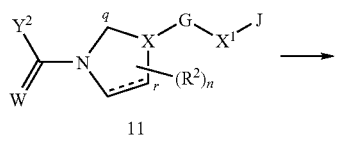

11
wherein Y$^2$ is Cl or imidazol-1-yl

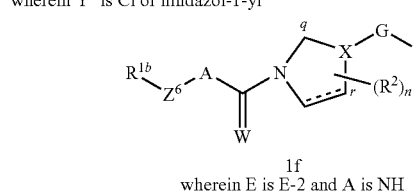

1f
wherein E is E-2 and A is NH

Imidoyl chlorides of Formula 2 (see Scheme 1) can be prepared from compounds of Formula 1f by treating with thionyl chloride, phosphorous oxychloride or phosphorous pentachloride in a solvent such as dichlormethane. For typical reactions conditions see, for example, W. Zielinski et al., *Heterocycles* 1998, 48, 319-327 and references given in Schemes 1 and 2. Also, Step B of Example 10 illustrates the preparation of a Compound of Formula 2.

As shown in Scheme 8, compounds of Formula 1g (Formula 1 wherein E is E-2, A is CHRR$^{15}$ and W is O) can be prepared by coupling of an acid chloride of Formula 12 with an amine of Formula 4 in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. In certain instances it is useful to use polymer-supported acid scavengers such as polymer-bound N,N-diisopropylethylamine and polymer-bound 4-(dimethylamino)pyridine. Acid salts of the Formula 4 amines can also be used in this reaction, provided that at least 2 equivalents of the acid scavenger is present. Typical acids used to form salts with amines include hydrochloric acid, oxalic acid and trifluoroacetic acid.

Scheme 8

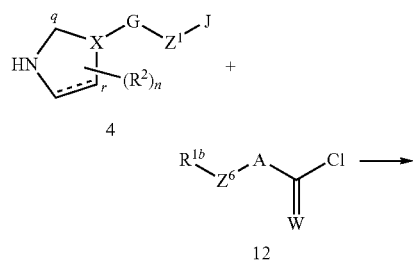

12

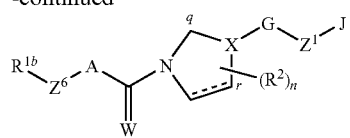

1g
wherein E is E-2 and A is CHR$^{15}$ and W is O

In a subsequent step, amides of Formula 1g can be converted to thioamides of Formula 1g wherein W is S using a variety of standard thiating reagents such as phosphorus pentasulfide or 2,4-bis(4-methoxyphenyl)-1,3-dithia-2,4-diphosphetane-2,4-disulfide (Lawesson's reagent).

An alternate procedure for the preparation of compounds of Formula 1g is depicted in Scheme 9 and involves coupling of an amine Formula 4 (or its acid salt) with an acid of Formula 13 in the presence of a dehydrative coupling reagent such as dicyclohexylcarbodiimide (DCC), 1-(3-dimethylaminopropyl)-3-ethylcarbodiimide hydro-chloride (EDC) or O-benzotriazol-1-yl-N,N,N',N'-tetramethyluronium hexafluorophosphate (HBTU). Polymer-supported reagents are also useful, such as polymer-bound cyclohexylcarbodiimide. The method of Scheme 9 is typically conducted in a suitable solvent such as dichloromethane or acetonitrile and in the presence of a base such as triethylamine or N,N-diisopropylethylamine at a temperature between about 0 and 40° C. Scheme 9 is illustrated in Step D of Example 6, Example 7 and Example 8.

Scheme 9

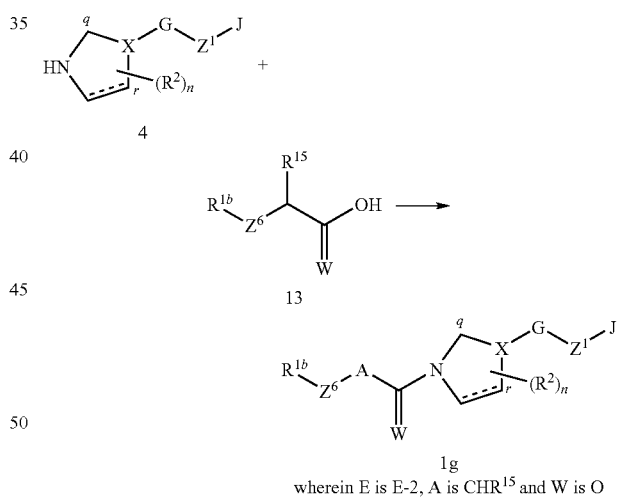

1g
wherein E is E-2, A is CHR$^{15}$ and W is O

As described above, amides of Formula 1g can be converted to thioamides of Formula 1g wherein W is S using a variety of standard thiating reagents.

Many acids of Formula 13 are known or can be prepared by methods known to one skilled in the art. Acid chlorides of Formula 12 can be readily prepared from acids of Formula 13 by numerous well-known methods.

As the synthetic literature includes many amide-forming methods, the synthetic procedures of Schemes 8 and 9 are simply representative examples of a wide variety of methods useful for the preparation of compounds Formula 1g.

Certain compounds of Formula 1g wherein W is O, Z$^6$ is a direct bond and R$^{1b}$ is cyano or a group linked through a heteroatom can be prepared by reacting a compound of Formula 14 and a haloacetamide of Formula 15 (wherein $Y^3$ is Cl, Br or I) as shown in Scheme 10. The reaction is carried out in the presence of a base such as sodium hydride or potassium carbonate and a solvent such as tetrahydrofuran, N,N-dimethylformamide or acetonitrile at a temperature between about 0 to 80° C. The haloacetamide of Formula 15 can be prepared by the reaction of an amine of Formula 4 with an α-halocarboxylic acid halide or an α-halocarboxylic acid or its anhydride, analogous to the amide-forming reactions described in Schemes 8 and 9.

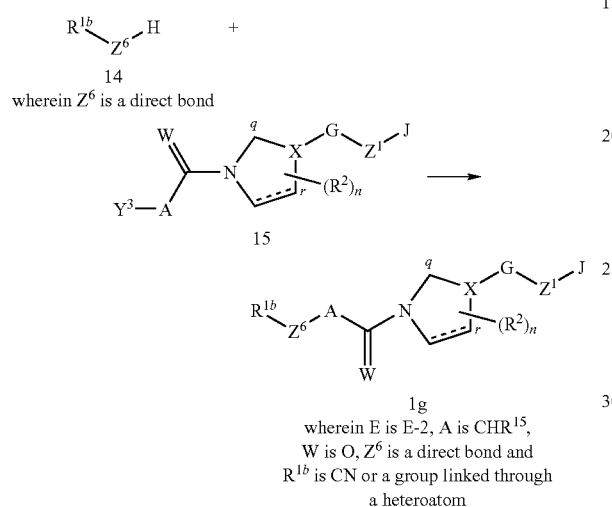

As shown in Scheme 11, compounds of Formula 1h (Formula 1 wherein E is E-2 and A is C(=O)) can be prepared by coupling an α-ketoacid chloride of Formula 16 with an amine of Formula 4 in the presence of a suitable acid scavenger, analogous to the method described in Scheme 8. The α-ketoacid chlorides can be prepared from the corresponding α-ketoacids by standard methods known in the art.

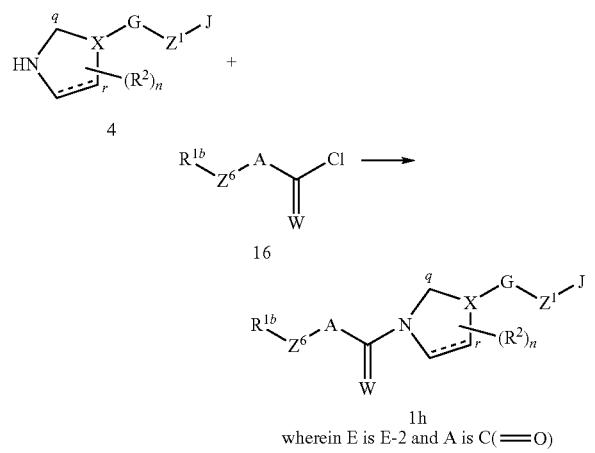

Alternately, is shown in Scheme 12, compounds of Formula 1h can be prepared by coupling of an amine of Formula 4 (or its acid salt) with an α-ketoacid of Formula 17 in the presence of a dehydrative coupling reagent, analogous to method described in Scheme 9. Many α-ketoacids of Formula 17 are known and can be prepared by methods known to one skilled in the art.

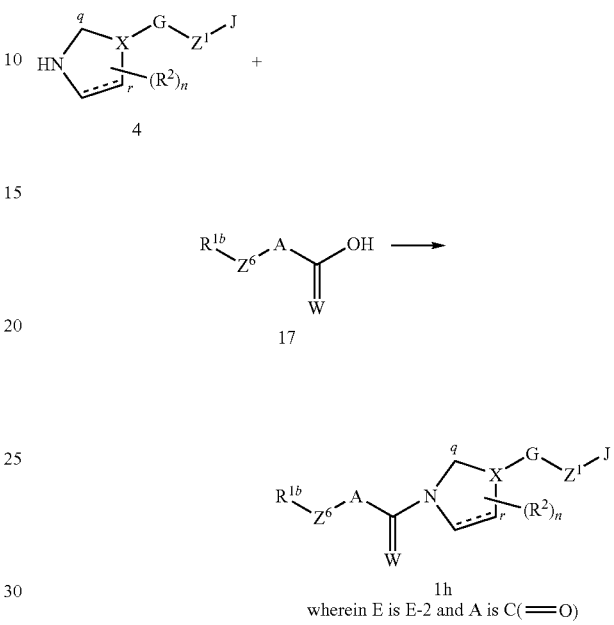

As shown in Scheme 13, compounds of Formula 1h wherein $R^{1b}$ is a group linked through a heteroatom can be prepared by reacting a compound of Formula 14 with an α-ketoacid chloride of Formula 18a in the presence of a suitable acid scavenger, analogous to method described in Scheme 8. The compounds of Formula 18a can be prepared from the corresponding amines of Formula 4 by treatment with oxalyl chloride in a solvent such chloroform or toluene at 0 to 110° C., or in a two-step procedure involving treatment with ethyl chlorooxoacetate in the presence of an acid scavenger to give the α-ketoesters of Formula 18a (e.g., L is OEt) followed by standard ester hydrolysis to the α-ketoacids of Formula 18b by methods as known in the art. One skilled in the art will also recognize that the compounds of Formula 1h can also be prepared by coupling of an amine of Formula 4 (or its acid salt) with an α-ketoacid of Formula 18b in the presence of a dehydrative coupling reagent, analogous to method described in Scheme 9.

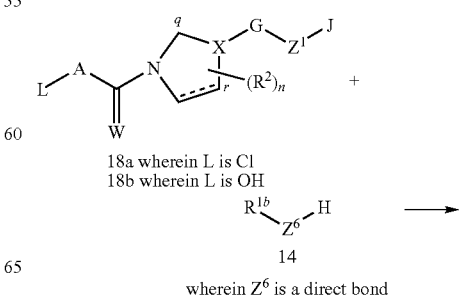

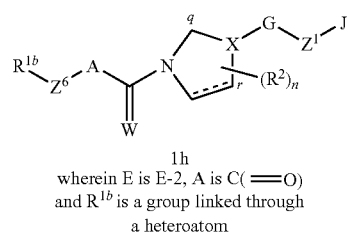

1h
wherein E is E-2, A is C(═O)
and R$^{1b}$ is a group linked through
a heteroatom As shown in Scheme 14, certain compounds of Formula 1i (Formula 1 wherein E is E-3 and A is CHR$^{15}$) can be prepared by reacting a sulfinyl, sulfonyl or sulfamoyl chloride of Formula 19 with an amine of Formula 4 in the presence of a suitable acid scavenger. The method of Scheme 14 is conducted in a solvent such as dichloromethane, tetrahydrofuran, acetonitrile or dimethylformamide at a temperature between about −20 and 100° C. Suitable acid scavengers include, for example, amine bases such as triethylamine, N,N-diisopropylethylamine and pyridine, hydroxides such as sodium and potassium hydroxide and carbonates such as sodium carbonate and potassium carbonate. Many compounds of Formula 19 are known or can be prepared by one skilled in the art. For leading references on the preparation of sulfinyl, sulfonyl and sulfamoyl chlorides and their conversion to sulfinamides, sulfonamides and sulfamides, respectively, see J. G. Tillett in *The Chemistry of Sulfinic Acids, Esters and their Derivatives*, S. Patai, Ed., John Wiley & Sons, 1990; *The Chemistry of Sulfonic Acids, Esters and their Derivatives*, S. Patai and Z. Rappoport, Eds., John Wiley & Sons, 1991; J. H. Youn et al., *Tetrahedron Letters* 1986, 27(13), 1493-1494 and references cited therein; *Comprehensive Organic Chemistry*, vol. 3, Neville Jones, Ed., Pergamon Press, Oxford, 1979.

Scheme 14

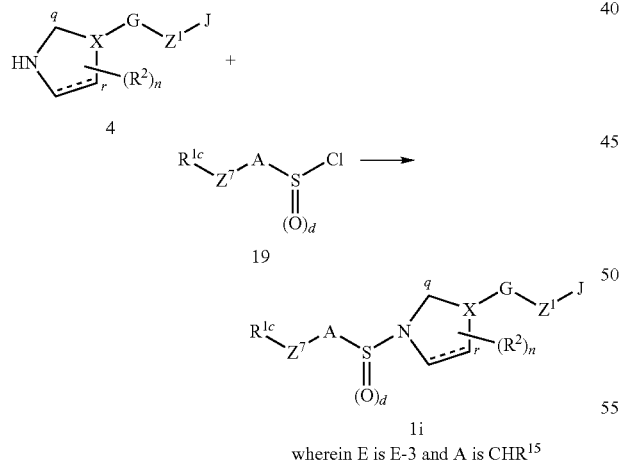

1i
wherein E is E-3 and A is CHR$^{15}$

A method for preparing compounds of Formula 1j (Formula 1 wherein E is E-3, A is NH and d is 2) is depicted in Scheme 15. As shown, a sulfamoyl chloride of Formula 20 is treated with an amine of Formula 10, analogous to the method described in Scheme 14. The sulfamoyl chlorides of Formula 20 can be prepared by treating the corresponding amines of Formula 4 with sulfuryl chloride by methods described in the references cited in Scheme 14.

Scheme 15

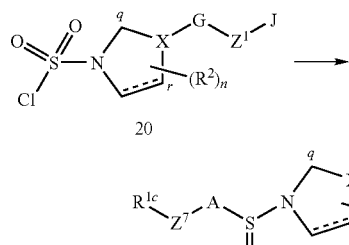

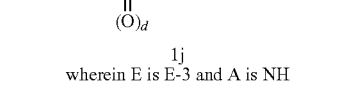

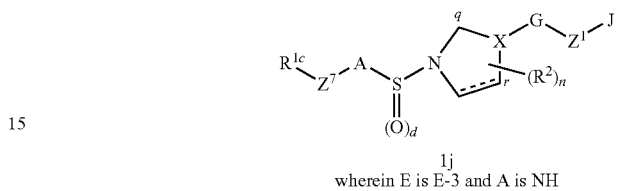

1j
wherein E is E-3 and A is NH

As shown in Scheme 16, compounds of Formula 1k (Formula 1 wherein E is E-4) can be prepared by reacting a sulfonimidoyl chloride of Formula 21 with an amine of Formula 4 in the presence of a suitable acid scavenger. The method of Scheme 16 is typically conducted in a suitable solvent such as dichloromethane, tetrahydrofuran, acetonitrile or dimethylformamide, at a temperature between about −20 and 100° C. Suitable acid scavengers include amine bases such as triethylamine, N,N-diisopropylethylamine and pyridine, hydroxides such as sodium and potassium hydroxide and carbonates such as sodium carbonate and potassium carbonate. Many compounds of Formula 21 are known and can be prepared methods disclosed in a variety of published references. For leading references on the preparation of sulfonimidoyl chlorides and their conversions to sulfonamidamides, see C. R. Johnson, *J. Organic Chem.* 1979, 44, 2055-2061; K. Okuma et al., *J. Organic Chemistry* 1988, 53, 4190-4193; C. R. Johnson in *Comprehensive Organic Chemistry*, vol. 3, part 11, Neville Jones, Ed., Pergamon Press, Oxford, 1979.

Scheme 16

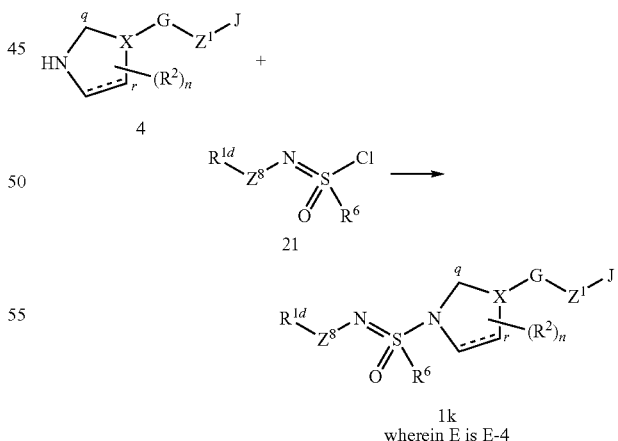

1k
wherein E is E-4

Compounds of Formula 1n (Formula 1 wherein E is E-1, E-2, E-3 or E-4 and the ring containing X is saturated) can be prepared from compounds of Formula 1m (Formula 1 wherein E is E-1, E-2, E-3 or E-4 and the ring containing X is unsaturated) by catalytic hydrogenation as shown in Scheme 17. Typical conditions involve exposing a compound of Formula 1m to hydrogen gas at a pressure of 70 to 700 kPa, preferably 270 to 350 kPa, in the presence of a metal catalyst such as palladium supported on an inert carrier such as activated carbon, in a weight ratio of 5 to 20% of metal to carrier, suspended in a solvent such as ethanol at an ambient temperature. This type of reduction is very well known; see, for example, *Catalytic Hydrogenation*, L. Cerveny, Ed., Elsevier Science, Amsterdam, 1986. One skilled in the art will recognize that other certain functionalities that may be present in compounds of Formula 1m can also be reduced under catalytic hydrogenation conditions, thus requiring a suitable choice of catalyst and conditions.

Scheme 17

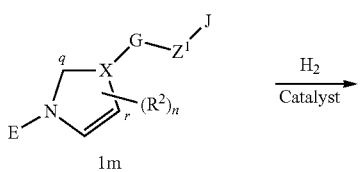
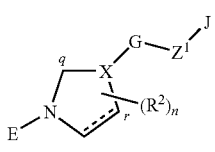

1m
wherein E is E-1, E-2, E-3 or E-4
and the ring containing X is unsaturated

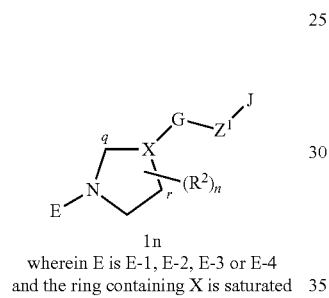

1n
wherein E is E-1, E-2, E-3 or E-4
and the ring containing X is saturated

Certain compounds of Formula 1p (Formula 1 wherein X is $X^1$, $X^5$, $X^7$ or $X^9$ and G is linked to the ring containing X via a carbon atom) can be prepared by displacement of an appropriate leaving group $Y^1$ on Formula 22 with a nitrogen-containing heterocycle of Formula 23 in the presence of a base as depicted in Scheme 18. Suitable bases include sodium hydride or potassium carbonate. The reaction is conducted in a suitable solvent such as N,N-dimethylformamide or acetonitrile at a temperature between about 0 and 80° C. Suitable leaving groups in the compounds of Formula 22 include nucleophic reaction leaving group such as halide (e.g., Cl, Br, I) or sulfonate (e.g., mesylate, triflate, p-toluenesulfonate), and the like. Compounds of Formula 22 can be prepared from the corresponding compounds wherein $Y^1$ is OH, using general methods known in the art.

Scheme 18

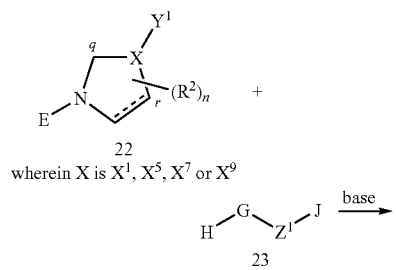

1p
wherein X is $X^1$, $X^5$, $X^7$ or $X^9$ and G is linked
to the ring containing X via a carbon atom Compounds of Formula 1q (Formula 1 wherein X is $X^2$ or $X^8$) can be prepared by reaction of a compound of Formula 24 with a heterocyclic halide or triflate (OS(O)$_2$CF$_3$) of Formula 25 as shown in Scheme 19. The reaction is carried out in the presence of a base such as potassium carbonate and in a solvent such as dimethylsulfoxide, N,N-dimethylformamide or acetonitrile at a temperature between about 0 to 80° C. Compounds of Formula 25 wherein $Y^4$ is triflate can be prepared from corresponding compounds wherein $Y^4$ is OH by methods known to one skilled in the art.

Scheme 19

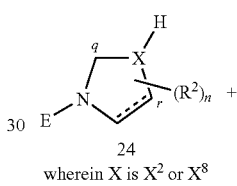

24
wherein X is $X^2$ or $X^8$

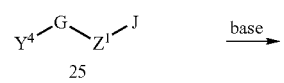

25

$Y^4$ is halide or triflate (OS(O)$_2$CF$_3$)

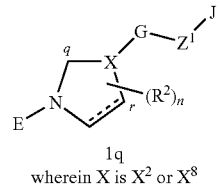

1q
wherein X is $X^2$ or $X^8$

Amines of Formula 4 can be prepared from the corresponding protected amines of Formula 26 wherein $Y^5$ is an amine-protecting group as shown in Scheme 20. A wide variety of amine-protecting groups are useful in the present method, as the only requirement is for the group to be displaceable during the reaction, thus generating a compound of Formula 4. For examples of appropriate protecting groups see T. W. Greene and P. G. M. Wuts, *Protective Groups in Organic Synthesis*, 2nd ed., John Wiley & Sons, Inc., New York, 1991. The protecting group can be removed and the amine isolated as either an acid salt or free-amine by general methods known in the art. One skilled in the art will also recognize that the protected amines of Formula 26 can be prepared by methods analogous to those described in Schemes 17, 18 and 19 above where the group E is replaced by $Y^5$ to give useful intermediates of Formula 26 for the preparation of compounds of Formula 1. The method of Scheme 20 is illustrated in Step B of Example 1 and Step C of Example 6.

Scheme 20

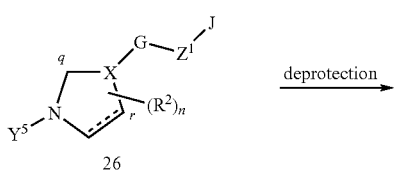

26 wherein $Y^5$ is an amine protecting group

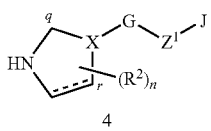

4

Compounds of Formula 26 can also be prepared by reaction of a suitably functionalized compound of Formula 27 with a suitably functionalized compound of Formula 28 as shown in Scheme 21. The functional groups $Y^6$ and $Y^7$ are selected from, but not limited to, moieties such as aldehydes, ketones, esters, acids, amides, thioamides, nitriles, amines, alcohols, thiols, hydrazines, oximes, amidines, amide, oximes, olefins, acetylenes, halides, alkyl halides, methanesulfonates, trifluoromethanesulfonates, boronic acids, boronates, and the like, which under the appropriate reaction conditions, will allow for the construction of various heterocyclic G-rings. As an example, reaction of a compound of Formula 27 where $Y^6$ is a thioamide group with a compound of Formula 28 where $Y^7$ is a bromoacetyl group will give a compound of Formula 26 where G is a thiazole ring. The synthetic literature describes many general methods for forming 5-membered heteroaromatic rings and 5-membered partially saturated heterocyclic rings (e.g., G-1 through G-59); see, for example, *Comprehensive Heterocyclic Chemistry*, vol. 4-6, A. R. Katritzky and C. W. Rees Eds., Pergamon Press, New York, 1984; *Comprehensive Heterocyclic Chemistry II*, vol. 2-4, A. R. Katritzky, C. W. Rees, and E. F. Scriven Eds., Pergamon Press, New York, 1996; and the series, *The Chemistry of Heterocyclic Compounds*, E. C. Taylor, Ed., John Wiley & Sons, New York. The use of intermediates of Formula 27 where X is $X^1$ and $Y^6$ is Br, I, methanesulfonate or trifluoromethanesulfonate to prepare organozinc reagents for use in cross-coupling reactions with aromatic rings has been described; see, for example, S. Bellotte, *Synlett* 1998, 379-380, and M. Nakamura et al., *Synlett* 2005, 1794-1798. One skilled in the art knows how to select the appropriate functional groups to construct the desired heterocyclic G rings. The method of Scheme 21 is also illustrated in Step B of Example 6.

Many compounds of Formula 27 and 28 are known and can be prepared by one skilled in the art.

Scheme 21

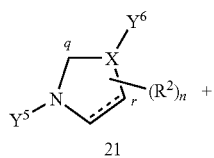

21

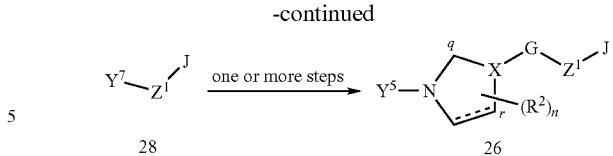

Certain compounds of Formula 26 (wherein $Z^1$ is O, S, or $NR^{21}$) can be prepared by displacement of an appropriate leaving group $Y^1$ on the G-ring of Formula 29 with a compound of Formula 30 in the presence of a base as depicted in Scheme 22. Suitable bases include sodium hydride or potassium carbonate. The reaction is carried out in a solvent such as N,N-dimethylformamide or acetonitrile at a temperature between about 0 to 80° C. Suitable leaving groups in the compounds of Formula 29 include nucleophic reaction leaving groups such as halide (e.g., Cl, Br, I) or sulfonate (e.g., mesylate, triflate, p-toluenesulfonate) and the like. Compounds of Formula 29 can be prepared from corresponding compounds wherein $Y^1$ is OH by general methods known in the art. Many of the compounds of Formula 30 are known and can be prepared by general methods known in the art.

Scheme 22

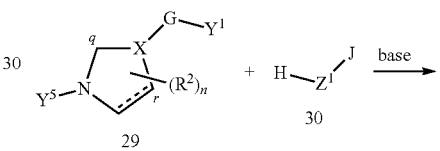

26

Certain compounds of Formula 26 (where $Z^1$ is O, S, or $NR^{21}$) can also be prepared by displacement of an appropriate leaving group $Y^1$ on the J ring of Formula 32 with a compound of Formula 30 in the presence of a base as depicted in Scheme 23. Suitable bases include sodium hydride or potassium carbonate. The reaction is carried out in a solvent such as N,N-dimethylformamide or acetonitrile at a temperature between about 0 to 80° C. Suitable leaving groups in the compounds of Formula 32 include nucleophic reaction leaving groups such as halide (e.g., Cl, Br, I) or sulfonate (e.g., mesylate, triflate, p-toluenesulfonate) and the like. Compounds of Formula 32 can be prepared from corresponding compounds wherein $Y^1$ is OH using general methods known in the art.

Scheme 23

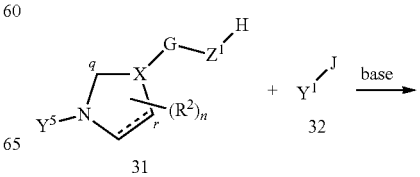

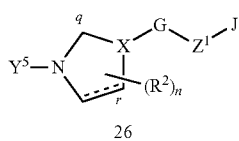

Compounds of Formula 26 can also be prepared by reaction of a suitably functionalized compound of Formula 33 with a suitably functionalized compound of Formula 34 as shown in Scheme 24. The functional groups $Y^6$ and $Y^7$ are selected from, but not limited to, moieties such as aldehydes, ketones, esters, acids, amides, thioamides, nitriles, amines, alcohols, thiols, hydrazines, oximes, amidines, amide oximes, olefins, acetylenes, halides, alkyl halides, methanesulfonates, trifluoromethanesulfonates, boronic acids, boronates, and the like, which, under the appropriate reaction conditions will allow the construction of various heterocyclic J-rings. As an example, reaction of a compound of Formula 33 where $Y^6$ is a chloro oxime moiety with a compound of Formula 34 where $Y^7$ is a vinyl or acetylene group in the presence of base will give a compound of Formula 26 where J is an isoxazoline or isoxazole, respectively. The method of Scheme 24 is illustrated in Step A of Example 1. Also, the synthetic literature includes many general methods for the formation of carbocyclic and heterocyclic rings and ring systems (for example, J-1 through J-82); see, for example, *Comprehensive Heterocyclic Chemistry*, vol. 4-6, A. R. Katritzky and C. W. Rees Eds., Pergamon Press, New York, 1984; *Comprehensive Heterocyclic Chemistry II*, vol. 2-4, A. R. Katritzky, C. W. Rees, and E. F. Scriven Eds., Pergamon Press, New York, 1996; the series, *The Chemistry of Heterocyclic Compounds*, E. C. Taylor, Ed., John Wiley & Sons, New York, and *Rodd's Chemistry of Carbon Compounds*, vol. 2-4, Elsevier, N.Y. General procedures for cycloaddition of nitrile oxides with olefins are well documented in the chemical literature. For relevant references see Lee, *Synthesis* 1982, 6, 508-509 and Kanemasa et al., *Tetrahedron* 2000, 56, 1057-1064 as well as references cited within. One skilled in the art knows how to select the appropriate functional groups to construct the desired heterocyclic J-ring. Many compounds of Formula 34 are known and can be prepared by general methods known in the art.

Scheme 24

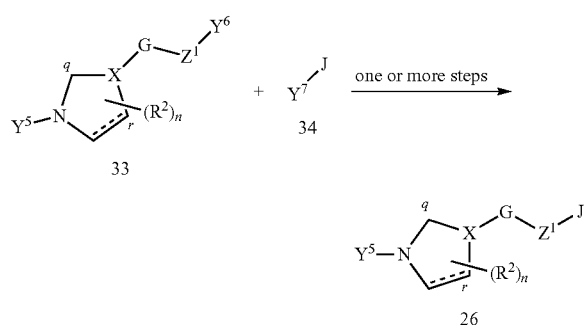

wherein $Y^6$ and $Y^7$ are functional groups suitable for construction of the desired heterocycle J.

An alternate preparation for the compounds of Formula 26 where $Z^1$ is a direct bond includes the well-known Suzuki reaction involving Pd-catalyzed cross-coupling of an iodide or bromide of Formula 35 or 38 with a boronic acid of Formula 36 or 37 as shown in Scheme 25. Many catalysts are useful for this type of transformation; one particularly useful catalyst is tetrakis(triphenylphosphine)palladium. Solvents such as tetrahydrofuran, acetonitrile, diethyl ether and dioxane are suitable. The Suzuki reaction and related coupling procedures offer many alternatives for creation of the G-J bond. For leading references see for example, C. A. Zificsak and D. J. Hlasta, *Tetrahedron* 2004, 60, 8991-9016. For a thorough review of palladium chemistry applicable to the synthesis of G-J bonds see J. J. Li and G. W. Gribble, Eds., *Palladium in Heterocyclic Chemistry: A Guide for the Synthetic Chemist*, Elsevier, Oxford, UK, 2000. Many other metal-catalyst cross-coupling reaction conditions known in the art are suitable for the preparation of compounds of Formula 26.

Scheme 25

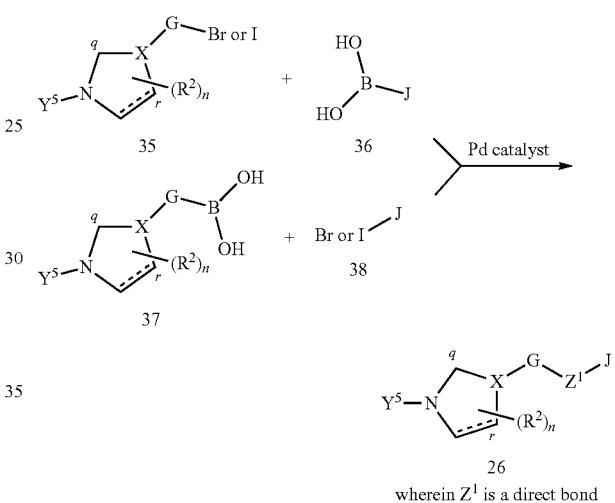

wherein $Z^1$ is a direct bond

One skilled in the art will recognize that many compounds of Formula 1 can be prepared directly by methods analogous to those described in Schemes 21 through 25 above where the group $Y^5$ is replaced by E. Thus, compounds corresponding to Formulae 27, 29, 31, 33, 35 and 37 in which $Y^5$ is replaced by E are useful intermediates for the preparation of compounds of Formula 1.

Thioamides of Formula 40 are particularly useful intermediates for preparing compounds of Formula 1 wherein X is $X^1$. A thioamide of Formula 40 can be prepared by the addition of hydrogen sulfide to the corresponding nitrile of Formula 39 as shown in Scheme 26.

Scheme 26

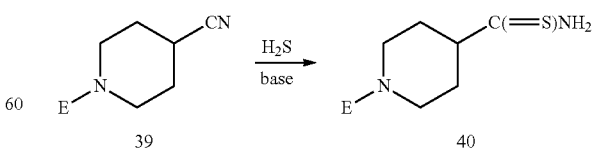

The method of Scheme 26 can be carried out by contacting a compound of Formula 39 with hydrogen sulfide in the presence of an amine such as pyridine, diethylamine or diethanolamine. Alternatively, hydrogen sulfide can be used in the form of its bisulfide salt with an alkali metal or ammonia. This type of reaction is well documented in the literature (e.g., see European Patent EP 696,581).

Halomethyl isoxazole ketones of Formula 44 are particularly useful intermediates for preparing certain chiral compounds of Formula 1 wherein J is, for example, selected from J-29-1 through J-29-12 as depicted in Exhibit A. Halomethyl isoxazole ketones of Formula 44 can be prepared by the multi-step reaction sequences shown in Scheme 27.

One skilled in the art will recognize that Scheme 27 can also be practiced without the use of a resolving agent, so that a compound of Formula 42 is converted directly to a racemic analog of Formula 41a, which can then be used to prepare racemic analogs of Formulae 43, 44 and certain racemic compounds of Formula 1 (e.g., compounds containing racemic analogs of J-29-1 through J-29-12).

aqueous acid, extracting, and concentrating. The crude ketones of Formula 43 are halogenated with a reagent such as sulfuryl chloride to afford the chloromethyl ketones of Formula 44 wherein $Y^3$ is Cl or molecular bromine to afford the corresponding bromomethyl ketones of Formula 44 wherein $Y^3$ is Br. The halomethyl ketones of Formula 44 can be purified by crystallization from a solvent such as hexanes or methanol, or can be used without further purification in the condensation reaction with thioamides.

Compounds of Formula 41 can be prepared by cycloaddition of hydroxamoyl chlorides of Formula 45 with an olefin of Formula 46, as shown in Scheme 28.

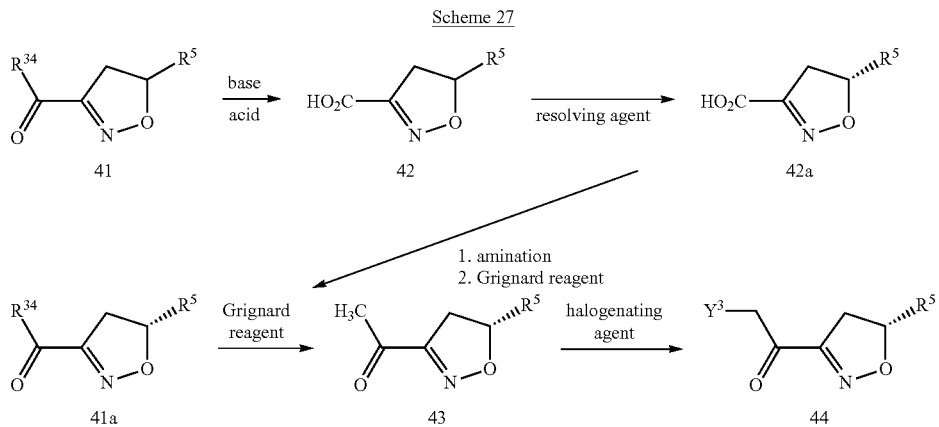

wherein $R^{34}$ is $C_2$-$C_8$ dialkylamino, 1-piperidinyl, 1-pyrrolidinyl or 4-morpholinyl $Y^3$ is Cl, Br or I and $R^5$ is as defined above in the Summary of the Invention.

The preparation of the racemic carboxylic acids of Formula 42 can be accomplished according to the well-known methods of basic or acidic hydrolysis of the corresponding compounds of Formula 41, preferably using a slight excess of sodium hydroxide in a water-miscible co-solvent such as methanol or tetrahydrofuran at a temperature between about 25 and 45° C. The product can be isolated by adjusting pH to about 1 to 3 and then filtering or extracting, optionally after removal of the organic solvent by evaporation. The racemic carboxylic acids of Formula 42 can be resolved by classical fractional crystallization of diastereomeric salts of suitable chiral amine bases such as cinchonine, dihydrocinchonine or a mixture thereof. A cinchonine-dihydrocinchonine mixture in about a 85:15 ratio is particularly useful, as it provides, for example, the (R)-configured carboxylic acids of Formula 42a, wherein $R^5$ is a substituted phenyl group, as the less soluble salt. Furthermore, these chiral amine bases are readily obtainable from commercial sources. The (R)-configured halomethyl ketone intermediates of Formula 44 afford the more fungicidally active final products of Formula 1 after coupling with thioamides of Formula 40. The halomethyl ketones of Formula 44 are obtained by first reacting amides of Formula 41 or 41a with one molar equivalent of a methylmagnesium halide (Grignard reagent) in a suitable solvent or solvent mixture such as tetrahydrofuran and toluene at a temperature between about 0 and 20° C. The crude ketone products of Formula 43 can be isolated by quenching with

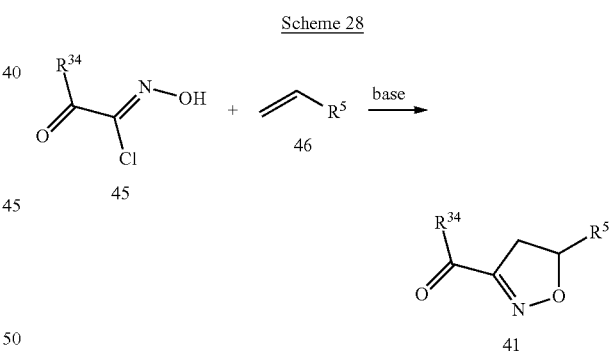

In this method, all three reacting components (i.e. the compounds of Formulae 45 and 46, and the base) are contacted so as to minimize hydrolysis or dimerization of the hydroxamoyl chloride of Formula 45. In one typical procedure, the base, which can either be a tertiary amine base such as triethylamine or an inorganic base such as an alkali metal or alkaline-earth carbonate, bicarbonate or phosphate, is mixed with the olefin derivative of Formula 46, and the hydroxamoyl chloride of Formula 45 is added gradually at a temperature at which the cycloaddition proceeds at a relatively rapid rate, typically between about 5 and 25° C. Alternatively, the base can be added gradually to the other two components (the compounds of Formulae 45 and 46). This alternative procedure is preferable when the hydroxamoyl chloride of Formula 45 is substantially insoluble in the reaction medium. The solvent in the reaction medium can be water or an inert organic solvent such as toluene, hexane or even the olefin derivative used in excess. The product can be separated from salt by-products by filtration or washing with water, followed by evaporation of the solvent. The crude product can be purified by crystallization, or the crude product can be used directly in the method of Scheme 27. Compounds of Formula 41 are precursors to the carboxylic acids of Formula 42, and are also useful for preparing the resolved enantiomers of the compounds of Formulae 41 (i.e. 41a), as shown in Scheme 27.

Certain compounds of Formula 1r (wherein J is substituted with —$Z^2Q$ and Q is substituted —$Z^3T^4$) can be prepared by one of several methods. In one method shown in Scheme 29, a compound of Formula 47 wherein $Y^3$ is a leaving group such as halogen, (e.g., Cl, Br or I) is reacted with a compound of Formula 48 wherein $Z^3$ is O, S or NH as shown in Scheme 29.

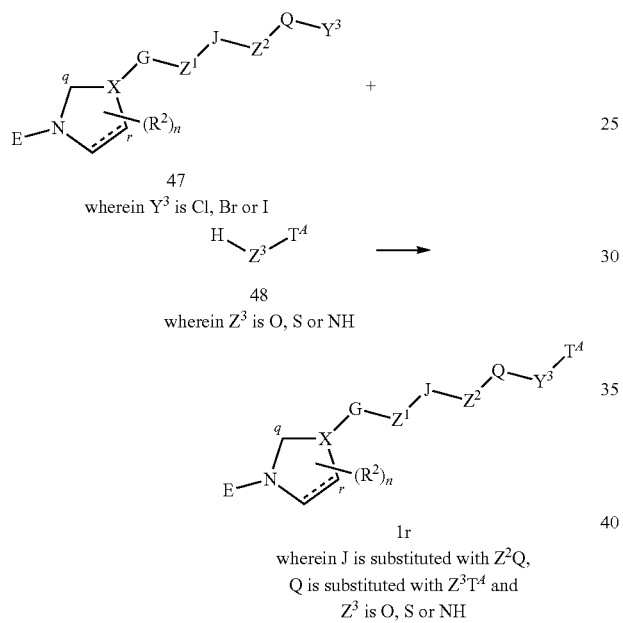

Scheme 29

47
wherein $Y^3$ is Cl, Br or I 48
wherein $Z^3$ is O, S or NH 1r
wherein J is substituted with $Z^2Q$,
Q is substituted with $Z^3T^4$ and
$Z^3$ is O, S or NH When $Z^3$ is O the reaction is the well-known Ullman ether synthesis, which is typically carried out in the presence of an inorganic base such as potassium carbonate or cesium carbonate and with a metal catalyst, for example, copper iodide. The reaction is run in a solvents such as dimethyl sulfoxide and N,N-dimethylformamide at a temperature between about room temperature and 150° C. Diaryl ethers of Formula 1r wherein $Z^3$ is O can also be prepared using palladium-catalyzed Buchwald-Hartwig reaction involving nucleophilic aromatic substitution or arylboronic acid diaryl ether methods. For a recent review of these methods, including the Ullman diaryl ether synthesis; see, for example, R. Frian and D. Kikeji, *Synthesis* 2006, 14, 2271-2285.

Conditions similar to those described for diaryl ethers can also be used to prepare compounds of Formula 1r where Z is S or NH. For a recent review of the preparation of sulfur and nitrogen analogs; see, for example, S. V. Ley and A. W Thomas *Angew. Chem., Int. Ed. Engl.* 2003, 42, 5400.

A similar copper catalyzed method can be used to prepare compounds of Formula 1r wherein $Z^3$ is a direct bond and $T^4$ is a heterocycle attached to Q through a nitrogen atom (e.g., $T^4$ is triazole or a salt thereof) as shown in Scheme 30.

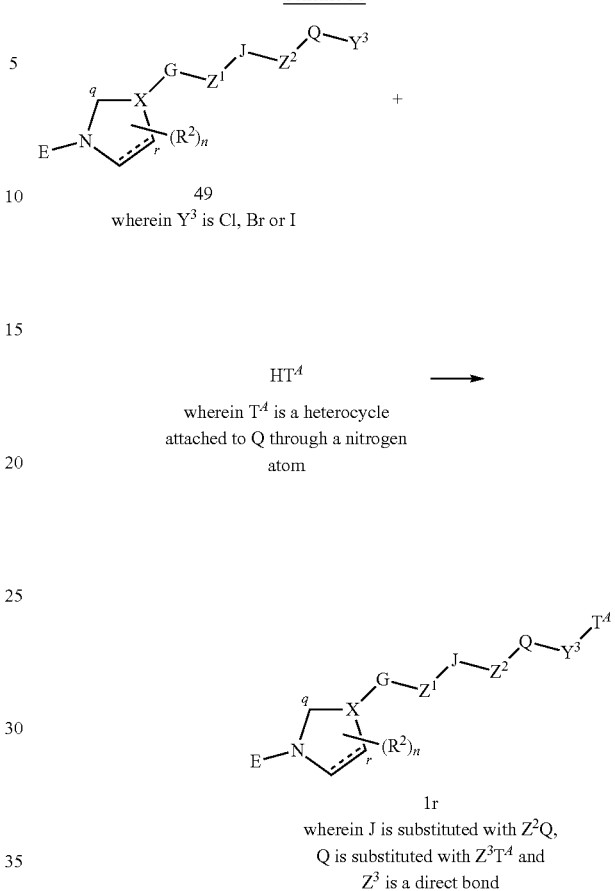

Scheme 30

49
wherein $Y^3$ is Cl, Br or I $HT^4$
wherein $T^4$ is a heterocycle attached to Q through a nitrogen atom 1r
wherein J is substituted with $Z^2Q$,
Q is substituted with $Z^3T^4$ and
$Z^3$ is a direct bond A ligand such as (1R,2R)—N,N-dimethyl-1,2-cyclohexenediamine may be used to increase the solubility and reactivity of the copper catalyst. The reaction is typically carried out in a solvent such as dimethylsulfoxide or in a mixed solvent such as dimethylsulfoxide-water at temperatures between about room temperature and 200° C. For leading reference; see, for example, Andersen et al., *Synlett* 2005, 14, 2209-2213.

Compounds of Formula 1r wherein $Z^3$ is a direct bond and $T^4$ is attached to Q through a carbon atom includes the well-known Suzuki reaction involving Pd-catalyzed cross-coupling as shown in Scheme 31.

Scheme 31

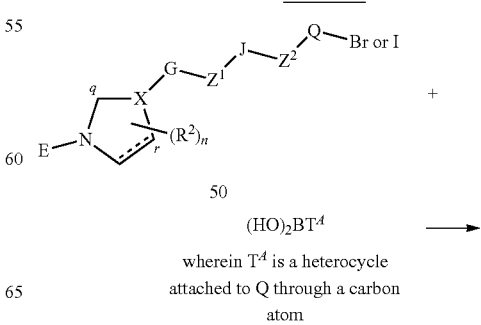

50

$(HO)_2BT^4$
wherein $T^4$ is a heterocycle attached to Q through a carbon atom

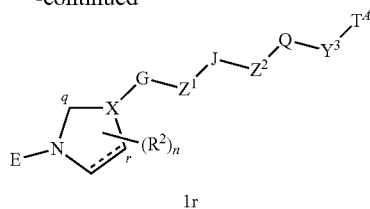

1r
wherein J is substituted with $Z^2Q$,
Q is substituted with $Z^3T^4$ and
$Z^3$ is a direct bond The conditions for coupling an iodide or bromide of Formula 50 with a boronic acid of Formula 51 are similar to those described in Scheme 25 above. Many catalysts are useful for this type of transformation; a typical catalyst is tetrakis(triphenylphosphine)palladium. Solvents such as tetrahydrofuran, acetonitrile, diethyl ether and dioxane are suitable. The Suzuki reaction and related coupling procedures offer many alternatives for creation of the $QT^4$ bond wherein $Z^3$ is a direct bond. For leading references; see, for example, C. A. Zificsak and D. J. Hlasta, *Tetrahedron* 2004, 60, 8991-9016. For a thorough review of palladium chemistry applicable to the synthesis of $Q\text{-}Z^3GA$ bonds; see, for example, J. J. Li and G. W. Gribble, editors, *Palladium in Heterocyclic Chemistry: A Guide for the Synthetic Chemist*, Elsevier: Oxford, UK, 2000. Many variations of catalyst type, base and reaction conditions are known in the art for this general method.

As shown in Scheme 32, preparation of the compounds of Formula 1r wherein $Z^3$ is an alkyne includes the well-known Sonogashira reaction using Pd-catalyzed cross-coupling of a halide of Formula 52 wherein $Y^3$ is a halogen such as iodine or bromide with an alkyne of Formula 53 in the presence of a metal catalyst and a base.

Scheme 32

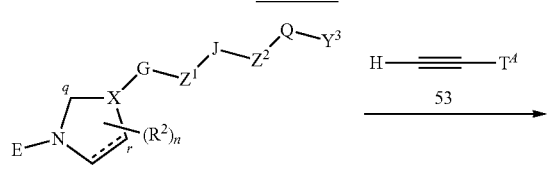

52
wherein $Y^3$ is Cl, Br or I 1r
wherein J is substituted with $Z^2Q$,
Q is substituted with $Z^3T^4$ and
$Z^3$ is alkyne Many catalysts are useful for this type of transformation; a typical catalyst is dichlorobis(tri-o-tolylphosphine)palladium (II). Suitable solvents include tetrahydrofuran, acetonitrile and ethyl acetate. Suitable metal catalysts include, for example, copper iodide. Typical bases include, for example, triethylamine or Hunig's base. For leading references; see, for example, I. B. Campbell, *Organocopper Reagents* 1994, 217-235.

As shown in Scheme 33, compounds of Formula 1r wherein $Z^3$ is —C≡C— can serve as starting materials to prepare compounds of Formula 1f wherein $Z^3$ is —$CH_2CH_2$— by reduction with hydrogen in the presence of a catalyst, for example, palladium on carbon.

Scheme 33

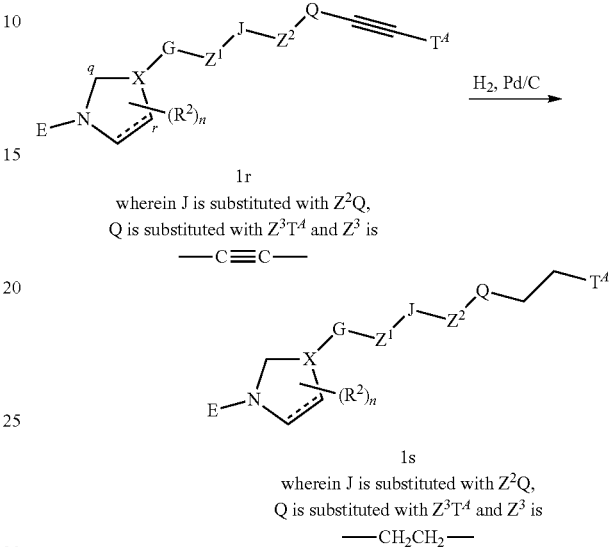

1r
wherein J is substituted with $Z^2Q$,
Q is substituted with $Z^3T^4$ and $Z^3$ is
—C≡C—

1s
wherein J is substituted with $Z^2Q$,
Q is substituted with $Z^3T^4$ and $Z^3$ is
—$CH_2CH_2$—

The reduction is typically carried out under an atmosphere of hydrogen at pressures from atmospheric to 700 kPa, preferably 400 kPa in a solvent such as ethyl acetate or ethanol using methods well-known to one skilled in the art.

As shown in Scheme 34, preparation of the certain compounds of Formula 1t wherein $Z^3$ is an —CH=CH— includes the well-known Heck reaction using Pd-catalyzed cross-coupling of iodine or bromide of Formula 53 wherein $Y^3$ with an alkene of Formula 54 in the presence of a metal catalyst and a base, such as triethylamine or sodium bicarbonate.

Scheme 34

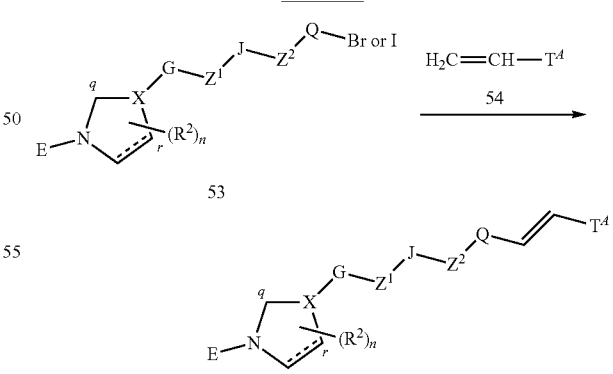

1t
wherein J is substituted with $Z^2Q$,
Q is substituted with $Z^3T^4$ and $Z^3$ is
—CH=CH—

Many catalysts are useful for this type of transformation; a typical catalyst is tris(dibenzylideneacetone)dipalladium.

Suitable solvents include N,N-dimethylformamide and acetonitrile. For a review of the Heck reaction; see, for example, W. Cabri and I. Candiani, *Acc. Chem Res.* 1995, 28, 2-7.

Compounds of Formula 1u wherein $Z^3$ is a direct bond and $T^4$ is a tetrazole linked to Q through carbon can be prepared from nitriles of Formula 55 as shown in Scheme 35.

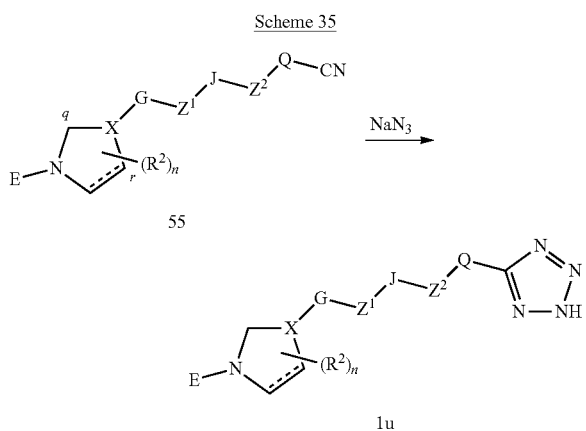

In this method a nitrile of Formula 55 is reacted with an azide such as sodium azide or trimethylsilyl azide in a solvent such at N,N-dimethylformamide or toluene at a temperature between about room temperature and 140° C. to form a compound of Formula 1u. For leading references; see, for example, B. Schmidt, D. Meid and D. Kieser, *Tetrahedron* 2006, 63, 492-496.

Reactions similar to those described in Schemes 31 and 32 can also be carried out on intermediates before coupling, for example, aldehydes of Formula 56, as shown in Scheme 36, are a useful starting materials to prepare the substituted aldehydes of Formula 57. Several starting aldehydes of Formula 48 are commercially available, for example, the ortho, meta and para isomers of fluorobenzaldehyde, chlorobenzaldehyde, bromobenzaldehyde and iodobenzaldehyde.

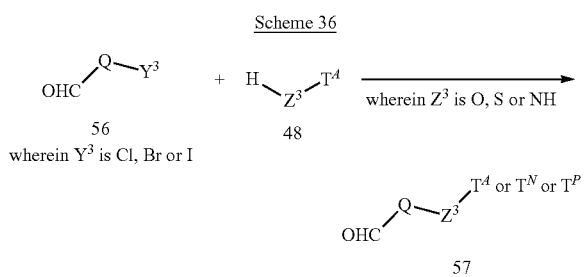

Similarly, the reactions described in Schemes 30-35 can also be used to prepare aldehydes derivatives of Formula 57; see, for example, W. Mansawat, et. al. *Tetrahedron Letters* 2007, 48(24), 4235-4238 for 2-(phenylthio)benzaldehyde; A. Cwik, Z. Hell, F. Figueras, *Advanced Synthesis & Catalysis* 2006, 348(4/5), 523-530 for 2-(2-phenylethenyl)benzaldehyde; T. Sakamoto, Y. Kondo, n. Miura, K. Hayashi, H. Yamanaka, *Heterocycles* 1986, 24(8), 2311-14 for 2-(phenylethynyl)benzaldehyde; and J. Rosevear, J. F. K. Wilshire, John F. K. *Australian Journal of Chemistry* 1991, 44(8), 1097-114 for 2-(1H-1,2,4-triazol-1-yl)benzaldehyde.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; John Wiley & Sons, New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "br m" means broad multiplet, and "br s" means broad singlet.

Example 1

Preparation of methyl 4-[4-(4,5-dihydro-5-phenyl-3-isoxazolyl)-2-thiazolyl]-N-(2,5-dimethylphenyl)-1-piperidinecarboximidothioate Step A: Preparation of 1,1-dimethylethyl 4-[4-(4,5-dihydro-5-phenyl-3-isoxazolyl)-2-thiazolyl)-1-piperidinecarboxylate To a mixture of 1,1-dimethylethyl 4-(4-formyl-2-thiazolyl)-1-piperidinecarboxylate (1.0 g, 3.4 mmol) in ethanol (5 mL) was added an aqueous solution of hydroxylamine (50 wt. %, 0.25 mL, 4.0 mmol). The reaction mixture was heated at 60° C. for 1 h, during which time the reaction mixture became homogeneous. The resulting reaction solution was cooled to room temperature and diluted with tetrahydrofuran (10 mL). Styrene (0.57 mL, 5 mmol) was added to the reaction mixture, followed by a portionwise addition of Clorox® (aqueous sodium hypochlorite solution) (10.5 mL) over 3 h. The reaction mixture was stirred overnight at room temperature, and then filtered. The solid collected by filtration was washed with water, diethyl ether and air dried to give the title compound as a white powder (610 mg). The filtrate was diluted with saturated aqueous sodium bicarbonate solution and extracted with diethyl ether. The extract was dried (MgSO$_4$) and concentrated under reduced pressure to give more of the title compound as a yellow oil (850 mg). The oil was diluted with diethyl ether (4 mL) and upon standing provided the title compound as a white solid (233 mg).

$^1$HNMR (CDCl$_3$) δ 1.47 (s, 9H), 1.7 (m, 2H), 2.1 (m, 2H), 2.85 (m, 2H), 3.2 (m, 1H), 3.45 (m, 1H), 3.84 (m, 1H) 4.2 (br s, 2H), 5.75 (m, 1H), 7.25-7.40 (m, 5H), 7.61 (s, 1H).

Step B: Preparation of 4-[4-(4,5-dihydro-5-phenyl-3-isoxazolyl)-2-thiazolyl]piperidine To a solution of 1,1-dimethylethyl 4-[4-(4,5-dihydro-5-phenyl-3-isoxazolyl)-2-thiazolyl)-1-piperidinecarboxylate (i.e. the product of Step A) (0.815 g, 1.97 mmol) in dichloromethane (50 mL) was added a solution of hydrogen chloride and diethyl ether (2 M, 10 mL, 20 mmol). The reaction mixture was stirred at room temperature for 1 h to give a gummy precipitate. Methanol was added to dissolve the precipitate, and the reaction mixture was stirred for an additional 1 h. The reaction mixture was concentrated under reduced pressure and partitioned between ethyl acetate and saturated aqueous sodium bicarbonate, the organic layer was dried (MgSO$_4$) and concentrated to give the title compound as a clear oil (0.31 g), which solidified on standing.

$^1$HNMR (CDCl$_3$) δ 1.65 (br s, 1H), 1.7 (m, 2H), 2.1 (m, 2H), 2.75 (m, 2H), 3.1-3.25 (m, 3H), 3.41 (m, 1H), 3.83 (m, 1H), 5.75 (m, 1H), 7.25-7.40 (m, 5H), 7.60 (s, 1H).

Step C: Preparation of 4-[4-(4,5-dihydro-5-phenyl-3-isoxazolyl)-2-thiazolyl]-N-(2,5-dimethylphenyl)-1-piperidinecarbothioamide To a solution of 4-[4-(4,5-dihydro-5-phenyl-3-isoxazolyl)-2-thiazolyl]piperidine (i.e. the product of Step B) (1.0 g, 3.2 mmol) in dichloromethane (10 mL) was added a solution of 2,5-dimethylphenyl isothiocyanate (0.52 g, 3.2 mmol) and dichloromethane (5 mL) over 1 minute. The reaction mixture was stirred at room temperature for 20 minutes, concentrated, dissolved in methyl acetate (4 mL), held at 0° C. overnight and filtered to give the title compound as a white powder (1.35 g) melting at 120-123° C.

$^1$H NMR (CDCl$_3$) δ 1.9 (m, 2H), 2.15 (m, 2H), 2.22 (s, 3H), 2.30 (s, 3H), 3.20 (m, 2H), 3.30 (m, 1H), 3.41 (m, 1H), 3.82 (m, 1H), 4.58 (m, 2H), 5.75 (m, 1H), 6.93 (m, 3H), 7.10 (m, 1H), 7.25-7.40 (m, 5H), 7.62 (s, 1H).

Step D: Preparation of methyl 4-[4-(4,5-dihydro-5-phenyl-3-isoxazolyl)-2-thiazolyl]-N-(2,5-dimethylphenyl)-1-piperdinecarboximidothioate A solution of 14-[4-(4,5-dihydro-5-phenyl-3-isoxazolyl)-2-thiazolyl]-N-(2,5-dimethylphenyl)-1-piperidinecarbothioamide (i.e. the product of Step C) (476 mg, 1.0 mmol) and methyl iodide (0.25 mL, 4.0 mmol) in dichloromethane (2 mL) was agitated at room temperature for 3 h. The reaction mixture was then diluted with dichloromethane, washed with saturated aqueous sodium bicarbonate, saturated aqueous sodium chloride, dried (MgSO$_4$), and concentrated to give a foamy white solid (480 mg). The solid was crystallized from methyl acetate/petroleum ether to give the title compound, a compound of the present invention, as a white powder (320 mg) melting at 114-116° C.

$^1$H NMR (CDCl$_3$) δ 1.9 (m, 2H), 2.08 (s, 3H), 2.12 (s, 3H), 2.1 (m, 2H), 2.28 (s, 3H), 3.05 (m, 2H), 3.30 (m, 1H), 3.42 (m, 1H), 3.82 (m, 1H), 4.28 (m, 2H), 5.75 (m, 1H), 6.57 (m, 1H), 6.75 (m, 1H), 7.0 (m, 1H), 7.25-7.40 (m, 5H), 7.63 (s, 1H).

Example 2

Preparation of N-[[4-[4-(4,5-dihydro-5-phenyl-3-isoxazolyl)-2-thiazolyl]-1-piperidinyl]methylene]-2,5-dimethylbenzenamine To a solution of trimethyl orthoformate (21.8 ml, 200 mmol), p-toluenesulfonic acid (380 mg, 2.0 mmol) in toluene (20 mL) at reflux, was added a solution of 2,5-dimethylaniline (2.5 mL, 20 mmol) in toluene (15 mL) over 1 h. After an additional 1 h, the reaction mixture was cooled to room temperature and allowed to stir overnight. The mixture washed with saturated aqueous sodium bicarbonate, saturated aqueous sodium chloride, and concentrated under reduced pressure to give an amber colored oil containing a small amount of solid. Filtration provided an oil (3.2 g) which was used without further purification. A mixture of the oil (326 mg, 2.0 mmol) and 4-[4-(4,5-dihydro-5-phenyl-3-isoxazolyl)-2-thiazolyl]piperidine (i.e. the product of Example 1, Step B) (313 mg, 1.0 mmol) in toluene (2 mL) was heated at 70° C. for 1 h, cooled and concentrated. The resulting solid was purified by column chromatography on silica gel using ethyl acetate-hexanes as eluant to provide the title compound, a compound of the present invention, as a foamy white solid (400 mg).

$^1$HNMR (CDCl$_3$) δ1.82 (m, 2H), 2.2 (m, 2H), 2.22 (s, 3H), 2.28 (s, 3H), 3.1 (br m, 2H), 3.30 (m, 1H), 3.41 (m, 1H), 3.82 (m, 1H), 4.1 (br m, 2H), 5.75 (m, 1H), 6.58 (m, 1H), 6.78 (m, 1H), 7.02 (m, 1H), 7.25-7.40 (m, 6H), 7.63 (s, 1H).

Example 3

Preparation of methyl 4-[4-(4,5-dihydro-5-phenyl-3-isoxazoly)-2-thiazolyl]-N-(2,5-dimethylphenyl)-1-piperidinecarboximidate A solution of methyl 4-[4-(4,5-dihydro-5-phenyl-3-isoxazolyl)-2-thiazolyl]-N-(2,5-dimethylphenyl)-1-piperidinecarboximidothioate (i.e. the product of Example 1, Step D) (0.10 g, 0.20 mmol) in methanol (5 mL) was heated in a Biotage® Creator XM microwave apparatus at 140° C. for 1.5 h. The reaction mixture was concentrated under reduced pressure. The resulting residue was purified by column chromatography on silica gel using 1:1 ethyl acetate-hexanes as eluant to provide the title compound, a compound of the present invention, as a foamy white solid (19 mg).

$^1$HNMR (CDCl$_3$) δ 1.66-1.75 (m, 2H), 1.97-2.01 (m, 2H), 2.11 (s, 3H), 2.25 (s, 3H), 2.76-2.82 (m, 2H), 3.10-3.15 (m, 1H), 3.38-3.44 (m, 1H), 3.68 (s, 3H), 3.80-3.82 (m, 1H), 3.84-3.88 (m, 2H), 5.71-5.76 (m, 1H), 6.61-6.67 (m, 2H), 6.97-6.99 (d, 1H), 7.30-7.34 (m, 1H), 7.36-7.40 (m, 4H), 7.60 (s, 1H).

Example 4

Preparation of 4-[4-(4,5-dihydro-5-phenyl-3-isoxazoly)-2-thiazolyl]-N-pentyl-1-piperidinecarboxamide A solution of 4-[4-(4,5-dihydro-5-phenyl-3-isoxazolyl)-2-thiazolyl]piperidine (i.e. the product of Example 1, Step B) (0.10 g, 0.32 mmol) and pentyl isocyanate (0.036 g, 0.32 mmol) in dichloromethane (10 mL) was stirred at room temperature overnight, then filtered and concentrated under reduced pressure to provide a white solid. The solid was slurried in diethyl ether, filtered and air-dried to provide the title compound, a compound of the present invention, as a white powder (0.081 g), melting at 132-134° C.

$^1$H NMR (CDCl$_3$) δ 0.90 (t, 3H), 1.30-1.34 (m, 4H), 1.49-1.53 (m, 2H), 1.72-1.82 (m, 2H), 2.14 (d, 2H), 2.94 (t, 2H), 3.20-3.26 (m, 3H), 3.39-3.45 (m, 1H), 3.80-3.88 (m, 1H), 4.03 (d, 2H), 4.44, (s, 1H), 5.74 (q, 1H), 7.32-7.34 (m, 1H), 7.35-7.41 (m, 4H), 7.61 (s, 1H).

Example 5

Preparation of 4-[4-(4,5-dihydro-5-phenyl-3-isoxazolyl)-2-thiazolyl]-N-2-propen-1-yl]-1-piperidinecarbothioamide A solution of 4-[4-(4,5-dihydro-5-phenyl-3-isoxazolyl)-2-thiazolyl]piperidine (i.e. the product of Example 1, Step B) (0.10 g, 0.32 mmol) and allyl isothiocyanate (0.027 g, 0.32 mmol) in dichloromethane (10 mL) was stirred at room temperature overnight, then filtered and concentrated under reduced pressure. The resulting solid was purified by column chromatography on silica gel using ethyl acetate as eluant to provide the title compound, a compound of the present invention, as a foamy white solid (85 mg).

$^1$H NMR (CDCl$_3$) δ 1.84-1.94 (m, 2H), 2.16-2.22 (m, 2H), 3.24 (t, 2H), 3.30-336 (m, 1H), 3.38-3.44 (m, 1H), 3.80-3.88 (m, 1H), 4.32-4.36 (m, 2H), 4.69 (d, 2H), 5.19 (t, 1H), 5.26 (s, 1H), 5.65 (s, 1H), 5.71-5.77 (m, 1H), 5.90-6.00 (m, 1H), 7.31-7.35 (m, 1H), 7.37-7.39 (m, 4H), 7.60 (s, 1H).

Example 6

Preparation of 1-[4-[4-[4,5-dihydro-5-(2-fluorophenyl)-3-isoxazolyl]-2-thiazolyl]-1-piperidinyl]-4,4,4-trifluoro-3-methyl-1-butanone Step A: 2-chloro-1-[4,5-dihydro-5-(2-fluorophenyl)-3-isoxazolyl]ethanone To a suspension of 2-fluorostyrene (2.78 g, 22.8 mmol) and sodium bicarbonate (2.88 g, 34.2 mmol) in anhydrous toluene (15 mL) heated at 55° C. was added 3-chloro-N-hydroxy-2-oxo-propanimidoyl chloride (1.78 g, 11.4 mmol). After 2 h at 55° C., the reaction mixture was cooled, filtered, and the filtrate was concentrated under reduced pressure. The resulting residue was purified by column chromatography on silica gel using 10% ethyl acetate in hexanes as eluant to provide the title compound as a yellow solid (2.35 g) melting at 42-44° C.

$^1$H NMR (CDCl$_3$) δ 3.24 (m, 1H), 3.62 (m, 1H), 4.73 (s, 2H), 6.02 (m, 1H), 7.18 (m, 1H), 7.26 (m, 1H), 7.36 (m, 2H).

Step B: 1,1-dimethylethyl 4-[4-(4,5-dihydro-5-(2-fluorophenyl)-3-isoxazolyl)-2-thiazolyl]-1-piperidinecarboxylate To a solution of 1-tert-butoxycarbonylpiperidine-4-carbothioamide (1 g, 4.10 mmol) in ethanol (10 mL) was added 2-chloro-1-[4,5-dihydro-5-(2-fluorophenyl)-3-isoxazolyl]ethanone (i.e. the product of Step A) (0.99 g) followed by pyridine (0.34 mL, 4.10 mmol). The reaction mixture was heated at 77° C. for 3 h, and then stirred at room temperature overnight. Ethanol was removed from the reaction mixture, and the remaining residue was diluted with ethyl acetate (50 mL). The organic layer was separated, washed with water, saturated aqueous sodium chloride solution, dried (MgSO$_4$) and concentrated under reduced pressure. The resulting oil was purified by column chromatography on silica gel to provide the title compound as a pale yellow sticky oil (1.11 g).

$^1$H NMR (CDCl$_3$) δ 1.46 (S, 9H), 1.65 (m, 2H), 2.04 (m, 2H), 2.82 (m, 1H), 3.24 (m, 1H), 3.40, (m, 1H), 4.02 (m, 2H), 5.98 (m, 1H), 7.08 (m, 2H), 7.27 (m, 1H), 7.35 (m, 1H), 7.61 (s, 1H).

$^{19}$F NMR (CDCl$_3$) δ 118.39 (1F).

Step C: 4-[4-[5-(2-fluorophenyl)-4,5-dihydro-3-isoxazolyl)-2-thiazolyl]piperidine hydrochloride To a solution of 1,1-dimethylethyl 4-[4-(4,5-dihydro-5-(2-fluorophenyl)-3-isoxazolyl)-2-thiazolyl]-1-piperidinecarboxylate (i.e. the product of Step B) (1.05 g, 2.43 mmol) in ethanol (20 mL) was added a solution of hydrogen chloride in ether (2 M, 12.2 mL). The reaction mixture was stirred at room temperature overnight and then concentrated under reduced pressure to provide the title compound as colorless solid (0.807 g)

$^1$H NMR (CDCl$_3$) δ 1.84 (m, 2H), 2.21 (m, 2H), 3.04 (m, 1H), 3.42 (m, 3H), 3.84 (m, 1H), 5.88 (m, 1H), 7.23 (m, 2H), 7.38 (m, 2H), 8.07 (s, 1H), 8.86 (br s, 1H), 9.02 (br s, 1H).

Step D: 1-[4-[4-[4,5-dihydro-5-(2-fluorophenyl)-3-isoxazolyl]-2-thiazolyl]-1-piperidinyl]-4,4,4-trifluoro-3-methyl-1-butanone To a solution of 4,4,4-trifluoro-3-methyl-butanoic acid (64 mg, 0.408 mmol) in dichloromethane (3 mL) was added 1-propanephosphonic acid cyclic anhydride solution (50% in ethyl acetate, 0.5 mL). After stirring for 5 minutes, 4-[4-[5-(2-fluorophenyl)-4,5-dihydro-3-isoxazolyl)-2-thiazolyl]piperidine hydrochloride (i.e. the product of Step C) (150 mg, 0.408 mmol), triethylamine (0.1 mL) and 4-dimethylaminopyridine (5 mg) were sequentially added The reaction mixture was stirred for 3 h, and then concentrated under reduced pressure. The resulting material was purified by column chromatography on silica gel to provide the title compound, a compound of the present invention, as an oil (151 mg).

$^1$H NMR (CDCl$_3$) δ 1.16 (m, 3H), 1.74 (m, 2H), 2.24 (m, 3H), 2.82 (m, 3H), 3.36 (m, 3H), 3.86, (m, 2H), 4.62 (m, 1H), 5.98 (m, 1H), 7.08 (m, 2H), 7.27 (m, 1H), 7.42 (m, 1H), 7.61 (s, 1H).

$^{19}$F NMR (CDCl$_3$) δ−118.39, −74.371, −73.851, −70.865.

Example 7

Preparation of 5-chloro-1-[4-[4-[4,5-dihydro-5-(2-fluorophenyl)-3-isoxazolyl]-2-thiazolyl]-1-piperidinyl]-1-pentanone To a solution of 5-chloropentanoic acid, (64 mg, 0.408 mmol) in dichloromethane (3 mL) was added 1-propanephosphonic acid cyclic anhydride solution (50% in ethyl acetate, 0.5 mL). After stirring for 5 minutes, 4-[4-[5-(2-fluorophenyl)-4,5-dihydro-3-isoxazolyl)-2-thiazolyl]piperidine hydrochloride (i.e. the product of Step C, Example 6) (150 mg, 0.408 mmol), triethylamine (0.1 mL) and 4-dimethylaminopyridine (5 mg) were sequentially added. The reaction mixture was stirred for 3 h, and then concentrated under reduced pressure. The resulting material was purified by column chromatography on silica gel to provide the title compound, a compound of the present invention, as an oil (126 mg).

$^1$HNMR (CDCl$_3$) δ 1.16 (m, 4H), 1.74 (m, 2H), 2.20 (m, 2H), 2.39 (m, 2H), 2.82 (m, 1H), 3.56 (m, 2H), 3.42 (m, 3H), 3.84, (m, 2H), 4.62 (m, 1H), 5.98 (m, 1H), 7.08 (m, 1H), 7.16 (m, 1H), 7.27 (m, 1H), 7.44 (m, 1H), 7.61 (s, 1H).

$^{19}$HNMR (CDCl$_3$) δ 118.39 (1F).

Example 8

Preparation of 1-[4-[4-[4,5-dihydro-5-(2-fluorophenyl)-3-isoxazolyl]-2-thiazolyl]-1-piperidinyl]-4-pentyn-1-one To a solution of 4-pentynoic acid (64 mg, 0.408 mmol) in dichloromethane (3 mL) was added 1-propanephosphonic acid cyclic anhydride solution (50% in ethyl acetate, 0.5 mL). After stirring for 5 minutes, 4-[4-[5-(2-fluorophenyl)-4,5-dihydro-3-isoxazolyl]-2-thiazolyl]piperidine hydrochloride (i.e. the product of Step C, Example 6) (150 mg, 0.408 mmol), triethylamine (0.1 mL) and 4-dimethylaminopyridine (5 mg) were sequentially added. The reaction mixture was stirred for 3 h and then concentrated under reduced pressure. The resulting material was purified by column chromatography on silica gel to provide the title compound, a compound of the present invention, as an oil (142 mg).

$^1$H NMR (CDCl$_3$) δ 1.78 (m, 2H), 2.21 (m, 2H), 2.39 (m, 2H), 2.59 (m, 3H), 2.82 (m, 1H), 3.46 (m, 3H), 3.84, (m, 2H), 4.62 (m, 1H), 5.98 (m, 1H), 7.08 (m, 1H), 7.16 (m, 1H), 7.26 (m, 1H), 7.44 (m, 1H), 7.61 (s, 1H).
$^{19}$F NMR (CDCl$_3$) δ 118.39 (1F).

Example 9

Preparation of 4-[4-(4,5-dihydro-5-phenyl-3-isoxazolyl)-2-thiazolyl]-N-(2,5-dimethylphenyl)-1-piperidinecarboximidamide

Step A: Preparation of 4-[4-(4,5-dihydro-5-phenyl-3-isoxazolyl)-2-thiazolyl]-N-(2,5-dimethylphenyl)-1-piperidinecarboxamide To a mixture of 4-[4-(4,5-dihydro-5-phenyl-3-isoxazolyl)-2-thiazolyl]piperidine (i.e. the product of Step B, Example 1) (1.56 g, 5.0 mmol) in dichloromethane (15 mL) was added 2,5-dimethylphenylisothiocyanate (0.736 g, 5.0 mmol) and 1,8-diazabicyclo[5.4.0]undec-7-ene (about 3-5 uL). The reaction mixture was stirred at room temperature for 30 minutes, concentrated under reduced pressure and purified by column chromatography on silica gel eluting with 0-100% ethyl acetate in hexanes as eluant to give the title compound as a white solid (1.25 g). A portion of the white solid was crystallized from methyl acetate to give the title compound as a white solid melting at 124-127° C. A another portion of the white solid was crystallized from i-propanol to give the title compound as a white solid melting at 141-144° C.

$^1$H NMR (CDCl$_3$): δ 1.85 (m, 2H), 1.99 (m, 2H), 2.21 (s, 3H), 2.31 (s, 3H), 3.08 (m, 2H), 3.25 (m, 1H), 3.42 (dd, 1H), 3.82 (dd, 1H), 4.15 (m, 2H), 5.78 (dd, 1H), 6.12 (br s, 1H), 6.82 (m, 1H), 7.02 (m, 1H), 7.2-7.4 (m, 5H), 7.46 (m, 1H), 7.62 (s, 1H).

Step B: Preparation of 4-[4-(4,5-dihydro-5-phenyl-3-isoxazolyl)-2-thiazolyl]-N-(2,5-dimethylphenyl)-1-piperidinecarboximidoyl chloride To a mixture of 4-[4-(4,5-dihydro-5-phenyl-3-isoxazolyl)-2-thiazolyl]-N-(2,5-dimethylphenyl)-1-piperidinecarboxamide (i.e. the product of Step A) (0.406 g, 0.88 mmol) in dichloromethane (10 mL) was added phosphorus pentachloride (0.208 g, 1.0 mmol). The reaction mixture was heated at 40° C. for 16 h, and then concentrated under reduced pressure to provide the title compound as a foamy white solid (0.52 g).

$^1$H NMR (CDCl$_3$): δ 2.22 (m, 2H), 2.27 (s, 3H), 2.32 (s, 3H), 2.50 (m, 2H), 3.45 (m, 1H), 3.63 (m, 1H), 3.82-3.95 (m, 3H), 4.87 (m, 2H), 5.78 (m, 1H), 7.02 (s, 1H), 7.1-7.2 (m, 2H), 7.3-7.40 (m, 5H), 7.71 (s, 1H).

Step C: Preparation of 4-[4-(4,5-dihydro-5-phenyl-3-isoxazolyl)-2-thiazolyl]-N-(2,5-dimethylphenyl)-1-piperidinecarboximidamide A mixture of 4-[4-(4,5-dihydro-5-phenyl-3-isoxazolyl)-2-thiazolyl]-N-(2,5-dimethylphenyl)-1-piperidinecarboximidoyl chloride (i.e. the product of Step B) (0.300 g, 0.63 mmol) in dichloromethane (4 mL) was added dropwise to a solution of ammonia in mathanol (7M, 10 ml) which was cooled to 0° C. The reaction mixture was stirred for 2 minutes, concentrated under reduced pressure, and the resulting tan solid portioned between dichloromethane and saturated aqueous sodium bicarbonate solution. The organic layer was dried and concentrated under reduced pressure to give of the title, a compound of the present invention, compound as a foamy white solid (0.25 g).

$^1$H NMR (CDCl$_3$): δ 1.90 (m, 2H), 2.15 (m, 2H), 2.18 (s, 3H), 2.27 (s, 3H), 3.07 (m, 2H), 3.25 (m, 1H), 3.41 (m, 1H), 3.82 (m, 2H), 4.02 (m, 2H), 5.75 (m, 1H), 6.72 (br s, 1H), 6.81 (br m, 1H), 7.03 (m, 1H), 7.3-7.42 (m, 5H), 7.61 (s, 1H).

Example 10

Preparation of 1-[4-[4-[5-(2,6-difluorophenyl)-4,5-dihydro-3-isoxazolyl]-2-thiazole]-1-piperidinyl]-2-(2,5-dimethylphenyl)-1,2-ethanedione

Step A: Preparation of 5-(2,6-difluorophenyl)-4,5-dihydro-N,N-dimethyl-3-isoxazolecarboxamide To a 1000-mL round bottom flask equipped with a mechanical stirrer, thermometer and addition funnel were added 2-(dimethylamino)-N-hydroxy-2-oxoethanimidoyl chloride (94.0 g, 0.62 mol) and a solution of 2,6-difluorostyrene (84.0 g, 0.60 mol) in chlorobenzene (275 g). The reaction mixture was cooled to 10° C., and then a solution of potassium bicarbonate (70 g, 0.70 mol) in water (350 mL) was added dropwise over 1 h while maintaining the temperature between 10 to 15° C. When gas chromatography analysis of the reaction mixture showed about 3% of 2-(dimethylamino)-N-hydroxy-2-oxo-ethanimidoyl chloride remaining, water (200 mL) was added to the reaction mixture, and the layers were separated. The organic layer was washed with water (300 mL) and concentrated under reduced pressure. Toluene was added to the resulting residue, and the mixture was concentrated under reduced pressure to provide the title compound as an oil (144g).

$^1$H NMR (CDCl$_3$): δ 3.1 (s, 3H), 3.3 (s, 3H), 3.4 (m, 1H), 3.57 (m, 1H), 6.0 (m, 1H), 6.95 (m, 2H), 7.35 (m, 1H).

Step B: Preparation of 1-(4,5-dihydro-5-(2,6-difluorophenyl)-3-isoxazolyl)ethanone To a 1000-mL flask equipped with thermometer and addition funnel were added 5-(2,6-difluorophenyl)-4,5-dihydro-N,N-dimethyl-3-isoxazolecarboxamide (i.e. the product of Step A) (80.0 g, 0.31 mol) and toluene (320 mL). The reaction mixture was cooled to −5° C., and a solution of methyl magnesium bromide (3.0 M in tetrahydrofuran, 120 mL, 0.36 mmol) was added dropwise while maintaining the temperature between −10 to −5° C. When gas chromatography analysis of the reaction mixture showed about 2% of 5-(2,6-difluorophenyl)-4,5-dihydro-N,N-dimethyl-3-isoxazolecarboxamide remaining, the reaction mixture was poured into a stirred solution of concentrated hydrochloric acid (80 mL) and water (320 mL) while maintaining the temperature between 10 to 30° C. The organic layer was separated, washed with saturated aqueous sodium chloride solution (80 mL), and then concentrated under reduced pressure. The resulting oil was crystallized from hexanes (100 mL), collected by filtration, washed with hexanes, and dried in a vacuum oven overnight at 23° C. to provide the title compound as a waxy, off-white solid (65 g), melting at 47-50° C.

$^1$H NMR (CDCl$_3$): δ 2.6 (s, 3H), 3.3 (m, 1H), 3.5 (m, 1H), 6.1 (m, 1H), 6.9 (m, 2H), 7.3 (m, 1H

Step C: Preparation of 2-bromo-1-(4,5-dihydro-5-(2,6-difluorophenyl)-3-isoxazolyl)ethanone To a 500-mL flask equipped with a mechanical stirrer, thermometer, addition funnel and scrubber were added 1-(4,5-dihydro-5-(2,6-difluorophenyl)-3-isoxazolyl)ethanone (i.e. the product of Step B) (60.0 g, 0.27 mmol) and dichloromethane (130 mL). The reaction mixture was heated at 33° C., and a solution of bromine (39.2 mL, 0.24 mol) in dichloromethane (100 mL) was added dropwise via the addition funnel. After about 5 mL of the bromine solution had been added, the addition was stopped and the reaction mixture was stirred at 33° C. for about 10 minutes, during which time the color of the reaction mixture changed from red to yellow. The reaction mixture was cooled to 5° C., and the remaining bromine solution was added dropwise over 90 minutes. After the addition was complete, the reaction mixture was washed with sodium bisulfite solution (3.5 g in 100 mL of water). The organic layer was concentrated under reduced pressure, hexanes were added, and the resulting solid precipitate was collected by filtration and washed with hexanes to provide the title compound as a brown solid (73 g), which was used without further purification

Step D: Preparation of 4-[4-[5-(2,6-difluorophenyl)-4,5-dihydro-3-isoxazolyl]-2-thiazolyl]piperidine A mixture of 1-tent-butoxycarbonylpiperidine-4-carbothioamide (7.33 g, 30 mmol) and 2-bromo-1-(4,5-dihydro-5-(2,6-difluorophenyl)-3-isoxazolyl)ethanone (i.e. the product of Step C) (9.12 g, 30 mmol) in acetone (100 mL) was heated at 45° C. for 3 h, and then stirred at room temperature overnight. The acetone solvent was evaporated, and the resulting residue was dissolved in dichloromethane (100 mL) and trifluoroacetic acid (40 mL). The mixture was stirred at room temperature for 3 h, and then concentrated under reduced pressure. The resulting oil was dissolved in aqueous hydrochloric acid solution (0.5 N, 200 mL) and extracted with ethyl acetate. The organic layer was basified by adding aqueous sodium hydroxide solution (10% in water). The organic layer was separated, washed with saturated aqueous sodium chloride solution, dried (MgSO$_4$), filtered and concentrated under reduced pressure to provide the title compound as a thick amber-colored oil (8.62 g, including residual ethyl acetate). The hydrochloric acid solution that had been extracted with ethyl acetate was subsequently basified by adding aqueous sodium hydroxide solution (50% in water) and then extracted with ethyl acetate. The organic layer was washed with saturated aqueous sodium chloride solution, dried (MgSO$_4$), filtered and concentrated under reduced pressure to provide more of the title product as an oil (1.33 g, including residual ethyl acetate).

$^1$H NMR (CDCl$_3$): δ 1.70-1.80 (m, 2H), 1.87 (br s, 1H), 2.22 (m, 2H), 2.77 (m, 2H), 3.18 (m, 3H), 3.62 (m, 1H), 3.80 (m, 1H), 6.05 (m, 1H), 6.92 (m, 2H), 7.30 (m, 1H), 7.64 (s, 1H).

Step E: Preparation of 2,5-dimethyl-α-oxobenzeneacetic acid

Two drops of 2-bromo-1,4-dimethylbenzene and an iodine crystal were add to magnesium turnings (1.7 g, 70.8 mmol). After heating to initiate the reaction, tetrahydrofuran (50 mL) was added, and then 2-bromo-1,4-dimethylbenzene (10 g, 54.1 mmol) was added dropwise the reaction mixture. The reaction was heated at reflux for an additional 1.5 h after the addition was complete, and then cooled to −65° C. and a solution of oxalyl chloride (5.2 mL, 7.6 g, 60 mmol) in THF (60 mL) was added dropwise. After 1 h the reaction mixture was warmed to 0° C., quenched with saturated aqueous ammonium chloride, poured into water and extracted with ethyl acetate (3×). The combined organic extracts were washed with saturated aqueous sodium chloride, dried (MgSO$_4$) and concentrated under reduced pressure. The crude mixture was taken up in ethyl acetate and extracted two times with sodium hydroxide (1 N). The combined aqueous layers were adjusted to pH 3 with HCl (1 N) and extracted with ethyl acetate (3×). The combined organic extracts were dried (MgSO$_4$) and concentrated under reduced pressure to provide the title compound as a tan solid (4.49 g).

$^1$H NMR (CDCl$_3$) δ 2.39 (s, 3H), 2.55 (s, 3H), 7.21 (d, 1H), 7.33 (d, 1H), 7.77 (s, 1H), 10.00 (br s, 1H, COOH).

Step F: Preparation of 1-[4-[4-[5-(2,6-difluorophenyl)-4,5-dihydro-3-isoxazolyl]-2-thiazole]-1-piperidinyl]-2-(2,5-dimethylphenyl)-1,2-ethanedione To a mixture of 2,5-dimethyl-α-oxo-benzeneacetic acid (i.e. the product of Step E) (199 mg, 1.1 mmol) in dichloromethane (5 mL) was added 4-[4-[5-(2,6-difluorophenyl)-4,5-dihydro-3-isoxazolyl]-2-thiazolyl]piperidine (i.e. the product of Step D) (390 mg, 1.1 mmol), 1-(3-dimethylaminopropyl)-3-ethylcarbodiimide hydrochloride (235 mg, 1.2 mmol), 1-hydroxy-1H-benzotriazole (13.5 mg, 0.1 mmol) and 4-methylmorpholine (123 μL, 1.1 mmol). The reaction mixture was stirred at room temperature overnight then poured into water and extracted with dichloromethane (3×). The combined organic extracts were dried (MgSO$_4$) and concentrated under reduced pressure. The resulting material was purified by flash column chromatography using a RediSep®Rf tube (manufactured by Teledyne Isco, Inc.) prepacked with 40 g of silica gel and ethyl acetate-hexanes as eluent to provide the title compound, a compound of the present invention, as an foamy white solid (158 mg).

$^1$H NMR (CDCl$_3$) δ 1.81-2.00 (m, 2H), 2.16 (d, 1H), 2.30 (d, 1H), 2.36 (s, 3H), 2.62 (s, 3H), 3.03-3.12 (m, 1H), 3.22-3.30 (m, 1H), 3.33-3.43 (m, 1H), 3.63 (dd, 1H), 3.67-3.75 (m, 1H), 3.80 (dd, 1H), 4.66-4.73 (m, 1H), 6.08 (dd, 1H), 6.92 (t, 2H), 7.20 (d, 1H), 7.27-7.34 (m, 2H), 7.51 (s, 1H), 7.67 (s, 1H).

$^{19}$F NMR (CDCl$_3$) δ −113.93 (t, 1F).

By the procedures described herein together with methods known in the art, the following compounds of Tables 1 to 13 can be prepared. The following abbreviations are used in the Tables which follow: t means tertiary, s or sec means secondary, n means normal, i means iso, c means cyclo, Me means methyl, Et means ethyl, Pr means propyl, i-Pr means isopropyl, Bu means butyl, Ph means phenyl, MeO means methoxy, EtO means ethoxy, MeS means methylthio, EtS means ethylthio, CN means, SO means sulfonyl, SO$_2$ means sulfonyl, cyano and Ph means phenyl.

TABLE 1

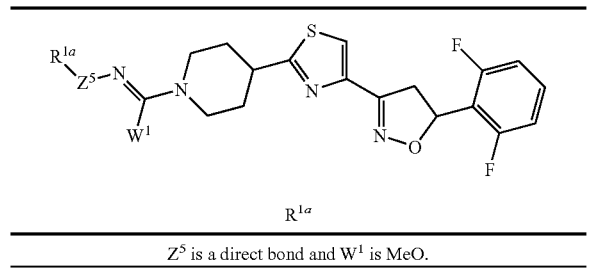

| R$^{1a}$ |
|---|
| Z$^5$ is a direct bond and W$^1$ is MeO. |
| phenyl |
| 2-methylphenyl |
| 2-methoxyphenyl |
| 2-chlorophenyl |
| 2-bromophenyl |
| 2-ethylphenyl |
| 2-ethoxyphenyl |
| 2-(methylthio)phenyl |
| 2-(ethylthio)phenyl |
| 2-(trifluoromethoxy)phenyl |
| 3-chlorophenyl |
| 3-bromophenyl |
| 3-iodophenyl |
| 3-methylphenyl |
| 2,5-dichlorophenyl |
| 5-bromo-2-chlorophenyl |
| 2-chloro-5-iodophenyl |
| 2-chloro-5-methylphenyl |
| 2-chloro-5-ethylphenyl |
| 2-chloro-5-propylphenyl |
| 2-chloro-5-i-propylphenyl |
| 2-chloro-5-(trifluoromethyl)phenyl |
| 2-chloro-5-(2,2,2-trifluoroethyl)phenyl |
| 2-chloro-5-(pentafluoroethyl)phenyl |
| 2-chloro-5-cyanophenyl |
| 2-chloro-5-nitrophenyl |
| 2-bromo-5-chlorophenyl |
| 2,5-dibromophenyl |
| 2-bromo-5-iodophenyl |
| 2-bromo-5-methylphenyl |
| 2-bromo-5-ethylphenyl |
| 2-bromo-5-propylphenyl |
| 2-bromo-5-i-propylphenyl |
| 2-bromo-5-(trifluoromethyl)phenyl |
| 2-bromo-5-(2,2,2-trifluoroethyl)phenyl |
| 2-bromo-5-(pentafluoroethyl)phenyl |
| 2-bromo-5-cyanophenyl |
| 2-bromo-5-nitrophenyl |
| 5-chloro-2-methylphenyl |
| 5-bromo-2-methylphenyl |
| 5-iodo-2-methylphenyl |
| 2,5-dimethylphenyl |
| 5-ethyl-2-methylphenyl |
| 2-methyl-5-propylphenyl |
| 5-i-propyl-2-methylphenyl |
| 2-methyl-5-(trifluoromethyl)phenyl |
| 2-methyl-5-(2,2,2-trifluoroethyl)phenyl |
| 2-methyl-5-(pentafluoroethyl)phenyl |
| 5-cyano-2-methylphenyl |
| 2-methyl-5-nitrophenyl |
| 5-chloro-2-methoxyphenyl |
| 5-bromo-2-methoxyphenyl |
| 5-iodo-2-methoxyphenyl |
| 2-methoxy-5-methylphenyl |
| 5-ethyl-2-methoxyphenyl |
| 2-methoxy-5-propylphenyl |
| 5-i-propyl-2-methoxyphenyl |
| 2-methoxy-5-(trifluoromethyl)phenyl |
| 2-methoxy-5-(2,2,2-trifluoroethyl)phenyl |
| 2-methoxy-5-(pentafluoroethyl)phenyl |
| 5-cyano-2-methoxyphenyl |
| 2-methoxy-5-nitrophenyl |

TABLE 1-continued

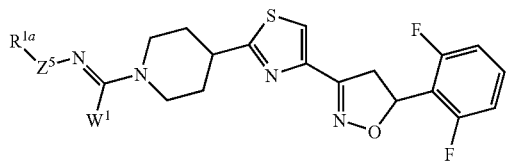

| R$^{1a}$ |
|---|
| 2,5-diethylphenyl |
| 3,5-dimethylpyrazol-1-yl |
| 3,5-dichloropyrazol-1-yl |
| 3,5-dibromopyrazol-1-yl |
| 3,5-bis-(trifluoromethyl)pyrazol-1-yl |
| 5-methyl-3-(trifluoromethyl)pyrazol-1-yl |
| 5-methyl-3-(2,2,2-trifluoroethyl)pyrazol-1-yl |
| 3,5-dimethyl-1,2,4-triazol-1-yl |
| 3,5-dichlorol-1,2,4-triazol-1-yl |
| 3,5-dibromo-1,2,4-triazol-1-yl |
| 2-chloro-5-(dimethylamino)phenyl |
| 2-chloro-5-(diethylamino)phenyl |
| 2-chloro-5-(cyclopropylamino)phenyl |
| 3-(methoxymethyl)phenyl |
| 2-chloro-5-(ethoxymethyl)phenyl |
| 2-chloro-5-(hydroxymethyl)phenyl |
| 2-chloro-5-(methoxycarbonyl)phenyl |
| 2-chloro-5-(ethylcarbonyl)phenyl |
| 2-chloro-5-(methylcarbonyloxy)phenyl |
| 2-chloro-5-(metylaminocarbonyl)phenyl |
| 2-chloro-5-(dimethylaminocarbonyl)phenyl |
| 2-methyl-5-(trimethylsilyl)phenyl |
| 3,5-dimethyl-2-thienyl |
| 3,5-dichloro-2-thienyl |
| 3,5-dimethy1-2-furyl |
| 1-methy1-2-pyrrolyl |
| 4-methyl-2-(trifluoromethyl)-5-thiazolyl |
| 4-(trifluoromethyl)-2-thiazolyl |
| 4-(trifluoromethyl)-2-oxazolyl |
| 4-methyl-2-(trifluoromethyl)-5-oxazolyl |
| 4-bromo-5-isothiazolyl |
| 4-bromo-5-isoxazolyl |
| 1-methyl-5-pyrazoly1 |
| 1-methyl-5-pyrazolyl |
| 1-methyl-5-imidazolyl |
| 1-methyl-4-(trifluoromethyl)-2-imidazolyl |
| 4-methyl-3-(1,3,4-triazolyl) |
| 2-methyl-3-(1,2,4-triazolyl) |
| 5-(trifluoromethyl)-2-(1,3,4-thiadiazolyl) |
| 5-(trifluoromethyl)-2-(1,3,4-oxadiazolyl) |
| 3-(trifluoromethyl)-5-(1,2,4-thiadiazolyl) |
| 3-(trifluoromethyl)-5-(1,2,4-oxadiazolyl) |
| 3-(trifluoromethyl)-1-(1,2,4-triazolyl) |
| 2,5-dimethyl-1-pyrrolyl |
| 1-methyl-3-(trifluoromethyl)pyrazol-5-yl |
| 3-(trifluoromethyl)pyrazol-1-yl |
| 5-butyl-2-methylphenyl |
| 5-hexyl-2-methylphenyl |
| 5-allyl-2-methylphenyl |
| 2-methyl-5-(4-methyl-3-pentenyl)phenyl |
| 2-methyl-5-propargylphenyl |
| 2-methyl-5-(3-methylpropargyl)phenyl |
| 5-cyclopropyl-2-methylphenyl |
| 5-cyclohexyl-2-methylphenyl |
| 2-methyl-5-(pentafluoroisopropyl)phenyl |
| 5-(3,3-dichloro-2-propen-1-yl)-2-methylphenyl |
| 2-methyl-5-(4,4,4-trifluoro-2-butyn-1-yl)phenyl |
| 5-(2,2-dichlorocyclopropan-1-yl)-2-methylphenyl |
| 2-methyl-5-(trifluoromethoxy)phenyl |
| 2-chloro-5-(i-butylthio)phenyl |
| 2-chloro-5-(ethylsulfonyl)phenyl |
| 2-chloro-5-(trifluoromethylthio)phenyl |
| 2-chloro-5-(trifluoromethylsulfonyl)phenyl |
| 2-chloro-5-(methylamino)phenyl |
| 2-chloro-5-(tert-butylamino)phenyl |
| 2,5-dimethyl-3-furyl |
| 2,5-dimethyl-3-thienyl |
| 2,5-dichloro-3-thienyl |
| 1,4-dimethyl-3-pyrrolyl |

TABLE 1-continued

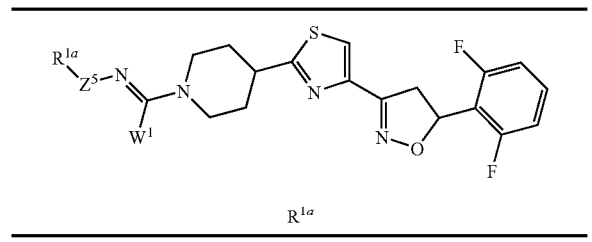

| $R^{1a}$ |
|---|
| 1,4-dimethyl-3-pyrazolyl |
| 1,3-dimethyl-4-pyrazolyl |
| 2,5-dimethyl-4-oxazolyl |
| 2,5-dimethyl-4-thiazolyl |
| 3-bromo-4-thiazolyl |
| 3-bromo-4-isoxazolyl |
| 1-methyl-4-imidazolyl |
| 5-(trifluoromethyl)-3-(1,2,4-oxadiazolyl) |
| 5-(trifluoromethyl)-3-(1,2,4-thiadiazolyl) |
| 2-bromo-1-(1,3,4-triazolyl) |
| 5-(trifluoromethyl)-3-(1,2,4-triazolyl) |
| 2-bromo-1-imidazolyl |
| 3,6-dimethyl-2-pyridyl |
| 2,5-dimethyl-3-pyridyl |
| 2,5-dimethyl-4-pyridyl |
| 3,6-dichloro-2-pyridyl |
| 2,5-dichloro-3-pyridyl |
| 2,5-dichloro-4-pyridyl |
| 4-bromo-3-pyridazinyl |
| 4-(trifluoromethyl)-2-pyrimidinyl |
| 3,6-dimethyl-2-pyrazinyl |
| 2,5-dimethyl-4-pyrimidinyl |
| 4-methoxy-5-pyrimidinyl |
| 3,6-dimethyl-4-pyridazinyl |
| 5-(trifluoromethyl)-3-(1,2,4-triazinyl) |
| 5-methoxy-6-(1,2,4-triazinyl) |
| 4-(trifluoromethyl)-2-(1,3,5-triazinyl) |
| 3,6-dimethyl-5-(1,2,4-triazinyl) |
| 1-methyl-4-(trifluoromethyl)imidazol-2-yl |
| cyano |
| methyl |
| ethyl |
| n-propyl |
| i-propyl |
| n-butyl |
| i-butyl |
| sec-butyl |
| t-butyl |
| n-amyl |
| i-amyl |
| t-amyl |
| n-hexyl |
| i-hexyl |
| 3,3,3-trimethylhex-1-yl |
| n-octyl |
| allyl |
| 3-methyl-2-buten-1yl |
| 4,4-dimetyl-2-pentyn-1-yl |
| 2,2,2-trifluoroethyl |
| 3,3,3-trifluoropropyl |
| 1,1-dichloro-1-propen-3-yl |
| 1,1,1-trifluoro-2-butyn-4-yl |
| cyclopropyl |
| cyclopentyl |
| cyclohexyl |
| cyclopropylmethyl |
| cyclohexylmethyl |
| 2,2-dimethylcyclohexyl |
| 2-methoxyethyl |
| 2-ethoxyethyl |
| 2-(t-butoxy)-ethyl |
| 2-cyclobutoxyethyl |
| 2-cyclohexylethyl |
| 2-(ethoxyethox)yethyl |
| 2-(methylthio)ethyl |
| 2-(methylsulfinyl)ethyl |
| 2-(methylsulfonyl)ethyl |
| 2-(methylamino)ethyl |
| 2,2,2-trifluoroethylaminoethyl |

TABLE 1-continued

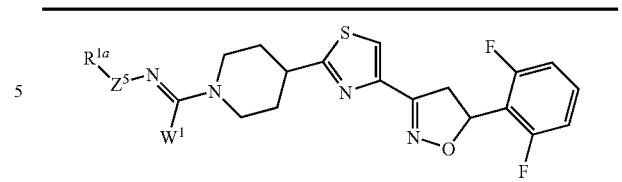

| $R^{1a}$ |
|---|
| 2-cyclohexylaminoethyl |
| methoxy |
| 2-chloroethyoxy |
| cyclohexyloxy |
| 2-chloropent-1-yloxy |
| cyclohexylmethoxy |
| allyloxy |
| 1-bromo-1-propen-3-yloxy |
| propargyloxy |
| 1,1,1-trifluoro-2-butyn-4-yloxy |
| 2-methoxyethoxy |
| trimethylsilyl |
| ethylamino |
| diethylamino |
| dimethylamino |
| 2,2,2-trifluoroethylamino |
| t-butylamino |
| N-methyl-N-butylamino |
| methylcarbonylamino |
| trifluoromethylcarbonylamino |
| methylsulfonylamino |
| chloromethylsulfonylamino |
| $Z^5$ is C(=O) and $W^1$ is MeO. |
| 2,5-dimethylphenyl |
| 2,5-dichlorophenyl |
| 2-methyl-5-chlorophenyl |
| 2-chloro-5-methylphenyl |
| 2-methyl-5-(trifluoromethyl)phenyl |
| 2,6-dichlorophenyl |
| methyl |
| i-propyl |
| i-butyl |
| 3,3,3-trifluoroprop-1-yl |
| cyclopropyl |
| i-propoxy |
| cyclohexyloxy |
| dimethylamino |
| diethylamino |
| (trifluoromethoxy)methyl |
| $Z^5$ is $S(O)_2$ and $W^1$ is MeO. |
| 2,5-dimethylphenyl |
| 2,5-dichlorophenyl |
| 2-methyl-5-chlorophenyl |
| 2-chloro-5-methylphenyl |
| 2-methyl-5-(trifluoromethyl)phenyl |
| 2,6-dichlorophenyl |
| methyl |
| i-propyl |
| i-butyl |
| trifluoromethyl |
| cyclopropyl |
| methoxy |
| cyclohexyloxy |
| dimethylamino |
| diethylamino |
| methoxymethyl |
| $Z^5$ is a direct bond and $W^1$ is EtO. |
| 2-methylphenyl |
| 2-methoxyphenyl |
| 3-chlorophenyl |
| 3-bromophenyl |
| 3-(trifluoromethyl)phenyl |
| 3-methylphenyl |
| 2,5-dichlorophenyl |
| 2-chloro-5-methylphenyl |
| 2-chloro-5-(trifluoromethyl)phenyl |

TABLE 1-continued

R$^{1a}$—Z$^5$—N=C(W$^1$)—[piperidine]—[thiazole]—[isoxazoline]—(2,6-difluorophenyl)

R$^{1a}$ 2,5-dibromophenyl
2-bromo-5-methylphenyl
2-bromo-5-(trifluoromethyl)phenyl
5-chloro-2-methylphenyl
5-bromo-2-methylphenyl
2-methyl-5-(trifluoromethyl)phenyl
5-chloro-2-methoxyphenyl
5-bromo-2-methoxyphenyl
2-methoxy-5-(trifluoromethyl)phenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichloro-1,2,4-triazol-1-yl
3,5-dibromo-1,2,4-triazol-1-yl
methyl
2-methylpropyl
3-methylbutyl
ethoxy
3,3,3-trifluoropropoxy
4,4,4-trifluorobutyl
Z$^5$ is a direct bond and W$^1$ is MeS.

2-methylphenyl
2-methoxyphenyl
3-chlorophenyl
3-bromophenyl
3-(trifluoromethyl)phenyl
3-methylphenyl
2,5-dichlorophenyl
2-chloro-5-methylphenyl
2-chloro-5-(trifluoromethyl)phenyl
2,5-dibromophenyl
2-bromo-5-methylphenyl
2-bromo-5-(trifluoromethyl)phenyl
5-chloro-2-methylphenyl
5-bromo-2-methylphenyl
2-methyl-5-(trifluoromethyl)phenyl
5-chloro-2-methoxyphenyl
5-bromo-2-methoxyphenyl
2-methoxy-5-(trifluoromethyl)phenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichloro-1,2,4-triazol-1-yl
3,5-dibromo-1,2,4-triazol-1-yl
methyl
2-methylpropyl
3-methylbutyl
ethoxy
3,3,3-trifluoropropoxy
4,4,4-trifluorobutyl
Z$^5$ is a direct bond and W$^1$ is EtS.

2-methylphenyl
2-methoxyphenyl
3-chlorophenyl
3-bromophenyl
3-(trifluoromethyl)phenyl
3-methylphenyl
2,5-dichlorophenyl
2-chloro-5-methylphenyl
2-chloro-5-(trifluoromethyl)phenyl
2,5-dibromophenyl

TABLE 1-continued

R$^{1a}$—Z$^5$—N=C(W$^1$)—[piperidine]—[thiazole]—[isoxazoline]—(2,6-difluorophenyl)

R$^{1a}$ 2-bromo-5-methylphenyl
2-bromo-5-(trifluoromethyl)phenyl
5-chloro-2-methylphenyl
5-bromo-2-methylphenyl
2-methyl-5-(trifluoromethyl)phenyl
5-chloro-2-methoxyphenyl
5-bromo-2-methoxyphenyl
2-methoxy-5-(trifluoromethyl)phenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichloro-1,2,4-triazol-1-yl
3,5-dibromo-1,2,4-triazol-1-yl
methyl
2-methylpropyl
3-methylbutyl
Ethoxy
3,3,3-trifluoropropoxy
4,4,4-trifluorobutyl
Z$^5$ is a direct bond and W$^1$ is NH$_2$.

2-methylphenyl
2-methoxyphenyl
3-chlorophenyl
3-bromophenyl
3-(trifluoromethyl)phenyl
3-methylphenyl
2,5-dichlorophenyl
2-chloro-5-methylphenyl
2-chloro-5-(trifluoromethyl)phenyl
2,5-dibromophenyl
2-bromo-5-methylphenyl
2-bromo-5-(trifluoromethyl)phenyl
5-chloro-2-methylphenyl
5-bromo-2-methylphenyl
2-methyl-5-(trifluoromethyl)phenyl
5-chloro-2-methoxyphenyl
5-bromo-2-methoxyphenyl
2-methoxy-5-(trifluoromethyl)phenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichlorol-1,2,4-triazol-1-yl
3,5-dibromo-1,2,4-triazol-1-yl
methyl
2-methylpropyl
3-methylbutyl
ethoxy
3,3,3-trifluoropropoxy
4,4,4-trifluorobutyl
Z$^5$ is a direct bond and W$^1$ is HONH—.

2-methylphenyl
2-methoxyphenyl
3-chlorophenyl
3-bromophenyl
3-(trifluoromethyl)phenyl
3-methylphenyl
2,5-dichlorophenyl
2-chloro-5-methylphenyl
2-chloro-5-(trifluoromethyl)phenyl
2,5-dibromophenyl
2-bromo-5-methylphenyl TABLE 1-continued

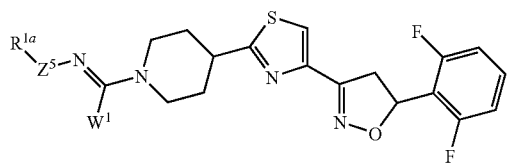

R(1a)

2-bromo-5-(trifluoromethyl)phenyl
5-chloro-2-methylphenyl
5-bromo-2-methylphenyl
2-methyl-5-(trifluoromethyl)phenyl
5-chloro-2-methoxyphenyl
5-bromo-2-methoxyphenyl
2-methoxy-5-(trifluoromethyl)phenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichlorol-1,2,4-triazol-1-yl
3,5-dibromo-1,2,4-triazol-1-yl
methyl
2-methylpropyl
3-methylbutyl
ethoxy
3,3,3-trifluoropropoxy
4,4,4-trifluorobutyl
$Z^5$ is a direct bond and $W^1$ is MeONH.

2-methylphenyl
2-methoxyphenyl
3-chlorophenyl
3-bromophenyl
3-(trifluoromethyl)phenyl
3-methylphenyl
2,5-dichlorophenyl
2-chloro-5-methylphenyl
2-chloro-5-(trifluoromethyl)phenyl
2,5-dibromophenyl
2-bromo-5-methylphenyl
2-bromo-5-(trifluoromethyl)phenyl
5-chloro-2-methylphenyl
5-bromo-2-methylphenyl
2-methyl-5-(trifluoromethyl)phenyl
5-chloro-2-methoxyphenyl
5-bromo-2-methoxyphenyl
2-methoxy-5-(trifluoromethyl)phenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichloro-1,2,4-triazol-1-yl
3,5-dibromo-1,2,4-triazol-1-yl
methyl
2-methylpropyl
3-methylbutyl
ethoxy
3,3,3-trifluoropropoxy
4,4,4-trifluorobutyl
$Z^5$ is a direct bond and $W^1$ is NCNH—.

2-methylphenyl
2-methoxyphenyl
3-chlorophenyl
3-bromophenyl
3-(trifluoromethyl)phenyl
3-methylphenyl
2,5-dichlorophenyl
2-chloro-5-methylphenyl
2-chloro-5-(trifluoromethyl)phenyl
2,5-dibromophenyl
2-bromo-5-methylphenyl
2-bromo-5-(trifluoromethyl)phenyl TABLE 1-continued

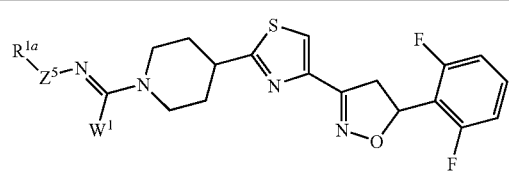

R(1a)

5-chloro-2-methylphenyl
5-bromo-2-methylphenyl
2-methyl-5-(trifluoromethyl)phenyl
5-chloro-2-methoxyphenyl
5-bromo-2-methoxyphenyl
2-methoxy-5-(trifluoromethyl)phenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichloro-1,2,4-triazol-1-yl
3,5-dibromo-1,2,4-triazol-1-yl
methyl
2-methylpropyl
3-methylbutyl
ethoxy
3,3,3-trifluoropropoxy
4,4,4-trifluorobutyl
$Z^5$ is a direct bond and $W^1$ is $H_2NNH$—.

2-methylphenyl
2-methoxyphenyl
3-chlorophenyl
3-bromophenyl
3-(trifluoromethyl)phenyl
3-methylphenyl
2,5-dichlorophenyl
2-chloro-5-methylphenyl
2-chloro-5-(trifluoromethyl)phenyl
2,5-dibromophenyl
2-bromo-5-methylphenyl
2-bromo-5-(trifluoromethyl)phenyl
5-chloro-2-methylphenyl
5-bromo-2-methylphenyl
2-methyl-5-(trifluoromethyl)phenyl
5-chloro-2-methoxyphenyl
5-bromo-2-methoxyphenyl
2-methoxy-5-(trifluoromethyl)phenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichloro-1,2,4-triazol-1-yl
3,5-dibromo-1,2,4-triazol-1-yl
methyl
2-methylpropyl
3-methylbutyl
ethoxy
3,3,3-trifluoropropoxy
4,4,4-trifluorobutyl

TABLE 2

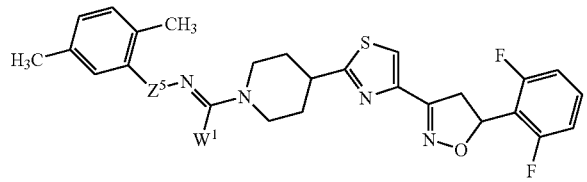

W$^1$

Z$^5$ is a direct bond.

ethoxy
propoxy
i-propoxy
i-butoxy
amyloxy
3,3-dimethylbutoxy
allyloxy
3 methyl-2-buten-1yloxy
2,2,2-trifluoroethoxy
3,3,3-trifluoropropoxy
1,1-dichloro-1-propen-3-yloxy
1,1,1-trifluoro-2-butyn-4-yloxy
cyclopropoxy
cyclopentoxy
cyclohexyloxy
cyclopropylmethoxy
cyclohexylmethoxy
2-methoxyethoxy
2-ethoxyethoxy
2-t-butoxyethoxy
2-cyclobutoxyethoxy
2-(ethoxyethoxy)ethoxy
2-(methylthio)ethoxy
2-(methylsulfinyl)ethoxy
2-(methylsulfonyl)ethoxy
2,2-(dimethylamino)ethoxy
2,2,2-(trifluoroethylamino)ethoxy
methylcarbonyloxy
t-butylcarbonyloxy
trifluoromethylcarbonyloxy
cyclopropylcarbonyloxy
methoxycarbonyloxy
methylaminocarbonyloxy
dimethylaminocarbonyloxy
methoxythio
ethoxythio
propylthio
i-propylthio
t-butylthio
allylsulfanyl
3-methyl-2-buten-1-ylthio
2,2,2-trifluoroethylthio
3,3,3-trifluoroethylthio
1,1-dichloro-1-propen-3-ylthio
1,1,1-trifluoro-2-butyn-4-ylthio
cyclopropylsulfanyl
cyclopentylthio
cyclohexylthio
cyclopropylmethylthio
cyclohexylmethylthio
2-methoxyethylthio
2-ethoxyethylthio
2-t-butoxyethylthio
2-cyclobutoxyethylthio
2-(ethoxyethoxyethyl)thio
H
methyl
ethyl
propyl
i-propyl
2-methylthioethylthio
2-metylsulfinylethylthio
2-methylsulfonylethylthio
2,2-dimethylaminoethylthio
2,2,2-trifluoroethylaminoethylthio
methylcarbonylthio

TABLE 2-continued

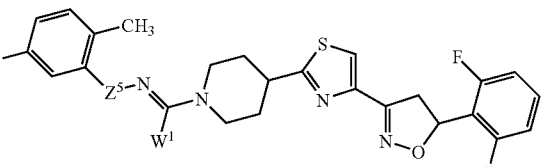

W$^1$ t-butylcarbonylthio
trifluoromethylcarbonylthio
cyclopropylcarbonylthio
methoxycarbonylthio
methylaminocarbonylthio
dimethylaminocarbonylthio
amino
hydroxyamino
cyanoamino
aminoamino
methylamino
ethylamino
i-propylamino
t-butylamino
3,3-dimethylbutylamino
allylamino
3-methyl-2-buten-1-ylamino
2,2,2-trifluoroethylamino
3,3,3-trifluoropropylamino
1,1-dichloro-1-propen-3-ylamino
1,1,1-trifluoro-2-butyn-4-ylamino
propargylamino
cyclopropylamino
cyclohexylamino
cyclopropylmethylamino
2-methoxyethylamino
2-ethoxyethylamino
2-t-butoxyethylamino
2-(ethoxyethoxy)ethylamino
methoxyamino
ethoxyamino
2,2,2-trifluoroethoxyamino
methylsulfonylamino
trifluoromethylsulfonylamino
methylaminoamino
ethylaminoamino
dimethylaminoamino
2,2,2-trifluoroethylaminoamino
dimethylamino
cyanoamino
N-methyl-N-butylamino
N-methyl-N-allylamino
N-methyl-N-propargylamino
N-methyl-N-cyclopropylamino
methoxyethyl
ethoxyethyl
methylcarbonyl
methoxycarbonyl
methylaminocarbonyl
dimethylaminocarbonyl
cyano
i-butyl
trifluoromethyl
methoxymethyl

TABLE 3

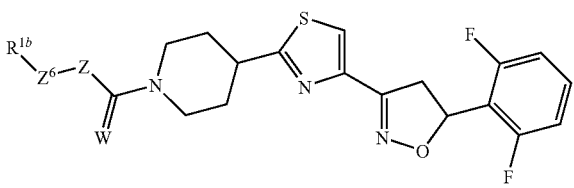

R$^{1b}$

| Z6 is a direct bond, A is C(=O) and W is O. |
| --- |
| 2-methylphenyl |
| 2-methoxyphenyl |
| 3-chlorophenyl |
| 3-bromophenyl |
| 3-(trifluoromethyl)phenyl |
| 3-methylphenyl |
| 2,5-dichlorophenyl |
| 2-chloro-5-methylphenyl |
| 2-chloro-5-(trifluoromethyl)phenyl |
| 2,5-dibromophenyl |
| 2-bromo-5-methylphenyl |
| 2-bromo-5-(trifluoromethyl)phenyl |
| 5-chloro-2-methylphenyl |
| 5-bromo-2-methylphenyl |
| 2-methyl-5-(trifluoromethyl)phenyl |
| 5-chloro-2-methoxyphenyl |
| 5-bromo-2-methoxyphenyl |
| 2-methoxy-5-(trifluoromethyl)phenyl |
| 2,5-dimethylphenyl |
| 3,5-dimethyl-2-thienyl |
| 3,5-dichloro-2-thienyl |
| 3,5-dimethyl-2-furyl |
| 4-methyl-2-(trifluoromethyl)-5-thiazolyl |
| 1-methyl-3-(trifluoromethyl)pyrazol-5-yl |
| 2,5-dimethyl-3-furyl |
| 2,5-dimethyl-3-thienyl |
| 2,5-dichloro-3-thienyl |
| 3,6-dimethyl-2-pyridyl |
| 2,5-dimethyl-3-pyridyl |
| 2,5-dimethyl-4-pyridyl |
| 3,6-dichloro-2-pyridyl |
| 2,5-dichloro-3-pyridyl |
| 2,5-dichloro-4-pyridyl |
| methyl |
| ethyl |
| n-propyl |
| i-propyl |
| n-butyl |
| i-butyl |
| sec-butyl |
| t-butyl |
| n-amyl |
| i-amyl |
| t-amyl |
| n-hexyl |
| i-hexyl |
| 3,3,3-trimethylhex-1-yl |
| n-octyl |
| allyl |
| 3-methyl-2-buten-1yl |
| 4,4-dimetyl-2-pentyn-1-yl |
| 4,4,4-trifluorobutyl |
| 3,3,3-trifluoropropyl |
| 1,1-dichloro-1-propen-3-yl |
| 1,1,1-trifluoro-2-butyn-4-yl |
| cyclopropyl |
| cyclopentyl |
| cyclohexyl |
| cyclopropylmethyl |
| cyclohexylmethyl |
| 2,2-dimethylcyclohexyl |
| 2-methoxyethyl |
| 2-ethoxyethyl |
| 2-t-butoxyethyl |
| 2-cyclobutoxyethyl |
| 2-cyclohexylethyl |

TABLE 3-continued

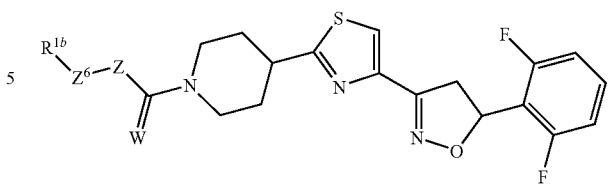

R$^{1b}$

| |
| --- |
| 2-(ethoxyethoxy)ethyl |
| 2-(methylthio)ethyl |
| 2-(methylsulfinyl)ethyl |
| 2-(methylsulfonyl)ethyl |
| 2-(methylamino)ethyl |
| 2-(2,2,2-trifluoroethyl)aminoethyl |
| 2-(cyclohexylamino)ethyl |
| methoxy |
| 2-chloroethoxy |
| ethoxy |
| 3,3,3-trifluoropropoxy |
| allyloxy |
| 1-bromo-1-propen-3-yloxy |
| propargyloxy |
| 1,1,1-trifluoro-2-butyn-4-yloxy |
| 2-methoxyethoxy |
| ethylamino |
| diethylamino |
| dimethylamino |
| 2,2,2-trifluoroethylamino |
| t-butylamino |
| N-methyl-N-butylamino |
| methylcarbonylamino |
| trifluoromethylcarbonylamino |
| methylsulfonylamino |
| chloromethylsulfonylamino |

| Z$^6$ direct bond A is HOCH— and W is O. |
| --- |
| methyl |
| ethyl |
| n-propyl |
| i-propyl |
| n-butyl |
| i-butyl |
| sec-butyl |
| t-butyl |
| n-amyl |
| i-amyl |
| t-amyl |
| n-hexyl |
| i-hexyl |
| 3,3,3-trimethylhex-1-yl |
| n-octyl |
| allyl |
| 3-methyl-2-buten-1-yl |
| 4,4-dimethyl-2-pentyn-1-yl |
| 2,2-dimethylcyclohexyl |
| 4,4,4-trifluorobut-1-yl |
| 3,3,3-trifluoropropyl |
| 1,1-dichloro-1-propen-3-yl |
| 1,1,1-trifluoro-2-butyn-4-yl |
| cyclopropyl |
| cyclopentyl |
| cyclohexyl |
| cyclopropylmethyl |
| cyclohexylmethyl |
| 2-(ethoxyethoxy)ethyl |
| 2-(methylthio)ethyl |
| 2-(metylsulfinyl)ethyl |
| 2-(methylsulfonyl)ethyl |
| 2-(methylamino)ethyl |
| 2-(2,2,2-trifluoroethylamino)ethyl |
| 2-cyclohexylethyl |
| 2-(ethoxyethoxy)ethyl |
| 2-methoxyethyl |
| 2-(2,2,2-trifluoroethoxy)ethyl |

| Z$^6$ is a direct bond, A is CH$_2$ and W is O. |
| --- |

TABLE 3-continued

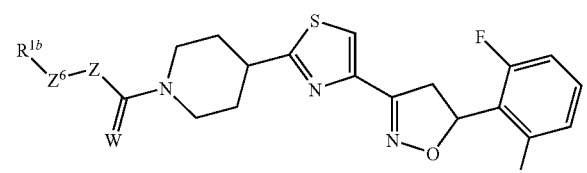

R$^{1b}$ cyano
methyl
ethyl
n-propyl
i-propyl
n-butyl
i-butyl
sec-butyl
t-butyl
n-amyl
i-amyl
t-amyl
n-hexyl
i-hexyl
3,3,3-trimethylhex-1-yl
n-octyl
allyl
3-methyl-2-buten-1-yl
4,4-dimethyl-2-pentyn-1-yl
4,4,4-trifluorobutyl
3,3,3-trifluoropropyl
1,1-dichloro-1-propen-3-yl
1,1,1-trifluoro-2-butyn-4-yl
cyclopropyl
cyclopentyl
cyclohexyl
cyclopropylmethyl
cyclohexylmethyl
2,2-dimethylcyclohexyl
2-methoxyethyl
2-ethoxyethyl
2-t-butoxyethyl
2-cyclobutoxyethyl
2-cyclohexylethyl
2-(ethoxyethoxy)ethyl
2-(methylthio)ethyl
2-(methylsulfinyl)ethyl
2-(methylsulfonyl)ethyl
2-(methylamino)ethyl
2,2,2-trifluoroethylaminoethyl
2-cyclohexylaminoethyl
methoxy
2-chloroethoxy
cyclohexyloxy
3,3,3-trifluoromethylpropoxy
cyclohexylmethoxy
allyloxy
1,1-dichloro-1-propen-3-yloxy
propargyloxy
1,1,1-trifluoro-2-butyn-4-yloxy
2-methoxyethoxy
trimethylsilyl
ethylamino
diethylamino
dimethylamino
2,2,2-trifluoroethylamino
t-butylamino
N-methyl-N-butylamino
methylcarbonylamino
trifluoromethylcarbonylamino
methylsulfonylamino
chloromethylsulfonylamino

TABLE 4

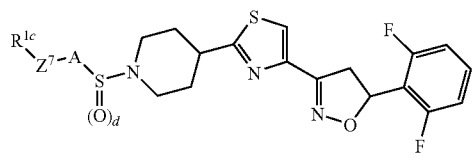

R$^{1bc}$

Z$^7$ is a direct bond, A is NH and d is 2.

2-methylphenyl
2-methoxyphenyl
3-chlorophenyl
3-bromophenyl
3-(trifluoromethyl)phenyl
3-methylphenyl
2,5-dichlorophenyl
2-chloro-5-methylphenyl
2-chloro-5-(trifluoromethyl)phenyl
2,5-dibromophenyl
2-bromo-5-methylphenyl
2-bromo-5-(trifluoromethyl)phenyl
5-chloro-2-methylphenyl
5-bromo-2-methylphenyl
2-methyl-5-(trifluoromethyl)phenyl
5-chloro-2-methoxyphenyl
5-bromo-2-methoxyphenyl
2-methoxy-5-(trifluoromethyl)phenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichloro-1,2,4-triazol-1-yl
3,5-dibromo-1,2,4-triazol-1-yl
methyl
2-methylpropyl
3-methylbutyl
ethoxy
3,3,3-trifluoropropoxy
4,4,4-trifluorobutyl Z$^7$ is direct bond, A is CH$_2$ and d is 1.

2,5-dichlorophenyl
2-chloro-5-methylphenyl
2-chloro-5-(trifluoromethyl)phenyl
2,5-dibromophenyl
5-chloro-2-methylphenyl
2-methyl-5-(trifluoromethyl)phenyl
2,5-dimethylphenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichloro-1,2,4-triazol-1-yl
3,5-dibromo-1,2,4-triazol-1-yl
2,5-dichlorophenyl
2-chloro-5-methylphenyl
2-chloro-5-(trifluoromethyl)phenyl
2,5-dibromophenyl
5-chloro-2-methylphenyl
2-methyl-5-(trifluoromethyl)phenyl
2,5-dimethylphenyl
3,5-dimethylpyrazol-1-yl
3,5-dichloropyrazol-1-yl
3,5-dibromopyrazol-1-yl
3,5-bis-(trifluoromethyl)pyrazol-1-yl
5-methyl-3-(trifluoromethyl)pyrazol-1-yl
3,5-dimethyl-1,2,4-triazol-1-yl
3,5-dichlorol-1,2,4-triazol-1-yl
3,5-dibromo-1,2,4-triazol-1-yl

TABLE 5

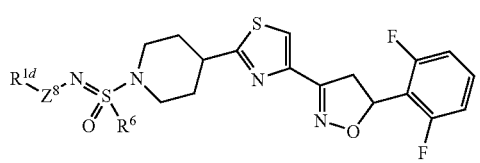

R$^{1d}$

Z$^8$ is a direct bond and R$^6$ is Me.

2-methylphenyl 2-methoxyphenyl 3-chlorophenyl 3-bromophenyl 3-(trifluoromethyl)phenyl 3-methylphenyl 2,5-dichlorophenyl 2-chloro-5-methylphenyl 2-chloro-5-(trifluoromethyl)phenyl 2,5-dibromophenyl 2-bromo-5-methylphenyl 2-bromo-5-(trifluoromethyl)phenyl 5-chloro-2-methylphenyl 5-bromo-2-methylphenyl 2-methyl-5-(trifluoromethyl)phenyl 5-chloro-2-methoxyphenyl 5-bromo-2-methoxyphenyl 2-methoxy-5-(trifluoromethyl)phenyl 3,5-dimethylpyrazol-1-yl 3,5-dichloropyrazol-1-yl 3,5-dibromopyrazol-1-yl 3,5-bis-(trifluoromethyl)pyrazol-1-yl 5-methyl-3-(trifluoromethyl)pyrazol-1-yl 3,5-dimethyl-1,2,4-triazol-1-yl 3,5-dichlorol-1,2,4-triazol-1-yl 3,5-dibromo-1,2,4-triazol-1-yl methyl 2-methylpropyl 3-methylbutyl ethoxy 3,3,3-trifluoropropoxy 4,4,4-trifluorobutyl

TABLE 6a

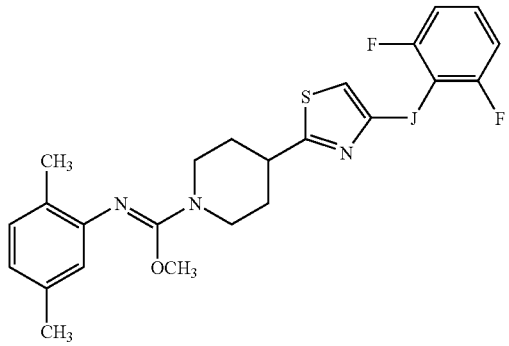

In Table 6a the structure of J (e.g. J-1) is shown in Exhibit 3 in the above Embodiments, wherein x is 1, R$^5$ is Q (i.e. —Z$_2$Q wherein Z$^2$ is a direct bond), and Q is 2,6-difluorophenyl as depicted in the structure immediately above. The thiazole ring in the above structure corresponds to G in Formula 1. The numbers in parentheses following J refer to the attachment points of the J ring to G (i.e. thiazole) and Q (i.e. 2,6-difluorophenyl). The first number is the ring position on J where G is attached, and the second number is the ring position on J where Q is attached.

| J |
|---|
| J-1 (2/4) |
| J-1 (2/5) |
| J-1 (4/2) |
| J-1 (5/2) |
| J-2 (2/4) |
| J-2 (2/5) |
| J-2 (4/2) |
| J-2 (5/2) |
| J-3 (4/1) |
| J-4 (2/4) |
| J-4 (2/5) |
| J-4 (4/2) |
| J-4 (5/2) |
| J-4 (3/5) |
| J-4 (5/3) |
| J-5 (2/5) |
| J-5 (4/2) |
| J-5 (5/2) |
| J-5 (3/5) |
| J-5 (5/3) |
| J-6 (2/4) |
| J-6 (3/5) |
| J-6 (2/5) |
| J-6 (4/2) |
| J-6 (5/2) |
| J-6 (4/2) |
| J-6 (5/3) |
| J-6 (3/1) |
| J-7 (5/3) |
| J-7 (3/5) |
| J-8 (5/3) |
| J-8 (3/5) |
| J-9 (4/1) |
| J-10 (3/5) |
| J-10 (5/3) |
| J-11 (3/5) |
| J-11 (5/3) |
| J-12 (3/1) |
| J-13 (1/4) |
| J-13 (4/1) |
| J-14 (5/3) |
| J-15 (2/5) |
| J-16 (2/5) |
| J-17 (4/2) |
| J-18 (5/2) |
| J-19 (2/4) |
| J-19 (4/2) |
| J-20 (2/4) |
| J-20 (2/5) |

TABLE 6a-continued

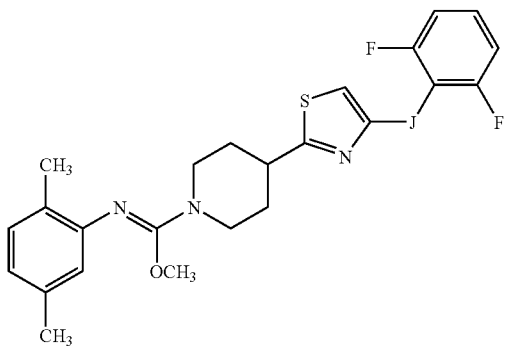

In Table 6a the structure of J (e.g. J-1) is shown in Exhibit 3 in the above Embodiments, wherein x is 1, $R^5$ is Q (i.e. —$Z_2$Q wherein $Z^2$ is a direct bond), and Q is 2,6-difluorophenyl as depicted in the structure immediately above. The thiazole ring in the above structure corresponds to G in Formula 1. The numbers in parentheses following J refer to the attachment points of the J ring to G (i.e. thiazole) and Q (i.e. 2,6-difluorophenyl). The first number is the ring position on J where G is attached, and the second number is the ring position on J where Q is attached.

| J |
|---|
| J-20 (2/6) |
| J-20 (3/5) |
| J-20 (4/2) |
| J20 (5/2) |
| J-21 (3/5) |
| J-21 (3/6) |
| J-21 (5/3) |
| J-22 (2/4) |
| J-22 (2/5) |
| J-22 (4/6) |
| J-22 (4/2) |
| J-22 (5/2) |
| J-23 (2/5) |
| J-23 (2/6) |
| J-24 (2/4) |
| J-24 (2/5) |
| J-24 (4/2) |
| J-24 (5/2) |
| J-25 (2/4) |
| J-25 (2/5) |
| J-25 (4/2) |
| J-25 (5/2) |
| J-26 (2/4) |
| J-26 (2/5) |
| J-26 (4/2) |
| J-26 (5/2) |
| J-26 (4/1) |
| J-27 (2/4) |
| J-27 (2/5) |
| J-27 (3/5) |
| J-27 (4/2) |
| J-27 (5/2) |
| J-27 (5/3) |
| J-28 (3/5) |
| J-28 (5/3) |
| J-29 (3/5) |
| J-29 (5/3) |
| J-30 (3/5) |
| J-30 (5/3) |
| J-30 (3/1) |
| J-30 (4/1) |
| J-31 (2/4) |
| J-31 (2/5) |
| J-31 (3/5) |
| J-31 (3/1) |
| J-31 (4/1) |
| J-31 (4/2) |
| J-31 (5/2) |
| J-32 (2/4) |

TABLE 6a-continued

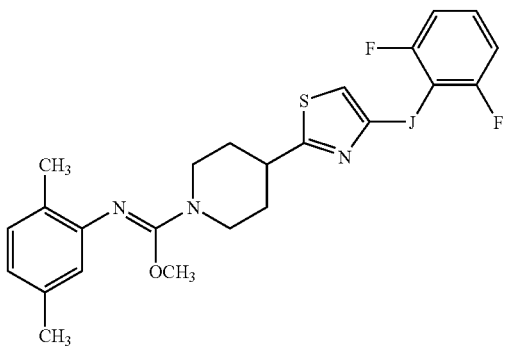

In Table 6a the structure of J (e.g. J-1) is shown in Exhibit 3 in the above Embodiments, wherein x is 1, $R^5$ is Q (i.e. —$Z_2$Q wherein $Z^2$ is a direct bond), and Q is 2,6-difluorophenyl as depicted in the structure immediately above. The thiazole ring in the above structure corresponds to G in Formula 1. The numbers in parentheses following J refer to the attachment points of the J ring to G (i.e. thiazole) and Q (i.e. 2,6-difluorophenyl). The first number is the ring position on J where G is attached, and the second number is the ring position on J where Q is attached.

| J |
|---|
| J-32 (2/5) |
| J-32 (3/5) |
| J-32 (5/3) |
| J-32 (5/2) |
| J-32 (4/2) |
| J-33 (2/4) |
| J-33 (2/5) |
| J-33 (3/5) |
| J-33 (5/3) |
| J-33 (5/2) |
| J-33 (4/2) |
| J-34 (1/3) |
| J-34 (1/4) |
| J-34 (3/5) |
| J-34 (3/1) |
| J-34 (4/1) |
| J-35 (4/1) |
| J-36 (1/3) |
| J-36 (3/1) |
| J-36 (3/5) |
| J-36 (5/3) |
| J-37 (2/5) |
| J-37 (5/2) |
| J-37 (2/4) |
| J-37 (4/2) |
| J-38 (2/5) |
| J-38 (5/2) |
| J-38 (2/4) |
| J-38 (4/2) |
| J-40 (3/5) |
| J-40 (5/3) |
| J-41 (1/3) |
| J-41 (1/4) |
| J-44 (1/3) |
| J-44 (2/4) |
| J-44 (2/5) |
| J-44 (2/6) |
| J-45 (2/4) |
| J-45 (2/5) |
| J-45 (2/6) |
| J-46 (2/4) |
| J-46 (2/5) |
| J-46 (4/2) |
| J-46 (5/2) |
| J-47 (2/4) |
| J-47 (2/5) |
| J-47 (4/2) |
| J-47 (5/2) |
| J-48 (3/5) |

TABLE 6a-continued

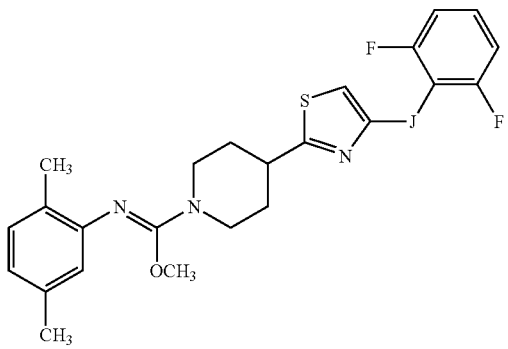

In Table 6a the structure of J (e.g. J-1) is shown in Exhibit 3 in the above Embodiments, wherein x is 1, $R^5$ is Q (i.e. —$Z_2$Q wherein $Z^2$ is a direct bond), and Q is 2,6-difluorophenyl as depicted in the structure immediately above. The thiazole ring in the above structure corresponds to G in Formula 1. The numbers in parentheses following J refer to the attachment points of the J ring to G (i.e. thiazole) and Q (i.e. 2,6-difluorophenyl). The first number is the ring position on J where G is attached, and the second number is the ring position on J where Q is attached.

| J |
|---|
| J-49 (2/4) |
| J-49 (2/5) |
| J-49 (4/2) |
| J-49 (5/2) |
| J-50 (2/6) |
| J-51 (2/6) |
| J-52 (2/6) |
| J-69 (1/3) |
| J-69 (1/4) |
| J-70 (1/3) |
| J-71 (2/4) |
| J-71 (4/2) |
| J-72 (2/4) |
| J-72 (4/2) |
| J-73 (2/4) |
| J-73 (4/2) |
| J-73 (1/3) |
| J-73 (1/4) |
| J-73 (4/1) |
| J-74 (3/5) |
| J-74 (5/3) |
| J-75 (3/5) |
| J-75 (5/3) |
| J-75 (2/4) |
| J-75 (2/5) |
| J-76 (3/6) |
| J-76 (6/3) |
| J-77 (3/5) |
| J-77 (5/3) |
| J-78 (1/3) |
| J-79 (1/3) |
| J-79 (3/1) |
| J-80 (1/3) |
| J-80 (3/1) |
| J-81 (3/5) |
| J-81 (5/3) |
| J-82 (3/5) |
| J-82 (3/6) |
| J-82 (5/3) |
| J-82 (6/3) |

TABLE 6b

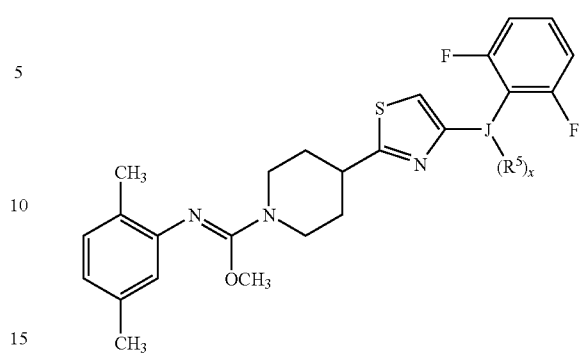

In Table 6b the structure of J (e.g. J-3) is shown in Exhibit 3 in the above Embodiments, wherein x is 2, one $R^5$ substituent is Q (i.e. —$Z^2$Q wherein $Z^2$ is a direct bond), and Q is 2,6-difluorophenyl as depicted in the structure immediately above. The other $R^5$ substituent is tabulated under the heading $(R^5)_x$. The thiazole ring in the above structure corresponds to G in Formula 1. The numbers in parentheses following J refer to the attachment points of the J ring to G (i.e. thiazole) and Q (i.e. 2,6-difluorophenyl). The first number is the ring position on J where G is attached, and the second number is the ring position on J where Q is attached.

| J | $(R^5)_x$ |
|---|---|
| J-3 (2/4) | 1-CH3 |
| J-3 (2/5) | 1-$CH_3$ |
| J-3 (4/2) | 1-$CH_3$ |
| J-3 (5/2) | 1-$CH_3$ |
| J-9 (5/3) | 1-$CH_3$ |
| J-9 (3/5) | 1-$CH_3$ |
| J-12 (3/5) | 1-$CH_3$ |
| J-12 (5/3) | 1-$CH_3$ |
| J-14 (3/5) | 1-$CH_3$ |
| J-39 (3/5) | 4-$CH_3$ |
| J-39 (5/3) | 4-$CH_3$ |
| J-74 (2/4) | 3-CH3 |
| J-74 (2/5) | 3-$CH_3$ |
| J-74 (4/2) | 3-$CH_3$ |
| J-74 (5/2) | 3-$CH_3$ |
| J-75 (3/5) | 2-$CH_3$ |
| J-75 (5/3) | 2-$CH_3$ |
| J-69 (1/3) | 4-F |
| J-69 (1/3) | 4-Cl |
| J-69 (1/3) | 4-OH |
| J-69 (1/3) | 4-$NH_2$ |
| J-69 (1/3) | 4-OEt |
| J-69 (1/3) | 4-OCF3 |
| J-69 (1/3) | 4-SMe |
| J-69 (1/3) | 4-SOMe |
| J-69 (1/3) | 4-$SO_2$Me |
| J-69 (1/3) | 4-$SCF_3$ |
| J-69 (1/3) | 4-$CH_2OCHF_2$ |
| J-69 (1/3) | 4-$CH_2OH$ |
| J-74 (2/5) | 3-C(=O)$CH_3$ |
| J-69 (1/3) | 4-OC(=O)$CH_3$ |
| J-69 (1/3) | 4-SC(=O)$CH_3$ |
| J-69 (1/3) | 4-C(=O)NHMe |

TABLE 6c

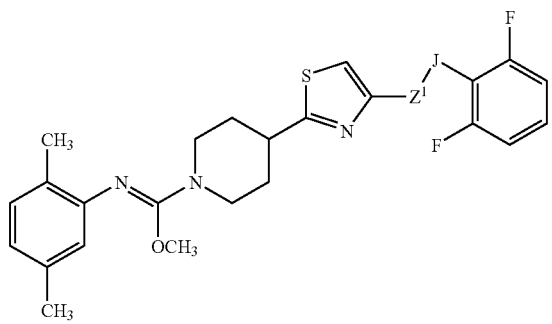

In Table 6c the structure of J (e.g. J-3) is shown in Exhibit 3 in the above Embodiments, wherein x is 1, $R^5$ is Q (i.e. —$Z^2$Q wherein $Z^2$ is a direct bond), and Q is 2,6-difluorophenyl as depicted in the structure immediately above. The numbers in parentheses following J refer to the attachment points of the J ring to $Z^1$ and Q (i.e. 2,6-difluorophenyl). The first number is the ring position on J where $Z^1$ is attached, and the second number is the ring position on J where Q is attached.

| $Z^1$ | J |
|---|---|
| $CH_2$ | J-3 (1/4) |
| $CH_2$ | J-6 (1/3) |
| $CH_2$ | J-9 (1/3) |
| $CH_2$ | J-12 (1/3) |
| $CH_2$ | J-17 (2/4) |
| $CH_2$ | J-18 (2/5) |
| $CH_2$ | J-26 (1/4) |
| $CH_2$ | J-30 (1/3) |
| $CH_2$ | J-30 (1/4) |
| $CH_2$ | J-31 (1/3) |
| $CH_2$ | J-31 (1/4) |
| $CH_2$ | J-35 (1/4) |
| $CH_2$ | J-36 (1/3) |
| $CH_2$ | J-42 (1/3) |
| $CH_2$ | J-42 (1/4) |

TABLE 6d

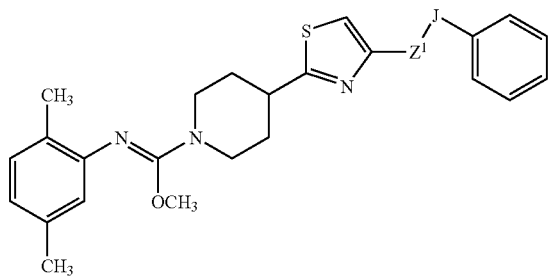

In Table 6d the structure of J (e.g. J-29) is shown in Exhibit 3 in the above Embodiments, wherein x is 1, $R^5$ is Q (i.e. —$Z^2$Q wherein $Z^2$ is a direct bond), and Q is phenyl as depicted in the structure immediately above. The numbers in parentheses following J refer to the attachment points of the J ring to $Z^1$ and Q (i.e. phenyl). The first number is the ring position on J where $Z^1$ is attached, and the second number is the ring position on J where Q is attached.

| $Z^1$ | J |
|---|---|
| O | J-29 (3/5) |
| S | J-29 (3/5) |
| S(=O) | J-29 (3/5) |
| S(=O)$_2$ | J-29 (3/5) |
| NH | J-29 (3/5) |
| N(Me) | J-29 (3/5) |
| N(n-Pr) | J-29 (3/5) |

TABLE 6d-continued

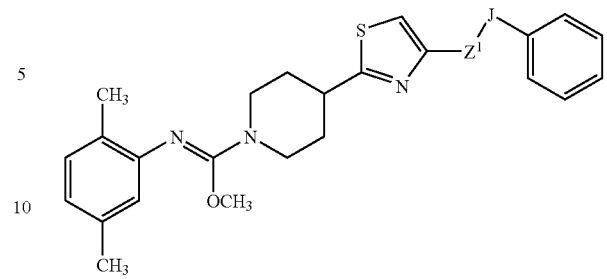

In Table 6d the structure of J (e.g. J-29) is shown in Exhibit 3 in the above Embodiments, wherein x is 1, $R^5$ is Q (i.e. —$Z^2$Q wherein $Z^2$ is a direct bond), and Q is phenyl as depicted in the structure immediately above. The numbers in parentheses following J refer to the attachment points of the J ring to $Z^1$ and Q (i.e. phenyl). The first number is the ring position on J where $Z^1$ is attached, and the second number is the ring position on J where Q is attached.

| $Z^1$ | J |
|---|---|
| $CH_2$ | J-29 (3/5) |
| CH(-i-Bu) | J-29 (3/5) |

TABLE 6e

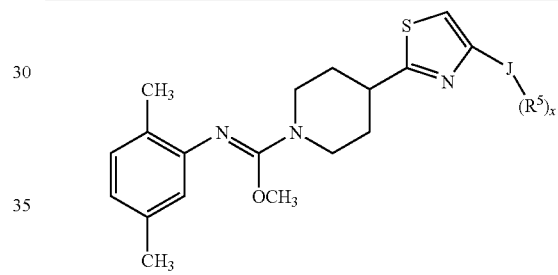

In Table 6e the structure of J (e.g. J-53) is shown in Exhibit 3 in the above Embodiments, wherein the $R^5$ substituents attached to the J ring are depicted as $(R^5)_x$ in the structure immediately above. The thiazole ring in the above structure corresponds to G in Formula 1. The number in parentheses following J refers to the attachment point of the J ring to G (i.e. thiazole).

| J | $(R^5)x$ |
|---|---|
| J-53 (2) | H |
| J-54 (2) | H |
| J-55 (2) | H |
| J-56 (2) | H |
| J-57 (2) | 1-Me |
| J-58 (3) | 1-Me |
| J-59 (2) | H |
| J-60 (2) | H |
| J-61 (2) | H |
| J-62 (2) | H |
| J-63 (3) | H |
| J-64 (2) | H |
| J-65 (3) | H |
| J-66 (6) | H |
| J-53 (2) | H |
| J-53 (2) | H |
| J-67 (2) | H |
| J-68 (2) | H |
| J-53 (2) | H |
| J-53 (2) | H |
| J-53 (2) | H |
| J-53 (2) | H |
| J-68 (2) | H |
| J-53 (2) | H |
| J-53 (2) | H |

TABLE 6e-continued

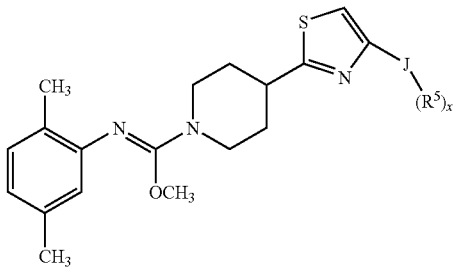

In Table 6e the structure of J (e.g. J-53) is shown in Exhibit 3 in the above Embodiments, wherein the $R^5$ substituents attached to the J ring are depicted as $(R^5)_x$ in the structure immediately above. The thiazole ring in the above structure corresponds to G in Formula 1. The number in parentheses following J refers to the attachment point of the J ring to G (i.e. thiazole).

| J | $(R^5)_x$ |
|---|---|
| J-53 (2) | H |
| J-53 (2) | H |
| J-53 (2) | H |
| J-53 (2) | H |
| J-53 (2) | H |
| J-53 (2) | H |
| J-29 (3) | 5-(4-Me-3-penten-1-yl) |
| J-29 (3) | 5-(3,3-di-Me-1-butyn-1-yl) |
| J-29 (3) | 5-(4-Me-c-hexyl) |
| J-29 (3) | 5-CF$_2$CF$_3$ |
| J-29 (3) | 5-(3,3-di-Cl-2-propen-1-yl) |
| J-29 (3) | 5-SiMe$_3$ |
| J-69 (1) | 4-S(=O)$_2$CH$_2$CF$_3$ |
| J-22 (2) | 4-NH-i-Bu |
| J-22 (2) | 4-N(Et)$_2$ |
| J-22 (2) | 4-NH-c-hexyl |
| J-69 (1) | 4-CH$_2$O-i-Pr |
| J-69 (1) | 4-C(=O)-i-Pr |
| J-29 (3) | 5-NHC(=O)CH$_3$ |
| J-29 (3) | 5-N(C(=O)CH$_3$)$_2$ |
| J-29 (3) | 5-N(Me)C(=O)Ph |
| J-29 (3) | 5-N(Et)C(=O)CH$_3$ |
| J-29 (3) | 5-N(Et)C(=O)Ph |
| J-29 (3) | 5-NHC(=O)OMe |
| J-29 (3) | 5-NHC(=O)OEt |
| J-29 (3) | 5-N(Me)(=O)OEt |
| J-69 (1) | 3-Cl |
| J-69 (1) | 3-Br |
| J-69 (1) | 3-I |
| J-69 (1) | 3-Me |
| J-69 (1) | 3-Et |
| J-69 (1) | 3-n-Pr |
| J-69 (1) | 3-i-Pr |
| J-69 (1) | 3-Bu |
| J-69 (1) | 3-i-Bu |
| J-69 (1) | 3-s-Bu |
| J-69 (1) | 3-t-Bu |
| J-69 (1) | 3-(CH$_2$)$_4$CH$_3$ |
| J-69 (1) | 3-(CH$_2$)$_2$CH(Me)$_2$ |
| J-69 (1) | 3-C(Me)$_2$(Et) |
| J-69 (1) | 3-c-Pr |
| J-69 (1) | 3-c-Bu |
| J-69 (1) | 3-c-pentyl |
| J-69 (1) | 3-c-hexyl |
| J-69 (1) | 3-OCF$_3$ |
| J-69 (1) | 3-O-i-Pr |
| J-69 (1) | 3-O-i-Bu |
| J-69 (1) | 3-Cl |
| J-69 (1) | 3-Br |
| J-69 (1) | 4-I |
| J-69 (1) | 4-Me |
| J-69 (1) | 4-Et |
| J-69 (1) | 4-n-Pr |
| J-69 (1) | 4-i-Pr |
| J-69 (1) | 4-n-Bu |
| J-69 (1) | 4-t-Bu |
| J-69 (1) | 4-(CH$_2$)$_4$CH$_3$ |

TABLE 6e-continued

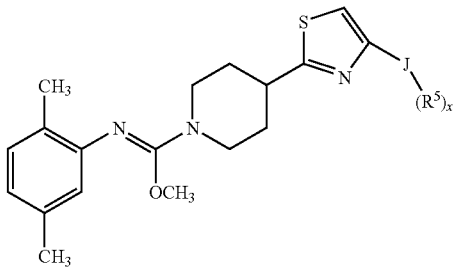

In Table 6e the structure of J (e.g. J-53) is shown in Exhibit 3 in the above Embodiments, wherein the $R^5$ substituents attached to the J ring are depicted as $(R^5)_x$ in the structure immediately above. The thiazole ring in the above structure corresponds to G in Formula 1. The number in parentheses following J refers to the attachment point of the J ring to G (i.e. thiazole).

| J | $(R^5)_x$ |
|---|---|
| J-69 (1) | 4-(CH$_2$)$_2$CH(Me)$_2$ |
| J-69 (1) | 4-C(Me)$_2$(Et) |
| J-69 (1) | 4-c-Pr |
| J-69 (1) | 4-c-Bu |
| J-69 (1) | 4-c-pentyl |
| J-69 (1) | 4-c-hexyl |
| J-69 (1) | 4-OCF$_3$ |
| J-69 (1) | 4-O-i-Pr |
| J-69 (1) | 4-O-i-Bu |
| J-69 (1) | 3,4-di-Cl |
| J-69 (1) | 3,4-di-Br |
| J-69 (1) | 3,4-di-Me |
| J-69 (1) | 3,4-di-Et |
| J-69 (1) | 3,4-di-OMe |
| J-69 (1) | 3,4-di-OEt |
| J-4 (2) | 5-i-Bu |
| J-5 (2) | 5-i-Bu |

TABLE 6f

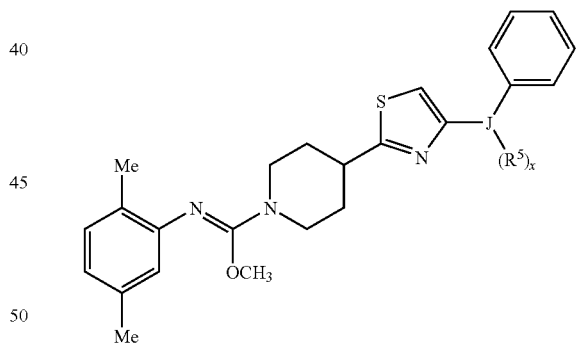

In Table 6f the structure of J (e.g. J-29) is shown in Exhibit 3 in the above Embodiments, wherein x is 2 or 3, one $R^5$ substituent is Q (i.e. —$Z^2$Q wherein $Z^2$ is a direct bond), and Q is phenyl as depicted in the structure immediately above. The other one or two $R^5$ substituents are tabulated under the heading $(R^5)_x$. The thiazole ring in the above structure corresponds to G in Formula 1. The numbers in parentheses following J refer to the attachment points of the J ring to G (i.e. thiazole) and Q (i.e. phenyl). The first number is the ring position on J where G is attached, and the second number is the ring position on J where Q is attached.

| J | $(R^5)_x$ |
|---|---|
| J-29 (3/5) | 4-CH$_3$ |
| J-29 (3/5) | 5-CH$_3$ |
| J-29 (3/5) | 4,5-di-Me |
| J-29 (3/5) | 4,4-di-Me |
| J-29 (3/5) | 5-Et |

TABLE 6f-continued

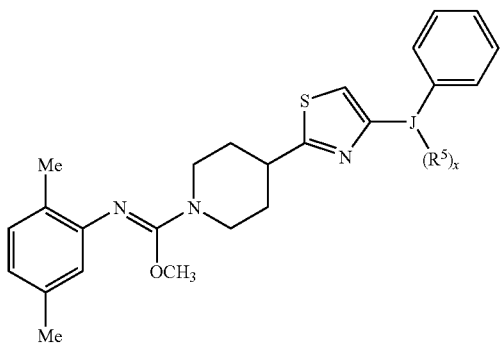

In Table 6f the structure of J (e.g. J-29) is shown in Exhibit 3 in the above Embodiments, wherein x is 2 or 3, one $R^5$ substituent is Q (i.e. —$Z^2$Q wherein $Z^2$ is a direct bond), and Q is phenyl as depicted in the structure immediately above. The other one or two $R^5$ substituents are tabulated under the heading $(R^5)_x$. The thiazole ring in the above structure corresponds to G in Formula 1. The numbers in parentheses following J refer to the attachment points of the J ring to G (i.e. thiazole) and Q (i.e. phenyl). The first number is the ring position on J where G is attached, and the second number is the ring position on J where Q is attached.

| J | $(R^5)_x$ |
|---|---|
| J-29 (3/5) | 5-(c-Pr) |
| J-29 (3/5) | 5-$CF_3$ |
| J-29 (3/5) | 5-OMe |

TABLE 6g

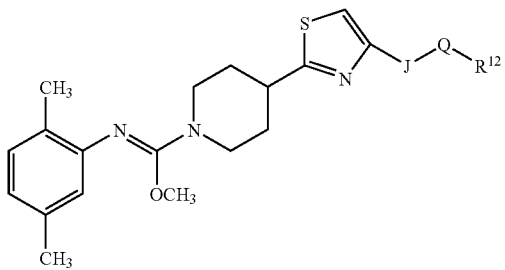

In Table 6g the structure of J (e.g. J-29) is shown in Exhibit 3 in the above Embodiments, wherein x is 1, and $R^5$ is Q (i.e. —$Z^2$Q wherein $Z^2$ is a direct bond) as depicted in the structure immediately above. The structure of Q is shown in Exhibit 4 in the above Embodiments, wherein p and q are 0, and the $R^{12}$ substituent attached to the ring in some instances of Q is depicted in the above structure. A dash "—" in the $R^{12}$ column indicates that no $R^{12}$ substituent is present on the Q ring. The thiazole ring in the above structure corresponds to G in Formula 1. The number in parentheses following J refer to the attachment points of the J ring to G (i.e. thiazole) and Q. The first number is the ring position on J where Q is attached, and the second number is the ring position on J where Q is attached.

| J | Q | $R^{12}$ |
|---|---|---|
| J-29 (3/5) | Q-1 | — |
| J-29 (3/5) | Q-2 | — |
| J-29 (3/5) | Q-3 | Me |
| J-29 (3/5) | Q-4 | — |
| J-29 (3/5) | Q-5 | — |
| J-29 (3/5) | Q-6 | — |
| J-29 (3/5) | Q-7 | — |
| J-29 (3/5) | Q-8 | — |
| J-29 (3/5) | Q-9 | — |
| J-29 (3/5) | Q-10 | Me |
| J-29 (3/5) | Q-11 | Me |
| J-29 (3/5) | Q-12 | Me |
| J-29 (3/5) | Q-13 | Me |

TABLE 6g-continued

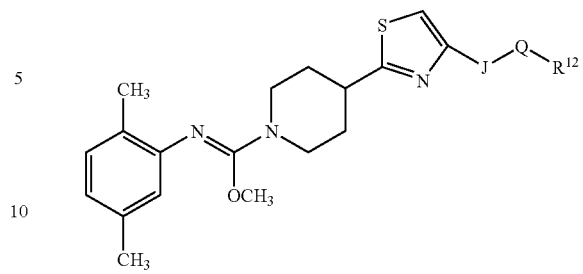

In Table 6g the structure of J (e.g. J-29) is shown in Exhibit 3 in the above Embodiments, wherein x is 1, and $R^5$ is Q (i.e. —$Z^2$Q wherein $Z^2$ is a direct bond) as depicted in the structure immediately above. The structure of Q is shown in Exhibit 4 in the above Embodiments, wherein p and q are 0, and the $R^{12}$ substituent attached to the ring in some instances of Q is depicted in the above structure. A dash "—" in the $R^{12}$ column indicates that no $R^{12}$ substituent is present on the Q ring. The thiazole ring in the above structure corresponds to G in Formula 1. The number in parentheses following J refer to the attachment points of the J ring to G (i.e. thiazole) and Q. The first number is the ring position on J where Q is attached, and the second number is the ring position on J where Q is attached.

| J | Q | $R^{12}$ |
|---|---|---|
| J-29 (3/5) | Q-14 | Me |
| J-29 (3/5) | Q-15 | — |
| J-29 (3/5) | Q-16 | — |
| J-29 (3/5) | Q-17 | — |
| J-29 (3/5) | Q-18 | — |
| J-29 (3/5) | Q-19 | — |
| J-29 (3/5) | Q-20 | — |
| J-29 (3/5) | Q-21 | Me |
| J-29 (3/5) | Q-22 | Me |
| J-29 (3/5) | Q-23 | Me |
| J-29 (3/5) | Q-24 | H |
| J-29 (3/5) | Q-25 | — |
| J-29 (3/5) | Q-26 | — |
| J-29 (3/5) | Q-27 | — |
| J-29 (3/5) | Q-28 | Me |
| J-29 (3/5) | Q-29 | — |
| J-29 (3/5) | Q-30 | — |
| J-29 (3/5) | Q-31 | Me |
| J-29 (3/5) | Q-32 | — |
| J-29 (3/5) | Q-33 | — |
| J-29 (3/5) | Q-34 | — |
| J-29 (3/5) | Q-35 | — |
| J-29 (3/5) | Q-36 | — |
| J-29 (3/5) | Q-36 | — |
| J-29 (3/5) | Q-37 | — |
| J-29 (3/5) | Q-38 | — |
| J-29 (3/5) | Q-39 | — |
| J-29 (3/5) | Q-40 | — |
| J-29 (3/5) | Q-41 | — |
| J-29 (3/5) | Q-42 | — |
| J-29 (3/5) | Q-43 | — |
| J-29 (3/5) | Q-44 | — |
| J-29 (3/5) | Q-46 | — |
| J-29 (3/5) | Q-48 | — |
| J-29 (3/5) | Q-49 | — |
| J-29 (3/5) | Q-50 | — |
| J-29 (3/5) | Q-51 | — |
| J-29 (3/5) | Q-52 | — |
| J-29 (3/5) | Q-53 | — |
| J-29 (3/5) | Q-54 | — |
| J-29 (3/5) | Q-55 | — |
| J-29 (3/5) | Q-56 | — |
| J-29 (3/5) | Q-57 | — |
| J-29 (3/5) | Q-58 | — |
| J-29 (3/5) | Q-59 | — |
| J-29 (3/5) | Q-60 | — |
| J-29 (3/5) | Q-61 | — |
| J-29 (3/5) | Q-61 | — |
| J-29 (3/5) | Q-61 | — |
| J-29 (3/5) | Q-62 | — |
| J-29 (3/5) | Q-63 | — |

TABLE 6g-continued

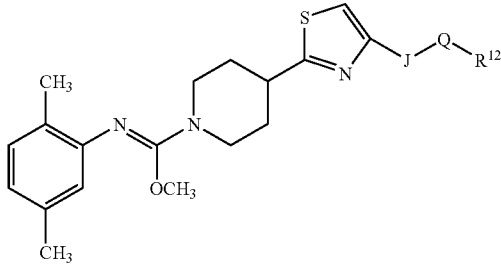

In Table 6g the structure of J (e.g. J-29) is shown in Exhibit 3 in the above Embodiments, wherein x is 1, and $R^5$ is Q (i.e. —$Z^2$Q wherein $Z^2$ is a direct bond) as depicted in the structure immediately above. The structure of Q is shown in Exhibit 4 in the above Embodiments, wherein p and q are 0, and the $R^{12}$ substituent attached to the ring in some instances of Q isdepicted in the above structure. A dash "—" in the $R^{12}$ column indicates that no $R^{12}$ substituent is present on the Q ring. The thiazole ring in the above structure corresponds to G in Formula 1. The number in parentheses following J refer to the attachment points of the J ring to G (i.e. thiazole) and Q. The first number is the ring position on J where Q is attached, and the second number is the ring position on J where Q is attached.

| J | Q | $R^{12}$ |
|---|---|---|
| J-29 (3/5) | Q-64 | — |
| J-29 (3/5) | Q-65 | — |
| J-29 (3/5) | Q-66 | — |
| J-29 (3/5) | Q-67 | — |
| J-29 (3/5) | Q-68 | — |
| J-29 (3/5) | Q-69 | — |

TABLE 6h

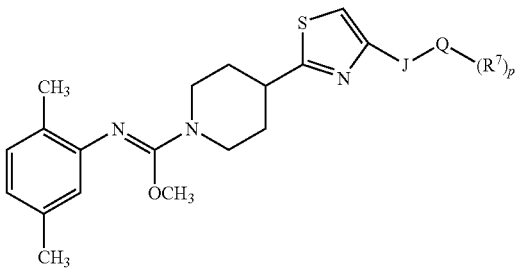

In Table 6h the structure of J (e.g. J-29) is shown in Exhibit 3 in the above Embodiments, wherein x is 1, and $R^5$ is Q (i.e. —$Z^2$Q wherein $Z^2$ is a direct bond) as depicted in the structure immediately above. The structure of Q is shown in Exhibit 4 in the above Embodiments, wherein q is 0, $R^{12}$ is H, p is 1 or 2, and the one or two $R^7$ substituents attached to the ring are depicted as $(R^7)_p$ in the above structure. The thiazole ring in the above structure corresponds to G in Formula 1. The number in parentheses following J refer to the attachment points of the J ring to G (i.e. thiazole) and Q. The first number is the ring position on J where G is attached, and the second number is the ring position on J where Q is attached.

| J | Q | $(R^7)_p$ |
|---|---|---|
| J-29 (3/5) | Q-45 | 2-Me |
| J-29 (3/5) | Q-45 | 3-Me |

TABLE 6h-continued

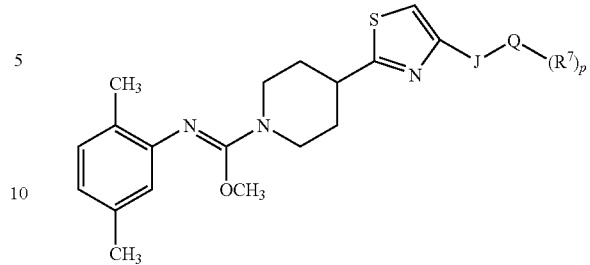

In Table 6h the structure of J (e.g. J-29) is shown in Exhibit 3 in the above Embodiments, wherein x is 1, and $R^5$ is Q (i.e. —$Z^2$Q wherein $Z^2$ is a direct bond) as depicted in the structure immediately above. The structure of Q is shown in Exhibit 4 in the above Embodiments, wherein q is 0, $R^{12}$ is H, p is 1 or 2, and the one or two $R^7$ substituents attached to the ring are depicted as $(R^7)_p$ in the above structure. The thiazole ring in the above structure corresponds to G in Formula 1. The number in parentheses following J refer to the attachment points of the J ring to G (i.e. thiazole) and Q. The first number is the ring position on J where G is attached, and the second number is the ring position on J where Q is attached.

| J | Q | $(R^7)_p$ |
|---|---|---|
| J-29 (3/5) | Q-45 | 4-Me |
| J-29 (3/5) | Q-45 | 2-Cl |
| J-29 (3/5) | Q-45 | 3-Cl |
| J-29 (3/5) | Q-45 | 4-Cl |
| J-29 (3/5) | Q-45 | 2-OMe |
| J-29 (3/5) | Q-45 | 3-OMe |
| J-29 (3/5) | Q-45 | 4-OMe |
| J-29 (3/5) | Q-45 | 2-Et |
| J-29 (3/5) | Q-45 | 3-i-Pr |
| J-29 (3/5) | Q-45 | 2,6-di-Me |
| J-29 (3/5) | Q-45 | 4-CH=$CH_2$ |
| J-29 (3/5) | Q-45 | 4-C≡CH |
| J-29 (3/5) | Q-45 | 4-c-Pr |
| J-29 (3/5) | Q-45 | 3-$CF_3$ |
| J-29 (3/5) | Q-45 | 3-$OCF_3$ |
| J-29 (3/5) | Q-45 | 4-Br |
| J-29 (3/5) | Q-45 | 3-OH |
| J-29 (3/5) | Q-45 | 3-$NH_2$ |
| J-29 (3/5) | Q-45 | 2-CN |
| J-29 (3/5) | Q-45 | 4-O-t-Bu |
| J-29 (3/5) | Q-45 | 4-SMe |
| J-29 (3/5) | Q-45 | 4-SCF3 |
| J-29 (3/5) | Q-45 | 3-S(=O)$_2$Me |
| J-29 (3/5) | Q-45 | 3-NHMe |
| J-29 (3/5) | Q-45 | 4-N(Me)$_2$ |
| J-29 (3/5) | Q-45 | 2-$CH_2$OMe |
| J-29 (3/5) | Q-45 | 3-C(=O)Me |
| J-29 (3/5) | Q-45 | 3-C(=O)$_2$Me |
| J-29 (3/5) | Q-45 | 3-C(=O)NHMe |
| J-29 (3/5) | Q-45 | 4-CO(=O)OMe |
| J-29 (3/5) | Q-45 | 4-SC(=O)Me |
| J-29 (3/5) | Q-45 | 3-C(=O)N(Me)$_2$ |
| J-29 (3/5) | Q-45 | 4-$SiMe_3$ |
| J-29 (3/5) | Q-45 | 2,6-di-Et |

TABLE 7

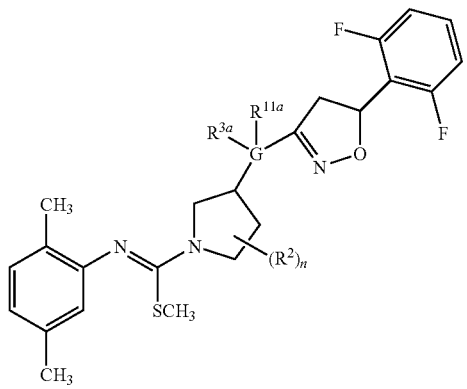

In Table 7 the structure of G (e.g. G-1) is shown in Exhibit 2 in the above Embodiments, wherein the $R^{3a}$ and $R^{11a}$ substituents occurring on some instances of the G ring are depicted in the structure immediately above, and the bond projecting to the left is bonded to X and the bond projecting to the right is bonded to the oxazole ring (corresponding to the J ring in Formula 1). A dash "—" in the $R^{11a}$ column indicates no $R^{11a}$ substituent is present on the G ring. A dash "—" in the $(R^2)_n$ column means that n is 0 and hydrogen is present at all available positions.

| X | $(R^2)_n$ | G | $R^{3a}$ | $R^{11a}$ |
|---|---|---|---|---|
| $X^1$ | — | G-1 | H | — |
| $X^1$ | — | G-2 | H | — |
| $X^1$ | — | G-3 | H | H |
| $X^1$ | — | G-4 | H | — |
| $X^1$ | — | G-5 | H | — |
| $X^1$ | — | G-6 | H | H |
| $X^1$ | — | G-7 | H | — |
| $X^1$ | — | G-8 | H | — |
| $X^1$ | — | G-9 | H | H |
| $X^1$ | — | G-10 | H | — |
| $X^1$ | — | G-11 | H | — |
| $X^1$ | — | G-12 | H | H |
| $X^1$ | — | G-13 | H | H |
| $X^1$ | — | G-14 | H | — |
| $X^1$ | — | G-15 | H | — |
| $X^1$ | — | G-16 | H | H |
| $X^1$ | — | G-17 | H | — |
| $X^1$ | — | G-18 | H | — |
| $X^1$ | — | G-19 | H | H |
| $X^1$ | — | G-20 | H | — |
| $X^1$ | — | G-21 | H | — |
| $X^1$ | — | G-22 | H | H |
| $X^1$ | — | G-23 | H | — |
| $X^1$ | — | G-24 | H | — |
| $X^1$ | — | G-25 | H | — |
| $X^1$ | — | G-26 | H | — |
| $X^1$ | — | G-27 | H | — |
| $X^1$ | — | G-28 | H | — |
| $X^1$ | — | G-29 | H | — |
| $X^1$ | — | G-30 | H | — |
| $X^1$ | — | G-31 | H | — |
| $X^1$ | — | G-32 | H | — |
| $X^1$ | — | G-33 | H | — |
| $X^1$ | — | G-34 | H | — |
| $X^1$ | — | G-35 | H | — |
| $X^1$ | — | G-36 | H | — |
| $X^1$ | — | G-37 | H | — |
| $X^1$ | — | G-38 | H | — |
| $X^1$ | — | G-39 | H | H |
| $X^1$ | — | G-40 | H | — |
| $X^1$ | — | G-41 | H | — |
| $X^1$ | — | G-42 | H | H |
| $X^1$ | — | G-43 | H | H |
| $X^1$ | — | G-44 | H | — |
| $X^1$ | — | G-45 | H | — |
| $X^1$ | — | G-46 | H | — |
| $X^1$ | — | G-47 | H | — |
| $X^1$ | — | G-48 | H | H |
| $X^1$ | — | G-49 | H | — |
| $X^1$ | — | G-50 | H | — |
| $X^1$ | — | G-51 | H | H |
| $X^1$ | — | G-52 | H | — |
| $X^1$ | — | G-53 | H | — |
| $X^1$ | — | G-54 | H | H |
| $X^1$ | — | G-55 | H | — |
| $X^1$ | — | G-56 | H | — |
| $X^1$ | — | G-57 | H | — |
| $X^1$ | — | G-58 | H | H |
| $X^1$ | — | G-59 | H | H |
| $X^1$ | — | G-2 | Me | — |
| $X^1$ | — | G-2 | Cl | — |
| $X^1$ | — | G-2 | F | — |
| $X^1$ | — | G-2 | $CF_3$ | — |
| $X^1$ | — | G-14 | n-Pr | — |
| $X^1$ | — | G-3 | H | Me |
| $X^1$ | — | G-3 | H | n-Pr |
| $X^1$ | — | G-26 | 5-Me | — |
| $X^1$ | 2-Me | G-1 | H | — |
| $X^1$ | 3-Me | G-1 | H | — |
| $X^1$ | 2,6-di-Me | G-1 | H | — |
| $X^1$ | 3,5-di-Me | G-1 | H | — |
| $X^1$ | 3-n-Bu | G-1 | H | — |
| $X^1$ | 4-MeO | G-1 | H | — |
| $X^1$ | 4-OH | G-1 | H | — |
| $X^1$ | 4-Cl | G-1 | H | — |
| $X^1$ | 4-Br | G-1 | H | — |
| $X^1$ | 4-CN | G-1 | H | — |
| $X^2$ | — | G-1 | H | — |
| $X^2$ | — | G-2 | H | — |
| $X^2$ | — | G-3 | H | H |
| $X^2$ | — | G-4 | H | — |
| $X^2$ | — | G-5 | H | — |
| $X^2$ | — | G-6 | H | H |
| $X^2$ | — | G-7 | H | — |
| $X^2$ | — | G-8 | H | — |
| $X^2$ | — | G-9 | H | H |
| $X^2$ | — | G-10 | H | — |
| $X^2$ | — | G-11 | H | — |
| $X^2$ | — | G-12 | H | H |
| $X^2$ | — | G-13 | H | H |
| $X^2$ | — | G-14 | H | — |
| $X^2$ | — | G-15 | H | — |
| $X^2$ | — | G-16 | H | H |
| $X^2$ | — | G-17 | H | — |
| $X^2$ | — | G-18 | H | — |
| $X^2$ | — | G-19 | H | H |
| $X^2$ | — | G-20 | H | — |
| $X^2$ | — | G-21 | H | — |

TABLE 7-continued

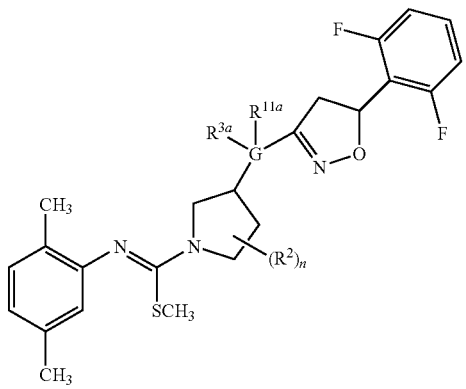

In Table 7 the structure of G (e.g. G-1) is shown in Exhibit 2 in the above Embodiments, wherein the $R^{3a}$ and $R^{11a}$ substituents occurring on some instances of the G ring are depicted in the structure immediately above, and the bond projecting to the left is bonded to X and the bond projecting to the right is bonded to the oxazole ring (corresponding to the J ring in Formula 1). A dash "—" in the $R^{11a}$ column indicates no $R^{11a}$ substituent is present on the G ring. A dash "—" in the $(R^2)_n$ column means that n is 0 and hydrogen is present at all available positions.

| X | $(R^2)_n$ | G | $R^{3a}$ | $R^{11a}$ |
|---|---|---|---|---|
| $X^2$ | — | G-22 | H | H |
| $X^2$ | — | G-23 | H | — |
| $X^2$ | — | G-24 | H | — |
| $X^2$ | — | G-31 | H | — |
| $X^2$ | — | G-32 | H | — |
| $X^2$ | — | G-33 | H | — |
| $X^2$ | — | G-34 | H | — |
| $X^2$ | — | G-35 | H | — |
| $X^2$ | — | G-37 | H | — |
| $X^2$ | — | G-38 | H | — |
| $X^2$ | — | G-39 | H | H |
| $X^2$ | — | G-40 | H | — |
| $X^2$ | — | G-41 | H | — |
| $X^2$ | — | G-42 | H | H |
| $X^2$ | — | G-43 | H | H |
| $X^2$ | — | G-44 | H | — |
| $X^2$ | — | G-45 | H | — |
| $X^2$ | — | G-46 | H | — |
| $X^2$ | — | G-47 | H | — |
| $X^2$ | — | G-48 | H | H |
| $X^2$ | — | G-49 | H | — |
| $X^2$ | — | G-50 | H | — |
| $X^2$ | — | G-51 | H | H |
| $X^2$ | — | G-52 | H | — |
| $X^2$ | — | G-53 | H | — |
| $X^2$ | — | G-54 | H | H |
| $X^2$ | — | G-2 | Me | — |
| $X^2$ | — | G-2 | Cl | — |
| $X^2$ | — | G-2 | F | — |
| $X^2$ | — | G-2 | $CF_3$ | — |
| $X^2$ | — | G-14 | n-Pr | — |
| $X^2$ | — | G-3 | H | Me |
| $X^2$ | — | G-3 | H | n-Pr |
| $X^2$ | 2-Me | G-1 | H | — |
| $X^2$ | 3-Me | G-1 | H | — |
| $X^2$ | 2,6-di-Me | G-1 | H | — |
| $X^2$ | 3,5-di-Me | G-1 | H | — |
| $X^2$ | 3-n-Bu | G-1 | H | — |
| $X^3$ | — | G-1 | H | — |
| $X^3$ | — | G-2 | H | — |
| $X^3$ | — | G-3 | H | H |
| $X^3$ | — | G-4 | H | — |
| $X^3$ | — | G-5 | H | — |
| $X^3$ | — | G-6 | H | H |
| $X^3$ | — | G-7 | H | — |
| $X^3$ | — | G-8 | H | — |
| $X^3$ | — | G-9 | H | H |
| $X^3$ | — | G-10 | H | — |
| $X^3$ | — | G-11 | H | — |

TABLE 7-continued

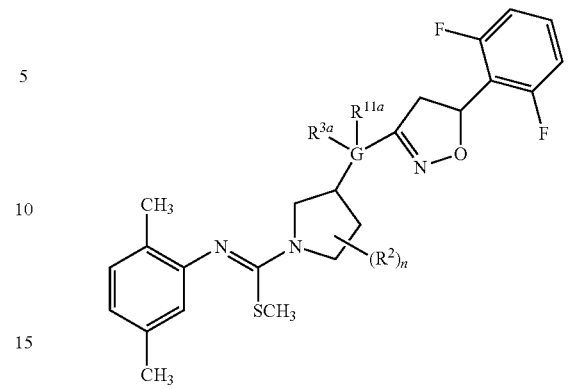

In Table 7 the structure of G (e.g. G-1) is shown in Exhibit 2 in the above Embodiments, wherein the $R^{3a}$ and $R^{11a}$ substituents occurring on some instances of the G ring are depicted in the structure immediately above, and the bond projecting to the left is bonded to X and the bond projecting to the right is bonded to the oxazole ring (corresponding to the J ring in Formula 1). A dash "—" in the $R^{11a}$ column indicates no $R^{11a}$ substituent is present on the G ring. A dash "—" in the $(R^2)_n$ column means that n is 0 and hydrogen is present at all available positions.

| X | $(R^2)_n$ | G | $R^{3a}$ | $R^{11a}$ |
|---|---|---|---|---|
| $X^3$ | — | G-12 | H | H |
| $X^3$ | — | G-13 | H | H |
| $X^3$ | — | G-14 | H | — |
| $X^3$ | — | G-15 | H | — |
| $X^3$ | — | G-16 | H | H |
| $X^3$ | — | G-17 | H | — |
| $X^3$ | — | G-18 | H | — |
| $X^3$ | — | G-19 | H | H |
| $X^3$ | — | G-20 | H | — |
| $X^3$ | — | G-21 | H | — |
| $X^3$ | — | G-22 | H | H |
| $X^3$ | — | G-23 | H | — |
| $X^3$ | — | G-24 | H | — |
| $X^3$ | — | G-31 | H | — |
| $X^3$ | — | G-32 | H | — |
| $X^3$ | — | G-33 | H | — |
| $X^3$ | — | G-34 | H | — |
| $X^3$ | — | G-35 | H | — |
| $X^3$ | — | G-37 | H | — |
| $X^3$ | — | G-38 | H | — |
| $X^3$ | — | G-39 | H | H |
| $X^3$ | — | G-40 | H | — |
| $X^3$ | — | G-41 | H | — |
| $X^3$ | — | G-42 | H | H |
| $X^3$ | — | G-43 | H | H |
| $X^3$ | — | G-44 | H | — |
| $X^3$ | — | G-45 | H | — |
| $X^3$ | — | G-46 | H | — |
| $X^3$ | — | G-47 | H | — |
| $X^3$ | — | G-48 | H | H |
| $X^3$ | — | G-49 | H | — |
| $X^3$ | — | G-50 | H | — |
| $X^3$ | — | G-51 | H | H |
| $X^3$ | — | G-52 | H | — |
| $X^3$ | — | G-53 | H | — |
| $X^3$ | — | G-54 | H | H |
| $X^3$ | — | G-2 | Me | — |
| $X^3$ | — | G-2 | Cl | — |
| $X^3$ | — | G-2 | F | — |
| $X^3$ | — | G-2 | $CF_3$ | — |
| $X^3$ | — | G-14 | n-Pr | — |
| $X^3$ | — | G-3 | H | Me |
| $X^3$ | — | G-3 | H | n-Pr |
| $X^3$ | 2-Me | G-1 | H | — |
| $X^3$ | 3-Me | G-1 | H | — |
| $X^3$ | 2,6-di-Me | G-1 | H | — |
| $X^3$ | 3,5-di-Me | G-1 | H | — |
| $X^3$ | 3-n-Bu | G-1 | H | — |
| $X^3$ | 5-Me | G-1 | H | — |

TABLE 7-continued

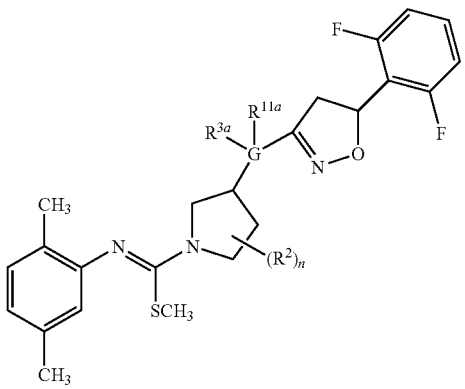

In Table 7 the structure of G (e.g. G-1) is shown in Exhibit 2 in the above Embodiments, wherein the $R^{3a}$ and $R^{11a}$ substituents occurring on some instances of the G ring are depicted in the structure immediately above, and the bond projecting to the left is bonded to X and the bond projecting to the right is bonded to the oxazole ring (corresponding to the J ring in Formula 1). A dash "—" in the $R^{11a}$ column indicates no $R^{11a}$ substituent is present on the G ring. A dash "—" in the $(R^2)_n$ column means that n is 0 and hydrogen is present at all available positions.

| X | $(R^2)_n$ | G | $R^{3a}$ | $R^{11a}$ |
|---|---|---|---|---|
| $X^3$ | 6-Me | G-1 | H | — |
| $X^4$ | — | G-1 | H | — |
| $X^5$ | — | G-1 | H | — |
| $X^6$ | — | G-1 | H | — |
| $X^7$ | — | G-1 | H | — |
| $X^8$ | — | G-1 | H | — |
| $X^9$ | — | G-1 | H | — |

TABLE 8

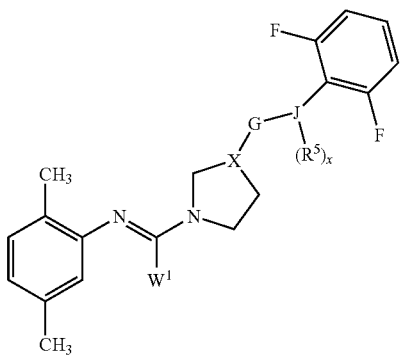

In Table 8 the structure of J (e.g. J-1) is shown in Exhibit 3 in the above Embodiments, wherein x is 1 or 2, one $R^5$ substituent is Q (i.e. —$Z^2$Q wherein $Z^2$ is a direct bond), and Q is 2,6-difluorophenyl as depicted in the structure immediately above. The other possible $R^5$ substituent is tabulated under the heading $(R^5)_x$. A dash "—" in the $(R^5)_x$ column means that no $R^5$ substituent other than Q is present. The structure of G (i.e. G-1 or G-2) is shown in Exhibit 2, wherein $R^{3a}$ is hydrogen. The number in parentheses following J refer to the attachment points of the J ring to G and Q (i.e. (2,6-difluorophenyl). The first number is the ring position on J where G is attached, and the second number is the ring position on J where Q is attached.

| X | G | J | $(R^5)_x$ | $W^1$ |
|---|---|---|---|---|
| $X^1$ | G-1 | J-1 (2/4) | — | methylthio |
| $X^1$ | G-1 | J-1 (2/4) | — | amino |
| $X^1$ | G-1 | J-1 (2/4) | — | hydroxyamino |

TABLE 8-continued

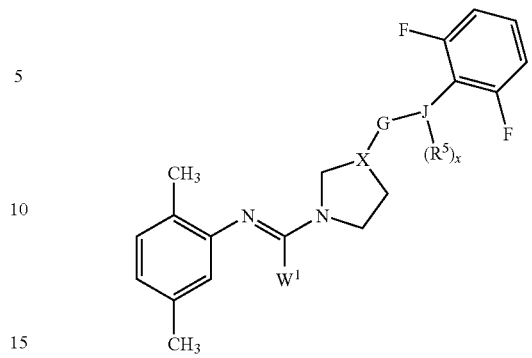

In Table 8 the structure of J (e.g. J-1) is shown in Exhibit 3 in the above Embodiments, wherein x is 1 or 2, one $R^5$ substituent is Q (i.e. —$Z^2$Q wherein $Z^2$ is a direct bond), and Q is 2,6-difluorophenyl as depicted in the structure immediately above. The other possible $R^5$ substituent is tabulated under the heading $(R^5)_x$. A dash "—" in the $(R^5)_x$ column means that no $R^5$ substituent other than Q is present. The structure of G (i.e. G-1 or G-2) is shown in Exhibit 2, wherein $R^{3a}$ is hydrogen. The number in parentheses following J refer to the attachment points of the J ring to G and Q (i.e. (2,6-difluorophenyl). The first number is the ring position on J where G is attached, and the second number is the ring position on J where Q is attached.

| X | G | J | $(R^5)_x$ | $W^1$ |
|---|---|---|---|---|
| $X^1$ | G-1 | J-1 (2/4) | — | methylhydroxyamino |
| $X^1$ | G-1 | J-1 (2/4) | — | cyanoamino |
| $X^1$ | G-1 | J-2 (2/4) | — | methylthio |
| $X^1$ | G-1 | J-2 (2/4) | — | amino |
| $X^1$ | G-1 | J-2 (2/4) | — | hydroxyamino |
| $X^1$ | G-1 | J-2 (2/4) | — | methylhydroxyamino |
| $X^1$ | G-1 | J-2 (2/4) | — | cyanoamino |
| $X^1$ | G-1 | J-3 (2/4) | 1-Me | methylthio |
| $X^1$ | G-1 | J-3 (2/4) | 1-Me | amino |
| $X^1$ | G-1 | J-3 (2/4) | 1-Me | hydroxyamino |
| $X^1$ | G-1 | J-3 (2/4) | 1-Me | methylhydroxyamino |
| $X^1$ | G-1 | J-3 (2/4) | 1-Me | cyanoamino |
| $X^1$ | G-1 | J-4 (2/5) | — | methylthio |
| $X^1$ | G-1 | J-4 (2/5) | — | amino |
| $X^1$ | G-1 | J-4 (2/5) | — | hydroxyamino |
| $X^1$ | G-1 | J-4 (2/5) | — | methylhydroxyamino |
| $X^1$ | G-1 | J-4 (2/5) | — | cyanoamino |
| $X^1$ | G-1 | J-11 (3/5) | — | methylthio |
| $X^1$ | G-1 | J-11 (3/5) | — | amino |
| $X^1$ | G-1 | J-11 (3/5) | — | hydroxyamino |
| $X^1$ | G-1 | J-11 (3/5) | — | methylhydroxyamino |
| $X^1$ | G-1 | J-11 (3/5) | — | cyanoamino |
| $X^1$ | G-1 | J-12 (3/5) | 1-Me | methylthio |
| $X^1$ | G-1 | J-12 (3/5) | 1-Me | amino |
| $X^1$ | G-1 | J-12 (3/5) | 1-Me | hydroxyamino |
| $X^1$ | G-1 | J-12 (3/5) | 1-Me | methylhydroxyamino |
| $X^1$ | G-1 | J-12 (3/5) | 1-Me | cyanoamino |
| $X^1$ | G-1 | J-15 (2/5) | — | methylthio |
| $X^1$ | G-1 | J-15 (2/5) | — | amino |
| $X^1$ | G-1 | J-15 (2/5) | — | hydroxyamino |
| $X^1$ | G-1 | J-15 (2/5) | — | methylhydroxyamino |
| $X^1$ | G-1 | J-15 (2/5) | — | cyanoamino |
| $X^1$ | G-1 | J-16 (2/5) | — | methylthio |
| $X^1$ | G-1 | J-16 (2/5) | — | amino |
| $X^1$ | G-1 | J-16 (2/5) | — | hydroxyamino |
| $X^1$ | G-1 | J-16 (2/5) | — | methylhydroxyamino |
| $X^1$ | G-1 | J-16 (2/5) | — | cyanoamino |
| $X^1$ | G-1 | J-22 (2/4) | — | methylthio |
| $X^1$ | G-1 | J-22 (2/4) | — | amino |
| $X^1$ | G-1 | J-22 (2/4) | — | hydroxyamino |
| $X^1$ | G-1 | J-22 (2/4) | — | methylhydroxyamino |
| $X^1$ | G-1 | J-22 (2/4) | — | cyanoamino |
| $X^1$ | G-1 | J-24 (2/4) | — | methylthio |
| $X^1$ | G-1 | J-24 (2/4) | — | amino |
| $X^1$ | G-1 | J-24 (2/4) | — | hydroxyamino |
| $X^1$ | G-1 | J-24 (2/4) | — | methylhydroxyamino |

TABLE 8-continued

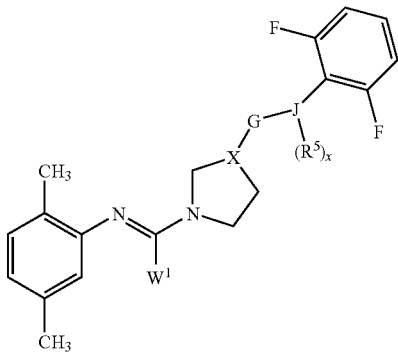

In Table 8 the structure of J (e.g. J-1) is shown in Exhibit 3 in the above Embodiments, wherein x is 1 or 2, one $R^5$ substituent is Q (i.e. —$Z^2$Q wherein $Z^2$ is a direct bond), and Q is 2,6-difluorophenyl as depicted in the structure immediately above. The other possible $R^5$ substituent is tabulated under the heading $(R^5)_x$. A dash "—" in the $(R^5)_x$ column means that no $R^5$ substituent other than Q is present. The structure of G (i.e. G-1 or G-2) is shown in Exhibit 2, wherein $R^{3a}$ is hydrogen. The number in parentheses following J refer to the attachment points of the J ring to G and Q (i.e. (2,6-difluorophenyl). The first number is the ring position on J where G is attached, and the second number is the ring position on J where Q is attached.

| X | G | J | $(R^5)_x$ | $W^1$ |
|---|---|---|---|---|
| $X^1$ | G-1 | J-24 (2/4) | — | cyanoamino |
| $X^1$ | G-1 | J-25 (2/4) | — | methylthio |
| $X^1$ | G-1 | J-25 (2/4) | — | amino |
| $X^1$ | G-1 | J-25 (2/4) | — | hydroxyamino |
| $X^1$ | G-1 | J-25 (2/4) | — | methylhydroxyamino |
| $X^1$ | G-1 | J-25 (2/4) | — | cyanoamino |
| $X^1$ | G-1 | J-26 (2/4) | — | methylthio |
| $X^1$ | G-1 | J-26 (2/4) | — | amino |
| $X^1$ | G-1 | J-26 (2/4) | — | hydroxyamino |
| $X^1$ | G-1 | J-26 (2/4) | — | methylhydroxyamino |
| $X^1$ | G-1 | J-26 (2/4) | — | cyanoamino |
| $X^1$ | G-1 | J-28 (3/5) | — | methylthio |
| $X^1$ | G-1 | J-28 (3/5) | — | amino |
| $X^1$ | G-1 | J-28 (3/5) | — | hydroxyamino |
| $X^1$ | G-1 | J-28 (3/5) | — | methylhydroxyamino |
| $X^1$ | G-1 | J-28 (3/5) | — | cyanoamino |
| $X^1$ | G-1 | J-30 (3/5) | — | methylthio |
| $X^1$ | G-1 | J-30 (3/5) | — | amino |
| $X^1$ | G-1 | J-30 (3/5) | — | hydroxyamino |
| $X^1$ | G-1 | J-30 (3/5) | — | methylhydroxyamino |
| $X^1$ | G-1 | J-30 (3/5) | — | cyanoamino |
| $X^1$ | G-1 | J-30 (3/5) | 1-Me | methylthio |
| $X^1$ | G-1 | J-30 (3/5) | 1-Me | amino |
| $X^1$ | G-1 | J-30 (3/5) | 1-Me | hydroxyamino |
| $X^1$ | G-1 | J-30 (3/5) | 1-Me | methylhydroxyamino |
| $X^1$ | G-1 | J-30 (3/5) | 1-Me | cyanoamino |
| $X^1$ | G-1 | J-37 (2/5) | 4-Ac | methylthio |
| $X^1$ | G-1 | J-37 (2/5) | 4-Ac | amino |
| $X^1$ | G-1 | J-37 (2/5) | 4-Ac | hydroxyamino |
| $X^1$ | G-1 | J-37 (2/5) | 4-Ac | methylhydroxyamino |
| $X^1$ | G-1 | J-37 (2/5) | 4-Ac | cyanoamino |
| $X^1$ | G-1 | J-38 (2/5) | 4-Ac | methylthio |
| $X^1$ | G-1 | J-38 (2/5) | 4-Ac | amino |
| $X^1$ | G-1 | J-38 (2/5) | 4-Ac | hydroxyamino |
| $X^1$ | G-1 | J-38 (2/5) | 4-Ac | methylhydroxyamino |
| $X^1$ | G-1 | J-38 (2/5) | 4-Ac | cyanoamino |
| $X^1$ | G-2 | J-1 (2/4) | — | methylthio |
| $X^1$ | G-2 | J-1 (2/4) | — | amino |
| $X^1$ | G-2 | J-1 (2/4) | — | hydroxyamino |
| $X^1$ | G-2 | J-1 (2/4) | — | methylhydroxyamino |
| $X^1$ | G-2 | J-1 (2/4) | — | cyanoamino |
| $X^1$ | G-2 | J-2 (2/4) | — | methylthio |
| $X^1$ | G-2 | J-2 (2/4) | — | amino |
| $X^1$ | G-2 | J-2 (2/4) | — | hydroxyamino |
| $X^1$ | G-2 | J-2 (2/4) | — | methylhydroxyamino |
| $X^1$ | G-2 | J-2 (2/4) | — | cyanoamino |
| $X^1$ | G-2 | J-3 (2/4) | 1-Me | methylthio |
| $X^1$ | G-2 | J-3 (2/4) | 1-Me | amino |
| $X^1$ | G-2 | J-3 (2/4) | 1-Me | hydroxyamino |
| $X^1$ | G-2 | J-3 (2/4) | 1-Me | methylhydroxyamino |
| $X^1$ | G-2 | J-3 (2/4) | 1-Me | cyanoamino |
| $X^1$ | G-2 | J-4 (2/5) | — | methylthio |
| $X^1$ | G-2 | J-4 (2/5) | — | amino |
| $X^1$ | G-2 | J-4 (2/5) | — | hydroxyamino |
| $X^1$ | G-2 | J-4 (2/5) | — | methylhydroxyamino |
| $X^1$ | G-2 | J-4 (2/5) | — | cyanoamino |
| $X^1$ | G-2 | J-11 (3/5) | — | methylthio |
| $X^1$ | G-2 | J-11 (3/5) | — | amino |
| $X^1$ | G-2 | J-11 (3/5) | — | hydroxyamino |
| $X^1$ | G-2 | J-11 (3/5) | — | methylhydroxyamino |
| $X^1$ | G-2 | J-11 (3/5) | — | cyanoamino |
| $X^1$ | G-2 | J-12 (3/5) | 1-Me | methylthio |
| $X^1$ | G-2 | J-12 (3/5) | 1-Me | amino |
| $X^1$ | G-2 | J-12 (3/5) | 1-Me | hydroxyamino |
| $X^1$ | G-2 | J-12 (3/5) | 1-Me | methylhydroxyamino |
| $X^1$ | G-2 | J-12 (3/5) | 1-Me | cyanoamino |
| $X^1$ | G-2 | J-15 (2/5) | — | methylthio |
| $X^1$ | G-2 | J-15 (2/5) | — | amino |
| $X^1$ | G-2 | J-15 (2/5) | — | hydroxyamino |
| $X^1$ | G-2 | J-15 (2/5) | — | methylhydroxyamino |
| $X^1$ | G-2 | J-15 (2/5) | — | cyanoamino |
| $X^1$ | G-2 | J-16 (2/5) | — | methylthio |
| $X^1$ | G-2 | J-16 (2/5) | — | amino |
| $X^1$ | G-2 | J-16 (2/5) | — | hydroxyamino |
| $X^1$ | G-2 | J-16 (2/5) | — | methylhydroxyamino |
| $X^1$ | G-2 | J-16 (2/5) | — | cyanoamino |
| $X^1$ | G-2 | J-22 (2/4) | — | methylthio |
| $X^1$ | G-2 | J-22 (2/4) | — | amino |
| $X^1$ | G-2 | J-22 (2/4) | — | hydroxyamino |
| $X^1$ | G-2 | J-22 (2/4) | — | methylhydroxyamino |
| $X^1$ | G-2 | J-22 (2/4) | — | cyanoamino |
| $X^1$ | G-2 | J-24 (2/4) | — | methylthio |
| $X^1$ | G-2 | J-24 (2/4) | — | amino |
| $X^1$ | G-2 | J-24 (2/4) | — | hydroxyamino |
| $X^1$ | G-2 | J-24 (2/4) | — | methylhydroxyamino |
| $X^1$ | G-2 | J-24 (2/4) | — | cyanoamino |
| $X^1$ | G-2 | J-25 (2/4) | — | methylthio |
| $X^1$ | G-2 | J-25 (2/4) | — | amino |
| $X^1$ | G-2 | J-25 (2/4) | — | hydroxyamino |
| $X^1$ | G-2 | J-25 (2/4) | — | methylhydroxyamino |
| $X^1$ | G-2 | J-25 (2/4) | — | cyanoamino |
| $X^1$ | G-2 | J-26 (2/4) | — | methylthio |

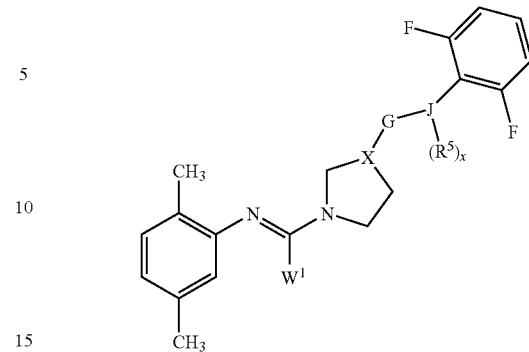

TABLE 8-continued

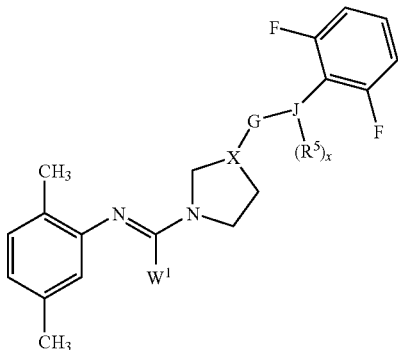

In Table 8 the structure of J (e.g. J-1) is shown in Exhibit 3 in the above Embodiments, wherein x is 1 or 2, one $R^5$ substituent is Q (i.e. —$Z^2$Q wherein $Z^2$ is a direct bond), and Q is 2,6-difluorophenyl as depicted in the structure immediately above. The other possible $R^5$ substituent is tabulated under the heading $(R^5)_x$. A dash "—" in the $(R^5)_x$ column means that no $R^5$ substituent other than Q is present. The structure of G (i.e. G-1 or G-2) is shown in Exhibit 2, wherein $R^{3a}$ is hydrogen. The number in parentheses following J refer to the attachment points of the J ring to G and Q (i.e. (2,6-difluorophenyl). The first number is the ring position on J where G is attached, and the second number is the ring position on J where Q is attached.

| X | G | J | $(R^5)_x$ | $W^1$ |
|---|---|---|---|---|
| $X^1$ | G-2 | J-26 (2/4) | — | amino |
| $X^1$ | G-2 | J-26 (2/4) | — | hydroxyamino |
| $X^1$ | G-2 | J-26 (2/4) | — | methylhydroxyamino |
| $X^1$ | G-2 | J-26 (2/4) | — | cyanoamino |
| $X^1$ | G-2 | J-28 (3/5) | — | methylthio |
| $X^1$ | G-2 | J-28 (3/5) | — | amino |
| $X^1$ | G-2 | J-28 (3/5) | — | hydroxyamino |
| $X^1$ | G-2 | J-28 (3/5) | — | methylhydroxyamino |
| $X^1$ | G-2 | J-28 (3/5) | — | cyanoamino |
| $X^1$ | G-2 | J-30 (3/5) | — | methylthio |
| $X^1$ | G-2 | J-30 (3/5) | — | amino |
| $X^1$ | G-2 | J-30 (3/5) | — | hydroxyamino |
| $X^1$ | G-2 | J-30 (3/5) | — | methylhydroxyamino |
| $X^1$ | G-2 | J-30 (3/5) | — | cyanoamino |
| $X^1$ | G-2 | J-30 (3/5) | 1-Me | methylthio |
| $X^1$ | G-2 | J-30 (3/5) | 1-Me | amino |
| $X^1$ | G-2 | J-30 (3/5) | 1-Me | hydroxyamino |
| $X^1$ | G-2 | J-30 (3/5) | 1-Me | methylhydroxyamino |
| $X^1$ | G-2 | J-30 (3/5) | 1-Me | cyanoamino |
| $X^1$ | G-2 | J-37 (2/5) | 4-Ac | methylthio |
| $X^1$ | G-2 | J-37 (2/5) | 4-Ac | amino |
| $X^1$ | G-2 | J-37 (2/5) | 4-Ac | hydroxyamino |
| $X^1$ | G-2 | J-37 (2/5) | 4-Ac | methylhydroxyamino |
| $X^1$ | G-2 | J-37 (2/5) | 4-Ac | cyanoamino |
| $X^1$ | G-2 | J-38 (2/5) | 4-Ac | methylthio |
| $X^1$ | G-2 | J-38 (2/5) | 4-Ac | amino |
| $X^1$ | G-2 | J-38 (2/5) | 4-Ac | hydroxyamino |
| $X^1$ | G-2 | J-38 (2/5) | 4-Ac | methylhydroxyamino |
| $X^1$ | G-2 | J-38 (2/5) | 4-Ac | cyanoamino |
| $X^1$ | G-2 | J-38 (2/5) | 4-Ac | hydroxyamino |
| $X^1$ | G-2 | J-38 (2/5) | 4-Ac | methylhydroxyamino |
| $X^1$ | G-2 | J-38 (2/5) | 4-Ac | cyanoamino |
| $X^2$ | G-1 | J-1 (2/4) | — | methylthio |
| $X^2$ | G-1 | J-1 (2/4) | — | amino |
| $X^2$ | G-1 | J-1 (2/4) | — | hydroxyamino |
| $X^2$ | G-1 | J-1 (2/4) | — | methylhydroxyamino |
| $X^2$ | G-1 | J-1 (2/4) | — | cyanoamino |
| $X^2$ | G-1 | J-2 (2/4) | — | methylthio |
| $X^2$ | G-1 | J-2 (2/4) | — | amino |
| $X^2$ | G-1 | J-2 (2/4) | — | hydroxyamino |
| $X^2$ | G-1 | J-2 (2/4) | — | methylhydroxyamino |
| $X^2$ | G-1 | J-2 (2/4) | — | cyanoamino |
| $X^2$ | G-1 | J-3 (2/4) | 1-Me | methylthio |
| $X^2$ | G-1 | J-3 (2/4) | 1-Me | amino |
| $X^2$ | G-1 | J-3 (2/4) | 1-Me | hydroxyamino |
| $X^2$ | G-1 | J-3 (2/4) | 1-Me | methylhydroxyamino |

TABLE 8-continued

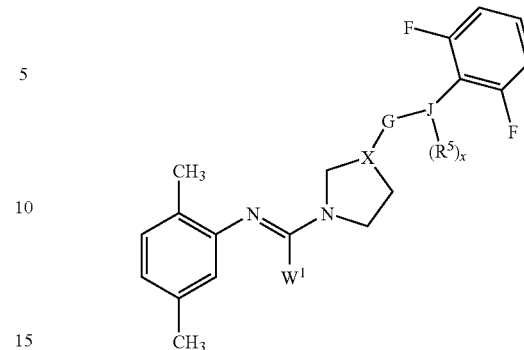

In Table 8 the structure of J (e.g. J-1) is shown in Exhibit 3 in the above Embodiments, wherein x is 1 or 2, one $R^5$ substituent is Q (i.e. —$Z^2$Q wherein $Z^2$ is a direct bond), and Q is 2,6-difluorophenyl as depicted in the structure immediately above. The other possible $R^5$ substituent is tabulated under the heading $(R^5)_x$. A dash "—" in the $(R^5)_x$ column means that no $R^5$ substituent other than Q is present. The structure of G (i.e. G-1 or G-2) is shown in Exhibit 2, wherein $R^{3a}$ is hydrogen. The number in parentheses following J refer to the attachment points of the J ring to G and Q (i.e. (2,6-difluorophenyl). The first number is the ring position on J where G is attached, and the second number is the ring position on J where Q is attached.

| X | G | J | $(R^5)_x$ | $W^1$ |
|---|---|---|---|---|
| $X^2$ | G-1 | J-3 (2/4) | 1-Me | cyanoamino |
| $X^2$ | G-1 | J-4 (2/5) | — | methylthio |
| $X^2$ | G-1 | J-4 (2/5) | — | amino |
| $X^2$ | G-1 | J-4 (2/5) | — | hydroxyamino |
| $X^2$ | G-1 | J-4 (2/5) | — | methylhydroxyamino |
| $X^2$ | G-1 | J-4 (2/5) | — | cyanoamino |
| $X^2$ | G-1 | J-11 (3/5) | — | methylthio |
| $X^2$ | G-1 | J-11 (3/5) | — | amino |
| $X^2$ | G-1 | J-11 (3/5) | — | hydroxyamino |
| $X^2$ | G-1 | J-11 (3/5) | — | methylhydroxyamino |
| $X^2$ | G-1 | J-11 (3/5) | — | cyanoamino |
| $X^2$ | G-1 | J-12 (3/5) | 1-Me | methylthio |
| $X^2$ | G-1 | J-12 (3/5) | 1-Me | amino |
| $X^2$ | G-1 | J-12 (3/5) | 1-Me | hydroxyamino |
| $X^2$ | G-1 | J-12 (3/5) | 1-Me | methylhydroxyamino |
| $X^2$ | G-1 | J-12 (3/5) | 1-Me | cyanoamino |
| $X^2$ | G-1 | J-15 (2/5) | — | methylthio |
| $X^2$ | G-1 | J-15 (2/5) | — | amino |
| $X^2$ | G-1 | J-15 (2/5) | — | hydroxyamino |
| $X^2$ | G-1 | J-15 (2/5) | — | methylhydroxyamino |
| $X^2$ | G-1 | J-15 (2/5) | — | cyanoamino |
| $X^2$ | G-1 | J-16 (2/5) | — | methylthio |
| $X^2$ | G-1 | J-16 (2/5) | — | amino |
| $X^2$ | G-1 | J-16 (2/5) | — | hydroxyamino |
| $X^2$ | G-1 | J-16 (2/5) | — | methylhydroxyamino |
| $X^2$ | G-1 | J-16 (2/5) | — | cyanoamino |
| $X^2$ | G-1 | J-22 (2/4) | — | methylthio |
| $X^2$ | G-1 | J-22 (2/4) | — | amino |
| $X^2$ | G-1 | J-22 (2/4) | — | hydroxyamino |
| $X^2$ | G-1 | J-22 (2/4) | — | methylhydroxyamino |
| $X^2$ | G-1 | J-22 (2/4) | — | cyanoamino |
| $X^2$ | G-1 | J-24 (2/4) | — | methylthio |
| $X^2$ | G-1 | J-24 (2/4) | — | amino |
| $X^2$ | G-1 | J-24 (2/4) | — | hydroxyamino |
| $X^2$ | G-1 | J-24 (2/4) | — | methylhydroxyamino |
| $X^2$ | G-1 | J-24 (2/4) | — | cyanoamino |
| $X^2$ | G-1 | J-25 (2/4) | — | methylthio |
| $X^2$ | G-1 | J-25 (2/4) | — | amino |
| $X^2$ | G-1 | J-25 (2/4) | — | hydroxyamino |
| $X^2$ | G-1 | J-25 (2/4) | — | methylhydroxyamino |
| $X^2$ | G-1 | J-25 (2/4) | — | cyanoamino |
| $X^2$ | G-1 | J-26 (2/4) | — | methylthio |
| $X^2$ | G-1 | J-26 (2/4) | — | amino |
| $X^2$ | G-1 | J-26 (2/4) | — | hydroxyamino |
| $X^2$ | G-1 | J-26 (2/4) | — | methylhydroxyamino |
| $X^2$ | G-1 | J-26 (2/4) | — | cyanoamino |

TABLE 8-continued

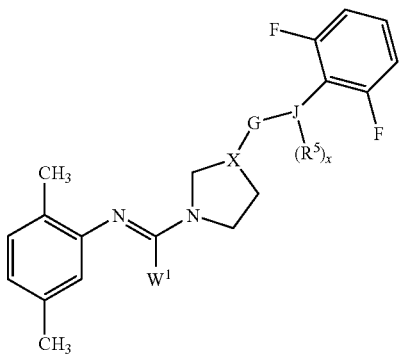
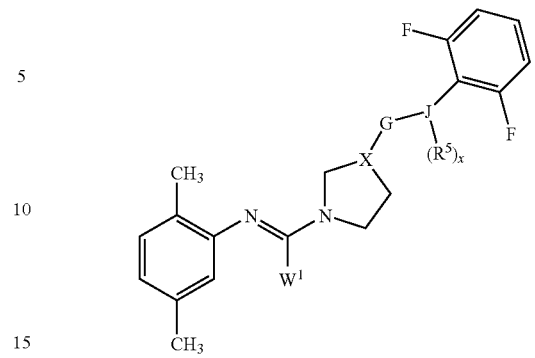

In Table 8 the structure of J (e.g. J-1) is shown in Exhibit 3 in the above Embodiments, wherein x is 1 or 2, one $R^5$ substituent is Q (i.e. —$Z^2$Q wherein $Z^2$ is a direct bond), and Q is 2,6-difluorophenyl as depicted in the structure immediately above. The other possible $R^5$ substituent is tabulated under the heading $(R^5)_x$. A dash "—" in the $(R^5)_x$ column means that no $R^5$ substituent other than Q is present. The structure of G (i.e. G-1 or G-2) is shown in Exhibit 2, wherein $R^{3a}$ is hydrogen. The number in parentheses following J refer to the attachment points of the J ring to G and Q (i.e. 2,6-difluorophenyl). The first number is the ring position on J where G is attached, and the second number is the ring position on J where Q is attached.

| X | G | J | $(R^5)_x$ | $W^1$ |
|---|---|---|---|---|
| $X^2$ | G-1 | J-28 (3/5) | — | methylthio |
| $X^2$ | G-1 | J-28 (3/5) | — | amino |
| $X^2$ | G-1 | J-28 (3/5) | — | hydroxyamino |
| $X^2$ | G-1 | J-28 (3/5) | — | methylhydroxyamino |
| $X^2$ | G-1 | J-28 (3/5) | — | cyanoamino |
| $X^2$ | G-1 | J-30 (3/5) | — | methylthio |
| $X^2$ | G-1 | J-30 (3/5) | — | amino |
| $X^2$ | G-1 | J-30 (3/5) | — | hydroxyamino |
| $X^2$ | G-1 | J-30 (3/5) | — | methylhydroxyamino |
| $X^2$ | G-1 | J-30 (3/5) | — | cyanoamino |
| $X^2$ | G-1 | J-30 (3/5) | 1-Me | methylthio |
| $X^2$ | G-1 | J-30 (3/5) | 1-Me | amino |
| $X^2$ | G-1 | J-30 (3/5) | 1-Me | hydroxyamino |
| $X^2$ | G-1 | J-30 (3/5) | 1-Me | methylhydroxyamino |
| $X^2$ | G-1 | J-30 (3/5) | 1-Me | cyanoamino |
| $X^2$ | G-1 | J-37 (2/5) | 4-Ac | methylthio |
| $X^2$ | G-1 | J-37 (2/5) | 4-Ac | amino |
| $X^2$ | G-1 | J-37 (2/5) | 4-Ac | hydroxyamino |
| $X^2$ | G-1 | J-37 (2/5) | 4-Ac | methylhydroxyamino |
| $X^2$ | G-1 | J-37 (2/5) | 4-Ac | cyanoamino |
| $X^2$ | G-1 | J-38 (2/5) | 4-Ac | methylthio |
| $X^2$ | G-1 | J-38 (2/5) | 4-Ac | amino |
| $X^2$ | G-1 | J-38 (2/5) | 4-Ac | hydroxyamino |
| $X^2$ | G-1 | J-38 (2/5) | 4-Ac | methylhydroxyamino |
| $X^2$ | G-1 | J-38 (2/5) | 4-Ac | cyanoamino |
| $X^2$ | G-2 | J-1 (2/4) | — | methylthio |
| $X^2$ | G-2 | J-1 (2/4) | — | amino |
| $X^2$ | G-2 | J-1 (2/4) | — | hydroxyamino |
| $X^2$ | G-2 | J-1 (2/4) | — | methylhydroxyamino |
| $X^2$ | G-2 | J-1 (2/4) | — | cyanoamino |
| $X^2$ | G-2 | J-2 (2/4) | — | methylthio |
| $X^2$ | G-2 | J-2 (2/4) | — | amino |
| $X^2$ | G-2 | J-2 (2/4) | — | hydroxyamino |
| $X^2$ | G-2 | J-2 (2/4) | — | methylhydroxyamino |
| $X^2$ | G-2 | J-2 (2/4) | — | cyanoamino |
| $X^2$ | G-2 | J-3 (2/4) | 1-Me | methylthio |
| $X^2$ | G-2 | J-3 (2/4) | 1-Me | amino |
| $X^2$ | G-2 | J-3 (2/4) | 1-Me | hydroxyamino |
| $X^2$ | G-2 | J-3 (2/4) | 1-Me | methylhydroxyamino |
| $X^2$ | G-2 | J-3 (2/4) | 1-Me | cyanoamino |
| $X^2$ | G-2 | J-4 (2/5) | — | methylthio |
| $X^2$ | G-2 | J-4 (2/5) | — | amino |
| $X^2$ | G-2 | J-4 (2/5) | — | hydroxyamino |
| $X^2$ | G-2 | J-4 (2/5) | — | methylhydroxyamino |
| $X^2$ | G-2 | J-4 (2/5) | — | cyanoamino |
| $X^2$ | G-2 | J-11 (3/5) | — | methylthio |
| $X^2$ | G-2 | J-11 (3/5) | — | amino |
| $X^2$ | G-2 | J-11 (3/5) | — | hydroxyamino |
| $X^2$ | G-2 | J-11 (3/5) | — | methylhydroxyamino |
| $X^2$ | G-2 | J-11 (3/5) | — | cyanoamino |
| $X^2$ | G-2 | J-12 (3/5) | 1-Me | methylthio |
| $X^2$ | G-2 | J-12 (3/5) | 1-Me | amino |
| $X^2$ | G-2 | J-12 (3/5) | 1-Me | hydroxyamino |
| $X^2$ | G-2 | J-12 (3/5) | 1-Me | methylhydroxyamino |
| $X^2$ | G-2 | J-12 (3/5) | 1-Me | cyanoamino |
| $X^2$ | G-2 | J-15 (2/5) | — | methylthio |
| $X^2$ | G-2 | J-15 (2/5) | — | amino |
| $X^2$ | G-2 | J-15 (2/5) | — | hydroxyamino |
| $X^2$ | G-2 | J-15 (2/5) | — | methylhydroxyamino |
| $X^2$ | G-2 | J-15 (2/5) | — | cyanoamino |
| $X^2$ | G-2 | J-16 (2/5) | — | methylthio |
| $X^2$ | G-2 | J-16 (2/5) | — | amino |
| $X^2$ | G-2 | J-16 (2/5) | — | hydroxyamino |
| $X^2$ | G-2 | J-16 (2/5) | — | methylhydroxyamino |
| $X^2$ | G-2 | J-16 (2/5) | — | cyanoamino |
| $X^2$ | G-2 | J-22 (2/4) | — | methylthio |
| $X^2$ | G-2 | J-22 (2/4) | — | amino |
| $X^2$ | G-2 | J-22 (2/4) | — | hydroxyamino |
| $X^2$ | G-2 | J-22 (2/4) | — | methylhydroxyamino |
| $X^2$ | G-2 | J-22 (2/4) | — | cyanoamino |
| $X^2$ | G-2 | J-24 (2/4) | — | methylthio |
| $X^2$ | G-2 | J-24 (2/4) | — | amino |
| $X^2$ | G-2 | J-24 (2/4) | — | hydroxyamino |
| $X^2$ | G-2 | J-24 (2/4) | — | methylhydroxyamino |
| $X^2$ | G-2 | J-24 (2/4) | — | cyanoamino |
| $X^2$ | G-2 | J-25 (2/4) | — | methylthio |
| $X^2$ | G-2 | J-25 (2/4) | — | amino |
| $X^2$ | G-2 | J-25 (2/4) | — | hydroxyamino |
| $X^2$ | G-2 | J-25 (2/4) | — | methylhydroxyamino |
| $X^2$ | G-2 | J-25 (2/4) | — | cyanoamino |
| $X^2$ | G-2 | J-26 (2/4) | — | methylthio |

TABLE 8-continued

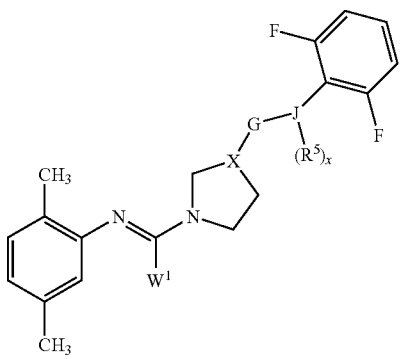

In Table 8 the structure of J (e.g. J-1) is shown in Exhibit 3 in the above Embodiments, wherein x is 1 or 2, one $R^5$ substituent is Q (i.e. —$Z^2$Q wherein $Z^2$ is a direct bond), and Q is 2,6-difluorophenyl as depicted in the structure immediately above. The other possible $R^5$ substituent is tabulated under the heading $(R^5)_x$. A dash "—" in the $(R^5)_x$ column means that no $R^5$ substituent other than Q is present. The structure of G (i.e. G-1 or G-2) is shown in Exhibit 2, wherein $R^{3a}$ is hydrogen. The number in parentheses following J refer to the attachment points of the J ring to G and Q (i.e. (2,6-difluorophenyl). The first number is the ring position on J where G is attached, and the second number is the ring position on J where Q is attached.

| X | G | J | $(R^5)_x$ | $W^1$ |
|---|---|---|---|---|
| $X^2$ | G-2 | J-26 (2/4) | — | amino |
| $X^2$ | G-2 | J-26 (2/4) | — | hydroxyamino |
| $X^2$ | G-2 | J-26 (2/4) | — | methylhydroxyamino |
| $X^2$ | G-2 | J-26 (2/4) | — | cyanoamino |
| $X^2$ | G-2 | J-28 (3/5) | — | methylthio |
| $X^2$ | G-2 | J-28 (3/5) | — | amino |
| $X^2$ | G-2 | J-28 (3/5) | — | hydroxyamino |
| $X^2$ | G-2 | J-28 (3/5) | — | methylhydroxyamino |
| $X^2$ | G-2 | J-28 (3/5) | — | cyanoamino |
| $X^2$ | G-2 | J-30 (3/5) | — | methylthio |
| $X^2$ | G-2 | J-30 (3/5) | — | amino |
| $X^2$ | G-2 | J-30 (3/5) | — | hydroxyamino |
| $X^2$ | G-2 | J-30 (3/5) | — | methylhydroxyamino |
| $X^2$ | G-2 | J-30 (3/5) | — | cyanoamino |
| $X^2$ | G-2 | J-30 (3/5) | 1-Me | methylthio |
| $X^2$ | G-2 | J-30 (3/5) | 1-Me | amino |
| $X^2$ | G-2 | J-30 (3/5) | 1-Me | hydroxyamino |
| $X^2$ | G-2 | J-30 (3/5) | 1-Me | methylhydroxyamino |
| $X^2$ | G-2 | J-30 (3/5) | 1-Me | cyanoamino |
| $X^2$ | G-2 | J-37 (2/5) | 4-Ac | methylthio |
| $X^2$ | G-2 | J-37 (2/5) | 4-Ac | amino |
| $X^2$ | G-2 | J-37 (2/5) | 4-Ac | hydroxyamino |
| $X^2$ | G-2 | J-37 (2/5) | 4-Ac | methylhydroxyamino |
| $X^2$ | G-2 | J-37 (2/5) | 4-Ac | cyanoamino |
| $X^2$ | G-2 | J-38 (2/5) | 4-Ac | methylthio |
| $X^2$ | G-2 | J-38 (2/5) | 4-Ac | amino |
| $X^2$ | G-2 | J-38 (2/5) | 4-Ac | hydroxyamino |
| $X^2$ | G-2 | J-38 (2/5) | 4-Ac | methylhydroxyamino |
| $X^2$ | G-2 | J-38 (2/5) | 4-Ac | cyanoamino |

TABLE 9

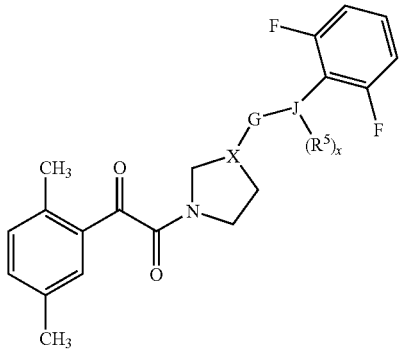

In Table 9 the structure of J (e.g. J-1) is shown in Exhibit 3 in the above Embodiments, wherein x is 1 or 2, one $R^5$ substituent is Q (i.e. —$Z^2$Q wherein $Z^2$ is a direct bond), and Q is 2,6-difluorophenyl as depicted in the structure immediately above. The other possible $R^5$ substituent is tabulated under the heading $(R^5)_x$. A dash "—" in the $(R^5)_x$ column means that no $R^5$ substituent other than Q is present. The structure of G (i.e. G-1 or G-2) is shown in Exhibit 2, wherein $R^{3a}$ is hydrogen. The number in parentheses following J refer to the attachment points of the J ring to G (i.e. thiazole) and Q (i.e. (2,6-difluorophenyl). The first number is the ring position on J where G is attached, and the second number is the ring position on J where Q is attached.

| X | G | J | $(R^5)_x$ | X | G | J | $(R^5)_x$ |
|---|---|---|---|---|---|---|---|
| $X^1$ | G-1 | J-1 (2/4) | — | $X^1$ | G-2 | J-38 (2/5) | 4-Ac |
| $X^1$ | G-1 | J-2 (2/4) | — | $X^2$ | G-1 | J-1 (2/4) | — |
| $X^1$ | G-1 | J-3 (2/4) | 1-Me | $X^2$ | G-1 | J-2 (2/4) | — |
| $X^1$ | G-1 | J-4 (2/5) | — | $X^2$ | G-1 | J-3 (2/4) | 1-Me |
| $X^1$ | G-1 | J-11 (3/5) | — | $X^2$ | G-1 | J-4 (2/5) | — |
| $X^1$ | G-1 | J-12 (3/5) | 1-Me | $X^2$ | G-1 | J-11 (3/5) | — |
| $X^1$ | G-1 | J-15 (2/5) | — | $X^2$ | G-1 | J-12 (3/5) | 1-Me |
| $X^1$ | G-1 | J-16 (2/5) | — | $X^2$ | G-1 | J-15 (2/5) | — |
| $X^1$ | G-1 | J-22 (2/4) | — | $X^2$ | G-1 | J-16 (2/5) | — |
| $X^1$ | G-1 | J-24 (2/4) | — | $X^2$ | G-1 | J-22 (2/4) | — |
| $X^1$ | G-1 | J-25 (2/4) | — | $X^2$ | G-1 | J-24 (2/4) | — |
| $X^1$ | G-1 | J-26 (2/4) | — | $X^2$ | G-1 | J-25 (2/4) | — |
| $X^1$ | G-1 | J-28 (3/5) | — | $X^2$ | G-1 | J-26 (2/4) | — |
| $X^1$ | G-1 | J-30 (3/5) | — | $X^2$ | G-1 | J-28 (3/5) | — |
| $X^1$ | G-1 | J-30 (3/5) | 1-Me | $X^2$ | G-1 | J-30 (3/5) | — |
| $X^1$ | G-1 | J-37 (2/5) | 4-Ac | $X^2$ | G-1 | J-30 (3/5) | 1-Me |
| $X^1$ | G-1 | J-38 (2/5) | 4-Ac | $X^2$ | G-1 | J-37 (2/5) | 4-Ac |
| $X^1$ | G-2 | J-1 (2/4) | — | $X^2$ | G-1 | J-38 (2/5) | 4-Ac |
| $X^1$ | G-2 | J-2 (2/4) | — | $X^2$ | G-2 | J-1 (2/4) | — |
| $X^1$ | G-2 | J-3 (2/4) | 1-Me | $X^2$ | G-2 | J-2 (2/4) | — |
| $X^1$ | G-2 | J-4 (2/5) | — | $X^2$ | G-2 | J-3 (2/4) | 1-Me |
| $X^1$ | G-2 | J-11 (3/5) | — | $X^2$ | G-2 | J-4 (2/5) | — |
| $X^1$ | G-2 | J-12 (3/5) | 1-Me | $X^2$ | G-2 | J-11 (3/5) | — |
| $X^1$ | G-2 | J-15 (2/5) | — | $X^2$ | G-2 | J-12 (3/5) | 1-Me |
| $X^1$ | G-2 | J-16 (2/5) | — | $X^2$ | G-2 | J-15 (2/5) | — |
| $X^1$ | G-2 | J-22 (2/4) | — | $X^2$ | G-2 | J-16 (2/5) | — |
| $X^1$ | G-2 | J-24 (2/4) | — | $X^2$ | G-2 | J-22 (2/4) | — |
| $X^1$ | G-2 | J-25 (2/4) | — | $X^2$ | G-2 | J-24 (2/4) | — |
| $X^1$ | G-2 | J-26 (2/4) | — | $X^2$ | G-2 | J-25 (2/4) | — |
| $X^1$ | G-2 | J-28 (3/5) | — | $X^2$ | G-2 | J-26 (2/4) | — |
| $X^1$ | G-2 | J-30 (3/5) | — | $X^2$ | G-2 | J-28 (3/5) | — |
| $X^1$ | G-2 | J-30 (3/5) | 1-Me | $X^2$ | G-2 | J-30 (3/5) | — |
| $X^1$ | G-2 | J-37 (2/5) | 4-Ac | $X^2$ | G-2 | J-30 (3/5) | 1-Me |
| $X^1$ | G-1 | J-1 (2/4) | — | $X^2$ | G-2 | J-37 (2/5) | 4-Ac |

TABLE 10

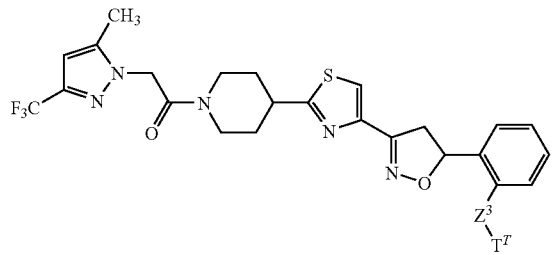

In Table 10 "$T^T$" indicates $T^A$, $T^N$ or $T^P$ and the structures of $T^A$, $T^N$ and $T^P$ (e.g., $T^A$-1, $T^N$-12 and $T^P$-20) are as shown in Exhibit 5 in the above Embodiments, wherein r is 0. When present, $R^{22}$ attached to $T^A$ and $T^N$ is methyl.

| $T^T$ | $T^T$ | $T^T$ | $T^T$ | $T^T$ | $T^T$ |
|---|---|---|---|---|---|
| \multicolumn{6}{c}{$Z^3$ is a direct bond.} | | | | | |
| $T^A$-1 | $T^A$-21 | $T^A$-41 | $T^N$-12 | $T^N$-32 | $T^P$-20 |
| $T^A$-2 | $T^A$-22 | $T^A$-42 | $T^N$-13 | $T^P$-1 | $T^P$-21 |
| $T^A$-3 | $T^A$-23 | $T^A$-43 | $T^N$-14 | $T^P$-2 | $T^P$-22 |
| $T^A$-4 | $T^A$-24 | $T^A$-44 | $T^N$-15 | $T^P$-3 | $T^P$-23 |
| $T^A$-5 | $T^A$-25 | $T^A$-45 | $T^N$-16 | $T^P$-4 | $T^P$-24 |
| TA-6 | $T^A$-26 | $T^A$-46 | $T^N$-17 | $T^P$-5 | $T^P$-25 |
| $T^A$-7 | $T^A$-27 | $T^A$-47 | $T^N$-18 | $T^P$-6 | $T^P$-26 |
| $T^A$-8 | $T^A$-28 | $T^A$-48 | $T^N$-19 | $T^P$-7 | $T^P$-27 |
| $T^A$-9 | $T^A$-29 | $T^A$-49 | $T^N$-20 | $T^P$-8 | $T^P$-28 |
| $T^A$-10 | $T^A$-30 | $T^N$-1 | $T^N$-21 | $T^P$-9 | $T^P$-29 |
| $T^A$-11 | $T^A$-31 | $T^N$-2 | $T^N$-22 | $T^P$-10 | $T^P$-30 |
| $T^A$-12 | $T^A$-32 | $T^N$-3 | $T^N$-23 | $T^P$-11 | $T^P$-31 |
| $T^A$-13 | $T^A$-33 | $T^N$-4 | $T^N$-24 | $T^P$-12 | $T^P$-32 |
| $T^A$-14 | $T^A$-34 | $T^N$-5 | $T^N$-25 | $T^P$-13 | $T^P$-33 |
| $T^A$-15 | $T^A$-35 | $T^N$-6 | $T^N$-26 | $T^P$-14 | $T^P$-34 |
| $T^A$-16 | $T^A$-36 | $T^N$-7 | $T^N$-27 | $T^P$-15 | $T^P$-35 |
| $T^A$-17 | $T^A$-37 | $T^N$-8 | $T^N$-28 | $T^P$-16 | |
| $T^A$-18 | $T^A$-38 | $T^N$-9 | $T^N$-29 | $T^P$-17 | |
| $T^A$-19 | $T^A$-39 | $T^N$-10 | $T^N$-30 | $T^P$-18 | |
| $T^A$-20 | $T^A$-40 | $T^N$-11 | $T^N$-31 | $T^P$-19 | |
| \multicolumn{6}{c}{$Z^3$ is O.} | | | | | |
| $T^A$-1 | $T^A$-21 | $T^A$-41 | $T^N$-12 | $T^N$-32 | $T^P$-20 |
| $T^A$-2 | $T^A$-22 | $T^A$-42 | $T^N$-13 | $T^P$-1 | $T^P$-21 |
| $T^A$-3 | $T^A$-23 | $T^A$-43 | $T^N$-14 | $T^P$-2 | $T^P$-22 |
| $T^A$-4 | $T^A$-24 | $T^A$-44 | $T^N$-15 | $T^P$-3 | $T^P$-23 |
| $T^A$-5 | $T^A$-25 | $T^A$-45 | $T^N$-16 | $T^P$-4 | $T^P$-24 |
| TA-6 | $T^A$-26 | $T^A$-46 | $T^N$-17 | $T^P$-5 | $T^P$-25 |
| $T^A$-7 | $T^A$-27 | $T^A$-47 | $T^N$-18 | $T^P$-6 | $T^P$-26 |
| $T^A$-8 | $T^A$-28 | $T^A$-48 | $T^N$-19 | $T^P$-7 | $T^P$-27 |
| $T^A$-9 | $T^A$-29 | $T^A$-49 | $T^N$-20 | $T^P$-8 | $T^P$-28 |
| $T^A$-10 | $T^A$-30 | $T^N$-1 | $T^N$-21 | $T^P$-9 | $T^P$-29 |
| $T^A$-11 | $T^A$-31 | $T^N$-2 | $T^N$-22 | $T^P$-10 | $T^P$-30 |
| $T^A$-12 | $T^A$-32 | $T^N$-3 | $T^N$-23 | $T^P$-11 | $T^P$-31 |
| $T^A$-13 | $T^A$-33 | $T^N$-4 | $T^N$-24 | $T^P$-12 | $T^P$-32 |
| $T^A$-14 | $T^A$-34 | $T^N$-5 | $T^N$-25 | $T^P$-13 | $T^P$-33 |
| $T^A$-15 | $T^A$-35 | $T^N$-6 | $T^N$-26 | $T^P$-14 | $T^P$-34 |
| $T^A$-16 | $T^A$-36 | $T^N$-7 | $T^N$-27 | $T^P$-15 | $T^P$-35 |
| $T^A$-17 | $T^A$-37 | $T^N$-8 | $T^N$-28 | $T^P$-16 | |
| $T^A$-18 | $T^A$-38 | $T^N$-9 | $T^N$-29 | $T^P$-17 | |
| $T^A$-19 | $T^A$-39 | $T^N$-10 | $T^N$-30 | $T^P$-18 | |
| $T^A$-20 | $T^A$-40 | $T^N$-11 | $T^N$-31 | $T^P$-19 | |
| \multicolumn{6}{c}{$Z^3$ is $CH_2$.} | | | | | |
| $T^A$-1 | $T^A$-21 | $T^A$-41 | $T^N$-12 | $T^N$-32 | $T^P$-20 |
| $T^A$-2 | $T^A$-22 | $T^A$-42 | $T^N$-13 | $T^P$-1 | $T^P$-21 |
| $T^A$-3 | $T^A$-23 | $T^A$-43 | $T^N$-14 | $T^P$-2 | $T^P$-22 |
| $T^A$-4 | $T^A$-24 | $T^A$-44 | $T^N$-15 | $T^P$-3 | $T^P$-23 |
| $T^A$-5 | $T^A$-25 | $T^A$-45 | $T^N$-16 | $T^P$-4 | $T^P$-24 |
| TA-6 | $T^A$-26 | $T^A$-46 | $T^N$-17 | $T^P$-5 | $T^P$-25 |
| $T^A$-7 | $T^A$-27 | $T^A$-47 | $T^N$-18 | $T^P$-6 | $T^P$-26 |
| $T^A$-8 | $T^A$-28 | $T^A$-48 | $T^N$-19 | $T^P$-7 | $T^P$-27 |
| $T^A$-9 | $T^A$-29 | $T^A$-49 | $T^N$-20 | $T^P$-8 | $T^P$-28 |
| $T^A$-10 | $T^A$-30 | $T^N$-1 | $T^N$-21 | $T^P$-9 | $T^P$-29 |
| $T^A$-11 | $T^A$-31 | $T^N$-2 | $T^N$-22 | $T^P$-10 | $T^P$-30 |
| $T^A$-12 | $T^A$-32 | $T^N$-3 | $T^N$-23 | $T^P$-11 | $T^P$-31 |
| $T^A$-13 | $T^A$-33 | $T^N$-4 | $T^N$-24 | $T^P$-12 | $T^P$-32 |
| $T^A$-14 | $T^A$-34 | $T^N$-5 | $T^N$-25 | $T^P$-13 | $T^P$-33 |

TABLE 10-continued

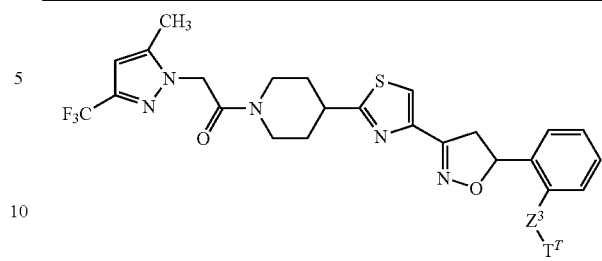

In Table 10 "$T^T$" indicates $T^A$, $T^N$ or $T^P$ and the structures of $T^A$, $T^N$ and $T^P$ (e.g., $T^A$-1, $T^N$-12 and $T^P$-20) are as shown in Exhibit 5 in the above Embodiments, wherein r is 0. When present, $R^{22}$ attached to $T^A$ and $T^N$ is methyl.

| $T^T$ | $T^T$ | $T^T$ | $T^T$ | $T^T$ | $T^T$ |
|---|---|---|---|---|---|
| $T^A$-15 | $T^A$-35 | $T^N$-6 | $T^N$-26 | $T^P$-14 | $T^P$-34 |
| $T^A$-16 | $T^A$-36 | $T^N$-7 | $T^N$-27 | $T^P$-15 | $T^P$-35 |
| $T^A$-17 | $T^A$-37 | $T^N$-8 | $T^N$-28 | $T^P$-16 | |
| $T^A$-18 | $T^A$-38 | $T^N$-9 | $T^N$-29 | $T^P$-17 | |
| $T^A$-19 | $T^A$-39 | $T^N$-10 | $T^N$-30 | $T^P$-18 | |
| $T^A$-20 | $T^A$-40 | $T^N$-11 | $T^N$-31 | $T^P$-19 | |
| \multicolumn{6}{c}{$Z^3$ is —C≡C—.} | | | | | |
| $T^A$-1 | $T^A$-21 | $T^A$-41 | $T^N$-12 | $T^N$-32 | $T^P$-20 |
| $T^A$-2 | $T^A$-22 | $T^A$-42 | $T^N$-13 | $T^P$-1 | $T^P$-21 |
| $T^A$-3 | $T^A$-23 | $T^A$-43 | $T^N$-14 | $T^P$-2 | $T^P$-22 |
| $T^A$-4 | $T^A$-24 | $T^A$-44 | $T^N$-15 | $T^P$-3 | $T^P$-23 |
| $T^A$-5 | $T^A$-25 | $T^A$-45 | $T^N$-16 | $T^P$-4 | $T^P$-24 |
| TA-6 | $T^A$-26 | $T^A$-46 | $T^N$-17 | $T^P$-5 | $T^P$-25 |
| $T^A$-7 | $T^A$-27 | $T^A$-47 | $T^N$-18 | $T^P$-6 | $T^P$-26 |
| $T^A$-8 | $T^A$-28 | $T^A$-48 | $T^N$-19 | $T^P$-7 | $T^P$-27 |
| $T^A$-9 | $T^A$-29 | $T^A$-49 | $T^N$-20 | $T^P$-8 | $T^P$-28 |
| $T^A$-10 | $T^A$-30 | $T^N$-1 | $T^N$-21 | $T^P$-9 | $T^P$-29 |
| $T^A$-11 | $T^A$-31 | $T^N$-2 | $T^N$-22 | $T^P$-10 | $T^P$-30 |
| $T^A$-12 | $T^A$-32 | $T^N$-3 | $T^N$-23 | $T^P$-11 | $T^P$-31 |
| $T^A$-13 | $T^A$-33 | $T^N$-4 | $T^N$-24 | $T^P$-12 | $T^P$-32 |
| $T^A$-14 | $T^A$-34 | $T^N$-5 | $T^N$-25 | $T^P$-13 | $T^P$-33 |
| $T^A$-15 | $T^A$-35 | $T^N$-6 | $T^N$-26 | $T^P$-14 | $T^P$-34 |
| $T^A$-16 | $T^A$-36 | $T^N$-7 | $T^N$-27 | $T^P$-15 | $T^P$-35 |
| $T^A$-17 | $T^A$-37 | $T^N$-8 | $T^N$-28 | $T^P$-16 | |
| $T^A$-18 | $T^A$-38 | $T^N$-9 | $T^N$-29 | $T^P$-17 | |
| $T^A$-19 | $T^A$-39 | $T^N$-10 | $T^N$-30 | $T^P$-18 | |
| $T^A$-20 | $T^A$-40 | $T^N$-11 | $T^N$-31 | $T^P$-19 | |
| \multicolumn{6}{c}{$Z^3$ is —$CH_2CH_2$—.} | | | | | |
| $T^A$-1 | $T^A$-21 | $T^A$-41 | $T^N$-12 | $T^N$-32 | $T^P$-20 |
| $T^A$-2 | $T^A$-22 | $T^A$-42 | $T^N$-13 | $T^P$-1 | $T^P$-21 |
| $T^A$-3 | $T^A$-23 | $T^A$-43 | $T^N$-14 | $T^P$-2 | $T^P$-22 |
| $T^A$-4 | $T^A$-24 | $T^A$-44 | $T^N$-15 | $T^P$-3 | $T^P$-23 |
| $T^A$-5 | $T^A$-25 | $T^A$-45 | $T^N$-16 | $T^P$-4 | $T^P$-24 |
| TA-6 | $T^A$-26 | $T^A$-46 | $T^N$-17 | $T^P$-5 | $T^P$-25 |
| $T^A$-7 | $T^A$-27 | $T^A$-47 | $T^N$-18 | $T^P$-6 | $T^P$-26 |
| $T^A$-8 | $T^A$-28 | $T^A$-48 | $T^N$-19 | $T^P$-7 | $T^P$-27 |
| $T^A$-9 | $T^A$-29 | $T^A$-49 | $T^N$-20 | $T^P$-8 | $T^P$-28 |
| $T^A$-10 | $T^A$-30 | $T^N$-1 | $T^N$-21 | $T^P$-9 | $T^P$-29 |
| $T^A$-11 | $T^A$-31 | $T^N$-2 | $T^N$-22 | $T^P$-10 | $T^P$-30 |
| $T^A$-12 | $T^A$-32 | $T^N$-3 | $T^N$-23 | $T^P$-11 | $T^P$-31 |
| $T^A$-13 | $T^A$-33 | $T^N$-4 | $T^N$-24 | $T^P$-12 | $T^P$-32 |
| $T^A$-14 | $T^A$-34 | $T^N$-5 | $T^N$-25 | $T^P$-13 | $T^P$-33 |
| $T^A$-15 | $T^A$-35 | $T^N$-6 | $T^N$-26 | $T^P$-14 | $T^P$-34 |
| $T^A$-16 | $T^A$-36 | $T^N$-7 | $T^N$-27 | $T^P$-15 | $T^P$-35 |
| $T^A$-17 | $T^A$-37 | $T^N$-8 | $T^N$-28 | $T^P$-16 | |
| $T^A$-18 | $T^A$-38 | $T^N$-9 | $T^N$-29 | $T^P$-17 | |
| $T^A$-19 | $T^A$-39 | $T^N$-10 | $T^N$-30 | $T^P$-18 | |
| $T^A$-20 | $T^A$-40 | $T^N$-11 | $T^N$-31 | $T^P$-19 | |

TABLE 11

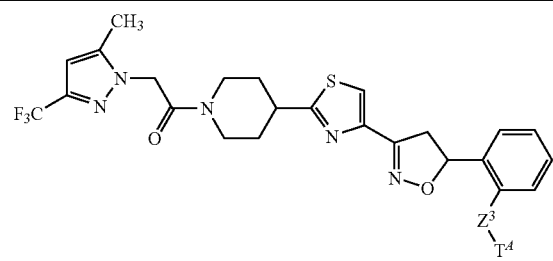

In Table 11 the structure of T⁴ (e.g., T⁴-18) is as shown in Exhibit 5 in the above Embodiments, wherein r is 0. In the radicals tabulated in the $Z^3$ column the bond projecting to the left is attached to the phenyl ring (corresponding to Q in Formula 1) and the bond projecting to the right is attached to $T^4$.

| $Z^3$ | $Z^3$ | $Z^3$ | $Z^3$ | $Z^3$ | $Z^3$ |
|---|---|---|---|---|---|
| \multicolumn{6}{c}{$T^4$ is $T^4$-18.} ||||||
| NH | C(=O) | S | —CH(CH₃)— | —CH=C(CH₃)— | —CH₂O— |
| NCH₃ | C(=S) | SO₂ | —CH(CF₃)— | | —OCH₂— |
| \multicolumn{6}{c}{$T^4$ is $T^4$-36.} ||||||
| NH | C(=O) | S | —CHCH₃— | —CH=C(CH₃)— | —CH₂O— |
| NCH₃ | C(=S) | SO₂ | —CHCF₃— | | —OCH₂— |
| \multicolumn{6}{c}{$T^4$ is $T^4$-49.} ||||||
| NH | C(=O) | S | —CHCH₃— | —CH=C(CH₃)— | —CH₂O— |
| NCH₃ | C(=S) | SO₂ | —CHCF₃— | | —OCH₂— |

TABLE 12

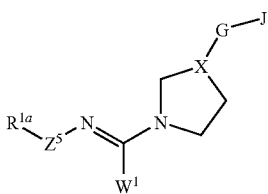

In Table 12 the structures of G (i.e. G-1) and J (e.g., J-29-1) are shown in Exhibits 2 and A, respectively, in the above Embodiments. The substituent $R^{3a}$ attached to some instances of the G ring is hydrogen.

| J | J | J | J | J | J |
|---|---|---|---|---|---|
| \multicolumn{6}{c}{$R^{1a}$ is 2,5-dimethylphenyl, $Z^5$ is a direct bond, $W^1$ is methoxy, X is $X^1$ and G is G-1.} ||||||
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |
| \multicolumn{6}{c}{$R^{1a}$ is 2,5-dichlorophenyl, $Z^5$ is a direct bond, $W^1$ is MeO, X is $X^1$ and G is G-1.} ||||||
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |

TABLE 12-continued

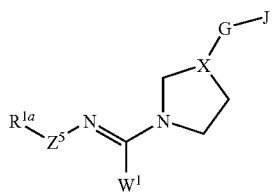

In Table 12 the structures of G (i.e. G-1) and J (e.g., J-29-1) are shown in Exhibits 2 and A, respectively, in the above Embodiments. The substituent $R^{3a}$ attached to some instances of the G ring is hydrogen.

| J | J | J | J | J | J |
|---|---|---|---|---|---|
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |
| \multicolumn{6}{c}{$R^{1a}$ is 3,5-dimethylpyrazole, $Z^5$ is a direct bond, $W^1$ is MeO, X is $X^1$ and G is G-1.} ||||||
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |
| \multicolumn{6}{c}{$R^{1a}$ is 5-methyl-3-trifluoromethylpyrazole, $Z^5$ is a direct bond, $W^1$ is MeO, X is $X^1$ and G is G-1.} ||||||
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |
| \multicolumn{6}{c}{$R^{1a}$ is 2,5-dimethylphenyl, $Z^5$ is a direct bond, $W^1$ is MeS, X is $X^1$ and G is G-1.} ||||||
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |
| \multicolumn{6}{c}{$R^{1a}$ is 2,5-dichlorophenyl, $Z^5$ is a direct bond, $W^1$ is MeS, X is $X^1$ and G is G-1.} ||||||
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |
| \multicolumn{6}{c}{$R^{1a}$ is 3,5-dimethylpyrazole, $Z^5$ is a direct bond, $W^1$ is MeS, X is $X^1$ and G is G-1.} ||||||
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |

TABLE 12-continued

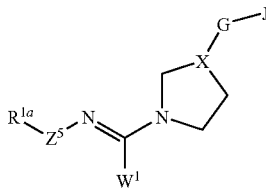

In Table 12 the structures of G (i.e. G-1) and J (e.g., J-29-1) are shown in Exhibits 2 and A, respectively, in the above Embodiments. The substituent $R^{3a}$ attached to some instances of the G ring is hydrogen.

| J | J | J | J | J | J |
|---|---|---|---|---|---|
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 5-methyl-3-trifluoromethylpyrazole, $Z^5$ is a direct bond, $W^1$ is MeS, X is $X^1$ and G is G-1.

| J | J | J | J | J | J |
|---|---|---|---|---|---|
| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-58 |
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 2,5-dimethylphenyl, $Z^5$ is a direct bond, $W^1$ is $NH_2$, X is $X^1$ and G is G-1.

| J | J | J | J | J | J |
|---|---|---|---|---|---|
| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-58 |
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 2,5-dichlorophenyl, $Z^5$ is a direct bond, $W^1$ is $NH_2$, X is $X^1$ and G is G-1.

| J | J | J | J | J | J |
|---|---|---|---|---|---|
| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-58 |
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 3,5-dimethylpyrazole, $Z^5$ is a direct bond, $W^1$ is $NH_2$, X is $X^1$ and G is G-1.

| J | J | J | J | J | J |
|---|---|---|---|---|---|
| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-58 |
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 5-methyl-3-trifluoromethylpyrazole, $Z^5$ is a direct bond, $W^1$ is $NH_2$, X is $X^1$ and G is G-1.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |

TABLE 12-continued

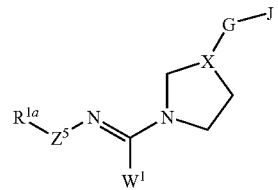

In Table 12 the structures of G (i.e. G-1) and J (e.g., J-29-1) are shown in Exhibits 2 and A, respectively, in the above Embodiments. The substituent $R^{3a}$ attached to some instances of the G ring is hydrogen.

| J | J | J | J | J | J |
|---|---|---|---|---|---|
| J-29-6  | J-29-16 | J-29-26 | J-29-36 | J-29-46 | J-29-58 |
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 2,5-dimethylphenyl, $Z^5$ is a direct bond, $W^1$ is NHOH, X is $X^1$ and G is G-1.

| J | J | J | J | J | J |
|---|---|---|---|---|---|
| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-58 |
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 2,5-dichlorophenyl, $Z^5$ is a direct bond, $W^1$ is NHOH, X is $X^1$ and G is G-1.

| J | J | J | J | J | J |
|---|---|---|---|---|---|
| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-58 |
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 3,5-dimethylpyrazole, $Z^5$ is a direct bond, $W^1$ is NHOH, X is $X^1$ and G is G-1.

| J | J | J | J | J | J |
|---|---|---|---|---|---|
| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-58 |
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 5-methyl-3-trifluoromethylpyrazole, $Z^5$ is a direct bond, $W^1$ is NHOH, X is $X^1$ and G is G-1.

| J | J | J | J | J | J |
|---|---|---|---|---|---|
| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-58 |
| J-29-7  | J-29-17 | J-29-27 | J-29-37 | J-29-47 | J-29-59 |
| J-29-8  | J-29-18 | J-29-28 | J-29-38 | J-29-48 | J-29-60 |
| J-29-9  | J-29-19 | J-29-29 | J-29-39 | J-29-49 |         |
| J-29-10 | J-29-20 | J-29-30 | J-29-40 | J-29-50 |         |

$R^{1a}$ is 2,5-dimethylphenyl, $Z^5$ is a direct bond, $W^1$ is NHOMe, X is $X^1$ and G is G-1.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |

TABLE 12-continued

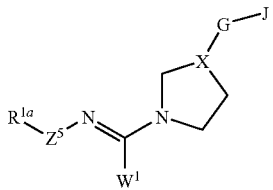

In Table 12 the structures of G (i.e. G-1) and J (e.g., J-29-1) are shown in Exhibits 2 and A, respectively, in the above Embodiments. The substituent $R^{3a}$ attached to some instances of the G ring is hydrogen.

| J | J | J | J | J | J |
|---|---|---|---|---|---|
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 2,5-dichlorophenyl, $Z^5$ is a direct bond, $W^1$ is NHOMe, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 3,5-dimethylpyrazole, $Z^5$ is a direct bond, $W^1$ is NHOMe, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 5-methyl-3-trifluoromethylpyrazole, $Z^5$ is a direct bond, $W^1$ is NHOMe, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 2,5-dimethylphenyl, $Z^5$ is a direct bond, $W^1$ is NHCN, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 2,5-dichlorophenyl, $Z^5$ is a direct bond, $W^1$ is NHCN, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |

TABLE 12-continued

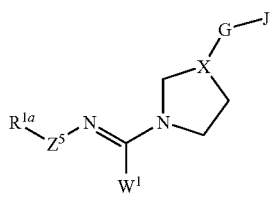

In Table 12 the structures of G (i.e. G-1) and J (e.g., J-29-1) are shown in Exhibits 2 and A, respectively, in the above Embodiments. The substituent $R^{3a}$ attached to some instances of the G ring is hydrogen.

| J | J | J | J | J | J |
|---|---|---|---|---|---|
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 3,5-dimethylpyrazole, $Z^5$ is a direct bond, $W^1$ is NHCN, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 5-methyl-3-trifluoromethylpyrazole, $Z^5$ is a direct bond, $W^1$ is NHCN, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 2,5-dimethylphenyl, $Z^5$ is a direct bond, $W^1$ is MeO, X is $X^2$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 2,5-dimethylphenyl, $Z^5$ is a direct bond, $W^1$ is MeS, X is $X^2$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |

TABLE 12-continued

In Table 12 the structures of G (i.e. G-1) and J (e.g., J-29-1) are shown in Exhibits 2 and A, respectively, in the above Embodiments. The substituent $R^{3a}$ attached to some instances of the G ring is hydrogen.

| J | J | J | J | J | J |
|---|---|---|---|---|---|
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 2,5-dimethylphenyl, $Z^5$ is a direct bond, $W^1$ is $NH_2$, X is $X^2$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 2,5-dimethylphenyl, $Z^5$ is a direct bond, $W^1$ is NHOH, X is $X^2$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 2,5-dimethylphenyl, $Z^5$ is a direct bond, $W^1$ is NHOMe, X is $X^2$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1a}$ is 2,5-dimethylphenyl, $Z^5$ is a direct bond, $W^1$ is NHCN, X is $X^2$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

TABLE 13

In Table 13 the structures of G (e.g., G-1) and J (e.g., J-29-1) are shown in Exhibits 2 and A, respectively, in the above Embodiments. The substituent $R^{3a}$ attached to some instances of the G ring is hydrogen.

$R^{1b}$ is 2,5-dimethylphenyl, $Z^6$ is a direct bond, A is C(=O), W is O, X is $X^1$ and G is G-1.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1b}$ is 2,5-dichlorophenyl, $Z^6$ is a direct bond, A is C(=O), W is O, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1b}$ is 4,4,4-trifluorobutyl, $Z^6$ is a direct bond, A is C(=O), W is O, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1b}$ is i-propyl, $Z^6$ is a direct bond, A is NH, W is O, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1b}$ is i-propyl, $Z^6$ is a direct bond, A is $CH_2$, W is O, X is $X^1$ and G is G-1.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |

TABLE 13-continued

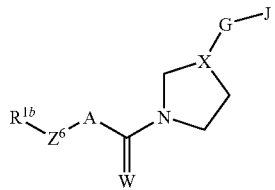

In Table 13 the structures of G (e.g., G-1) and J (e.g., J-29-1) are shown in Exhibits 2 and A, respectively, in the above Embodiments. The substituent $R^{3a}$ attached to some instances of the G ring is hydrogen.

| J | J | J | J | J | J |
|---|---|---|---|---|---|
| J-29-10 | J-29-20 | J-29-30 | J-29-40 | J-29-50 | |

$R^{1b}$ is i-propyl, $Z^6$ is a direct bond, A is CHOH, W is O, X is $X^1$ and G is G-1.

| J-29-1 | J-29-11 | J-29-21 | J-29-31 | J-29-41 | J-29-51 |
|---|---|---|---|---|---|
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

$R^{1b}$ is 3,3,3-trifluoropropoxy, $Z^6$ is a direct bond, A is $CH_2$, W is O, X is $X^1$ and G is G-1.

| J-29-1 | J-29-11 | J-29-21 | J-29-31 | J-29-41 | J-29-51 |
|---|---|---|---|---|---|
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-58 |
| J-29-7 | J-29-17 | J-29-27 | J-29-37 | J-29-47 | J-29-59 |
| J-29-8 | J-29-18 | J-29-28 | J-29-38 | J-29-48 | J-29-60 |
| J-29-9 | J-29-19 | J-29-29 | J-29-39 | J-29-49 | |
| J-29-10 | J-29-20 | J-29-30 | J-29-40 | J-29-50 | |

Formulation/Utility

A compound of Formula 1 of this invention (including N-oxides and salts thereof) will generally be used as a fungicidal active ingredient in a composition, i.e. formulation, with at least one additional component selected from the group consisting of surfactants, solid diluents and liquid diluents, which serve as a carrier. Compounds within the scope of exclusion of proviso (a) of Formula 1 can also be used. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, pills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto vegetable seeds as seed treatments before planting to protect developing roots and other subterranean plant parts and/or foliage through systemic uptake.

The formulations will typically contain effective amounts of active ingredient, diluent and surfactant within the following approximate ranges in the Formulation Table which add up to 100 percent by weight.

Formulation Table

| | Weight Percent | | |
|---|---|---|---|
| | Active Ingredient | Diluent | Surfactant |
| Water-Dispersible and Water-soluble Granules, Tablets and Powders. | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents, Seventh Edition*, John Wiley and Sons, New York, 1987.

Compositions of this invention may also contain formulation auxiliaries and additives, known to those skilled in the art as formulation aids. Such formulation auxiliaries and additives may control: pH (buffers), foaming during processing (antifoams such polyorganosiloxanes (e.g., Rhodorsil® 416)), sedimentation of active ingredients (suspending agents), viscosity (thixotropic thickeners), in-container microbial growth (antimicrobials), product freezing (antifreezes), color (dyes/pigment dispersions (e.g., Pro-lzed® Colorant Red)), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and, usually, grinding as in a hammer mill or fluid-energy mill. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 25 | 98.5% |
| silica aerogel | 0.5% |
| synthetic amorphous fine silica | 1.0% |

Example B

| Wettable Powder | |
|---|---|
| Compound 34 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 44 | 10.0% |
| attapulgite granules (low volatile matter, 0.71/0.30 mm; U.S.S. No. 25-50 sieves) | 90.0% |

Example D

| Extruded Pellet | |
|---|---|
| Compound 75 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 77 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 67 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| Compound 52 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Formulations such as those in the Formulation Table above are typically diluted with water to form aqueous compositions suitable for convenient application. Aqueous compositions for direct applications to the plant or portion thereof (e.g., spray tank compositions) typically at least about 1 ppm or more (e.g., from 1 ppm to 300 ppm) of the compound(s) of this invention.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans*, *Phytophthora megasperma*, *Phytophthora parasitica*, *Phytophthora cinnamomi* and *Phytophthora capsici*, *Pythium* diseases such as *Pythium aphanidermatum*, and diseases in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae*, *Guignardia* diseases such as *Guignardia bidwell*, *Venturia* diseases such as *Venturia inaequalis*, *Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligena* and *Podosphaera leucotricha*, *Pseudocercosporella herpotrichoides*, *Botrytis* diseases such as *Botrytis cinerea*, *Monilinia fructicola*, *Sclerotinia* diseases such as *Sclerotinia sclerotiorum*, *Magnaporthe grisea*, *Phomopsis viticola*, *Helminthosporium* diseases such as *Helminthosporium tritici repentis*, *Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondite*, *Puccinia striiformis*, *Puccinia hordei*, *Puccinia graminis* and *Puccinia arachidis*), *Hemileia vastatrix* and *Phakopsora pachyrhizi*; other pathogens including *Rhizoctonia* spp. (such as *Rhizoctonia solani*); *Fusarium* diseases such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and *Cercospora beticola*; and other genera and species closely related to these pathogens. In addition to their fungicidal activity, the compositions or combinations also have activity against bacteria such as *Erwinia amylovora*, *Xanthomonas campestris*, *Pseudomonas syringae*, and other related species.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a fungicidally effective amount of a compound of Formula 1 and a biologically effective amount of at least one additional biologically active compound or agent and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

Of note is a composition which in addition to the compound of Formula 1 include at least one fungicidal compound selected from the group consisting of the classes (1) methyl benzimidazole carbamate (MBC) fungicides; (2) dicarboximide fungicides; (3) demethylation inhibitor (DMI) fungicides; (4) phenylamide fungicides; (5) amine/morpholine fungicides; (6) phospholipid biosynthesis inhibitor fungicides; (7) carboxamide fungicides; (8) hydroxy(2-amino-) pyrimidine fungicides; (9) anilinopyrimidine fungicides; (10) N-phenyl carbamate fungicides; (11) quinone outside inhibitor (QoI) fungicides; (12) phenylpyrrole fungicides; (13) quinoline fungicides; (14) lipid peroxidation inhibitor fungicides; (15) melanin biosynthesis inhibitors-reductase (MBI-R) fungicides; (16) melanin biosynthesis inhibitors-dehydratase (MBI-D) fungicides; (17) hydroxyanilide fungicides; (18) squalene-epoxidase inhibitor fungicides; (19) polyoxin fungicides; (20) phenylurea fungicides; (21) quinone inside inhibitor (QiI) fungicides; (22) benzamide fungicides; (23) enopyranuronic acid antibiotic fungicides; (24) hexopyranosyl antibiotic fungicides; (25) glucopyranosyl antibiotic: protein synthesis fungicides; (26) glucopyranosyl antibiotic: trehalase and inositol biosynthesis fungicides; (27) cyanoacetamideoxime fungicides; (28) carbamate fungicides; (29) oxidative phosphorylation uncoupling fungicides; (30) organo tin fungicides; (31) carboxylic acid fungicides; (32) heteroaromatic fungicides; (33) phosphonate fungicides; (34) phthalamic acid fungicides; (35) benzotriazine fungicides; (36) benzene-sulfonamide fungicides; (37) pyridazinone fungicides; (38) thiophene-carboxamide fungicides; (39) pyrimidinamide fungicides; (40) carboxylic acid amide (CAA) fungicides; (41) tetracycline antibiotic fungicides; (42) thiocarbamate fungicides; (43) benzamide fungicides; (44) host plant defense induction fungicides; (45) multi-site contact activity fungicides; (46) fungicides other than classes (1) through (45); and salts of compounds of classes (1) through (46).

Further descriptions of these classes of fungicidal compounds are provided below.

(1) "Methyl benzimidazole carbamate (MBC) fungicides" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(2) "Dicarboximide fungicides" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

(3) "Demethylation inhibitor (DMI) fungicides" (Fungicide Resistance Action Committee (FRAC) code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole and uniconazole. The imidazoles include clotrimazole, imazalil, oxpoconazole, prochloraz, pefurazoate and triflumizole. The pyrimidines include fenarimol and nuarimol. The piperazines include triforine. The pyridines include pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(4) "Phenylamide fungicides" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl and metalaxyl-M/mefenoxam. The oxazolidinones include oxadixyl. The butyrolactones include ofurace.

(5) "Amine/morpholine fungicides" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(6) "Phospholipid biosynthesis inhibitor fungicides" (Fungicide Resistance Action Committee (FRAC) code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(7) "Carboxamide fungicides" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamides, furan carboxamides, oxathiin carboxamides, thiazole carboxamides, pyrazole carboxamides and pyridine carboxamides. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include furametpyr, penthiopyrad, bixafen, N-[2-(1S,2R)-[1, 1'-bicyclopropyl]-2-ylphenyl]-3-(difluoromethyl)-1-methyl-1H-pyrazole-4-carboxamide and N-[2-(1,3-dimethylbutyl)phenyl]-5-fluoro-1,3-dimethyl-1H-pyrazole-4-carboxamide. The pyridine carboxamides include boscalid.

(8) "Hydroxy(2-amino-)pyrimidine fungicides" (Fungicide Resistance Action Committee (FRAC) code 8) inhibit nucleic acid synthesis by interfering with adenosine deaminase. Examples include bupirimate, dimethirimol and ethirimol.

(9) "Anilinopyrimidine fungicides" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(10) "N-Phenyl carbamate fungicides" (Fungicide Resistance Action Committee (FRAC) code 10) inhibit mitosis by binding to β-tubulin and disrupting microtubule assembly. Inhibition of microtubule assembly can disrupt cell division, transport within the cell and cell structure. Examples include diethofencarb.

(11) "Quinone outside inhibitor (QoI) fungicides" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_O$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071) and picoxystrobin. The methoxycarbamates include pyraclostrobin. The oximinoacetates include kresoxim-methyl and trifloxystrobin. The oximinoacetamides include dimoxystrobin, metominostrobin, orysastrobin, α-[methoxyimino]-N-methyl-2-[[[1-[3-(trifluoromethyl)phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide. The oxazolidinediones include famoxadone. The dihydrodioxazines include fluoxastrobin. The imidazolinones include fenamidone. The benzylcarbamates include pyribencarb.

(12) "Phenylpyrrole fungicides" (Fungicide Resistance Action Committee (FRAC) code 12) inhibit a MAP protein kinase associated with osmotic signal transduction in fungi. Fenpiclonil and fludioxonil are examples of this fungicide class.

(13) "Quinoline fungicides" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen is an example of this class of fungicide.

(14) "Lipid peroxidation inhibitor fungicides" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintozene, tecnazene and tolclofos-methyl. The 1,2,4-thiadiazole fungicides include etridiazole.

(15) "Melanin biosynthesis inhibitors-reductase (MBI-R) fungicides" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(16) "Melanin biosynthesis inhibitors-dehydratase (MBI-D) fungicides" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(17) "Hydroxyanilide fungicides (Fungicide Resistance Action Committee (FRAC) code 17) inhibit C4-demethylase which plays a role in sterol production. Examples include fenhexamid.

(18) "Squalene-epoxidase inhibitor fungicides" (Fungicide Resistance Action Committee (FRAC) code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(19) "Polyoxin fungicides" (Fungicide Resistance Action Committee (FRAC) code 19) inhibit chitin synthase. Examples include polyoxin.

(20) "Phenylurea fungicides" (Fungicide Resistance Action Committee (FRAC) code 20) are proposed to affect cell division. Examples include pencycuron.

(21) "Quinone inside inhibitor (QiI) fungicides" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(22) "Benzamide fungicides" (Fungicide Resistance Action Committee (FRAC) code 22) inhibit mitosis by binding to β-tubulin and disrupting microtubule assembly Inhibition of microtubule assembly can disrupt cell division, transport within the cell and cell structure. Examples include zoxamide.

(23) "Enopyranuronic acid antibiotic fungicides" (Fungicide Resistance Action Committee (FRAC) code 23) inhibit growth of fungi by affecting protein biosynthesis. Examples include blasticidin-S.

(24) "Hexopyranosyl antibiotic fungicides" (Fungicide Resistance Action Committee (FRAC) code 24) inhibit growth of fungi by affecting protein biosynthesis. Examples include kasugamycin.

(25) "Glucopyranosyl antibiotic: protein synthesis fungicides" (Fungicide Resistance Action Committee (FRAC) code 25) inhibit growth of fungi by affecting protein biosynthesis. Examples include streptomycin.

(26) "Glucopyranosyl antibiotic: trehalase and inositol biosynthesis fungicides" (Fungicide Resistance Action Committee (FRAC) code 26) inhibit trehalase in inositol biosynthesis pathway. Examples include validamycin.

(27) "Cyanoacetamideoxime fungicides (Fungicide Resistance Action Committee (FRAC) code 27) include cymoxanil.

(28) "Carbamate fungicides" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(29) "Oxidative phosphorylation uncoupling fungicides" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(30) "Organo tin fungicides" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

(31) "Carboxylic acid fungicides" (Fungicide Resistance Action Committee (FRAC) code 31) inhibit growth of fungi by affecting deoxyribonucleic acid (DNA) topoisomerase type II (gyrase). Examples include oxolinic acid.

(32) "Heteroaromatic fungicides" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

(33) "Phosphonate fungicides" (Fungicide Resistance Action Committee (FRAC) code 33) include phosphorus acid and its various salts, including fosetyl-aluminum.

(34) "Phthalamic acid fungicides" (Fungicide Resistance Action Committee (FRAC) code 34) include teclofthalam.

(35) "Benzotriazine fungicides" (Fungicide Resistance Action Committee (FRAC) code 35) include triazoxide.

(36) "Benzene-sulfonamide fungicides" (Fungicide Resistance Action Committee (FRAC) code 36) include flusulfamide.

(37) "Pyridazinone fungicides" (Fungicide Resistance Action Committee (FRAC) code 37) include diclomezine.

(38) "Thiophene-carboxamide fungicides" (Fungicide Resistance Action Committee (FRAC) code 38) are proposed to affect ATP production. Examples include silthiofam.

(39) "Pyrimidinamide fungicides" (Fungicide Resistance Action Committee (FRAC) code 39) inhibit growth of fungi by affecting phospholipid biosynthesis and include diflumetorim.

(40) "Carboxylic acid amide (CAA) fungicides" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valiphenal. The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(41) "Tetracycline antibiotic fungicides" (Fungicide Resistance Action Committee (FRAC) code 41) inhibit growth of fungi by affecting complex 1 nicotinamide adenine dinucleotide (NADH) oxidoreductase. Examples include oxytetracycline.

(42) "Thiocarbamate fungicides (b42)" (Fungicide Resistance Action Committee (FRAC) code 42) include methasulfocarb.

(43) "Benzamide fungicides" (Fungicide Resistance Action Committee (FRAC) code 43) inhibit growth of fungi by delocalization of spectrin-like proteins. Examples include acylpicolide fungicides such as fluopicolide and fluopyram.

(44) "Host plant defense induction fungicides" (Fungicide Resistance Action Committee (FRAC) code P) induce host plant defense mechanisms. Host plant defense induction fungicides include benzo-thiadiazole, benzisothiazole and thiadiazole-carboxamide fungicides. The benzo-thiadiazoles include acibenzolar-5-methyl. The benzisothiazoles include probenazole. The thiadiazole-carboxamides include tiadinil and isotianil.

(45) "Multi-site contact fungicides" inhibit fungal growth through multiple sites of action and have contact/preventive activity. This class of fungicides includes: (45.1) "copper fungicides" (Fungicide Resistance Action Committee (FRAC) code M1)", (45.2) "sulfur fungicides" (Fungicide Resistance Action Committee (FRAC) code M2), (45.3) "dithiocarbamate fungicides" (Fungicide Resistance Action Committee (FRAC) code M3), (45.4) "phthalimide fungicides" (Fungicide Resistance Action Committee (FRAC) code M4), (45.5) "chloronitrile fungicides" (Fungicide Resistance Action Committee (FRAC) code M5), (45.6) "sulfamide fungicides" (Fungicide Resistance Action Committee (FRAC) code M6), (45.7) "guanidine fungicides" (Fungicide Resistance Action Committee (FRAC) code M7), (45.8) "triazine fungicides" (Fungicide Resistance Action Committee (FRAC) code M8) and (45.9) "quinone fungicides" (Fungicide Resistance Action Committee (FRAC) code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazine fungicides" include anilazine. "Quinone fungicides" include dithianon.

(46) "Fungicides other than fungicides of classes (1) through (45)" include certain fungicides whose mode of action may be unknown. These include: (46.1) "thiazole carboxamide fungicides" (Fungicide Resistance Action Committee (FRAC) code U5), (46.2) "phenyl-acetamide fungicides" (Fungicide Resistance Action Committee (FRAC) code U6), (46.3) "quinazolinone fungicides" (Fungicide Resistance Action Committee (FRAC) code U7) and (46.4) "benzophenone fungicides" (Fungicide Resistance Action Committee (FRAC) code U8). The thiazole carboxamides include ethaboxam. The phenyl-acetamides include cyflufenamid and N-[[(cyclopropylmethoxy)amino][6-(difluoromethoxy)-2,3-difluorophenyl]-methylene]benzeneacetamide. The quinazolinones include proquinazid and 2-butoxy-6-iodo-3-propyl-4H-1-benzopyran-4-one. The benzophenones include metrafenone. The (b46) class also includes bethoxazin, neo-asozin (ferric methanearsonate), pyrrolnitrin, quinomethionate, N-[2-[4-[[3-(4-chlorophenyl)-2-propyn-1-yl]oxy]-3-methoxy-phenyl]ethyl]-3-methyl-2-[(methylsulfonyl)amino]butanamide, N-[2-[4-[[3-(4-chloro-phenyl)-2-propyn-1-yl]oxy]-3-methoxyphenyl]ethyl]-3-methyl-2-[(ethylsulfonyl)amino]-butanamide, 2-[[2-fluoro-5-(trifluoromethyl)phenyl]thio]-2-[3-(2-methoxyphenyl)-2-thiazo-lidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl) [1,2,4]triazolo[1,5-a]pyrimidine, N-(4-chloro-2-nitrophenyl)-N-ethyl-4-methylbenzenesulfonamide, N-[[(cyclopropylmethoxy)-amino][6-(difluoromethoxy)-2,3-difluorophenyl]methylene]benzeneacetamide, N'-[4-[4-chloro-3-(trifluoromethyl)phenoxy]-2,5-dimethylphenyl]-N-ethyl-N-methylmethanimidamide and 1-[(2-propenylthio)carbonyl]-2-(1-methylethyl)-4-(2-methylphenyl)-5-amino-1H-pyrazol-3-one.

Therefore of note is a mixture (i.e. composition) comprising a compound of Formula 1 and at least one fungicidal compound selected from the group consisting of the aforedescribed classes (1) through (46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (1) through (46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are: insecticides such as abamectin, acephate, acetamiprid, amidoflumet (S-1955), avermectin, azadirachtin, azinphos-methyl, bifenthrin, bifenazate, 3-bromo-1-(3-chloro-2-pyridinyl)-N-[4-cyano-2-methyl-6-[(methylamino)carbonyl]phenyl]-1H-pyrazole-5-carboxamide, buprofezin, carbofuran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, flpronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

The rate of application required for effective control (i.e. "biologically effective amount") will depend on such factors as the plant diseases to be controlled, the location, time of year, host crop, ambient moisture, temperature, and the like. One skilled in the art can easily determine through simple experimentation the biologically effective amount necessary for the desired level of plant disease control.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Of note is a combination of a compound of Formula 1 with at least one other fungicidal active ingredient. Of particular note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to compound of Formula 1 include at least one compound selected from the group consisting of (1) alkylenebis(dithiocarbamate) fungicides; (2) cymoxanil; (3) phenylamide fungicides; (4) pyrimidinone fungicides; (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Pyrimidinone fungicides (group (4)) include compounds of Formula A1

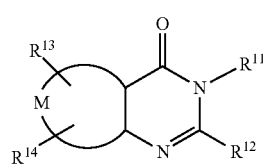

A1 wherein M forms a fused phenyl, thiophene or pyridine ring; $R^{11}$ is $C_1$-$C_6$ alkyl; $R^{12}$ is $C_1$-$C_6$ alkyl or $C_1$-$C_6$ alkoxy; $R^{13}$ is halogen; and $R^{14}$ is hydrogen or halogen.

Pyrimidinone fungicides are described in PCT Patent Application Publication WO 94/26722 and U.S. Pat. Nos. 6,066,638, 6,245,770, 6,262,058 and 6,277,858. Of note are pyrimidinone fungicides selected from the group: 6-bromo- 3-propyl-2-propyloxy-4(3H)-quinazolinone, 6,8-diiodo-3-propyl-2-propyloxy-4(3H)-quinazolinone, 6-iodo-3-propyl-2-propyloxy-4(3H)-quinazolinone (proquinazid), 6-chloro-2-propoxy-3-propyl-thieno[2,3-c/]pyrimidin-4(3H)-one, 6-bromo-2-propoxy-3-propylthieno[2,3-c/]pyrimidin-4(3H)-one, 7-bromo-2-propoxy-3-propylthieno[3,2-c/]pyrimidin-4(3H)-one, 6-bromo-2-propoxy-3-propylpyrido[2,3-d]pyrimidin-4(3H)-one, 6,7-dibromo-2-propoxy-3-propyl-thieno[3,2-d]pyrimidin-4(3H)-one, and 3-(cyclopropylmethyl)-6-iodo-2-(propylthio)pyrido-[2,3-d]pyrimidin-4(3H)-one.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin and trifloxystrobin are known to have this mode of action (H. Sauter et al., *Angew. Chem. Int. Ed.* 1999, 38, 1328-1349). Other fungicidal compounds that inhibit the $bc_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin Of further note are combinations of compounds of Formula 1 with azoxystrobin, kresoxim-methyl, trifloxystrobin, pyraclostrobin, picoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, hexaconazole, ipconazole, metconazole, penconazole, propiconazole, proquinazid, prothioconazole, tebuconazole, triticonazole, famoxadone, prochloraz, penthiopyrad and boscalid (nicobifen).

Preferred for better control of plant diseases caused by fungal plant pathogens (e.g., lower use rate or broader spectrum of plant pathogens controlled) or resistance management are mixtures of a compound of this invention with a fungicide selected from the group: azoxystrobin, kresoxim-methyl, trifloxystrobin, pyraclostrobin, picoxystrobin, dimoxystrobin, metominostrobin/fenominostrobin, quinoxyfen, metrafenone, cyflufenamid, fenpropidine, fenpropimorph, cyproconazole, epoxiconazole, flusilazole, metconazole, propiconazole, proquinazid, prothioconazole, tebuconazole, triticonazole, famoxadone and penthiopyrad.

Specifically preferred mixtures (compound numbers refer to compounds in Index Table A-B) are selected from the group: combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with azoxystrobin, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with kresoxim-methyl, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with trifloxystrobin, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with pyraclostrobin, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with picoxystrobin, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with dimoxystrobin, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with metominostrobin/fenominostrobin, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with quinoxyfen, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with metrafenone, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with cyflufenamid, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with fenpropidine, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with fenpropimorph, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with cyproconazole, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with epoxiconazole, combinations of C Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with flusilazole, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with metconazole, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with propiconazole, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with prothioconazole, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with tebuconazole, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with triticonazole, combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with famoxadone, and combinations of Compound 3, Compound 14, Compound 15, Compound 16, Compound 17, Compound 20, Compound 25, Compound 26, Compound 31, Compound 34, Compound 39, Compound 40, Compound 44, Compound 52, Compound 65, Compound 67, Compound 68, Compound 70, Compound 71, Compound 72, Compound 73, Compound 75 or Compound 77 with penthiopyrad.

The following TESTS demonstrate the control efficacy of compounds of this invention on specific pathogens. The pathogen control protection afforded by the compounds is not limited, however, to these species. See Index Tables A-B for compound descriptions. The following abbreviations are used in the Index Tables which follow: t is tertiary, i is iso, c is cyclo, Me is methyl, Bu is butyl, t-Bu is tent-butyl, Ph is phenyl and OMe is methoxy, The abbreviation "Ex." stands for "Example" and is followed by a number indicating in which example the compound is prepared. In the following table a dash ("-") in the $(R^7)_j$ indicates j is 0 and hydrogen is present at all available positions. Index Tables A-B lists the molecular weight of the highest isotopic abundance parent ion (M+1) formed by addition of $H^+$ (molecular weight of 1) to the molecule, observed by mass spectrometry using atmospheric pressure chemical ionization ($AP^+$).

INDEX TABLE A

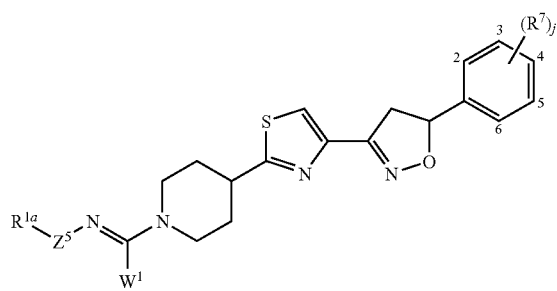

$Z^5$ is a direct bond.

| Cmpd. | $R^{1a}$ | $W^1$ | $(R^7)_j$ | AP+ (M + 1) | M.P. (° C.) |
|---|---|---|---|---|---|
| 1 (Ex. 1) | 2,5-di-Me-Ph | SMe | — | 491 | ** |
| 2 (Ex. 2) | 2,5-di-Me-Ph | H | — | 445 | ** |
| 3 (Ex. 3) | 2,5-di-Me-Ph | OMe | — | 475 | ** |
| 21[a] | 2,5-di-Me-Ph | H | — | 445 | |
| 22 | 2,5-di-Me-Ph | Cl | — | | *** |
| 23 (Ex. 9) | 2,5-di-Me-Ph | $NH_2$ | — | 460 | ** |
| 24 | 2,5-di-Me-Ph | $NMe_2$ | — | 488 | |
| 25 | 2,5-di-Me-Ph | NHOH | 2,6-di-F | 512 | |
| 26[b] | 2,5-di-Me-Ph | SMe | 2,6-di-F | 527 | |
| 27 | 2,5-di-Me-Ph | NHC(=O)Me | — | 502 | |
| 28 | 2,5-di-Me-Ph | NHMe | — | 474 | |
| 29 | 2,5-di-Me-Ph | OEt | — | 489 | |
| 30 | 2,5-di-Me-Ph | 4-morpholinyl | — | 530 | |
| 31 | 2,5-di-Me-Ph | $NH_2$ | 2,6-di-F | 496 | |
| 32 | 2,5-di-Me-Ph | CN | — | 470 | |
| 34 | 2,5-di-Me-Ph | NHOMe | 2,6-di-F | 526 | |
| 35 | 2,5-di-Me-Ph | NHMe | 2,6-di-F | 510 | |
| 38 | 2,5-di-Me-Ph | $NMe_2$ | 2,6-di-F | 524 | |
| 39 | 2,5-di-Me-Ph | NHOEt | 2,6-di-F | 540 | |
| 42 | 2,5-di-Me-Ph | NHCN | 2,6-di-F | 521 | |

** See synthesis example for $^1$H NMR data.

*** See Index Table C for $^1$H NMR data.

[a] HCl salt.

[b] HI salt.

INDEX TABLE B

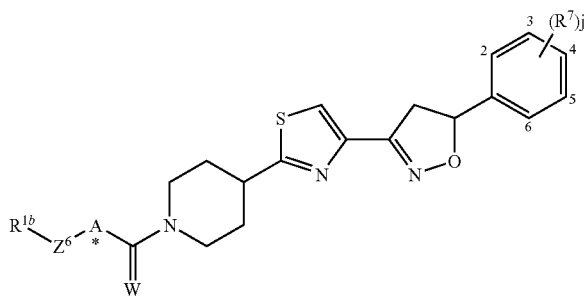

| Cmpd. | $R^{1b}$ | A | W | $(R^7)_j$ | $AP^+(M+1)$ | M.P. (° C.) |
|---|---|---|---|---|---|---|
| $Z^6$ is a direct bond. | | | | | | |
| 4 (Ex. 4) | $CH_3(CH_2)_4$ | NH | O | — | 427 | ** |
| 5 (Ex. 5) | $CH_2=CHCH_2$ | NH | S | — | 413 | ** |
| 6 (Ex. 6) | $CF_3CH(Me)$ | $CH_2$ | O | 2-F | 470 | ** |
| 7 (Ex. 7) | $ClCH_2(CH_2)_2$ | $CH_2$ | O | 2-F | 450 | ** |
| 8 (Ex. 8) | $CH\equiv CCH_2$ | $CH_2$ | O | 2-F | 412 | ** |
| 9 | c-hexyl | NH | O | — | 439 | |
| 10 | $Ph-CH_2$ | NH | O | — | 447 | |
| 11 | $CH_3$ | NMe | O | — | 385 | |
| 12 | $CH_3CH_2$ | NEt | O | — | 413 | |
| 13 | $CH_3CH_2$ | NH | O | — | 385 | |
| 14 | n-Pr | NH | O | — | 399 | |
| 15 | i-Pr | NH | O | — | 399 | 159-161 |
| 16 | t-Bu | NH | O | — | 413 | 174-176 |
| 17 | $CH_3CH_2CH(Me)$ | NH | O | — | 413 | 128-130 |
| 18 | $EtOC(=O)CH_2$ | NH | O | — | 443 | 109-110 |
| 19 | c-pentyl | NH | O | — | 425 | 173-175 |
| 20 | c-hexyl-$CH_2$ | NH | O | — | 453 | 148-150 |
| 40 | 2,5-di-Me-Ph | C(=O) | O | 2-F | 492 | |
| 41 | 5-Me-3-$CF_3$-pyrazol-1-yl | C(=O) | O | 2-F | 536 | |
| 43 | 5-Me-3-$CF_3$-pyrazol-1-yl | C(=O) | O | 2,6-di-F | 554 | |
| 45 | Ph | C(=O) | O | 2-F | 464 | |
| 46 | 2-thienyl | C(=O) | O | 2-F | 470 | |
| 47 | 2-furanyl | C(=O) | O | 2-F | 454 | |
| 48 | Et | CH(OH) | O | 2,6-di-F | 436 | |
| 49 | i-Pr | CH(OH) | O | 2,6-di-F | 450 | |
| $50^c$ | $PhCH_2$ | CH(OH) | O | 2,6-di-F | 498 | |
| 51 | 2,4,6-tri-Me-Ph | C(=O) | O | 2-F | 506 | |
| 52 (Ex. 10) | 2,5-di-Me-Ph | C(=O) | O | 2,6-di-F | 510 | ** |
| 53 | $CF_3$ | CH(OH) | O | 2,6-di-F | 476 | |
| $54^d$ | i-Pr | CH(OH) | O | 2,6-di-F | 450 | |
| $55^c$ | i-Pr | CH(OH) | O | 2,6-di-F | 450 | |
| $56^c$ | i-Bu | CH(OH) | O | 2,6-di-F | 464 | |
| 57 | i-Bu | CH(OH) | O | 2,6-di-F | 464 | |
| 58 | n-Bu | CH(OH) | O | 2,6-di-F | 464 | |
| $59^c$ | c-hexyl | CH(OH) | O | 2,6-di-F | 490 | |
| $60^d$ | c-hexyl | CH(OH) | O | 2,6-di-F | 490 | |
| 61 | n-hexyl | CH(OH) | O | 2,6-di-F | 492 | |
| 63 | CN | $CH_2$ | O | 2,6-di-F | 417 | |
| 64 | MeC(=O)O | $CH_2$ | O | 2,6-di-F | 450 | |
| 65 | Me | C(=O) | O | 2,6-di-F | 420 | |
| 66 | Et | C(=O) | O | 2,6-di-F | 434 | |
| 67 | n-Pr | C(=O) | O | 2,6-di-F | 448 | |
| 68 | i-Pr | C(=O) | O | 2,6-di-F | 448 | |
| 69 | i-Bu | C(=O) | O | 2,6-di-F | 462 | |
| 70 | s-Bu | C(=O) | O | 2,6-di-F | 462 | |
| 71 | 2-thienyl | C(=O) | O | 2,6-di-F | 448 | |
| 72 | 2-furanyl | C(=O) | O | 2,6-di-F | 472 | |
| 73 | $CH_3(CH_2)_4$ | $CH_2$ | O | 2,6-di-F | 462 | |
| 74 | $CF_3CH_2O$ | $CH_2$ | O | 2,6-di-F | 490 | |
| 75 | $CF_3CH_2CH_2O$ | $CH_2$ | O | 2,6-di-F | 504 | |
| 76 | 3-$CF_3$-c-hex-1-yl | $CH_2$ | O | 2,6-di-F | 542 | |
| 77 | $CF_3CH_2OCH_2$ | $CH_2$ | O | 2,6-di-F | 504 | |
| $Z^6$ is $S(=O)_2$. | | | | | | |
| 33 | 2,5-di-Me-Ph | NH | O | — | 523 | |
| 62 | Me | $CH_2$ | O | 2,6-di-F | 470 | |

INDEX TABLE B-continued

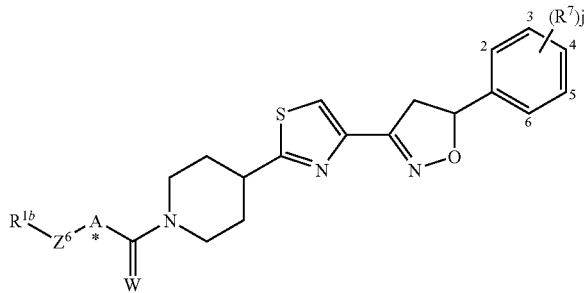

| Cmpd. | $R^{1b}$ | A | W | $(R^7)_j$ | $AP^+(M+1)$ | M.P. (° C.) |
|---|---|---|---|---|---|---|
| $Z^6$ is C(=O) | | | | | | |
| 36 | 2,5-di-Me-Ph | NH | O | 2,6-di-F | 524 | |
| 37 | 2,5-di-Me-Ph | NH | O | 2-F | 507 | |

** See synthesis example for $^1$H NMR data.
$^c$S-isomer at the carbon atom denoted by the asterisk "*" in the structure above.
$^d$R-isomer at the carbon atom denoted by the asterisk "*" in the structure above.

INDEX TABLE C

| Compound No. | $^1$H NMR Data (CDCl$_3$ solution unless indicated otherwise)$^a$ |
|---|---|
| 22 | δ 2.22 (m, 2H), 2.27 (s, 3H), 2.32 (s, 3H), 2.50 (m, 2H), 3.45 (m, 1H), 3.63 (m, 1H), 3.82-3.95 (m, 3H), 4.87 (m, 2H), 5.78 (m, 1H), 7.02 (s, 1H), 7.1-7.2 (m, 2H), 7.3-7.40 (m, 5H), 7.71 (s, 1H). |

BIOLOGICAL EXAMPLES OF THE INVENTION

General protocol for preparing test suspensions for Test A-C: The test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-C. Spraying a 200 ppm test suspension to the point of run-off on the test plants was equivalent to a rate of 500 g/ha.

Test A

Grape seedlings were inoculated with a spore suspension of *Plasmopara viticola* (the causal agent of grape downy mildew) and incubated in a saturated atmosphere at 20° C. for 24 h. After a short drying period, the test suspension was sprayed to the point of run-off on the grape seedlings, which were then moved to a growth chamber at 20° C. for 5 days, after which time the grape seedling were placed back into a saturated atmosphere at 20° C. for 24 h. Upon removal, visual disease ratings were made.

Test B

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test C

Tomato seedlings were inoculated with a spore suspension of *Phytophthora infestans* (the causal agent of tomato late blight) and incubated in a saturated atmosphere at 20° C. for 17 h. After a short drying period, the test suspension was sprayed to the point of run-off on the tomato seedlings, which were then moved to a growth chamber at 20° C. for 4 days, after which time visual disease ratings were made.

In addition to Tests A-C, the compounds were also sprayed on 2 separate sets of tomato plants, which were inoculated with *Botrytis cinerea* or *Alternaria solani* 24 h after treatment, and wheat plants, which were inoculated with *Erysiphe graminis* f. sp. *tritici* 24 h after treatment. Test compounds did not show noticeable activity against these additional pathogens under the test conditions at the application rates tested.

Results for Tests A-C are given in Table A. In the table, a rating of 100 indicates 100% disease control and a rating of 0 indicates no disease control (relative to the controls). A dash (-) indicates no test results, "*" indicates compound was tested at 40 ppm and "**" indicates compound was tested at 10 ppm.

TABLE A

| Cmpd No. | Test A | Test B | Test C |
|---|---|---|---|
| 1* | 96 | 97 | 53 |
| 2 | 17 | 88 | 0 |
| 3* | 99 | 100 | 99 |
| 4* | 86 | 100 | 76 |
| 5* | 83 | 99 | 73 |
| 6 | 0 | 33 | 0 |
| 7 | 98 | 100 | 71 |
| 8 | 46 | 40 | 0 |
| 9 | 0 | 57 | 0 |
| 10 | 25 | 93 | 24 |
| 11 | 0 | 0 | 0 |
| 12 | 8 | 40 | 0 |
| 13 | 57 | 99 | 0 |
| 14 | 88 | 100 | 99 |
| 15 | 86 | 100 | 91 |
| 16 | 86 | 100 | 95 |
| 17* | 86 | 100 | 95 |
| 18* | 39 | 63 | 26 |
| 19* | 67 | 100 | 63 |
| 20* | 95 | 100 | 93 |
| 21 | 0 | 95 | 0 |

TABLE A-continued

| Cmpd No. | Test A | Test B | Test C |
|---|---|---|---|
| 23** | 79 | 100 | 33 |
| 24* | 79 | 97 | 39 |
| 25* | 100 | 100 | 99 |
| 26* | 99 | 100 | 93 |
| 27* | 4 | 99 | 58 |
| 28* | 43 | 95 | 0 |
| 29* | 92 | 99 | 80 |
| 30* | 58 | 64 | 17 |
| 31* | 99 | 100 | 97 |
| 32* | 31 | 58 | 0 |
| 33* | 0 | 0 | 0 |
| 34* | 100 | 100 | 97 |
| 35* | 0 | 86 | 26 |
| 36* | 0 | 99 | 99 |
| 37* | 0 | 63 | 0 |
| 38* | 8 | 33 | 0 |
| 39* | 99 | 100 | 97 |
| 40* | 99 | 100 | 98 |
| 41* | 17 | 26 | 0 |
| 42* | 99 | 100 | 99 |
| 43* | 0 | 25 | 0 |
| 44* | 100 | 100 | 99 |
| 45* | 0 | 0 | 0 |
| 46* | 0 | 0 | 0 |
| 47* | 85 | 33 | 0 |
| 48* | 88 | 100 | 91 |
| 49* | 97 | 98 | 100 |
| 50* | 0 | 87 | 0 |
| 51* | 0 | 52 | 0 |
| 52* | 100 | 100 | 96 |
| 53* | — | 100 | 95 |
| 54* | — | 100 | 99 |
| 55** | 10 | 100 | 99 |
| 56* | 98 | 84 | 50 |
| 57* | — | 100 | 97 |
| 58* | — | 100 | 99 |
| 59* | — | 99 | 83 |
| 60* | — | 100 | 73 |
| 61* | — | 100 | 47 |
| 62* | 99 | 99 | 95 |
| 63* | 94 | 100 | 92 |
| 64* | 80 | 100 | 68 |
| 65* | 88 | 100 | 99 |
| 66* | — | 100 | 99 |
| 67* | 100 | 100 | 99 |
| 68* | 99 | 100 | 93 |
| 69* | 99 | 84 | 64 |
| 70* | 100 | 100 | 88 |
| 71* | 99 | 100 | 94 |
| 72* | 100 | 100 | 99 |
| 73* | 99 | 100 | 99 |
| 74** | 100 | 10 | 97 |
| 75** | 100 | 100 | 97 |
| 76* | 66 | 67 | 0 |
| 77** | 100 | 100 | 99 |

What is claimed is:

1. A compound selected from the compounds of Formula 1 and N-oxides and salts thereof,

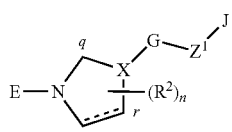

wherein
E is a radical selected from the group consisting of

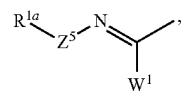
E-1

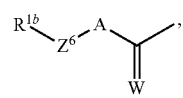
E-2

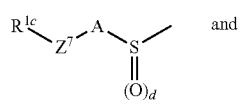
E-3

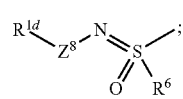
E-4

A is $CHR^{15}$, $NR^{16}$ or $C(=O)$;
G is an optionally substituted 5-membered heterocyclic ring;
J is J-29 wherein the bond shown projecting to the left is bonded to $Z^1$ in Formula 1 and to an available carbon atom ring member in the J ring; and x is an integer from 0 to 5

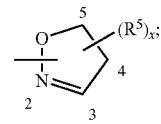

$W^1$ is $OR^{30}$, $SR^{31}$, $NR^{32}R^{33}$ or $R^{28}$;
W is O or S;
X is a radical selected from

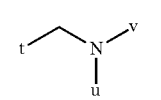
X¹ and

X² wherein the bond of $X^1$ or $X^2$ which is identified with "t" is connected to the carbon atom identified with "q" of Formula 1, the bond which is identified with "u" is connected to the carbon atom identified with "r" of Formula 1, and the bond which is identified with "v" is connected to G Formula 1;
$Z^1$ is a direct bond, O, $C(=O)$, $S(O)_m$, $CHR^{20}$ or $NR^{21}$;
$Z^5$, $Z^6$, $Z^7$ and $Z^8$ independently are a direct bond, $C(=O)$ or $S(O)_2$;
$R^{1a}$, $R^{1b}$, $R^{1c}$ and $R^{1d}$ independently are an optionally substituted phenyl, an optionally substituted naphthalenyl or an optionally substituted 5- to 6-membered heteroaromatic ring; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_4$-$C_{10}$ halocycloalkylalkyl, $C_5$-$C_{10}$ alkylcycloalkylalkyl, $C_2$-$C_8$ alkoxyalkyl, $C_2$-$C_8$ haloalkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ haloalkylthioalkyl, $C_2$-$C_8$ alkylsulfinylalkyl, $C_2$-$C_8$ alkylsulfonylalkyl, $C_3$-$C_8$ alkoxycarbonylalkyl, $C_3$-$C_8$ haloalkoxycarbonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ haloalkenyloxy, $C_2$-$C_8$ alkynyloxy, $C_3$-$C_8$ haloalkynyloxy, $C_2$-$C_8$ alkoxyalkoxy, $C_2$-$C_8$ alkylcarbonyloxy, $C_2$-$C_8$ haloalkylcarbonyloxy, $C_1$-$C_8$ alkylthio, $C_1$-$C_8$ haloalkylthio, $C_3$-$C_8$ cycloalkylthio, $C_3$-$C_{10}$ trialkylsilyl, $C_1$-$C_8$ alkylamino, $C_2$-$C_8$ dialkylamino, $C_1$-$C_8$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_8$ alkylsulfonylamino, $C_1$-$C_8$ haloalkylsulfonylamino, pyrrolidinyl, piperidinyl or morpholinyl;

each $R^2$ is independently halogen, cyano, hydroxy, $C_1$-$C_4$ alkyl, $C_1$-$C_4$ alkenyl, $C_1$-$C_4$ haloalkyl or $C_1$-$C_4$ alkoxy; or two $R^2$ groups are taken together as $C_1$-$C_4$ alkylene or $C_2$-$C_4$ alkenylene to form a bridged bicyclic or fused bicyclic ring system; or two $R^2$ groups attached to adjacent ring carbon atoms joined by a double bond are taken together as —CH=CH—CH=CH— optionally substituted with up to 3 substituents independently selected from halogen, cyano, hydroxy, amino, nitro, $C_1$-$C_4$ alkyl, $C_1$-$C_4$ haloalkyl, $C_1$-$C_4$ alkoxy and $C_1$-$C_4$ haloalkoxy;

$R^6$ is $C_1$-$C_4$ alkyl, $C_1$-$C_4$ haloalkyl or $C_2$-$C_4$ alkoxyalkyl;

each $R^5$ is independently H, halogen, cyano, hydroxy, amino, nitro, —CHO, —C(=O)OH, —C(=O)NH$_2$, —NR$^{25}$R$^{26}$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_8$ alkylaminoalkyl, $C_3$-$C_8$ dialkylaminoalkyl, $C_2$-$C_6$ haloalkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_2$-$C_6$ haloalkoxyalkyl, $C_1$-$C_6$ hydroxyalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_8$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylsulfonylamino, $C_1$-$C_6$ haloalkylsulfonylamino or —Z$^2$Q;

each $Z^2$ is independently a direct bond, —O—, —C(=O)—, —S(O)$_m$—, —CHR$^{20}$— or —NR$^{21}$—;

each Q is independently phenyl, benzyl, naphthalenyl, a 5- to 6-membered heteroaromatic ring or an 8- to 11-membered heteroaromatic bicyclic ring system, each optionally substituted with up to 2 substituents independently selected from R$^{7a}$ on carbon atom or nitrogen atom ring members, and each optionally substituted with up to 5 substituents independently selected from R$^7$ on carbon atom ring members and R$^{12}$ on nitrogen atom ring members; or a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(=O)$_s$, (=NR$^{23}$)$_f$ and SiR$^{17}$R$^{18}$, and each ring or ring system optionally substituted with up to 2 substituents independently selected from R$^{7a}$ on carbon atom or nitrogen atom ring members, and each optionally substituted with up to 5 substituents independently selected from R$^7$ on carbon atom ring members and R$^{12}$ on nitrogen atom ring members;

each R$^{7a}$ is independently —Z$^3$T$^A$, —Z$^3$T$^N$ or —Z$^3$T$^P$;

each Z$^3$ is independently a direct bond, O, NR$^{22}$, C(=O), C(=S), S(O)$_m$, CHR$^{20}$, —CHR$^{20}$—CHR$^{20}$—, —CR$^{24}$=CR$^{27}$—, —OCHR$^{20}$— or —CHR$^{20}$O—;

each T$^A$ is independently phenyl, phenylethynyl or a 5- to 6-membered heteroaromatic ring, each optionally substituted with up to 5 substituents independently selected from R$^{29}$ on carbon atom ring members, and each optionally substituted with up to 2 substituents independently selected from R$^{22}$ on nitrogen atom ring members;

each T$^N$ is independently a 3- to 7-membered nonaromatic ring including ring members selected from the group consisting of C(R$^{29}$)$_2$, O, S, NR$^{22}$, —C(R$^{29}$)=CC(R$^{29}$)—, —C(R$^{29}$)=N—, —N=N—, C(=O), C(=S), C=C—, C(=NR$^{23}$), S(=O)$_s$(=NR$^{23}$)$_f$ and SiR$^{17}$R$^{18}$;

each T$^P$ is independently an 8- to 10-membered aromatic or a 7- to 11-membered nonaromatic bicyclic ring system, said ring system including ring members selected from the group consisting of C(R$^{29}$)$_2$, O, S, NR$^{22}$, —C(R$^{29}$)=CC(R$^{29}$)—, —C(R$^{29}$)=N—, —N=N—, C(=O), C(=S), —C=C—, C(=NR$^{23}$), S(=O)$_s$(=NR$^{23}$)$_f$ and SiR$^{17}$R$^{18}$;

each R$^7$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_6$-$C_{14}$ cycloalkylcycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ alkylsulfonyl, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or R[5] and R[7] are taken together with the atoms linking R[5] and R[7] to form an optionally substituted 5- to 7-membered ring containing ring members selected from carbon atoms and optionally up to 3 heteroatoms selected from up to 1 O, up to 1 S and up to 1 N, and up to 3 ring members selected from C(=O), C(=S), S(=O)$_s$(=NR$^{23}$)$_f$ and SiR$^{17}$R$^{18}$;

each R$^{12}$ is independently H, $C_1$-$C_3$ alkyl, $C_1$-$C_3$ alkylcarbonyl, $C_1$-$C_3$ alkoxy or $C_1$-$C_3$ alkoxycarbonyl;

R$^{15}$ is H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl;

R$^{16}$ is H, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkylsulfonyl or $C_1$-$C_4$ haloalkylsulfonyl;

each R$^{17}$ and R$^{18}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

each R$^{20}$, R$^{22}$, R$^{24}$ and R$^{27}$ is independently H, alkyl or $C_1$-$C_4$ haloalkyl;

each R$^{21}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each R$^{23}$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_1$-$C_6$ alkoxy, $C_1$-$C_6$ haloalkoxy, $C_1$-$C_6$ alkylamino, $C_2$-$C_8$ dialkylamino, $C_1$-$C_6$ haloalkylamino or phenyl;

each R$^{25}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each R$^{26}$ is independently $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl or —Z$^4$Q;

each Z$^4$ is independently O, C(=O), S(O)$_m$, or CHR$^{20}$;

R$^{28}$ is H, halogen, cyano, $C_1$-$C_4$ alkyl, $C_1$-$C_4$ haloalkyl, $C_2$-$C_4$ alkoxyalkyl, $C_2$-$C_4$ alkylcarbonyl, $C_2$-$C_4$ alkoxycarbonyl, $C_2$-$C_3$ alkylaminocarbonyl or $C_3$-$C_6$ dialkylaminocarbonyl;

each R$^{29}$ is independently H, halogen, cyano, hydroxy, amino, nitro, —CHO, —C(=O)OH, —C(=O)NH$_2$, —SO$_2$NH$_2$, —C(=S)NH$_2$, —C(=O) NHCN, —O(=O)NHOH, —SH, —SO$_2$NHCN, —SO$_2$NHOH, —OCN, —SCN, —SF$_5$, —NHCHO, —NHNH$_2$, —N$_3$, —NHOH, —NHCN, —NHC(=O)NH$_2$, —N=C=O, —N=C=S, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{12}$ alkylcycloalkylalkyl, $C_3$-$C_8$ cycloalkenyl, $C_3$-$C_8$ halocycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_{10}$ dialkylaminoalkyl, $C_2$-$C_8$ haloalkylaminoalkyl, $C_4$-$C_{10}$ cycloalkylaminoalkyl, $C_4$-$C_{10}$ cycloalkylcarbonyl, $C_4$-$C_{10}$ cycloalkylaminocarbonyl, $C_2$-$C_7$ cyanoalkyl, $C_1$-$C_6$ hydroxyalkyl, $C_4$-$C_{10}$ cycloalkenylalkyl, $C_2$-$C_8$ haloalkoxyalkyl, $C_2$-$C_8$ alkoxyhaloalkyl, $C_2$-$C_8$ haloalkoxyhaloalkyl, $C_4$-$C_{10}$ halocycloalkoxyalkyl, $C_4$-$C_{10}$ cycloalkenyloxyalkyl, $C_4$-$C_{10}$ halocycloalkenyloxyalkyl, $C_3$-$C_{10}$ dialkoxyalkyl, $C_4$-$C_{12}$ trialkoxyalkyl, $C_3$-$C_8$ alkoxyalkenyl, $C_3$-$C_8$ alkoxyalkynyl, $C_3$-$C_{10}$ halodialkylaminoalkyl, $C_5$-$C_{12}$ cycloalkyl(alkyl)aminoalkyl, $C_2$-$C_8$ alkyl(thiocarbonyl), $C_3$-$C_{10}$ alkoxyalkylcarbonyl, $C_3$-$C_{10}$ alkoxycarbonylalkyl, $C_2$-$C_8$ haloalkoxycarbonyl, $C_3$-$C_{10}$ alkoxyalkoxycarbonyl, $C_2$-$C_8$ (alkylthio)carbonyl, $C_2$-$C_8$ alkoxy(thiocarbonyl), $C_2$-$C_8$ alkylthio(thiocarbonyl), $C_2$-$C_8$ alkylamino(thiocarbonyl), $C_3$-$C_{10}$ dialkylamino(thiocarbonyl), $C_3$-$C_{10}$ alkoxy(alkyl)aminocarbonyl, $C_2$-$C_8$ alkylsulfonylaminocarbonyl, $C_2$-$C_8$ haloalkylsulfonylaminocarbonyl, $C_2$-$C_8$ alkylamidino, $C_3$-$C_{10}$ dialkylamidino, $C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ haloalkylcarbonyloxy, $C_4$-$C_{10}$ cycloalkylcarbonyloxy, $C_3$-$C_{10}$ alkylcarbonylalkoxy, $C_3$-$C_8$ cycloalkylthio, $C_3$-$C_8$ cycloalkylsulfonyl, $C_3$-$C_8$ cycloalkenyloxy, $C_3$-$C_8$ halocycloalkenyloxy, $C_2$-$C_8$ haloalkoxyalkoxy, $C_2$-$C_8$ alkoxyhaloalkoxy, $C_2$-$C_8$ haloalkoxyhaloalkoxy, $C_3$-$C_{10}$ alkoxycarbonylalkoxy, $C_2$-$C_8$ alkyl(thiocarbonyl)oxy, $C_2$-$C_8$ alkylcarbonylthio, $C_2$-$C_8$ alkyl(thiocarbonyl)thio, $C_3$-$C_8$ cycloalkylsulfinyl, $C_3$-$C_{10}$ halotrialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, $C_1$-$C_6$ haloalkylamino, $C_2$-$C_8$ halodialkylamino, $C_3$-$C_8$ cycloalkylamino, $C_2$-$C_8$ haloalkylcarbonylamino, $C_1$-$C_6$ haloalkylsulfonylamino, $C_4$-$C_{10}$ cycloalkylalkylamino, $C_4$-$C_{10}$ cycloalkyl(alkyl)amino, $C_3$-$C_{10}$ alkoxycarbonylalkylamino, $C_1$-$C_6$ alkoxyamino, $C_1$-$C_6$ haloalkoxyamino, $C_4$-$C_{12}$ dialkylimido, $C_2$-$C_8$ alkoxycarbonylamino, $C_2$-$C_8$ haloalkoxycarbonylamino, $C_2$-$C_8$ alkylaminocarbonylamino, $C_3$-$C_{10}$ dialkylaminocarbonylamino, $C_3$-$C_{10}$ alkylaminocarbonyl(alkyl)amino, $C_4$-$C_{12}$ dialkylaminocarbonyl(alkyl)amino, $C_2$-$C_8$ alkylamino(thiocarbonyl)amino, $C_3$-$C_{10}$ dialkylamino(thiocarbonyl)amino, $C_3$-$C_{10}$ alkylamino(thiocarbonyl)alkylamino or $C_4$-$C_{12}$ dialkylamino(thiocarbonyl)alkylamino;

each R$^{30}$ and R$^{31}$ is independently $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_4$-$C_8$ halocycloalkylalkyl, $C_5$-$C_8$ alkylcycloalkylalkyl, $C_2$-$C_6$ alkoxyalkyl, $C_4$-$C_8$ cycloalkoxyalkyl, $C_3$-$C_6$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_6$ dialkylaminoalkyl, $C_2$-$C_6$ haloalkylaminoalkyl, $C_4$-$C_8$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_2$-$C_6$ alkylaminocarbonyl, $C_3$-$C_8$ dialkylaminocarbonyl or $C_4$-$C_8$ cycloalkylaminocarbonyl;

$R^{32}$ is H, cyano, hydroxy, amino, $C_1$-$C_6$ alkyl, $C_3$-$C_6$ alkenyl, $C_3$-$C_6$ alkynyl, $C_1$-$C_6$ haloalkyl, $C_3$-$C_6$ haloalkenyl, $C_3$-$C_6$ haloalkynyl, $C_3$-$C_6$ cycloalkyl, $C_4$-$C_8$ cycloalkylalkyl, $C_2$-$C_6$ alkoxyalkyl, $C_1$-$C_6$ alkoxy, $C_1$-$C_6$ haloalkoxy, $C_1$-$C_6$ alkylsulfonyl, $C_1$-$C_6$ haloalkylsulfonyl, $C_2$-$C_6$ alkylcarbonyl, $C_2$-$C_6$ haloalkylcarbonyl, $C_1$-$C_6$ alkylamino, $C_2$-$C_8$ dialkylamino, $C_1$-$C_6$ haloalkylamino or $C_2$-$C_8$ halodialkylamino;

$R^{33}$ is H, $C_1$-$C_6$ alkyl, $C_3$-$C_6$ alkenyl, $C_3$-$C_6$ alkynyl, $C_1$-$C_6$ haloalkyl or $C_3$-$C_6$ cycloalkyl; or $R^{32}$ and $R^{33}$ are taken together as —(CH$_2$)$_4$—, —(CH$_2$)$_5$— or —(CH$_2$)$_2$O(CH$_2$)$_2$—;

d is 1 or 2;

each m is independently 0, 1 or 2;

n is 0, 1 or 2; and s and f are independently 0, 1 or 2 in each instance of S(=O)$_s$(=NR$^{23}$)$_f$ provided that the sum of s and f is 1 or 2;

provided that:

(i) when $Z^6$ is a direct bond, and A is CHR$^{15}$ or NR$^{16}$, then R$^{1b}$ is other than an optionally substituted phenyl, optionally substituted naphthalenyl or an optionally substituted 5- to 6-membered herteroaromatic ring;

(ii) when A is C(=O), then E is E-2, $Z^6$ is a direct bond and W is O; and (iii) when E is E-3, R$^{1c}$ is unsubstituted phenyl, X is X$^1$ and the ring containing X is saturated, G is an unsubstituted thiazole ring connected at the 2-position to X and at the 4-position to Z$^1$ in Formula 1, Z$^7$ is a direct bond, A is CHR$^{15}$, R$^{15}$ is H, d is 2 and J is an isoxazole ring connected at the 4-position to Z$^1$ and substituted at the 5-position with methyl and at its 3-position with meta-substituted phenyl, then Z$^1$ is O, C(=O), S(O)$_m$, CHR$^{20}$ or NR$^{21}$.

2. A compound of claim 1 wherein

E is E-1 or E-2;

G is a 5-membered heterocyclic ring optionally substituted with up to 2 substituents selected from R$^3$ on carbon ring members and selected from R$^{11}$ on nitrogen ring members;

each R$^3$ is independently halogen, $C_1$-$C_3$ alkyl or $C_1$-$C_3$ haloalkyl;

each R$^{11}$ is independently $C_1$-$C_3$ alkyl;

Z$^1$ is a direct bond, CHR$^{20}$ or NR$^{21}$;

each R$^{21}$ is independently H, $C_1$-$C_3$ alkyl, $C_1$-$C_3$ alkylcarbonyl or $C_2$-$C_3$ alkoxycarbonyl;

R$^{1a}$, R$^{1b}$ and R$^{1c}$ independently are optionally substituted phenyl, optionally substituted naphthalenyl or an optionally substituted 5- or 6-membered heteroaromatic ring; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_2$-$C_8$ haloalkylthioalkyl, $C_3$-$C_8$ cycloalkyl, $C_2$-$C_8$ alkoxyalkyl, $C_2$-$C_8$ haloalkoxyalkyl, $C_3$-$C_8$ alkoxycarbonylalkyl, $C_3$-$C_8$ haloalkoxycarbonylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ alkylcarbonyloxy, $C_2$-$C_8$ haloalkylcarbonyloxy, $C_3$-$C_{10}$ dialkylaminoalkyl, $C_1$-$C_8$ alkoxy, $C_1$-$C_8$ haloalkoxy, $C_1$-$C_8$ alkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl;

each R$^2$ is independently halogen, cyano, hydroxy, $C_1$-$C_2$ alkyl, $C_1$-$C_2$ haloalkyl or $C_1$-$C_2$ alkoxy;

R$^5$ is independently H, halogen, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_3$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —NR$^{25}$R$^{26}$ or —Z$^2$Q;

each R$^{26}$ is independently $C_1$-$C_3$ alkyl or —Z$^4$Q;

each $Z^4$ is independently C(=O) or S(=O)$_2$;

each $Z^2$ is independently a O, C(=O), S(O)$_2$, CHR$^{20}$ or NR$^{21}$;

each Q is independently phenyl, benzyl, naphthalenyl, a 5- to 6-membered heteroaromatic ring or an 8- to 11-membered heteroaromatic bicyclic ring system, each optionally substituted with up to 1 substituent independently selected from R$^{7a}$ on carbon atom or nitrogen atom ring members, and each optionally substituted with up to 5 substituents independently selected from R$^7$ on carbon atom ring members and R$^{12}$ on nitrogen atom ring members; or a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(=O)$_s$(=NR$^{23}$)$_f$ and SiR$^{17}$R$^{18}$, and each ring or ring system optionally substituted with up to 1 substituent independently selected from R$^{7a}$ on carbon atom or nitrogen atom ring members, and each optionally substituted with up to 5 substituents independently selected from R$^7$ on carbon atom ring members and R$^{12}$ on nitrogen atom ring members:

each R$^7$ is independently halogen, cyano, hydroxy, amino, nitro, $C_1$-$C_3$ alkyl, $C_1$-$C_3$ haloalkyl, $C_1$-$C_2$ alkoxy or $C_1$-$C_2$ haloalkoxy; or R$^5$ and R$^7$ are taken together with the atoms linking R5 and R7 to form an optionally substituted 5- to 7-membered ring containing ring members selected from carbon atoms and optionally up to 3 heteroatoms selected from up to 1 O, up to 1 S and up to 1 N, and up to 2 ring members selected from C(=O), C(=S), S(=O)$_s$(=NR$^{23}$)$_f$ and SiR$^{17}$R$^{18}$, the ring optionally substituted with substituents selected from R$^8$;

each R$^8$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsily8;

each $R^{7a}$ is independently —$Z^3T^4$;

each $R^{29}$ is independently H, halogen, cyano, hydroxy, $C_1$-$C_2$ alkyl, $C_1$-$C_2$ haloalkyl, $C_1$-$C_2$ alkoxy or $C_1$-$C_2$ haloalkoxy;

each $T^4$ is independently selected from $T^4$-18 and $T^4$-49 wherein the bond shown projecting to the left is bonded to $Z^3$ in Formula 1 and; r is 0, 1, 2, 3, 4 or 5

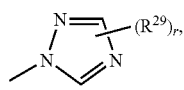

T⁴-18

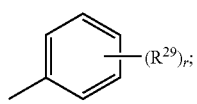

T⁴-49

$R^{15}$ is H, halogen, cyano, hydroxy, —CHO, $C_1$-$C_4$ alkyl, $C_1$-$C_4$ haloalkyl, $C_1$-$C_4$ alkoxy or $C_2$-$C_5$ alkoxycarbonyl; and $R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl.

3. A compound of claim 2 wherein

G is one of G-1 through G-59 wherein the bond projecting to the left is bonded to X, and the bond projecting to the right is bonded to $Z^1$ in Formula 1

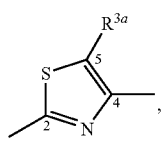

G-1

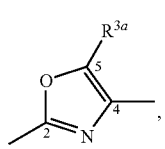

G-2

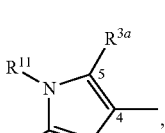

G-3

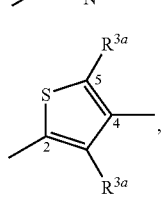

G-4

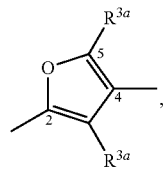

G-5

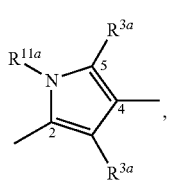

G-6

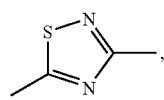

G-7

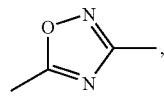

G-8

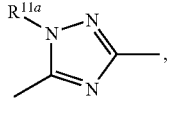

G-9

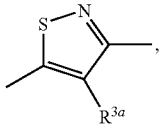

G-10

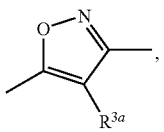

G-11

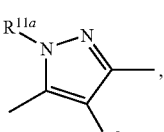

G-12

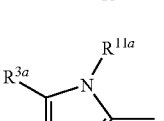

G-13

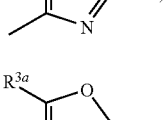

G-14

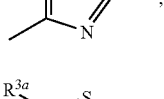

G-15

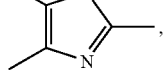

| | |
|---|---|
| 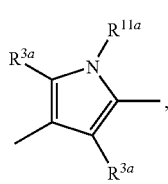 G-16 | 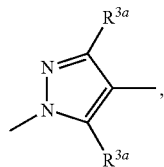 G-27 |
| 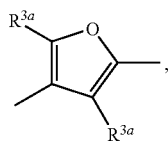 G-17 | 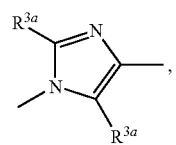 G-28 |
| 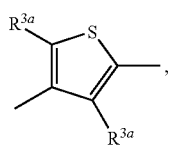 G-18 | 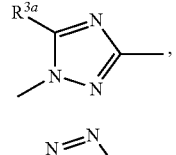 G-29 |
| 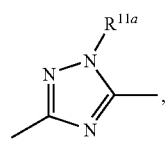 G-19 | 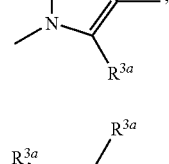 G-30 |
| 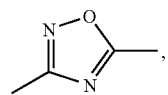 G-20 | 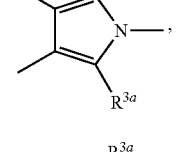 G-31 |
| 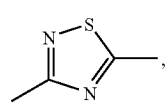 G-21 | 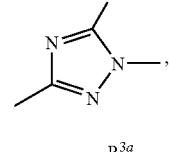 G-32 |
| 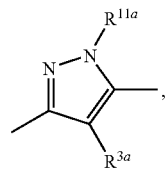 G-22 | 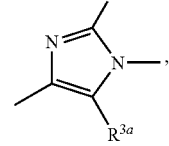 G-33 |
| 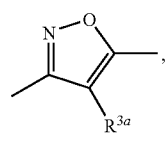 G-23 | 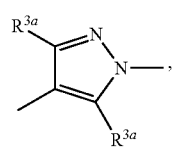 G-34 |
| 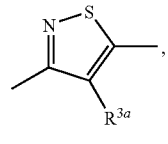 G-24 | 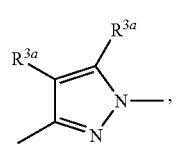 G-35 |
| 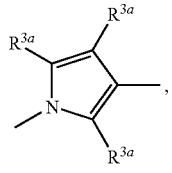 G-25 | 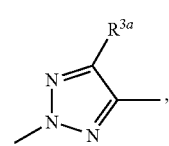 G-36 |
| 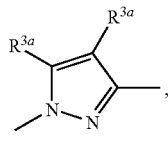 G-26 | |

-continued
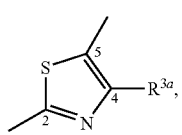 G-37
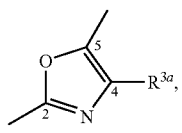 G-38
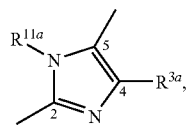 G-39
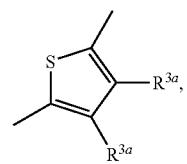 G-40
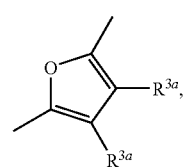 G-41
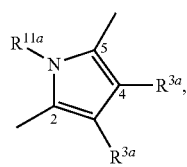 G-42
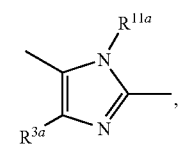 G-43
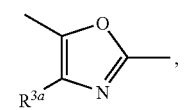 G-44
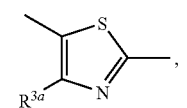 G-45
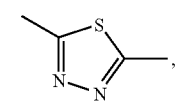 G-46
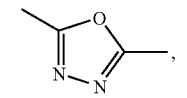 G-47
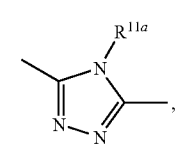 G-48
-continued
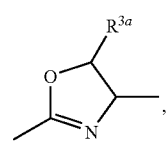 G-49
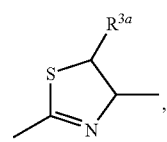 G-50
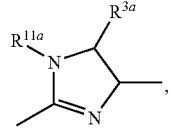 G-51
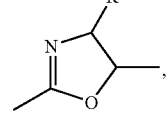 G-52
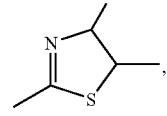 G-53
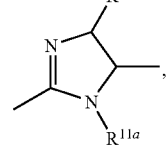 G-54
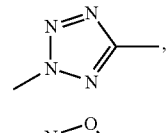 G-55
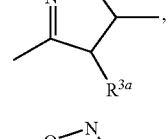 G-56
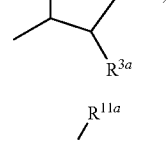 G-57
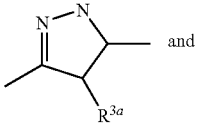 and G-58
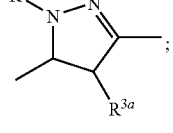 ; G-59 each $R^{3a}$ is independently selected from H and $R^3$;
$R^{11a}$ is selected from H and $R^{11}$;
x is and integer from 0 to 3;
$Z^1$ is a direct bond or $CHR^{20}$;
each $R^{21}$ is independently H or methyl;
$Z^5$ and $Z^6$ independently are each a direct bond;
$R^{1a}$ and $R^{1b}$ independently are phenyl, naphthalenyl or a 5- or 6-membered heteroaromatic ring, each optionally substituted with up to 3 substituents selected from $R^{4a}$ on carbon ring members and $R^{4b}$ on nitrogen ring members; or cyano, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_2$-$C_8$ haloalkylthioalkyl, $C_3$-$C_8$ cycloalkyl, $C_2$-$C_8$ alkoxyalkyl, $C_2$-$C_8$ haloalkoxyalkyl, $C_3$-$C_8$ alkoxycarbonylalkyl, $C_3$-$C_8$ haloalkoxycarbonylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_2$-$C_8$ alkylcarbonyloxy, $C_2$-$C_8$ haloalkylcarbonyloxy, $C_3$-$C_{10}$ dialkylaminoalkyl, $C_1$-$C_8$ alkoxy, $C_1$-$C_8$ haloalkoxy, $C_1$-$C_8$ alkylthio, $C_3$-$C_{10}$ trialkylsilyl, $C_1$-$C_8$ alkylamino, $C_2$-$C_8$ dialkylamino, $C_2$-$C_8$ alkylcarbonylamino, pyrrolidinyl, piperidinyl or morpholinyl;
each $R^{4a}$ is independently halogen, cyano, hydroxy, amino, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_2$-$C_8$ dialkylaminocarbonyl or $C_3$-$C_6$ trialkylsilyl;
each $R^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl;
each $R^2$ is independently cyano, hydroxy, methyl or methoxy;
each $R^5$ is independently H, halogen, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —$NR^{25}R^{26}$ or —$Z^2Q$;
each $Z^2$ is independently a direct bond or $NR^{21}$—;
Q is one of Q-1 through Q-106 wherein p is an teger from 0 to 5 and q is an integer from 0 to 2

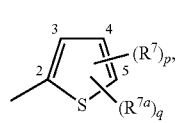

Q-1

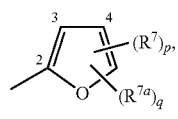

Q-2

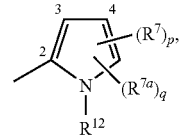

Q-3

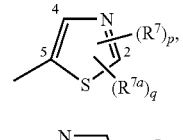

Q-4

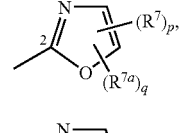

Q-5

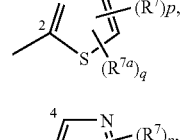

Q-6

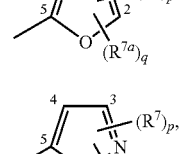

Q-7

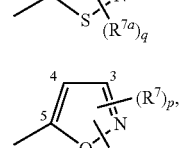

Q-8

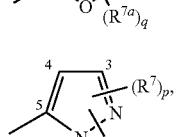

Q-9

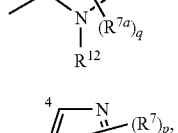

Q-10

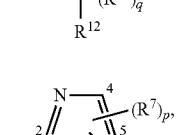

Q-11

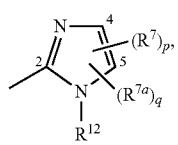

Q-12

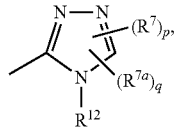

Q-13

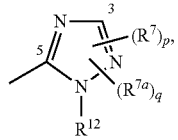

Q-14

-continued
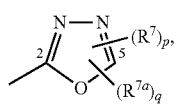 Q-15
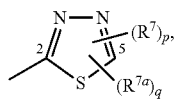 Q-16
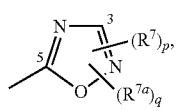 Q-17
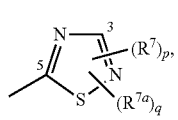 Q-18
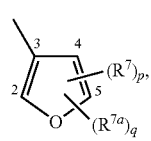 Q-19
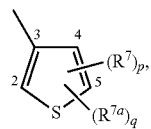 Q-20
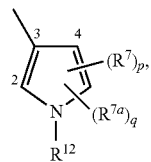 Q-21
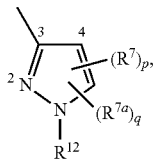 Q-22
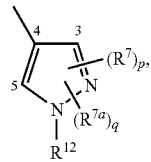 Q-23
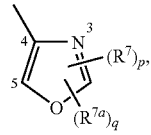 Q-24
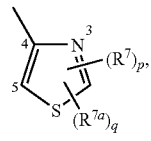 Q-25
-continued
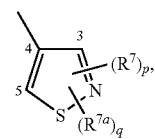 Q-26
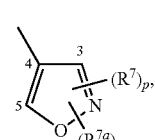 Q-27
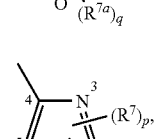 Q-28
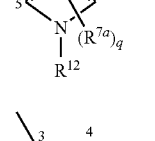 Q-29
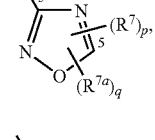 Q-30
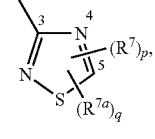 Q-31
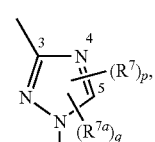 Q-32
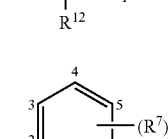 Q-33
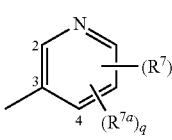 Q-34
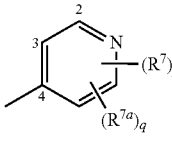 Q-35
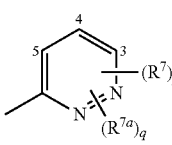

-continued

| Q-36 |
| Q-37 |
| Q-38 |
| Q-39 |
| Q-40 |
| Q-41 |
| Q-42 |
| Q-43 |
| Q-44 |
| Q-45 |

-continued

| Q-46 |
| Q-47 |
| Q-48 |
| Q-49 |
| Q-50 |
| Q-51 |
| Q-52 |
| Q-53 |
| Q-54 |
| Q-55 |
| Q-56 |
| Q-57 |

-continued
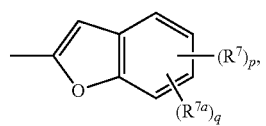 Q-58
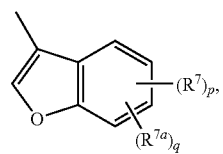 Q-59
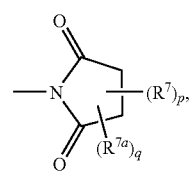 Q-60
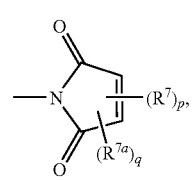 Q-61
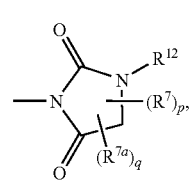 Q-62
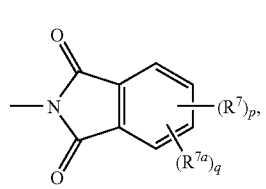 Q-63
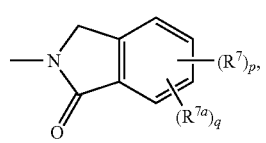 Q-64
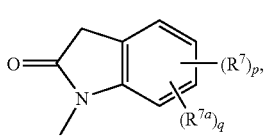 Q-65
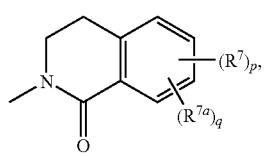 Q-66
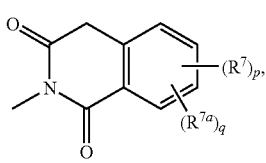 Q-67
-continued
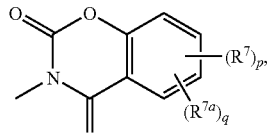 Q-68
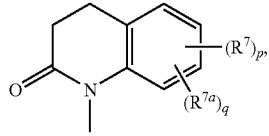 Q-69
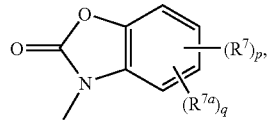 Q-70
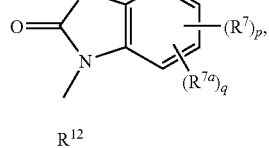 Q-71
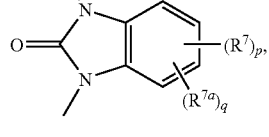 Q-72
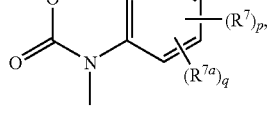 Q-73
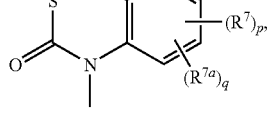 Q-74
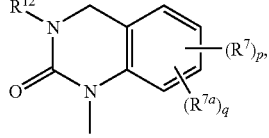 Q-75
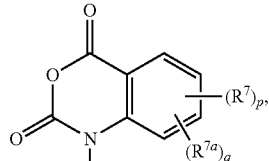 Q-76
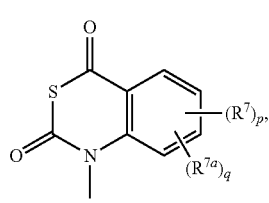 Q-77

-continued
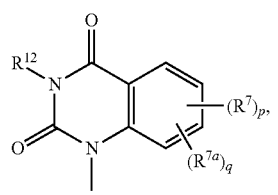 Q-78
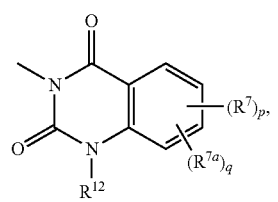 Q-79
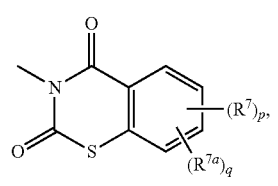 Q-80
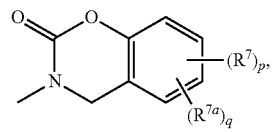 Q-81
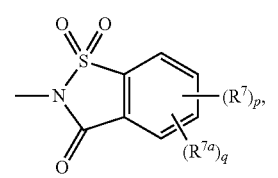 Q-82
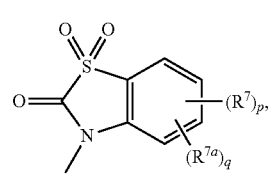 Q-83
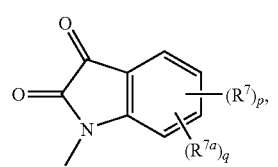 Q-84
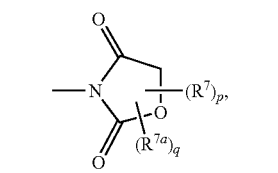 Q-85
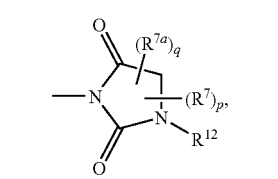 Q-86
-continued
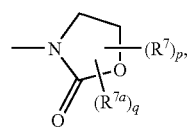 Q-87
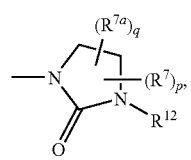 Q-88
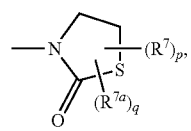 Q-89
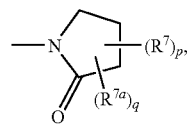 Q-90
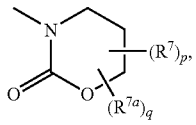 Q-91
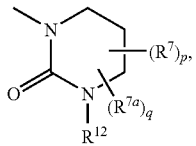 Q-92
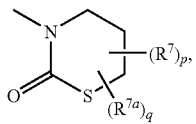 Q-93
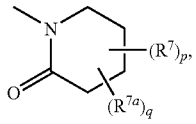 Q-94
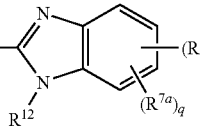 Q-95
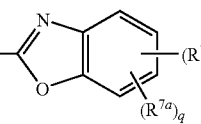 Q-96
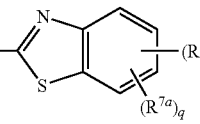 Q-97

-continued

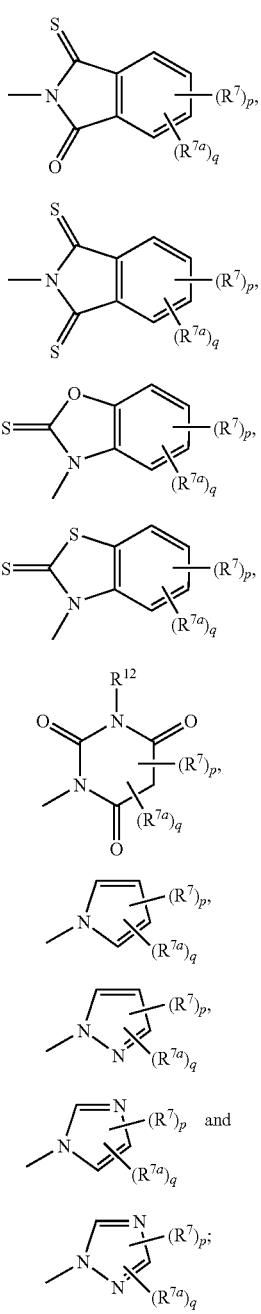

each R⁷ is independently halogen, cyano, hydroxy, $C_1$-$C_3$ alkyl, $C_1$-$C_3$ haloalkyl, $C_1$-$C_2$ alkoxy or $C_1$-$C_2$ haloalkoxy;
each R²⁹ is independently H, halogen, $C_1$-$C_2$ alkyl, $C_1$-$C_2$ haloalkyl or $C_1$-$C_2$ alkoxy;
R¹⁵ is H, halogen, cyano, hydroxy, methyl, methoxy or methoxycarbonyl;
R¹⁶ is H, methyl, methylcarbonyl or methoxycarbonyl;
R²⁸ is H, halogen, cyano or $C_1$-$C_4$ alkyl;
each R³⁰ and R³¹ is independently selected from $C_1$-$C_6$ alkyl, $C_3$-$C_4$ alkenyl, $C_3$-$C_4$ alkynyl, $C_1$-$C_4$ haloalkyl, $C_3$-$C_6$ haloalkenyl, $C_3$-$C_6$ haloalkynyl, $C_2$-$C_6$ alkoxyalkyl and $C_3$-$C_6$ cycloalkyl;
R³² is H, cyano, hydroxy, amino, $C_1$-$C_6$ alkyl or $C_1$-$C_6$ alkoxy; and R³³ is H or $C_1$-$C_6$ alkyl.

4. A compound of claim 3 wherein

G is selected from G-1, G-2, G-7, G-8, G-14, G-15, G-23, G-24, G-26, G-27, G-36, G-37, G-38, G-49, G-50 and G-55;

G is unsubstituted;

x is an integer from 0 to 2;

W is O;

Z¹ is a direct bond;

R¹ᵃ and R¹ᵇ independently are selected from U-1 through U-50 wherein when R⁴ is attached to a carbon ring member, said R⁴ is selected from R⁴ᵃ, and when R⁴ is attached to a nitrogen ring member, said R⁴ is selected from R⁴ᵇ, and k is 0, 1 or 2; or alkyl, $C_2$-$C_5$ alkenyl, $C_2$-$C_5$ haloalkyl, $C_2$-$C_5$ haloalkenyl, $C_2$-$C_5$ haloalkylthioalkyl, $C_2$-$C_5$ alkoxyalkyl, $C_2$-$C_5$ haloalkoxyalkyl, $C_2$-$C_5$ alkylthioalkyl, $C_2$-$C_5$ alkylaminoalkyl, $C_2$-$C_5$ alkylcarbonyloxy, $C_2$-$C_5$ haloalkylcarbonyloxy, $C_2$-$C_5$ alkoxy, $C_2$-$C_5$ haloalkoxy, $C_2$-$C_5$ alkylthio, $C_2$-$C_5$ alkylamino or $C_2$-$C_5$ alkylcarbonylamino

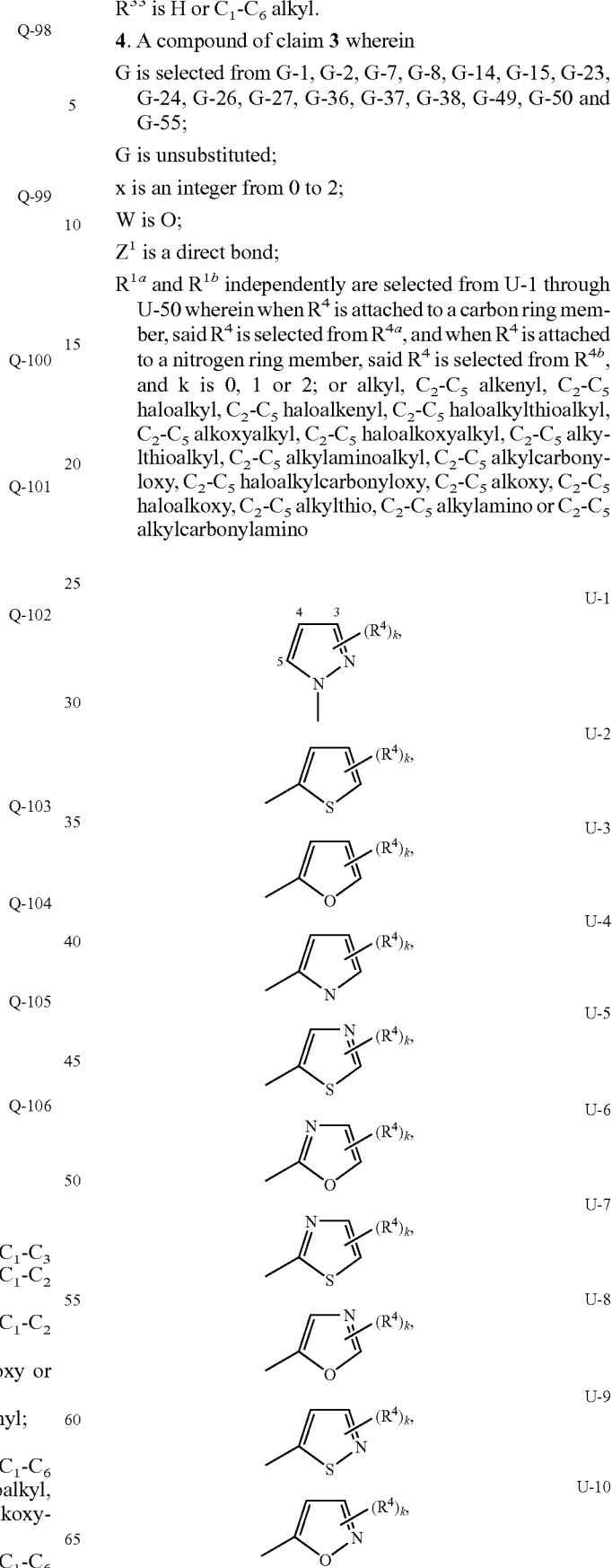

| | |
|---|---|
| U-11 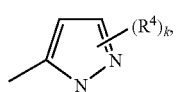 | U-24 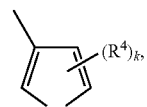 |
| U-12 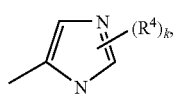 | U-25 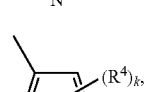 |
| U-13 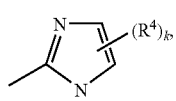 | U-26 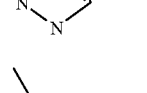 |
| U-14 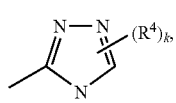 | U-27 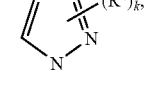 |
| U-15 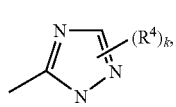 | U-28 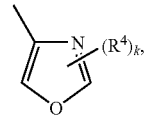 |
| U-16 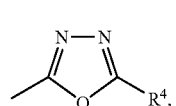 | U-29 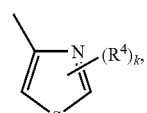 |
| U-17 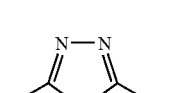 | U-30 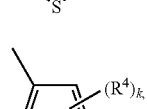 |
| U-18 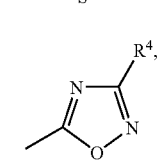 | U-31 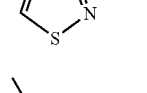 |
| U-19 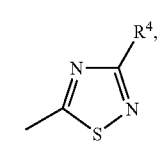 | U-32 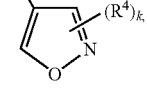 |
| U-20 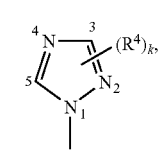 | U-33 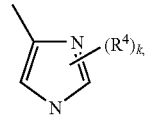 |
| U-21 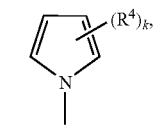 | U-34 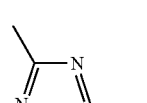 |
| U-22 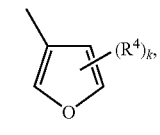 | U-35 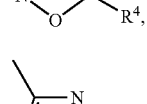 |
| U-23 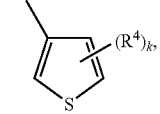 | 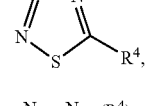 |
| | 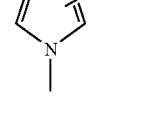 |
| | 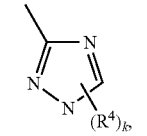 |

-continued

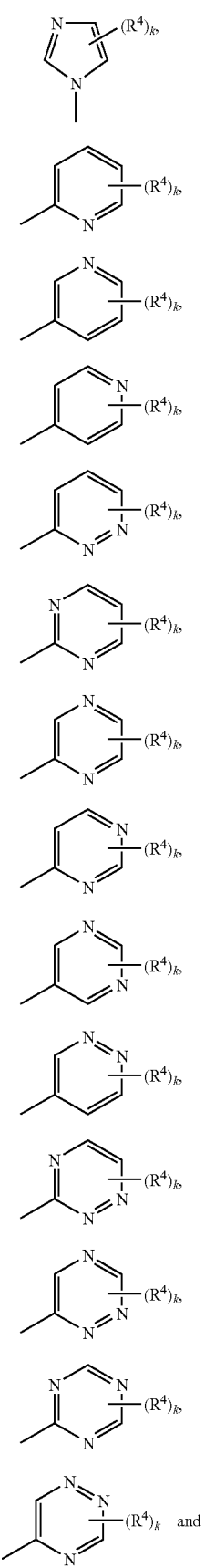

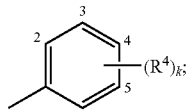

each $R^5$ is independently H, halogen, cyano, $C_1$-$C_6$ alkyl, $C_1$-$C_6$ haloalkyl, $C_1$-$C_6$ alkoxy, $C_1$-$C_6$ haloalkoxy, —$NR^{25}R^{26}$ or —$Z^2Q$;
each $Z^2$ is a direct bond;
each Q is independently Q-1, Q-20, Q-32 through Q-34, Q-45 through Q-47, Q-60 through Q-73, Q-76 through Q-79, Q-84 through Q-94 and Q-98 through Q-106;
p is an integer from 0 to 3;
q is an integer from 0 to 1;
each $R^7$ is independently F, Cl, cyano, hydroxy, methyl or methoxy;
$R^{28}$ is H, halogen or cyano;
each $R^{30}$ and $R^{31}$ is independently selected from $C_1$-$C_6$ alkyl, $C_3$-$C_4$ alkenyl, $C_3$-$C_4$ alkynyl and $C_1$-$C_4$ haloalkyl;
$R^{32}$ is selected H, cyano, hydroxy, amino, $C_1$-$C_3$ alkyl or $C_1$-$C_3$ alkoxy;
$R^{33}$ is selected from H or methyl; and
n is 0.

5. A compound of claim 4 wherein
G is selected from G-2, G-15, G-26, G-27, G-36, G-37 and G-38;
X is $X^1$ or $X^2$; and the ring comprising X is saturated;
$R^{1a}$ and $R^{1b}$ independently are selected from U-1 through U-3, U-11, U-13, U-20, U-22, U-23, U-36 through U-39 and U-50 in Exhibit 1 wherein when $R^4$ is attached to a carbon ring member, said $R^4$ is selected from $R^{4a}$, and when $R^4$ is attached, to a nitrogen ring member, said $R^4$ is selected from $R^{4b}$, and k is 0, 1 or 2; or $C_3$-$C_5$ alkyl, $C_3$-$C_5$ alkenyl, $C_3$-$C_5$ haloalkyl, $C_3$-$C_5$ haloalkenyl, $C_2$-$C_4$ haloalkylthioalkyl, $C_2$-$C_4$ alkoxyalkyl, $C_2$-$C_4$ haloalkoxyalkyl, $C_2$-$C_4$ alkylthioalkyl, $C_2$-$C_4$ alkylaminoalkyl, $C_2$-$C_3$ alkylcarbonyloxy, $C_2$-$C_3$ haloalkylcarbonyloxy, $C_2$-$C_4$ alkoxy, $C_2$-$C_4$ haloalkoxy, $C_2$-$C_4$ alkylthio, $C_2$-$C_4$ alkylamino or $C_2$-$C_3$ alkylcarbonylamino;
each $R^5$ is independently H, halogen, cyano, $C_1$-$C_6$ alkyl, $C_1$-$C_6$ haloalkyl, $C_1$-$C_6$ alkoxy, $C_1$-$C_6$ haloalkoxy or —$Z^2Q$;
Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100 and Q-101 through Q-106;
$R^{28}$ is Cl, F or cyano;
each $R^{30}$ and $R^{31}$ is independently selected from $C_1$-$C_4$ alkyl;
$R^{32}$ is H, cyano, hydroxy, $C_1$-$C_2$ alkyl or $C_1$-$C_2$ alkoxy; and
$R^{33}$ is H.

6. A compound of claim 5 wherein
G is selected from G-1, G-2, G-15, G-26 and G-36;
J is any one of J-29-1 to J-29-60

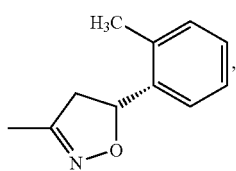

-continued
J-29-2
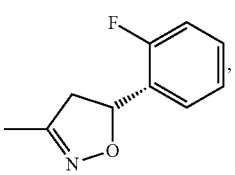
J-29-3
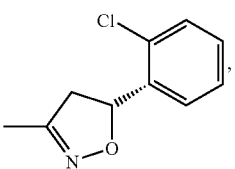
J-29-4
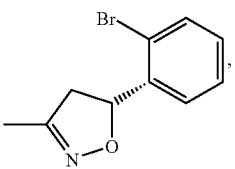
J-29-5
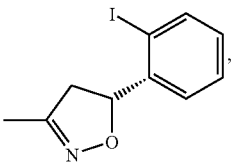
J-29-6
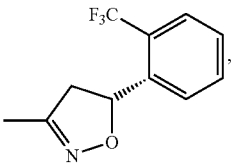
J-29-7
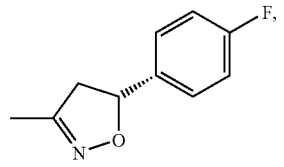
J-29-8
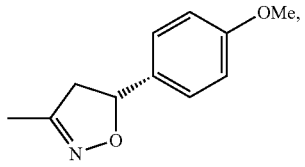
J-29-9
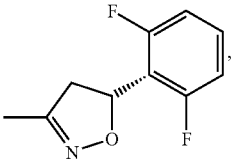
J-29-10
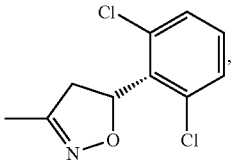
-continued
J-29-11
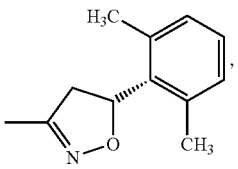
J-29-12
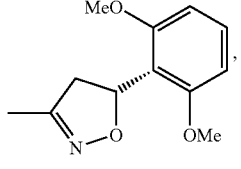
J-29-13
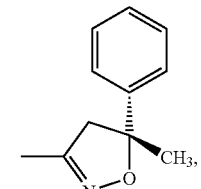
J-29-14
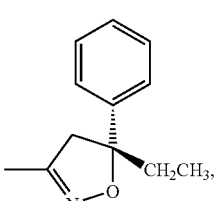
J-29-15
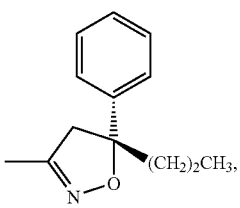
J-29-16
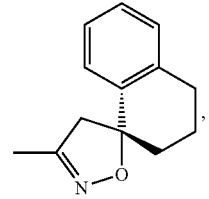
J-29-17
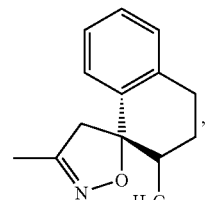
J-29-18
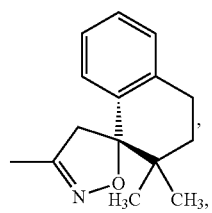

| | |
|---|---|
| J-29-19 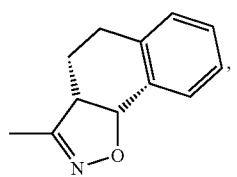 | J-29-27 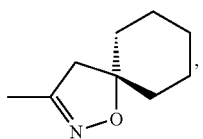 |
| J-29-20 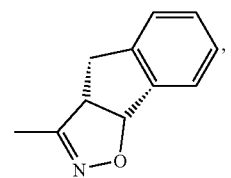 | J-29-28 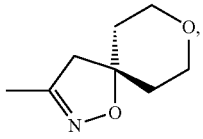 |
| J-29-21 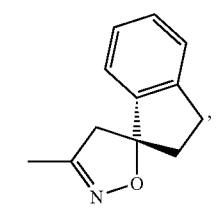 | J-29-29 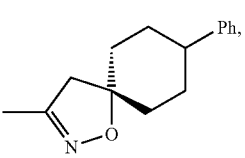 |
| J-29-22 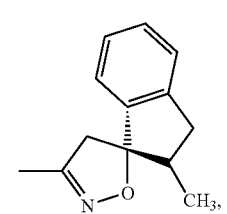 | J-29-30 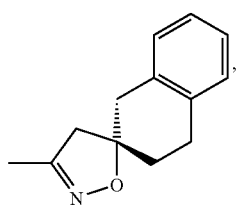 |
| J-29-23 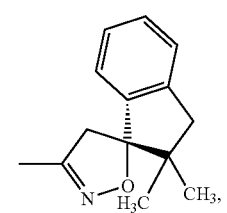 | J-29-31 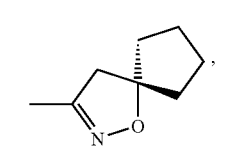 |
| J-29-24 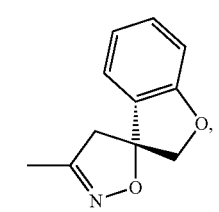 | J-29-32 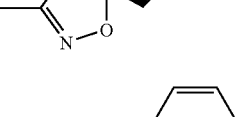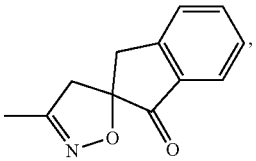 |
| J-29-25 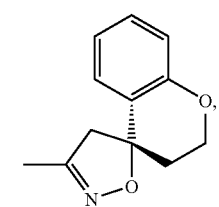 | J-29-33 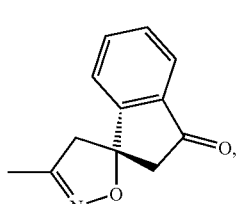 |
| J-29-26 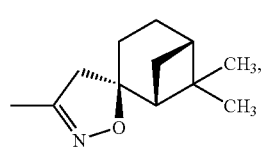 | J-29-34 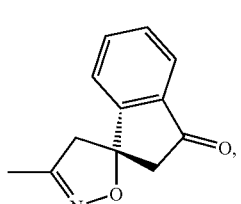 |
| | J-29-35 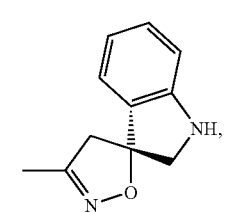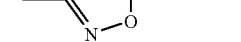 |

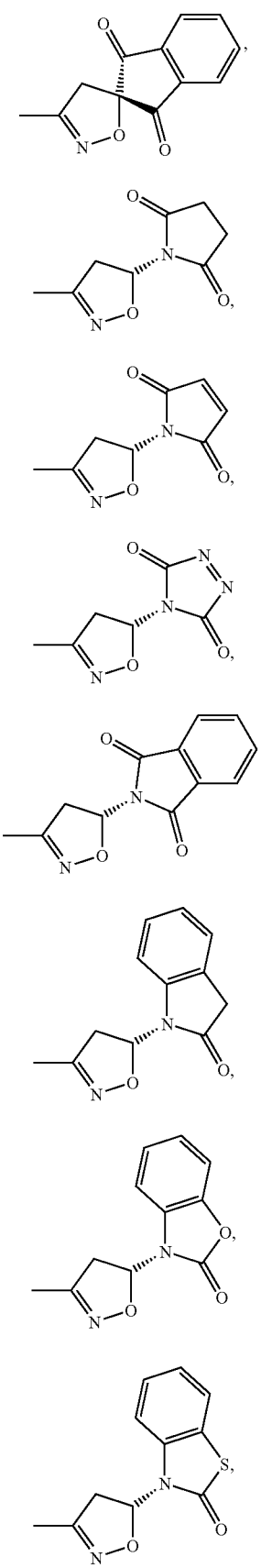
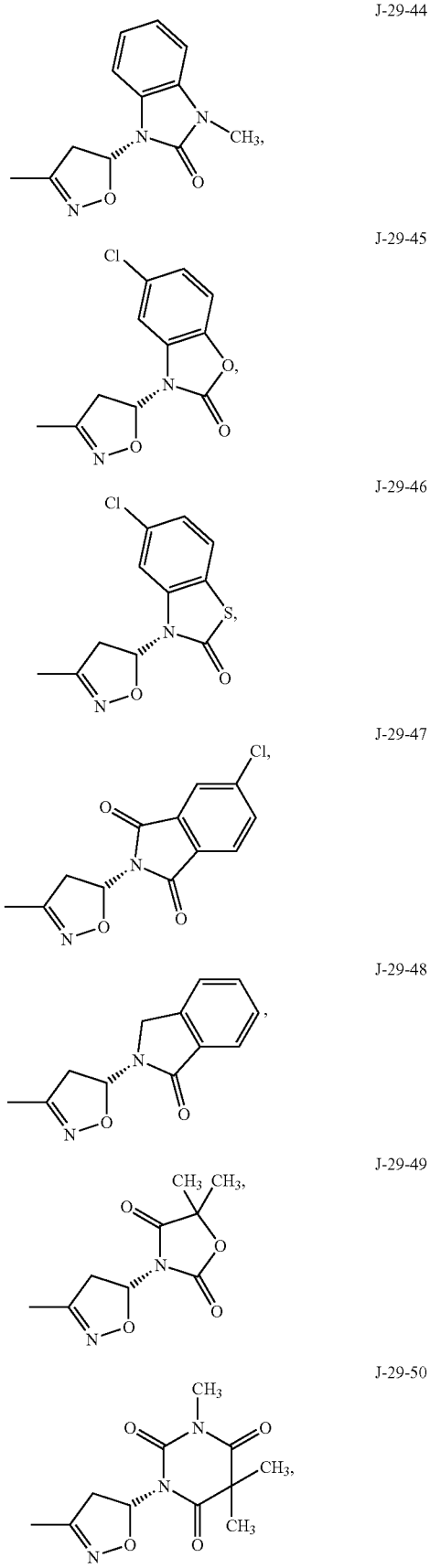

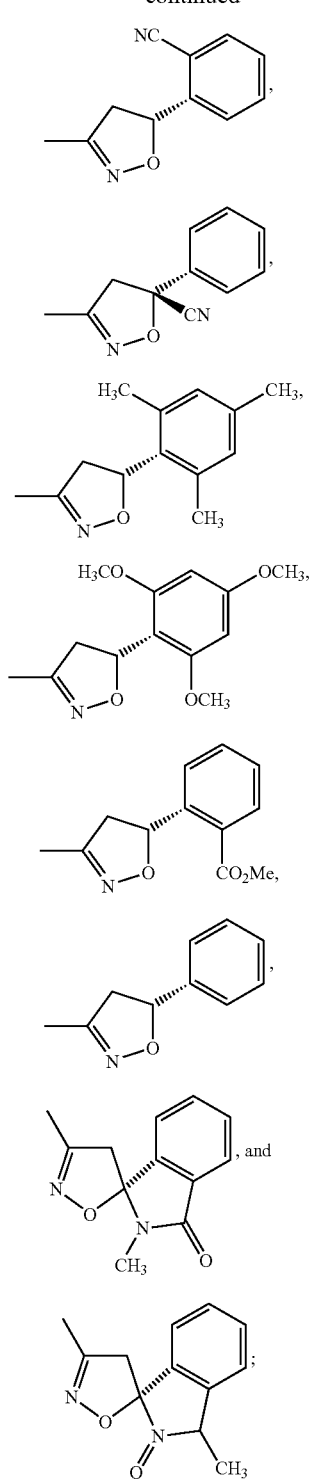

X is $X^1$;

$R^{1a}$ and $R^{1b}$ are each selected from U-1, U-20 and U-50 in Exhibit 1 wherein when $R^4$ is selected from $R^{4a}$, and k is 0, 1 or 2; or $C_3$-$C_5$ haloalkyl, $C_3$-$C_5$ haloalkenyl, $C_3$-$C_5$ haloalkylthioalkyl, $C_3$-$C_5$ haloalkoxyalkyl, $C_2$-$C_3$ haloalkylcarbonyloxy or $C_2$-$C_4$ haloalkoxy;

each $R^5$ is independently cyano, $C_1$-$C_6$ alkyl, $C_1$-$C_6$ alkoxy or —$Z^2Q$;

Q is selected from Q-45, Q-63, Q-64, Q-65, Q-68, Q-69, Q-70, Q-71, Q-72, Q-84 and Q-85; and each $R^{30}$ and $R^{31}$ is independently ethyl or methyl.

7. A compound of claim 1 selected from the group consisting of:

methyl 4-[4-(2,3-dihydrospiro[1H-indene-1,5'(4'H)-isoxazol]-3'-yl)-2-thiazolyl]-N-(2,5-dimethylphenyl)-1-piperidinecarboximidate, methyl 4-[4-[5-(2,6-difluorophenyl)-4,5-dihydro-3-isoxazolyl]-2-thiazolyl]-N-(2,5-dimethylphenyl)-1-piperidinecarboximidate, methyl 4-[4-[4,5-dihydro-5-(2-oxo-3(2H)-benzoxazolyl)-3-isoxazolyl]-2-thiazolyl]-N-(2,5-dimethylphenyl)-1-piperidinecarboximidate, methyl N-(2,5-dimethylphenyl)-4-[4-[5-(2,6-dimethyylphenyl)-4,5-dihydro-3-isoxazolyl]-2-thiazolyl]-1-piperidinecarboximidate, methyl 4-[4-(3',4''-dihydrospiro[isoxazole-5(4H),1'(2'H)-naphthalen]-3-yl)-2-thiazolyl]-N-(2,5-dimethylphenyl)-1-piperidinecarboximidate, methyl N-(2,5-dimethylphenyl)-4-[4-[5-(2-fluorophenyl)-4,5-dihydro-3-isoxazolyl]-2-thiazolyl]-1-piperidinecarboximidate, methyl 4-[4-(5-cyano-4,5-dihydro-5-phenyl-3-isoxazolyl)-2-thiazolyl]-N-(2,5-dimethylphenyl)-1-piperidinecarboximidate, methyl 4-[4-[5-(2-cyanophenyl)-4,5-dihydro-3-isoxazolyl]-2-thiazolyl]-N-(2,5-dimethylphenyl)-1-piperidinecarboximidate, and 4-[4-(4,5-dihydro-5-phenyl-3-isoxazolyl)-2-thiazolyl]-N-(2,5-dimethylphenyl)-1-piperidinecarboximidamide.

8. A compound of claim 1 wherein A is C(═O).

9. A compound of claim 1 wherein A is $CHR^{15}$ or $NR^{16}$.

10. A method for controlling plant diseases caused by Oomycete fungal plant pathogens comprising applying to the plant or portion thereof, or to the plant seed or seedling, a fungicidally effective amount of a compound of claim 1.

11. A fungicidal composition comprising (1) a compound of claim 1; and (2) at least one other fungicide.

12. A fungicidal composition comprising (1) a fungicidally effective amount of a compound of claim 1; and (2) at least one additional component selected from the group consisting of surfactants, solid diluents and liquid diluents.

* * * * *

UNITED STATES PATENT AND TRADEMARK OFFICE
CERTIFICATE OF CORRECTION

PATENT NO. : 8,349,870 B2
APPLICATION NO. : 12/863875
DATED : January 8, 2013
INVENTOR(S) : Balreddy Kamireddy, Robert James Pasteris and Mary Ann Hanagan It is certified that error appears in the above-identified patent and that said Letters Patent is hereby corrected as shown below:

In the Claims:

Column 264, lines 28-29, Claim 1, "bonded to $Z^1$ in Formula 1 and to an available carbon atom ring member in the J ring; and x is an integer" should read --bonded to $Z^1$ in Formula 1; and x is an integer--.

Column 270, lines 54-55, Claim 2, "R5 and R7" should read --$R^5$ and $R^7$--.

Column 277, line 54, Claim 3, "p is an teger" should read --p is an integer--.

Column 288, line 17, Claim 4, "or alkyl," should read --or $C_2$-$C_5$ alkyl,--.

Column 292, line 29, Claim 5, "G is selected from G-2, G-15, G-26, G-27, G-36, G-37 and" should read --G is selected from G-1, G-2, G-15, G-26, G-27, G-36, G-37 and--.

Column 292, line 34, Claim 5, "U-50 in Exhibit 1 wherein" should read --U-50 wherein--.

Column 300, lines 2-3, Claim 6, "U-50 in Exhibit 1 wherein when $R^4$ is selected" should read --U-50 wherein $R^4$ is selected--.

Signed and Sealed this
Sixteenth Day of July, 2013

Teresa Stanek Rea
*Acting Director of the United States Patent and Trademark Office*